United States Patent [19]
Silverman et al.

[11] Patent Number: 5,866,787
[45] Date of Patent: Feb. 2, 1999

[54] TRANSGENIC PLANTS CO-EXPRESSING A FUNCTIONAL HUMAN 2-5A SYSTEM

[75] Inventors: Robert H. Silverman, Shaker Heights, Ohio; Amitava Mitra, Lincoln, Nebr.

[73] Assignee: Cleveland Clinic Foundation, Cleveland, Ohio

[21] Appl. No.: 487,797

[22] Filed: Jun. 7, 1995

Related U.S. Application Data

[63] Continuation-in-part of Ser. No. 198,973, Feb. 18, 1994, abandoned, which is a continuation-in-part of Ser. No. 28,086, Mar. 8, 1993, abandoned.

[51] Int. Cl.$^6$ .............................. A01H 5/00; C12N 5/04; C12N 15/82
[52] U.S. Cl. .................. 800/205; 435/69.1; 435/172.3; 435/320.1; 435/418; 435/419; 536/23.2; 536/23.5; 800/DIG. 43
[58] Field of Search ........................... 800/205, DIG. 43; 435/69.1, 172.3, 240.4, 240.49, 252.3, 320.1, 418, 419; 536/23.2, 23.5

[56] References Cited

U.S. PATENT DOCUMENTS 5,063,159  11/1991  Revel et al. ........................ 435/252.3

FOREIGN PATENT DOCUMENTS

WO 93/19187  9/1993  WIPO ........................... C12N 15/54

OTHER PUBLICATIONS

Gura: Science, 270:575–577 (Oct. 27, 1995).
Nejidat et al.: Physiologia Plantarum, 80:662–668 (1990).
Gergerich et al.: Phytopathology, 78(3):270–272 (1988).
Cuozzo et al.: Bio/Technology, 6:549–557 (May 1988).
Ogawa et al. Nature Biotechnology 14:1566–1569, Nov. 1996.
Sarchenko et al (Sep. 1992) Dokl Akad Nauk Ukr 0(9):145–148, Abstract.
Devash et al (1985) Biochemistry 24:593–599.
Jacobsen, H. et al.: Virology, 125:496–501 (1983).
Jacobsen, H. et al.: Proc. Natl. Acad. Sci. USA, 80:4954–4958 (Aug. 1983).
Silverman, R.H. et al.: Local Organ. Comm. of 5th Ann. Meeting of Interf. Res. (The Biol. of Interf. Syst. 1988), 183–186 (1989).
Ferbus, D. et al.: Mol. & Cell Biochem., 62:51–55 (1984).
Eppstein D. A. et al.: J. Biol. Chem., 257(22):13390–13397 (1982).
Hovanessian, A.G. et al.: J. Biol. Chem., 263(10):4945–4949 (1988).
Hovanessian, A.G. et al.: EMBO J., 6(5):1273–1280 (1987).
Hearl, W.G. et al.: J. Virol., 61(5):1586–1592 (1987).
Wreschner, D.H. et al: Nature, 289(5796):414–417 (Jan. 29, 1981).
Debois, M.F. et al.: Ann. Ins. Pasteur/Virol., 1987.
Silverman, R.H. et al.: J. Biol. Chem., 263(15) 7336–7341 (May 25, 1988).

Yang–Feng, T.L. et al.: Genomics, 19:173–176 (1994).
Dong, B. et al.: J. Biol. Chem., 269(19):14153–14158 (May 13, 1994).
Hassel, H.A. et al.: EMBO J., 12(8):3297–3304 (1993).
Zhou, A. et al.: Cell, 72:753–765 (Mar. 12, 1993).
William. B.R.G. et al.: Local Org. Comm. of 5th Ann. Meet. of Interf. Res. (The Biol. of Interf. Syst.), 159–162 (1988).
Sawai, H. et al.: J. Biol. Chem., 288(3):1671–1677 (Feb. 10, 1983).
Torrence, P.F. et al.: J. Biol. Chem., 263(3):1131–1139 (Jan. 25, 1988).
Lesiak, K. et al.: J. Biol. Chem., 258(21):13082–13088 (Nov. 10, 1983).
Black, R.J. et al.: FEBS Letters, 191(1):154–158 (Oct. 1985).
Sawai, H. et al.: J. Biol. Chem., 258(3)1671–1677 (Feb. 1, 1983).
Torrence, P.F. et al.: Proc. Natl. Acad. Sci. USA, 78(1):5993–5997 (Oct. 1981).
Lesiak, K. et al.: J. Biol. Chem., 262(5):1961–1965 (Feb. 15, 1987).
Lesiak, K. et al.: Bioconjugate Chem., 467–472 (Nov./Dec., 1993).
Jacobsen, H.J. et al.: Virology, 125:496–501 (1983).
SenGupta, D.N. et al.: Proc. Natl. Acad. Sic. USA, 87:7492–7496 (Oct. 1990).
Silverman, R.H.: Anal. Biochem., 144:450–460 (1985).
Krause, D. et al.: J. Interf. Res., 13:13–16 (1993).
Krause, D. et al.: J. Biol. Chem., 260(16):9501–9507 (Aug. 5, 1985).
Kraus, D. et al.: J. Biol. Chem., 261(15):6836–6839 (May 25, 1986).
Maheshwari, R.K. et al.: Science, 219:1339–1341 (Mar. 18, 1983).
Nolan–Sorden, N.L.: Anal. Biochem., 184:298–304 (1990).
SenGupta, D.N.: Proc. Natl. Acad. Sci. USA, 87:7492–7496 (Oct. 1990).
Silverman, R.H.: Eur. J. Biochem., 126:333–341 (1982).
Ryseicki, G.: J. Interf. Res., 9:649–657 (1989).
Wreschner, D.H. et al.: Nucelic Acids Res., 9(7):1571–1581 (1981).
Cayley, P.J. et al.: Cell. Resp. to Mol. Modul., 347–360.

(List continued on next page.)

Primary Examiner—Elizabeth F. McElwain
Attorney, Agent, or Firm—Rothwell, Figg, Ernst & Kurz, PC

[57]  ABSTRACT

Novel transgenic plants having the ability to express a functional 2-5A system, i.e., a 2-5A synthetase which produces 5'-phosphorylated, 2',5'-linked oligoadenylates (2-5A) in response to double stranded RNA (dsRNA), and a 2-5A-dependent (RNase L), are disclosed. The novel transgenic plants expressing the functional 2-5A system, such as novel transgenic tobacco plants, are immune to and resistant against viral infection. When the novel transgenic tobacco plants are exposed to three different types of plant viruses, i.e., TMV, TEV and AIMV, such viral exposure leads to necrotic local lesions in such transgenic tobacco plants instead of typical systemic infections.

16 Claims, 37 Drawing Sheets

OTHER PUBLICATIONS

Torrence, P.F. et al.: *Proc. Natl. Acad. Sci. USA,* 90:1300–1304 (Feb. 1993).
Silverman, R.H. et al.: *Biol. of Interf. System,* 189–200 (1983).
Silverman, R.H. et al.: *J. Virology,* 46(3):1051–1055 (Jun. 1983).
Grimley, P.M. et al.: *Cancer Res.,* 144:3480–3488 (Aug. 1984).
SenGupta, D.N. et al.: *Nucleic Acids Res.,* 17(3):969–978 (1989).
Silverman, R.H.: *J. Interf. Res.,* 14:101–104 (1994).
Kerr, I.M.: *Phil. Trans. R. Soc. Lond.,* B299:59–67 (1982).
Meurs, E. et al.: *Ann. Inst. Pasteur/Virol.,* 137E:251–272 (1986).
Schmidt, A. et al.: *Nat. Immun. Cell Growth Regul.,* 6:19–27 (1987).
Dieffenbach, C.W. et al.: *J. Biol. Chem.,* 264(22):13281–13288 (1989).
Suhadolnik, R.J. et al.: *Biochem.,* 27:8846–8851 (1988).
Wells, J.A. et al.: *J. Biol. Chem.,* 259(2):1363–1370 (Jan. 25, 1984).
Reid, T.R. et al.: *Anal. Biochem.,* 135:000–000 (1983).
Hersh, C.L. et al.: *J. Biol. Chem.,* 259(3):1727–1730 (Feb. 10, 1984).
Iwata, A. et al.: *J. Biochem.,* 104:247–250 (1988).
Shimizu, N. et al.: *J. Biochem.,* 94:1421–1428 (1983).
Orlic, D. et al.: *Exp. Hematol.,* 13:821–826 (1985).
Orlic, D. et al.: *Blood Cells,* 10:193–210 (1984).
Lewis, J.A. et al.: *Viology,* 133:464–469 (1984).
Mengheri, E. et al.: *FEBS,* 157(2):301–305 (Jul. 1983).
Lewis, J.A. et al.: *Eur. J. Biochem.,* 86:497–509 (1978).
Lewis, J.A. et al.: *Proc. Natl. Acad. Sci. USA.,* 80:26–30 (Jan. 1983).
Schattner, A. et al.: *J. Interf. Res.,* 1(4):587–594 (1981).
Weissenbach, J. et al.: *Proc. Natl. Acad. Sci. USA,* (77)(12):7152–7156 (Dec. 1980).
Revel, M. et al.: *Texas Reports on Biology and Medicine,* 41:452–462 (1981–1982).
Revel, M.: "*Molecular Mechanisms Involved in the Intiviral Effects of Interferon,*" 101–163.
Revel, M. et al.: *Cell. Resp. Mol. Modul.,* 361–384.
Wallach, D. et al.: *Nature,* 287:68–90 (Sep. 1980).
Revel, M. et al.: *Ann. Rev. Biochem.,* 47:1079–1126 (1978).
Chernajovsky, Y. et al.: *Eur. J. Biochem.,* 96:35–41 (1979).
Wallach, D. et al.: *Interferons,* 449–463 (1982).
Kimchi, A. et al.: *Proc. Natl. Acad. Sci. USA,* 76(7):3208–3212 (Jul. 1979).
Kimchi, A. et al.: *Anti–Mitogenic Func. of Interf.–Induced (2'–5')Oligo(adenylate . . . ,* 5–10 (1980).
Zilberstein, A. et al.: *Proc. natl. Acad. Sci. USA,* 75(1):4734–4738 (Oct. 1978).
Kimchi, A. et al.: *FEBS,* 134(2):212–216 (Nov. 1981).
Chebath, J. et al.: *J. Biol. Chem.,* 262(8)3852–3857 (Mar. 15, 1987).
Rappoport, S. et al.: *FEBS,* 149(1):47–50 (Nov. 1982).
Panet, A. et al.: *Virology,* 114:567–572 (1981).
Epstein, D.A. et al.: *Eur. J. Biochem.,* 118:9–15 (1981).
Sen, G.C.: *Pharmac. Ther.,* 23:235–257 (1984).
Kumar, R. et al.: *J. Virol.,* 62(2)641–643 (Feb. 1988).
Salzberg, S. et al.: *Mol. Cell. Biol,* 3(10):1759–1765 (Oct. 1983).
Panet, A.: *Mol. Cell. Ciochem.,* 52:153–160 (1983).
Lewis, J.A.: *Virology,* 162:118–127 (1988).
Neth, R. et al.: Reprint from *Modern Trends in Human Leukemia III* (Springer–Verlag Berlin Heidelberg Ny 1979).
Kemchi, A. et al.: *Nature,* 282:20–27 (Dec. 1979).
Sen, G.C. et al.: *J. Biol. Chem.,* 253(17):5915–5921 (Sep. 10, 1978).
Shimizu, N. et al.: *J. Biol. Chem.,* 254(23):12034–12037 (Dec. 10, 1979).
Schmidt, A. et al.: *Proc. natl. Acad. Sci. USA,* 76(10):4788–4792 (Oct. 1979).
Revel, M. et al.: "*Studies on Interef. Action: Snyth., Degrad. & Biol. Act. of (2'–5') Oligo–Isoadenylate,*" 1–18.
Lengyel, P. et al.: *J. Interf. Res.,* 7:511–519 (1987).
Floyd–Smith, G. et al.: *J. Interf. Res.,* 8:517–525 (1988).
Kerr, I.M. et al.: *Proc. Natl. Acad. Sci. USA,* 75(1):256–260 (Jan. 1978).
Salehzada, T. et al.: *J. Biol. Chem.,* 266(9):5808–5813 (Mar. 25, 1991).
Hovanessian, A.G. et al.: *Nature,* 268:537–538 (Aug. 1977).
Salehzada, T. et al.: *Anal. Biochem.,* 196:410–414 (1991).
Williams, B.R.G. et al.: *Nature,* 276:88–90 (Nov. 1978).
Roberts, W.K. et al.: *Proc. Natl. Acad. Sci. USA,* 73(9):3136–3140 (Sep. 1976).
Kerr, I.M. et al.: *Nature,* 268:537–542.
Salehzada, T. et al.: *J. Biol. Chem.,* 268(11):7733–7740 (Apr. 15, 1993).
Lengyel, P.: *Proc. Natl. Acad. Sci. USA,* 90:5893–5895 (Jul. 1993).
Cayley, P.J. et al.: *Piochem. Biophys. Res. Comm.,* 108(3):1243–1250 (Oct. 15, 1982).
Kerr, I.M. et al.: *Eur. J. Biochem.,* 69:551–561 (1976).
Kumar, R. et al.: *J. Virol.,* 62(9):3175–3181 (Sep. 1988).
Shaila, S. et al.: *gen. Virol.,* 37:535–546 (1977).
Brown, G.E. et al.: *Biochem. Biophys. Res. Commun.,* 69(1):114–122(1976).
Sen, G.C. et al. *Nature,* 264:370–373 (Nov. 25, 1976).
Hanks, S.K. et al.: *Science,* 241:42–52 (Jul. 1988).
Singh, H. et al.: *Cell,* 52:415–423 (Feb. 12, 1988).
Singh, H. et al.: *BioTech.,* 7(3):252–261 (1989).
Baglioni, C. et al.: *Nature,* 273:684–687 (Jun. 1978).
Apirion, D.: "*Isolation, Genetic Mappern and Some Characterization of a Mutation in ESCHERICHIA COLI . . . ,*" 659–671 (Dec. 1978).
Goldblum, K. et al.: *J. Bacteriology,* 146:128–132 (Apr. 1981).
Slattery, E. et al.: *Proc. natl. Acad. Sci. USA,* 76(10):4778–4782 (Oct. 1979).
Nilsen, T.W. et al.: *J. Biol. Chem.,* 256(21):10751–10754 (Nov. 10, 1981).
Williams, B.R.G. et al.: *FEBS,* 105(1):47–52 (Sep. 1979).
Floyd–Smith, G.: *J. Cell. Biochem.,* 38:13–21 (1988).
Schmidt, A. et al.: *FEBS,* 95(2):257–264 (Nov. 1978).
Hovanessian, A.G. et al.: *Eur. J. Biochem.,* 84:149–159 (1978).
Clemens, M.J. et al. *Cell,* 13:565–572 (Mar. 1978).
Sen, G.C. et al.: *J. Biol. Chem.,* 267(8):5017–5020 (Mar. 15, 1992).
Nilsen, T.W. et al.: *Proc. Natl. Acad. Sci. USA,* 76(6):2600–2604 (Jun. 1979).
Ratner, L. et al.: *Eur. J. Biochem,* 79:565–577 (1977).
Baglioni, C. et al.: *J. Biol. Chem.,* 255(18)8390–8393 (Sep. 25, 1980).
Williams, B.R.G. et al.: *Nature,* 282(5739):582–586 (Dec. 6, 1979).
Williams, B.R.G. et al.: "*The 2–5A (pppA2' p5'A2' p5' A) System in Interferon–treated and Control Cells*".

Floyd–Smith, G. et al.: *Science,* 212:1030–1032 (May 1981).
Ratner, L. et al.: *Biochem. Biophys. Res. Commun.,* 81(3):947–954 (Apr. 14, 1978).
Coccia, E.M. et al.: *Virology,* 179:228–233 (1990).
Berg, J.M.: *J. Biol. Chem.,* 265(12):6513–6516 (Apr. 25, 1990).
Evans, R.M. et al.: *Cell,* 52:1–3 (Jan. 15, 1988).
Belasco, J. et al.: *Gene,* 72:15–23 (1988).
Fry, D.C. et al.: *Proc. Natl. Acad. Sci. USA,* 83:907–911 (Feb. 1986).
Walker, J.E. et al.: *EMBO,* 1(8):945–951 (1982).
Krupinski, J. et al.: *Science,* 244:1558–1564 (1989).
Au, D.C. et al.: *Biochem.,* 28:2772–2776 (1989).
Glaser, P. et al.: *EMBO,* 8(3):967–972 (1989).
Imai, J. et al.: *J. Biol. Chem.,* 260(3):1390–1393 (Feb. 10, 1985).
Watling, D. et al.: *EMBO,* 4(2):431–436 (1985).
Pestka, S. et al.: *Ann. Rev. Biochem.,* 56:727–777 (1987).
Lengyel, P.: *Ann. Rev. Biochem.,* 51:251–282 (1982).
Floyd–Smith, G. et al.: *Science,* 212:1030–1032 (May 1981).
Night, M. et al.: *Nature,* 288(5787):189–192 (Nov. 13, 1980).
Deutscher, M.P.: *J. Biol. Chem.,* 268(18:13011–13014 (Jun. 25, 1993).
Cedergren, R. et al.: *FEBS,* 226(1)63–66 (Dec. 1987).
Floyd–Smith, G. et al.: *Meth. Enzymology,* 119:489–499 (1986).
Farrell, P.J. et al.: *Proc. Natl. Acad. Sci. USA,* 75(12):5893–5897 (Dec. 1978).
Bisbal, C. et al.: *Eur. J. Biochem.,* 179:595–602 (1989).
Brawerman, G.: *Cell,* 57:9–10 (Apr. 7, 1989).
Mackie, G.A.: *J. Bacteriology,* 178(8)2488–2497 (Apr. 1991).
Xia, Z. et al.: *J. Biol. Chem.,* 265(12):6517–6520 (Apr. 25, 1990).
Saraste, M. et al.: *TIBS,* 15 (Nov. 1990).
Deutscher, M.P. et al.: *Cell,* 40:731–732 (Apr. 1985).
Cormack, R.S. et al.: *Proc. natl. Acad. Sci. USA,* 90:9006–9010 (Oct. 1993).
Bouvet, P. et al.: *Nature,* 360:488–491 (Dec. 3, 1992).
Claverie–Martin, F. et al.: *J. Biol. Chem.,* 266(5):2843–2851 (Feb. 15, 1991).
Mudd, E.A. et al.: *EMBO,* 7(11):3601–3607 (1988).
Ehretsmann, C.P. et al.: *Genes & Develop.,* 6:149–159 (1992).
Taraseviciene, L. et al.: *Mol. Microbiol.,* 5(4):851–855 (1991).
Chauhan, A.K. et al.: *Nucleic Acids Res.,* 19(1)125–129 (1991).
Babitzke, P. et al.: *Proc. Natl. Acad. Sci. USA,* 88:1–5 (Jan. 1991).
Mudd, E.A. et al.: *Mol. Microbiol.,* 4(12):2127–2135 (1990).
Bouvet, P. et al. : *Nature,* 360:488–491 (Dec. 3, 1992).
Silverman, R.H. et al.: *Eur. J. Biochem.,* 124:131–138 (1982).
Hovanessian, A.G. et al.: *Meth. Enzymol.,* 79:184–199 (1981).
Goswami, B.B. et al.: *J. Biol. Chem.,* 259(3):1371–1374 (Feb. 10, 1984).
Sharma, O.K. et al.: *Proc. Natl. Acad. Sci. USA,* 78(4):2221–2224 (Apr. 1981).
Goswami, B.B. et al.: *J. Biol. Chem.,* 257(12):6867–6870 (Jun. 25, 1982).
Sharma, O.K. et al.: *FEBS 0601,* 158(2):298–300 (Jul. 1983).
Sen, G.C. et al.: *J. Virology,* 45(3):1017–1027 (Mar. 1983).
Sen, G.C. et al.: *J. gen Virol.,* 64:2213–2220 (1983).
Sawai, H. et al.: *J. Biochem.,* 101:339–346 (1987).
Taira, H. et al.: *J. Interf. Res.,* 5:583–596 (1985).
Salzberg, S. et al.: *Mol. Cell. Biol.,* 3(10):1759–1765 (Oct. 1983).
David, S. et al.: *J. Virology,* 63(3):1116–1122 (Mar. 1989).
Affabris, E. et al.: *Virology,* 125:508–512 (1983).
Mechti, N. et al.: *J. Biol. Chem.,* 259(5)3261–3265 (Mar. 10, 1984).
Miyamoto, N.G. et al.: *Virology,* 107:461–475 (1980).
Miyamoto, N.G. et al.: *J. Biol. Chem.,* 258(24):15232–15237 (Dec. 25, 1983).
Eppstein, D.A. et al.: *Virology,* 98:9–19 (1979).
Benech, P. et al.: *Mol. Cell. Biol.,* 7(12):4498–4504 (Dec. 1987).
Cohen, B. et al.: *EMBO,* 7(5):1411–1419 (1988).
Mory, Y. et al.: *J. Interf. Res.,* 9:295–304 (1989).
Imai, J. et al.: *J. Biol. Chem.,* 257(21):12739–12745 (Nov. 10, 1982).
Krause, D. et al.: *Eur. J. Biochem.,* 146:611–618 (1985).
Silverman, R.H. et al.: *Eur. J. Biochem,* 115:79–85 (1981).
Wreschner, D.H. et al.: *Eur. J. Biochem.,* 124:261–268 (1982).
Wreschner, D.H. et al. *Eur. J. Biochem.,* 172:333–340 (1988).
Penn, L.J.Z. et al.: *J. Virology,* 49(3):748–753 (Mar. 1984).
Saunders, M.E. et al.: *EMBO,* 4(7):1761–1768 (1985).
Lesiak, K. et al.: *Biochem. Biophys. Res. Commun.,* 126(2):917–921 (Jan. 31, 1985).
Kitade, Y. et al.: *Nucl. Acids Res.,* 19(15):4103–4108 (1991).
Torrence, P.F. et al.: *FEB 04463,* 212(2):267–270 (Feb. 1987).
Alster, D. et al.: *Biochem. Biophys. Res. Commun.,* 141(2):555–561 (Dec. 15, 1986).
Lesiak, K. et al.: *J. Med. Chem.,* 1015–1022 (Jun. 1986).
Ilson, D.H. et al.: *J. Interf. Res.,* 6:05–12 (1986).
Torrence, P.F. et al.: *FEB 04463,* 212(2):267–270 (Feb. 1987).
Jamoulle, J.C. et al.: *Biochem.,* 23:3063–3069 (1984).
Imai, J. et al.: *Biochem,* 23:766–774 (1984).
Eppstein, D.A. et al.: *J. Biol. Chem.,* 260(6):3666–3671 (Mar. 25, 1985).
Johnston, M.I. et al.: *Biochem. Biophys. Res. Commun.,* 97(2):375–383 (Nov. 28, 1980).
Torrence, P.F. et al.: *J. Med. Chem.,* 27:726–733 (1984).
Imai, J. et al.: *Org. Chem.,* 1418–1420 (May 3, 1985).
Silverman, R.H. et al.: *The Biology of the Interferon System 1984,* Kirchner et al., eds. 1985 Elsevier Science Publishers B.V., pp. 141–145.
Silverman, R. et al: In, *Inteferons as cell growth inhibitors & antitumor factors.* (Friedman et al., eds.) A.R. Liss, NY, NY pp. 143–150(1986).
Williams BRG, (1983). *The Biochemical action of interferon. In: Interferon and Cancer,* K. Sikora ed, Elsevier, Amsterdam, pp. 33–52.
Doetsch, P.W. et al.: *Proc. Natl. Acad. Sci. USA,* 78:1–9 (1981).
Henderson, E.E. et al.: *Virology,* 122:198–201 (1982).
Wu, J.M. et al.: *Biochem. & Biophys. Res. Comm.,* 86(3):648–653 (1979).

Lee, C. et al.: *FEBS* 157(1):205–209 (Jun. 1983).
Doetsch, P. et al.: *Nature,* 291:355–358 (May 1981).
Suhadolnik, R.J. et al.: *Biochemistry,* 22:4153–4158 (1983).
Kariko, K. et al.: *Biochemistry,* 26:7127–7135 (1987).
Kariko, K. et al.: *Biochemistry,* 26:7136–7142 (1987).
Suhadolnik, R.J. et al.: *Biochemistry,* 26:7143–7149 (1987).
Suhadolnik, R.J. et al.: *Biochemistry,* 27:8840–8846 (1988).
Suhadolnik, R.J. et al.: *Biochem. & Biophys. Res. Comm.,* 111(1):205–212 (1983).
Black, P.L. et al.: *J. Immun.,* 135(5):2773–2777 (Nov. 1984).
Lee, C. et al.: *Biochemistry,* 24(3):551–555 (Jan. 1985).
Knight, M. et al.: *Meth. Enzymology,* 79:217–227 (1981).
Williams, B.R.G. et al.: *Meth. Enzymology,* 79:199–208 (1981).
Kerr, I.M. et al.: *Adv. Cyclic Nucleo. Res.,* 14:469–478.
Gribaudo, G. et al.: *J. Virol.,* 65(4):1478–1757 (Apr. 1991).
Suhadolnik, R.J. et al.: *Biochemistry,* 22:(?):4153–4157 (1983).
Justesen, J. et al.: *Proc. Natl. Acad. Sci. USA,* 77:4618–4622 (1980).
Ono, M. et al.: *J. Mol. Biol.,* 129:343–357 (1979).
LeBleu, B. et al.: *Mechanisms of Interferon Action: Biochem. & Genetic Appr.,* 47–94.
Pai, E.F. et al.: *Nature,* 341:209–214 (Sep. 1989).
St. Laurent, G. et al.: *Cell,* 95–102 (1983).
Saraste, M. et al.: *TIBS,* 15:430–434 (Nov. 1990).
Rozen, F. et al.: *Mol. & Cell. Biol.,* 9(9):4061–4063 (Sep. 1989).
Schroder, H.C. et al.: *FASEB J.,* 4:3124–3130 (Oct. 1990).
Suhadolnik, R.J. et al.: *Nucleosides, Nucleotides, and their Biol. Appl.,* pp. 147–179 (Academic Press 1983).
Torrence, P.F. et al.: *J. Medicinal Chem.,* 27(6):726–733 (1984).
Torrence, P.F. et al.: *Proc. Natl. Acad. Sci. USA,* 78(10):5993–5997 (Oct. 1981).
Torrence, P.F. et al.: *FEBS,* 130(2):291–296 (Aug. 1981).
Imai, J. et al.: *J. Biol. Chem.,* 257(21):12739–12745 (Nov. 1982).
Morag, A. et al.: *Lancet,* p. 744 (Mar. 27, 1982).
Shulman, L. et al.: *Nature,* 288:98–100 (Nov. 1980).
Lesiak, K. et al.: *FEBS,* 151(2):291–296 (Jan. 1983).
deClercq, E. et al.: *UPHAR 9th Int'l Congress of Pharma.,* London 1984, Paton et al. eds. (vol. 1), pp. 307–317.
Williams, B.R.G. et al.: *Biol. of Interf. Syst.,* 1981, Elsevier, De Mayer et al. eds., pp. 111–114.
Silverman, R.H. et al.: In *Lymphokines & Interf.: A Practical Approach,* Clemens et al. eds., IRL Press, Wash. D.C. 1987, pp. 149–193.
Justesen, J. et al.: *Nucleic Acids Res.,* 8(14):? (1980).
Torrence, P.F. et al.: *Chemica Scripta,* 26:191–197 (1986).
Torrence, P.F. et al.: *Molec. Aspects Med.,* 5:129–171 (1982).
Chousterman, S. et al.: *J. Biol. Chem.,* 262(10):4806–4811 (Apr. 1987).
Chelbi–Alix, M.K. et al.: *J. Biol. Chem.,* 260(13):7960–7964 (Jul. 1985).
Besancon, F. et al.: *Biochem. & Biophys. Res. Comm.,* 103(1):16–24 (Nov. 1981).
Lab, M. et al.: *Biochem. & Biophys. Res. Comm.,* 105(2):412–418 (Mar. 1982).
Dougherty, J.P. et al.: *J. Biol. Chem.,* 255(9):3813–3816 (May 1980).
Mory, Y. et al.: *J. Interf. Res.,* 9:295–304 (1989).
Chebath, J. et al.: *Nature,* 330:587–588 (Dec. 1987).
Ghosh, S. K. et al.: *J. Biol. Chem.,* 266(23):15293–15299 (Aug. 1991).
Minks, M.A. et al.: *J. Biol. Chem.,* 254(20):10180–10183 (Oct. 1979).
Wu, J.M. et al.: *AIDS Res.,* 2(2):127–131 (1986).
Schroder, H.C. et al.: *J. Biol. Chem.,* 264(10):5669–5673 (Apr. 1989).
Schroder, H.C. et al.: *AIDS Res. & Human Retrov.,* 6(5):659–672 (1990).
Schroder, H.C. et al.: *Biol. Chem. Hoppe–Seyler,* 369:985–995 (Sep. 1988).
Agy, M.B. et al.: *Virology,* 177:251–258 (1990).
Suhadolnik, R.J. et al.: *Photoaffinity,* 27(24):8840–8846 (1988).
Read, S.E., et al.: *J. Infect. Dis.,* 152(3):466–472 (Sep. 1985).
Ghora, B.K. et al.: *Cell,* 15:1055–1066 (Nov. 1978).
Samanta, H. et al.: *J. Biol. Chem.,* 255(20)9807–9813 (Oct. 1980).
Broeze, R.J. et al.: *J. Interf. Res.,* 1(2):191–201 (1981).
Yang, K. et. al.: *J. Biol. Chem.,* 256(17):9324–9328 (Sep. 1981).
Cayley, P.J. et al.: *Eur. J. Biochem.,* 143:165–174 (1984).
Brown, R.E. et al.: *Meth. in Enzymology,* 79:208–216 (1981).
Hersh, C.L. et al.: *J. Biol. Chem.,* 259(3):1731–1737 (Feb. 1984).
Rice, A.P. et al.: *J. Virol.,* 50(1):220–228 (Apr. 1984).
Rice, A.P. et al.: *J. Virol.,* 56(3):1041–1044 (Dec. 1985).
Williams, B.R.G. et al.: *Eur. J. Biochem.,* 92:455–462 (1978).
Cayley, P.J. et al.: *Eur. J. Biochem.,* 122:601–608 (1982).
Reid, T.R. et al.: *Anal. Biochem.,* 136:136–141 (1984).
Williams, B.R.G. et al.: *Nucleic Acids Res.,* 6(4):1335–1350 (Apr. 1979).
Foster, G.R. et al.: *Proc. natl. Acad. Sci. USA,* 88:2888–2892 (Apr. 1991).
Cayley, P.J. et al.: *Eur. J. Biochem.,* 122:601–608 (1982).
Cayley, P.J. et al.: *Interferons,* ??:143–157 (Academic Press 1992).
Lebleu, B. et al.: *Proc. Natl. Acad. Sci. USA,* 73(9):3107–3111 (Sep. 1976).
Bisbal, C. et al.: *Biochemistry,* 26:5172–5178 (1987).
Mechti, N. et al.: *Differentiation,* 29:136–139 (1985).
Bayard, B. et al.: *Biochemistry,* 25:3730–3736 (1986).
Stark, G.R. et al.: *Nature,* 278:471–473 (Mar. 1979).
Hovanessian, A.G. et al.: *Proc. Natl. Acad. Sci. USA,* 76(&):3261–3265 (Jul. 1979).
Buffet–Janvresse, C. et al.: *J. Interf. Res.,* 6:85–96 (1986).
Ogunkolade, W. et al.: *J. Interf. Res.,* 7:245–254 (1987).
Riviere, Y. et al.: *Ann. Immunol. (Inst. Pasteur),* 135(C):333–343 (1984).
Marcovistz, R. et al: *J. gen. Virol.,* 65:995–997 (1984).
Hovanessian, A.G. et al.: *Virology,* 104:195–204 (1980).
Laurence, L. et al.: *Virology* 143:290–299 (1985).
Chapekar, M.S. et al.: *Biochem. & Biophys. Res. Commun.,* 151(3):1180–1187 (Mar. 1988).
Floyd–Smith, G. et al.: *Proc. of Soc. for Exper. Bio. & Medicine,* 189:329–337 (1988).
Esteban, M. et al.: *J. gen. Virol.,* 67:801–808 (1986).
Paez, E. et al.: *J. Virol.,* 56(1):75–84 (Oct. 1985).
Paez, E. et al.: *Virology,* 134:12–28 (1984).
Paez, E. et al.: *Virology,* 134:29–39 (1984).
Esteban, M. et al.: *Virology,* 134:40–51 (1984).

Santoro, M.G. et al.: *Biochem. & Biophys. Res. Commun.,* 116(2):442–448 (Oct. 1983).
Benavente, J. et al.: *J. Virol.,* 51(3):866–871 (Sep. 1984).
Eppstein, D.A. et al.: *Nature,* 302:723–724 (Apr. 1983).
Eppstein, D.A. et al.: *Virology,* 131:341–354 (1983).
Eppstein, D.A. et al.: *J. Interf. Res.,* 3(3):305–311 (1983).
Eppstein, D.A. et al.: *J. Biol. Chem.,* 261(13):5999–6003 (May 1986).
Drocourt, J. et al.: *Nucleic Acids Res.,* 10(6):2163–2174 (1982).
Rice, A.P. et al.: *J. Virol.,* 54(3):894–898 (Jun. 1985).
Jamoulle, J.–C. et al.: *Biochemistry,* 26:376–383 (1987).
Torrence, P.F. et al.: *Analyt. Biochem.,* 129:103–110 (1983).
Johnston, M.I. et al.: *J. Biol. Chem.,* 262(17):8377–8382 (Jun. 1987).
Mittnacht, S. et al.: *J. gen. Virol.,* 68:2945–2951 (1987).
Defilippi, P. et al.: *FEBS 3525,* 198(20):326–332 (Mar. 1986).
Ankel, H. et al.: *J. gen. Virol.,* 66:2355–2364 (1985).
Hovanessian, A.G.: *J. Interf. Res.,* 11:199–205 (1991).
Marie, I. et al.: *J. Biol. Chem.,* 267(14):9933–9939 (1992).
Hovanessian, A.G. et al.: *Virology,* 101:81–90 (1980).
Hovanessian, A.G. et al.: *EMBO,* 6(5):1273–1280 (1987).
Flenniken, A.M. et al.: *J. Virol.,* 62(9):3077–3083 (Sep. 1988).
Wood, J.N. et al.: *Nature,* 282:74–76 (Nov. 1979).
Hovanessian, A.G. et al.: *J. Interf. Res.,* 1(2):179–190 (1981).
Hovanessian, A.G. et al.: *Proc. Natl. Acad. Sci. USA,* 76(7):3261–3265 (Jul. 1979).
Galabru, J. et al.: *J. gen. Virol.,* 66:711–718 (1985).
Buffet–Janvresse, C. et al.: *Proc. of Soc. for Exp. Biol. & Medicine,* 175:169–175 (1984).
Knight, Jr., E. et al.: *Proc. Natl. Acad. Sci. USA,* 82:1151–1154 (Feb. 1985).
Kimchi, A.: *J. Interf. Res.,* 1(4):559–569 (1981).
Cleveland, D. W. et al.: *J. Biol. Chem.,* 252(3):1102–1106 (Feb. 1977).
Bayard, B. et al.: *Eur. J. Biochem.,* 142:291–298 (1984).
Bisbal, C. et al.: *Biochemistry,* 26:5172–5178 (1987).
Bayard, B. et al.: *Eur. J. Biochem.,* 151:319–325 (1985).
Baynard, B. et al.: *Biochemistry,* 25:3730–3736 (1985).
Baglioni, C. et al.: *Biochemistry,* 18(9):1765–1770 (1979).
Nilsen, T.W. et al.: *J. Virol.,* 42(3):1039–1045 (Jun. 1982).
Baglioni, C. et al.: *J. Biol. Chem.,* 256(7):3253–3257 (Apr. 1981).
Nilsen, T.W. et al.: *Biochemistry,* 19:5574–5579 (1980).
Baglioni, C. et al.: *Biochemistry,* 20:758–762 (1981).
Nilsen, T.W. et al.: *Virology,* 122:498–502 (1982).
Nilsen, T.W. et al.: *Molecular & Cellular Biol.,* 3(1):64–69 (Jan. 1983).
Baglioni, C. et al.: *Cell,* 17:255–264 (Jun. 1979).
Nilsen, T.W. et al.: *Molecular & Cellular Biol.,* 2(2):154–160 (Feb. 1982).
Baglioni, C. et al.: *J. Virol.,* 52(3):865–871 (Dec. 1984).
Williams, G.J. et al.: *Virology,* 151:233–242 (1986).
Minks, M.A. et al.: *Nucleic Acids Res.,* 6(2):767–780 (Feb. 1979).
Baglioni, C.: Chapter 8, *The Molecular Mediators of Interferon Action,* pp. 153–168.
Nilsen, T.W. et al.: *J. Biol. Chem.,* 256(15):7806–7811 (Aug. 1981).
Nilsen, T.W. et al.: *J. Biol. Chem.,* 257(4):1602–1605 (Feb. 1982).
Verhaegen, M. et al.: *Proc. Natl. Acad. Sci. USA,* 77(8):4479–4483 (Aug. 1980).
Verhaegen–Lewalle, M. et al.: *Eur. J. Biochem.,* 126:639–643 (1982).
Vandenbussche, P. et al.: *Virology,* 111:11–22 (1981).
Chebath, J. et al.: *Nature,* 330:587–588 (Dec. 1987).
Chebath, J. et al.: *J. Biol. Chem.* 262(8):3852–3857 (1987).
Sperling, J. et al.: *Proc. Natl. Acad. Sci. USA,* 88:10377–10381 (Dec. 1991).
Alarcon, B. et al.: *J. Virol.,* 52(1):183–187 (Oct. 1984).
Cailla, H. et al.: *Radioimmunoassay and Related Procedures in Medicine 1982,* Int'l Atomic Energy Agency Vienna, 1982.
Cailla, H. et al.: *Proc. Natl. Acad. Sci. USA,* 79:4742–4746 (Aug. 1982).
Marti, J. et al.: *Nucleosides & Nucleotides,* 7(4):479–495 (1988).
Trujillo, M.A. et al.: *Eur. J. Biochem.,* 169:167–173 (1987).
Laurence, L. et al.: *Proc. Natl. Acad. Sci. USA,* 81:2322–2326 (Apr. 1984).
Hovanessian, A.G. et al.: *Eur. J. Biochem.,* 93:515–526 (1979).
Kerr, I.M. et al.: *The Biology of the Interferon System 1983,* Elsevier: De Maeyer et al. eds., pp. 213–222.
Etienne–Smekens, M. et al.: *FEBS L.,* 125(2):146–150 (Mar. 1981).
Smekens–Etienne, M. et al.: *Eur. J. Biochem.,* 130:269–273 (1983).
Wathelet, M. et al.: *FEBS L.,* 196(1):113–120 (Feb. 1986).
Verhaegen–Lewalle, M. et al.: *J. Virol.,* ?:425–434 (1981).
Haugh, M.C. et al.: *Eur. J. Biochem.,* 132:77–84 (1983).
Martin, E.M. et al.: *Eur. J. Biochem.,* 95:295–307 (1979).
Squire, J. et al.: *Genomics,* 19:174–175 (1994).
Fujihara, M. et al.: *J. Interf. Res.,* 9:691–707 (1989).
Squire, J. et al.: *Genomics* (Dec.), pp. 17–19.
Hassel, B.A. et al.: *EMBO,* 12(8):3297–3304 (1993).
Nilsen, T.W. et al.: *Nature,* 286:178–181 (Jul. 1980).
Krishnan, I. et al.: *Nature,* 285:485–488 (Jun. 1980).
Krishnan, I. et al.: *Mol. & Cell. Biol.,* 1(10):932–938 (Oct. 1981).
Krishnan, I. et al.: *Proc. Natl. Acad. Sci. USA,* 77(11):6506–6510 (Nov. 1980).
Krishnan, I. et al.: *Virology,* 111:666–670 (1981).
Minks, M.A. et al.: *J. Biol. Chem.,* 254(12):5058–5064 (Jun. 1979).
Minks, M.A. et al.: *J. Biol. Chem.,* 255(13):6403–6407 (Jul. 1980).
West, D.K. et al.: *Mol. & Cell. Biol.,* 2(11):1436–1443 (Nov. 1982).
Ball, L.A.: *Virology,* 94:282–296 (1979).
Ball, L.A. et al.: *Proc. Natl. Acad. Sci. USA,* 75(3):1167–1171 (Mar. 1978).
Creasey, A.A. et al.: In press, *Molecular and Cellular Biology* (1983), pp. 1–28.
Eds. William, B.R.G. and Silverman, R.H.: *The 2–5A System,* Proc. of 6th Int'l Symp. of Res. Inst. Hosp. for Sick Children, Toronto, Ontario, Canada, Jun. 3–5, 1985.
Young, et al.: *Science,* 222:778–782 (1983).
Gerald, et al.: *Biochem. Biophys. Acta.,* 866:1–14 (1986).
Murhammer, et al.: *Appl. Biochem. Biotechnol.,* 31:283–310 (1991).
Silverman, et al.: *J. Cell. Biochem.,* Suppl. 16B:163 (1992).
Hassel, et al.: *J. Cell. Biochem.,* Suppl. 17C:177 (1993).
Hassel, et al.: *J. Interferon Res.* 12(Suppl. 1):S42 (1992).
Zhou, et al.: *J. Interferon Res.,* 12(Suppl. 1):S57 (1992).

Silverman, et al.: *J. Cell. Biol. Supplement 16B,* See Abstract G 520, p. 163 (1992).

Meurs, E. et al.: *Cell,* 62:379–390 (Jul. 27, 1990).

Meurs, E. et al.: *J. Virology,* 66(10):5805–5814 (1992).

Lee, S.B. et al.: *Virology,* 193:1037–1041 (1993).

Lomonossof, G.P.: Virus Resistance Mediated by a Non-structural Viral Gene Sequence, Chapter 5, pp. 79–91 (1993) IN: *Transgenic Plants,* ed. Hiatt, A. Marcel Dekker, Inc., NY, NY.

Herrera–Estrella, L. et al.: Agrobacterium as a Vector System for the Introduction of Genes into Plants, Chapter 5 pp. 61–92, IN: *Plant Genetic Engineering,* ed. Dodds, J.H., Chambridge University Press, NY, NY (1985).

Mukherjee, A.B. et al.: *Biochemical Pharmacology,* 48(1):1–10 (1994).

Yang, N.S.: *Critical Reviews in Biotechnology,* 12(4):335–356 (1992).

Deng, T. et al.: *Gene,* 93:229–234 (1990).

Seilhamer, J.J. et al.: *J. Cell Biochem.,* 39:327–337 (1989).

Bekkers, A.C.A.P.A. et al.: *Biochimica et Biophysica Acta,* 1089:345–351 (1991).

Luckow et al.: *Biotechnology,* 6:47–55 (1988).

Seidah et al.: *DNA Cell Biol.,* 11:283–289 (1992).

THE 2-5A SYSTEM

FIG. 3B1

```
-103 aatcccaacttacactcaaagctt
ctttgattaagtgctaggagataaattgcatttctcaaggaaaagctaaaagtggtagcaggtggcatttaccgtc ATG GAG AGC AGG GAT CAT AAC AAC CCC CAG GAG GGA CCC ACG TCC TCC AGC GGT AGA AGG    60
Met Glu Ser Arg Asp His Asn Asn Pro Gln Glu Gly Pro Thr Ser Ser Ser Gly Arg Arg    20

GCT GCA GTG GAA GAC AAT CAC TTG CTG ATT AAA GCT GTT CAA AAC GAA GAT GTT GAC CTG   120
Ala Ala Val Glu Asp Asn His Leu Leu Ile Lys Ala Val Gln Asn Glu Asp Val Asp Leu    40

GTC CAG CAA TTG CTG GAA GGT GGA GCC AAT GTT AAT TTC CAG GAA GAG GGG GGC TGG       180
Val Gln Gln Leu Leu Glu Gly Gly Ala Asn Val Asn Phe Gln Glu Glu Gly Gly Trp        60

ACA CCT CTG CAT AAC GCA GTA CAA ATG AGC AGG GAG GAC ATT GTG GAA CTT CTG CGT       240
Thr Pro Leu His Asn Ala Val Gln Met Ser Arg Glu Asp Ile Val Glu Leu Leu Arg        80

CAT GGT GCT GAC CCT GTT CTG AGG AAG AAT GGG GCC ACG CTT TTT ATC CTC GCA GCG       300
His Gly Ala Asp Pro Val Leu Arg Lys Asn Gly Ala Thr Leu Phe Ile Leu Ala Ala       100

ATT GCG GGG AGC GTG AAG CTG CTG AAA CTT TTC CTT TCT AAA GGA GCA GAT GTC AAT GAG   360
Ile Ala Gly Ser Val Lys Leu Leu Lys Leu Phe Leu Ser Lys Gly Ala Asp Val Asn Glu   120

TGT GAT TTT TAT GGC TTC ACA GCC TTC ATG GAA GCC GCT GTG TAT GGT GTG AAG GAT       420
Cys Asp Phe Tyr Gly Phe Thr Ala Phe Met Glu Ala Ala Val Tyr Gly Val Lys Val Ala   140

CTA AAA TTC CTT TAT AGA GGA GCA AAT GTG AAT GTT AGG CGA AAG ACA AAG GAG GAT       480
Leu Lys Phe Leu Tyr Arg Gly Ala Asn Val Asn Leu Arg Arg Lys Thr Lys Glu Asp       160

CAA GAG CGG CTG AGG AAA GGA CTG AGG GCC ACA GCT CTC ATG GAC GCT GAA AAA GGA CAC   540
Gln Glu Arg Leu Arg Lys Gly Leu Arg Ala Thr Ala Leu Met Asp Ala Glu Lys Gly His   180

GTA GAG GTC TTG AAG ATT CTC CTT GAT GAG ATG GGG GCA GAT GTA AAC GCC TGT GAC AAT   600
Val Glu Val Leu Lys Ile Leu Leu Asp Glu Met Gly Ala Asp Val Asn Ala Cys Asp Asn   200
```

FIG. 3B2

```
ATG GGC AGA AAT GCC TTG ATC CAT GCT CTC CTG AGC TCT GAC GAT AGT GAT GTG GAG GCT    660
Met Gly Arg Asn Ala Leu Ile His Ala Leu Leu Ser Ser Asp Asp Ser Asp Val Glu Ala    220

ATT ACG CAT CTG CTG GAC CAT GGG GCT GAT GTC AAT GTG AGG GGA GAA AGA GGG AAG        720
Ile Thr His Leu Leu Asp His Gly Ala Asp Val Asn Val Arg Gly Glu Arg Gly Lys        240

ACT CCC CTG ATC CTG GCA GTG GAG AAG AAG CAC TTG GGT TTG GTG CAG AGG CTT CTG GAG    780
Thr Pro Leu Ile Leu Ala Val Glu Lys Lys His Leu Gly Leu Val Gln Arg Leu Leu Glu    260

CAA GAG CAC ATA GAG ATT AAT GAC ACA GAC AGT GAT GGC AAA ACA GCA CTG CTG CTT GCT    840
Gln Glu His Ile Glu Ile Asn Asp Thr Asp Ser Asp Gly Lys Thr Ala Leu Leu Leu Ala    280

GTT GAA CTC AAA CTG AAG AAA ATC GCC GAG TTG CTG TGC AAA CGT GGA GCC AGT ACA GAT    900
Val Glu Leu Lys Leu Lys Lys Ile Ala Glu Leu Leu Cys Lys Arg Gly Ala Ser Thr Asp    300

TGT GGG GAT CTT GTT ATG ACA GCG AGG CGG AAT TAT GAC CAT TCC CTT GTG AAG GTT CTT    960
Cys Gly Asp Leu Val Met Thr Ala Arg Arg Asn Tyr Asp His Ser Leu Val Lys Val Leu    320

CTC TCT CAT GGA GCC AAA GAA GAT TTT CAC CCT CCT GCT GAA GAC TGG AAG CCT CAG AGC   1020
Leu Ser His Gly Ala Lys Glu Asp Phe His Pro Pro Ala Glu Asp Trp Lys Pro Gln Ser    340

TCA CAC TGG GGG GCA GCC CTG AAG GAT CTC CAC AGA ATA TAC CGC ATG ATT GGC AAA       1080
Ser His Trp Gly Ala Ala Leu Lys Asp Leu His Arg Ile Tyr Arg Met Ile Gly Lys        360

CTC AAG TTC TTT ATT GAT GAA AAA TAC AAA ATT GCT GAT ACT TCA GAA GGA GGC ATC TAC   1140
Leu Lys Phe Phe Ile Asp Glu Lys Tyr Lys Ile Ala Asp Thr Ser Glu Gly Gly Ile Tyr    380

CTG GGG TTC TAT GAG AAG CAA GAA GTA GCT GTG AAG ACG TTC TGT GAG GGC AGC CCA CGT   1200
Leu Gly Phe Tyr Glu Lys Gln Glu Val Ala Val Lys Thr Phe Cys Glu Gly Ser Pro Arg    400

GCA CAG CGG GAA GTC TCT TGT CTG CAA AGC AGC CGA GAG AAC AGT CAC TTG GTG ACA TTC   1260
Ala Gln Arg Glu Val Ser Cys Leu Gln Ser Ser Arg Glu Asn Ser His Leu Val Thr Phe    420
```

FIG. 3B3

| | | | | | | | | | | | |
|---|---|---|---|---|---|---|---|---|---|---|---|
|TAT|GGG|AGT|GAG|AGC|CAC|AGG|GGC|CAC|TTG|TTT|GTG|TGT|GTC|ACC|CTC|TGT|GAG|CAG|ACT|1320|
|Tyr|Gly|Ser|Glu|Ser|His|Arg|Gly|His|Leu|Phe|Val|Cys|Val|Thr|Leu|Cys|Glu|Gln|Thr|440|

CTG GAA GCG TGT TTG GAT GTG CAC AGA GGG GAA AAT GAG GAA GAT GAA TTT 1380
Leu Glu Ala Cys Leu Asp Val His Arg Gly Glu Asn Glu Glu Asp Glu Phe 460

GCC CGA AAT GTC CTG TCA TCT ATA TTT AAG GCT GTT CAA GAA CTA CAC TTG TCC TGT GGA 1440
Ala Arg Asn Val Leu Ser Ser Ile Phe Lys Ala Val Gln Glu Leu His Leu Ser Cys Gly 480

TAC ACC CAC CAG GAT CTG CAA CCA CAA AAC ATC TTA ATA GAT TCT AAG AAA CGT GCT CAC 1500
Tyr Thr His Gln Asp Leu Gln Pro Gln Asn Ile Leu Ile Asp Ser Lys Lys Arg Ala His 500

CTG GCA GAT TTT GAT AAG AGC ATC AAG TGG GCT GGA GAT CCA CAG GAA GTC AAG AGA GAT 1560
Leu Ala Asp Phe Asp Lys Ser Ile Lys Trp Ala Gly Asp Pro Gln Glu Val Lys Arg Asp 520

CTA GAG GAC CTT GGA CGG CTG GTC TAT GTG GTA AAG GTT GTA AAG GGA AGC ATC TCA TTT GAG 1620
Leu Glu Asp Leu Gly Arg Leu Val Tyr Val Val Lys Gly Ser Ile Ser Phe Glu 540

GAT CTG AAA GCT CAA AGT AAT GAA GAG GTG GTT CAA CTT TCT CCA GAT GAG GAA ACT AAG 1680
Asp Leu Lys Ala Gln Ser Asn Glu Glu Val Val Gln Leu Ser Pro Asp Glu Glu Thr Lys 560

GAC CTC ATT CAT CGT CTC TTC CAT CCT GGG GAA CAT GTG AGG GAC TGT CTG AGT GAC CTG 1740
Asp Leu Ile His Arg Leu Phe His Pro Gly Glu His Val Arg Asp Cys Leu Ser Asp Leu 580

CTG GGT CAT CCC TTC TTT TGG ACT TGG GAG AGC CGC TAT AGG ACG CTT CGG AAT GTG GGA 1800
Leu Gly His Pro Phe Phe Trp Thr Trp Glu Ser Arg Tyr Arg Thr Leu Arg Asn Val Gly 600

AAT GAA TCC GAC ATC AAA ACA CGA AAA TCT GAA AGT AAG CTT ATC CTC AGA CTA CTG CAA CCT 1860
Asn Glu Ser Asp Ile Lys Thr Arg Lys Ser Glu Ser Lys Ile Leu Arg Leu Leu Gln Pro 620

GGG CCT TCT GAA CAT TCC AAA AGT TTT GAC AAG TGG ACG ACT ATT AAT GAA TGT GTT 1920
Gly Pro Ser Glu His Ser Lys Ser Phe Asp Lys Trp Thr Thr Lys Ile Asn Glu Cys Val 640

FIG. 3B4

```
ATG AAA AAA ATG AAT AAG TTT TAT GAA AAA AGA GGC AAT TTC TAC CAG AAC ACT GTG GGT    1980
Met Lys Lys Met Asn Lys Phe Tyr Glu Lys Arg Gly Asn Phe Tyr Gln Asn Thr Val Gly     660

GAT CTG CTA AAG TTC ATC CGG AAT TTG GGA GAA CAC ATT GAT GAA GAA AAG CAT AAA AAG    2040
Asp Leu Leu Lys Phe Ile Arg Asn Leu Gly Glu His Ile Asp Glu Glu Lys His Lys Lys     680

ATG AAA TTA AAA ATT GGA GAC CCT TCC CTG TAT TTT CAG AAG ACA TTT CCA GAT CTG GTG    2100
Met Lys Leu Lys Ile Gly Asp Pro Ser Leu Tyr Phe Gln Lys Thr Phe Pro Asp Leu Val     700

ATC TAT GTC TAC ACA AAA CTA CAG AAC ACA GAA TAT AGA AAG CAT TTC CCC CAA ACC CAC    2160
Ile Tyr Val Tyr Thr Lys Leu Gln Asn Thr Glu Tyr Arg Lys His Phe Pro Gln Thr His     720

AGT CCA AAC AAA CCT CAG TGT GAT GGA GCT GGT GGG GCC AGT GGG TTG GCC AGC CCT GGG    2220
Ser Pro Asn Lys Pro Gln Cys Asp Gly Ala Gly Gly Ala Ser Gly Leu Ala Ser Pro Gly     740

TGC 2223  tgatggactgattgctggagttcagggaactacttattagctgtagagtccttggcaaatcacaacat    2292
Cys  741 tctgggcctttaactcaccaggttgctgttgtgaggatgagttgcatagctgatgtcagtccctgcatcgtg           2367
tattccatatgtctataacaaaagcaatatataccagactacactagtccataagcttacccactaactggga         2442
ggacattctgctaagattccttttgtcaattgcaccaaaagaatgagtgcctgacccctaatgctgcatatgtt       2517
acaattctctcactcacttaatttcccaatgatcttgcaaaaacaggattatcatcccatttaagaactgaggaacc    2592
tgagactcagagagtgtgagctactggcccagattattcaatttatacctgcacttataaatttatgtggtg         2667
ttattggtacctctcatttggcaccttaaaactcttaactatctttccaggctcttccagatgaggcccaaaacat     2742
atatagggggttccaggaatctcattcattcattcagtatttattgagcatctagtataagtctgggcactggatg    2817
catgaatt  2825
```

FIG. 4A

P-loop cores- ▬  Cys-rich- ▨  PK homology- ▩

```
Human  - MESRDHNNPQ EGPTSSSGRR AAVEDNHLLI KAVQNEDVDL VQQLLEGGAN VNFQEEEGGW  60
         ::         :: ::     :         ::         ::           :: ::
Murine - METPDYNTPQ GGTPSAGSQR TVVEDDSSLI KAVQKGDVVR VQQLLEKGAD ANACEDTWGW  60

Human  - TPLHNAVQMS REDIVELLLR HGADPVLRKK NGATLFILAA IAGSVKLLKL FLSKGADVNE 120
         ::::::::::      :::::: ::::::::   :::::::::  ::: ::::::
Murine - TPLHNAVQAG RVDIVNLLLS HGADPHRRKK NGATPFIIAG IQGDVKLLEI LLSCGADVNE 120

Human  - CDFYGFTAFM EAAVYGKVKA LKFLYKRGAN VNLRRKTKED QERLRKGGAT ALMDAAAEKGH 180
         ::  ::::::  ::       :::  :::::: :::::      :::::::::: ::: :::::
Murine - CDENGFTAFM EAAERGNAEA LRFLFAKGAN VNLRRQTTKD KRRLKQGGAT ALMSAAEKGH 180

Human  - VEVLKILLDE MGADVNACDN MGRNALIHAL LSSDDSDVEA ITHLLLDHGA DVNVRGERGK 240
         :::::::::  ::::::: :: ::::::::::    :  ::::::   : : :: ::::::::::
Murine - LEVLRILLND MKAEVDARDN MGRNALIRTL LNWDCENVEE ITSILIQHGA DVNVRGERGK 240

Human  - TPLILAVEKK HLGLVQRLLE QEHIEINDTD SDGKTALLLA VELKLKKIAE LLCKRGASTD 300
         :::::  ::: ::::::::::      ::  :  ::::::::  :::::  ::   :: ::::
Murine - TPLIAAVERK HTGLVQMLLS REGINIDARD NEGKTALLIA VDKQLKEIVQ LLLEKGA-DK 299

Human  - CGDLVMTARR NYDHSLVKVL LSHGAKEDFH PPAEDWKPQS SHWGAALKDL HRIYRPMIGK 360
         ::::: :::: :::  :::::  :::::::::   ::      ::::::::: ::::::::::
Murine - CDDLVWIARR NHDYHLVKLL LPYVANPDTD PPAGDWSPHS SRWGTALKSL HSMTRPMIGK 359

Human  - LKFFIDEKYK IADTSEGGIY LGFYEKQEVA VKTFCEGSPR AQREVSCLQS SRENSHLVTF 420
         :::::  ::: :  :::: :: :: :::  :: ::::::::::  :::::::::  ::::::::
Murine - LKIFIHDDYK IAGTSEGAVY LGIYDNREVA VKVFRENSPR GCKEVSCLRD CGDHSNLVAF 419
```

FIG. 4B

| | | | | |
|---|---|---|---|---|
| Human  — | YGSESHRGHL | FVCVTLCEQT LEACLDVHRG EDVENEEDEF ARNVLSSIFK AVQELHLSCG | 480 |
| Murine — | YGREDDKGCL | YVCVSLCEWT LEEFLRLPRE EPVENGEDKF AHSILLSIFE GVQKLHLH-G | 478 |
| Human  — | YTHQDLQPQN | ILIDSKKKRAH LADFDKSIKW AGDPQEVKRD LEDLGRLVLY VVKKGSISFE | 540 |
| Murine — | YSHQDLQPQN | ILIDSKKAVR LADFQSIRW MGESQMVRRD LEDLGRLVLY VVMKGEIPFE | 538 |
| Human  — | DLKAQSNEEV | VQLSPDEETK DLIHRLFHPG EHVRDCLSDL LGHPFFWTWE SRYRTLRNVG | 600 |
| Murine — | TLKTQNDEVL | LTMSPDEETK DLIHCLFSPG ENVKNCLVDL LGHPFFWTWE NRYRTLRNVG | 598 |
| Human  — | NESDIKTRKS | ESEILRLLQP GPSEHSKSFD KWTTKINECV MKKMNKFYEK R-GNFYQNTV | 659 |
| Murine — | NESDIKVRKC | KSDLLRLLQH QTLEPPRSFD QWTSKIDKNV MDEMNHFYEK RKKNPYQDTV | 658 |
| Human  — | GDLLKFIRNL | GEHIDEEKHK KMKLKIGDPS LYFQKTFPDL VIYVYTKLQN TEYRKHFPQT | 719 |
| Murine — | GDLLKFIRNI | GEHINEEKKR G-------- ---------- ---------- ---------- | 679 |
| Human  — | HSPNKPQCDG | AGGASGLASP GC  741 | |

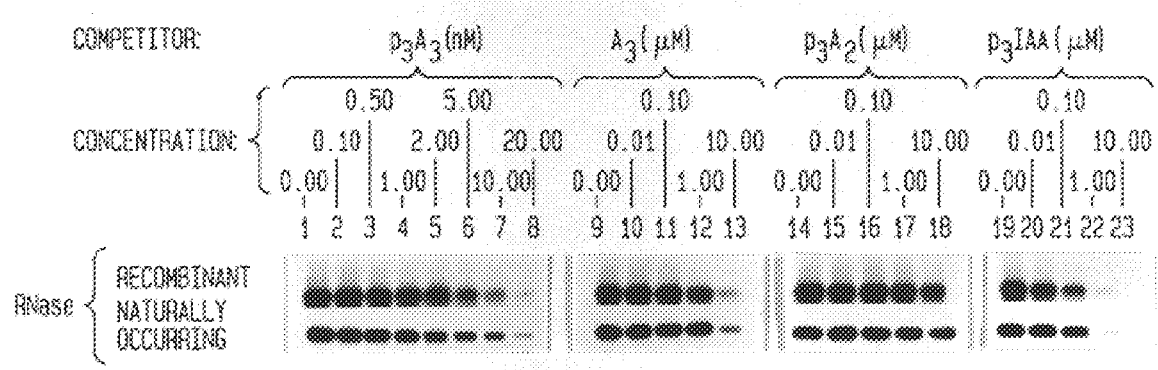

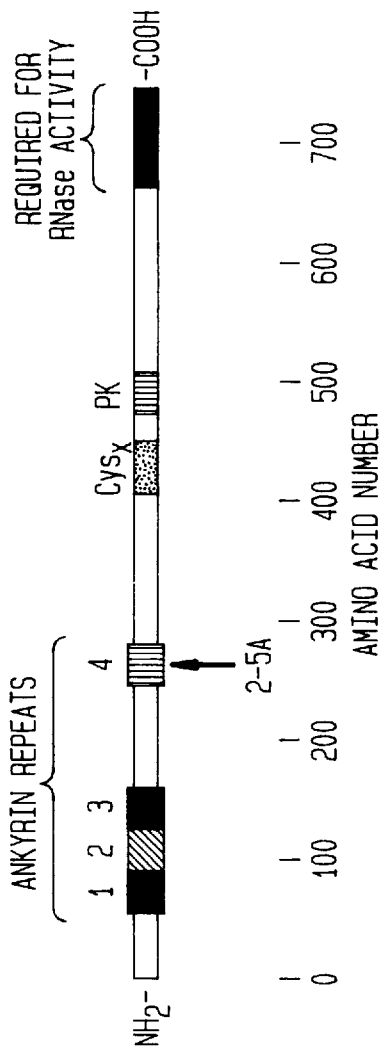

FIG. 18

ID SEQ NO 8

| | | | | | | |
|---|---|---|---|---|---|---|
| 1 | cagtttctgg | agcaaattca | gtttgccttc | ctggatttgt | aaattgtaat | gacctcaaaa |
| 61 | ctttagcagt | tcttccatct | gactcaggtt | tgcttctctg | gcggtcttca | gaatcaacat |
| 121 | ccacacttcc | gtgattatct | gcgtgcattt | tggacaaagc | ttccaaccag | gatacgggaa |
| 181 | gaagaaatgg | ctggtgatct | ttcagcaggt | ttcttcatgg | aggaacttaa | tacataccgt |
| 241 | cagaagcagg | gagtagtact | taaatatcaa | gaactgccta | attcaggacc | tccacatgat |
| 301 | aggaggttta | catttcaagt | tataatagat | ggaagagaat | ttccagaagg | tgaaggtaga |
| 361 | tcaaagaagg | aagcaaaaaa | tgccgcagcc | aaattagctg | ttgagatact | taataaggaa |
| 421 | aagaaggcag | ttagtccttt | attattgaca | acaacgaatt | cttcagaagg | attatccatg |
| 481 | gggaattaca | taggccttat | caatagaatt | gcccagaaga | aaagactaac | tgtaaattat |
| 541 | gaacagtgtg | catcggggt | gcatgggcca | gaaggatttc | attataaatg | caaaatggga |
| 601 | cagaaagaat | atagtattgg | tacaggttct | actaaacagg | aagcaaaaca | attggccgct |
| 661 | aaacttgcat | atcttcagat | attatcagaa | gaaacctcag | tgaaatctga | ctacctgtcc |
| 721 | tctggttctt | ttgctactac | gtgtgagtcc | caaagcaact | ctttagtgac | cagcacactc |
| 781 | gcttctgaat | catcatctga | aggtgacttc | tcagcagata | catcagagat | aaattctaac |
| 841 | agtgacagtt | taaacagttc | ttcgttgctt | atgaatggtc | tcagaaataa | tcaaaggaag |
| 901 | gcaaaaagat | ctttggcacc | cagatttgac | cttcctgaca | tgaaagaaac | aaagtatact |
| 961 | gtggacaaga | ggtttggcat | ggattttaaa | gaaatagaat | taattggctc | aggtggattt |
| 1021 | ggccaagttt | tcaaagcaaa | acacagaatt | gacggaaaga | cttacgttat | taaacgtgtt |
| 1081 | aaatataata | acgagaaggc | ggagcgtgaa | gtaaaagcat | tggcaaaact | tgatcatgta |
| 1141 | aatattgttc | actacaatgg | ctgttgggat | ggatttgatt | atgatcctga | gaccagtgat |
| 1201 | gattctcttg | agagcagtga | ttatgatcct | gagaacagca | aaaatagttc | aaggtcaaag |
| 1261 | actaagtgcc | ttttcatcca | aatggaattc | tgtgataaag | ggaccttgga | acaatggatt |
| 1321 | gaaaaaagaa | gaggcgagaa | actagacaaa | gttttggctt | tggaactctt | tgaacaaata |
| 1381 | acaaaagggg | tggattatat | acattcaaaa | aaattaattc | atagagatct | taagccaagt |
| 1441 | aatatattct | tagtagatac | aaaacaagta | aagattggag | actttggact | tgtaacatct |
| 1501 | ctgaaaaatg | atggaaagcg | aacaaggagt | aggggaactt | tgcgatacat | gagcccagaa |
| 1561 | cagatttctt | cgcaagacta | tggaaaggaa | gtggacctct | acgctttggg | gctaattctt |
| 1621 | gctgaacttc | ttcatgtatg | tgacactgct | tttgaaacat | caaagttttt | cacagaccta |
| 1681 | cgggatggca | tcatctcaga | tatatttgat | aaaaaagaaa | aaactcttct | acagaaatta |
| 1741 | ctctcaaaga | aacctgagga | tcgacctaac | acatctgaaa | tactaaggac | cttgactgtg |
| 1801 | tggaagaaaa | gcccagagaa | aaatgaacga | cacacatgtt | agagcccttc | tgaaaaagta |
| 1861 | tcctgcttct | gatatgcagt | tttccttaaa | ttatctaaaa | tctgctaggg | aatatcaata |
| 1921 | gatatttacc | ttttatttta | atgtttcctt | taatttttta | ctatttttac | taatcttct |
| 1981 | gcagaaacag | aaaggttttc | ttcttttttgc | ttcaaaaaca | ttcttacatt | ttacttttc |
| 2041 | ctggctcatc | tctttatttt | tttttttt | ttttaaagac | agagtctcgc | tctgttgccc |
| 2021 | aggctggagt | gcaatgacac | agtcttggct | cactgcaact | tctgcctctt | gggttcaagt |
| 2061 | gattctcctg | cctcagcctc | ctgagtagct | ggattacagg | catgtgccac | ccacccaact |
| 2221 | aattttgtg | tttttaataa | agacagggtt | tcaccatgtt | ggccaggctg | gtctcaaact |
| 2281 | cctgacctca | agtaatccac | ctgcctcggc | ctcccaaagt | gctgggatta | cagggatgag |
| 2341 | ccaccgcgcc | cagcctcatc | tctttgttct | aaagatggaa | aaaccacccc | caaatttct |
| 2401 | ttttatacta | ttaatgaatc | aatcaattca | tatctattta | ttaaatttct | accgctttta |
| 2461 | ggccaaaaaa | atgtaagatc | gttctctgcc | tcacatagct | tacaagccag | ctggagaaat |
| 2521 | atggtactca | ttaaaaaaaa | aaaaaaaag | tgatgtacaa | cc | |

FIG. 19

ID SEQ NO: 9

MAGDLSAGFFMEELNTYRQKQGVVLKYQELPNSGPPHDRRFTFQVIID
GREFPEGEGRSKKEAKNAAAKLAVEILNKEKKAVSPLLLTTTNSSEGLS
MGNYIGLINRIAQKKRLTVNYEQCASGVHGPEGFHYKCKMGQKEYSIG
TGSTKQEAKQLAAKLAYLQILSEETSVKSDYLSSGSFATTCESQSNSLV
TSTLASESSSEGDFSADTSEINSNSDSLNSSSLLMNGLRNNQRKAKRS
LAPRFDLPDMKETKYTVDKRFGMDFKEIELIGSGGFGQVFKAKHRIDG
KTYVIKRVKYNNEKAEREVKALAKLDHVNIVHYNGCWDGFDYDPETSD
DSLESSDYDPENSKNSSRSKTKCLFIQMEFCDKGTLEQWIEKRRGEKL
DKVLALELFEQITKGVDYIHSKKLIHRDLKPSNIFLVDTKQVKIGDFGLVT
SLKNDGKRTRSKGTLRYMSPEQISSQDYGKEVDLYALGLILAELLHVCD
TAFETSKFFTDLRDGIISDIFDKKEKTLLQKLLSKKPEDRPNTSEILRTLT
VVWKKSPEKNERHTC

FIG. 20A

ID SEQ NO: 10

```
              10         20         30         40         50
  1 AACTGAAACC AACAGCAGTC CAAGCTCAGT CAGCAGAAGA GATAAAAGCA 60         70         80         90        100
 51 AACAGGTCTG GGAGGCAGTT CTGTTGCCAC TCTCTCTCCT GTCAATGATG 10         20         30         40         50
101 GATCTCAGAA ATACCCCAGC CAAATCTCTG GACAAGTTCA TTGAAGACTA 60         70         80         90        100
151 TCTCTTGCCA GACACGTGTT TCCGCATGCA AATCGACCAT GCCATTGACA 10         20         30         40         50
201 TCATCTGTGG GTTCCTGAAG GAAAGGTGCT TCCGAGGTAG CTCCTACCCT 60         70         80         90        100
251 GTGTGTGTGT CCAAGGTGGT AAAGGGTGGC TCCTCAGGCA AGGGCACCAC 10         20         30         40         50
301 CCTCAGAGGC CGATCTGACG CTGACCTGGT TGTCTTCCTC AGTCCTCTCA 60         70         80         90        100
351 GCACTTTTCA GGATCAGTTA AATCGCCGGG GAGAGTTCAT CCAGGAAATT 10         20         30         40         50
401 AGGAGACAGC TGGAAGCCTG TCAAAGAGAG AGAGCACTTT CCGTGAAGTT 60         70         80         90        100
451 TGAGGTCCAG GCTCCACGCT GGGGCAACCC CCGTGCGCTC AGCTTCGTAC 10         20         30         40         50
501 TGAGTTCGCT CCAGCTCGGG GAGGGGGTGG AGTTCGATGT GCTGCCTGCC 60         70         80         90        100
551 TTTGATGCCC TGGGTCAGTT GACTGGCAGC TATAAACCTA ACCCCCAAAT 10         20         30         40         50
601 CTATGTCAAG CTCATCGAGG AGTGCACCGA CCTGCAGAAA GAGGGCGAGT 60         70         80         90        100
651 TCTCCACCTG CTTCACAGAA CTACAGAGAG ACTTCCTGAA GCAGCGCCCC 10         20         30         40         50
701 ACCAAGCTCA AGAGCCTCAT CCGCCTAGTC AAGCACTGGT ACCAAAATTG 60         70         80         90        100
751 TAAGAAGAAG CTTGGGAAGC TGCCACCTCA GTATGCCCTG GAGCTCCTGA 10         20         30         40         50
801 CGGTCTATGC TTGGGAGCGA GGGAGCATGA AAACACATTT CAACACAGCC 60         70         80         90        100
851 CAAGGATTTC GGACGGTCTT GGAATTAGTC ATAAACTACC AGCAACTCTG
```

FIG. 20B

```
              10         20         30         40         50
 901 CATCTACTGG ACAAAGTATT ATGACTTTAA AAACCCCATT ATTGAAAAGT
              60         70         80         90        100
 951 ACCTGAGAAG GCAGCTCACG AAACCCAGGC CTGTGATCCT GGACCCGGCG
              10         20         30         40         50
1001 GACCCTACAG GAAACTTGGG TGGTGGAGAC CCAAAGGGTT GGAGGCAGCT
              60         70         80         90        100
1051 GGCACAAGAG GCTGAGGCCT GGCTGAATTA CCCATGCTTT AAGAATTGGG
              10         20         30         40         50
1101 ATGGGTCCCC AGTGAGCTCC TGGATTCTGC TGGCTGAAAG CAACAGTACA
              60         70         80         90        100
1151 GACGATGAGA CCGACGATCC CAGGACGTAT CAGAAATATG GTTACATTGG
              10         20         30         40         50
1201 AACACATGAG TACCCTCATT TCTCTCATAG ACCCAGCACG CTCCAGGCAG
              60         70         80         90        100
1251 CATCCACCCC ACAGGCAGAA GAGGACTGGA CCTGCACCAT CCTCTGAATG
              10         20         30         40         50
1301 CCAGTGCATC TTGGGGGAAA GGGCTCCAGT GTTATCTGGA CCAGTTCCTT
              60         70         80         90        100
1351 CATTTTCAGG TGGGACTCTT GATCCAGAGA AGACAAAGCT CCTCAGTGAG
              10         20         30         40         50
1401 CTGGTGTATA ATCCAAGACA GAACCCAAGT CTCCTGACTC CTGGCCTTCT
              60         70         80         90        100
1451 ATGCCCTCTA TCCTATCATA GATAACATTC TCCACAGCCT CACTTCATTC
              10         20         30         40         50
1501 CACCTATTCT CTGAAAATAT TCCCTGAGAG AGAACAGAGA GATTTAGATA
              60         70         80         90        100
1551 AGAGAATGAA ATTCCAGCCT TGACTTTCTT CTGTGCACCT GATGGGAGGG
              10         20         30         40         50
1601 TAATGTCTAA TGTATTATCA ATAACAATAA AAATAAAGCA AATACCAAAA
```

FIG. 21

ID SEQ NO: 11

```
            10         20         30         40         50
    1234567890 1234567890 1234567890 1234567890 1234567890
    MMDLRNTPAK SLDKFIEDYL LPDTCFRMQI DHAIDIICGF LKERCFRGSS  50
    YPVCVSKVVK GGSSGKGTTL RGRSDADLVV FLSPLTTFQD QLNRRGEFTQ 100
    EIRRQLEACQ RERALSVKFE VQAPRWGNPR ALSFVLSSLQ LGEGVEFDVL 150
    PAFDALGQLT GSYKPNPQIY VKLIEECTDL QKEGEFSTCG TELQRDFLKQ 200
    RPTKLKSLIR LVKHWTQNCK KKLGKLPPQY ALELLTVYAW ERGSMKTHFN 250
    TAQGFRTVLE LVINYQQLCI YWIKYYDFKN PIIEKYLRRQ LTKPRPVILK 300
    PADPTGNLGG GDPKGWRQLA QEAEAWLNYP CFKNWDGSPV SSWILLAESN 350
    STDDETDDPR TYQKYGYIGT HEYPHFSHRP STLQAASTPQ AEEDWTCTIL 400
```

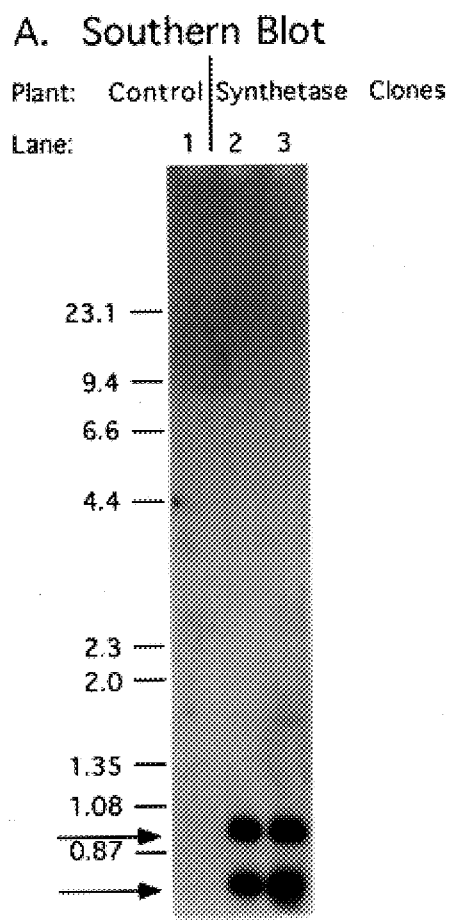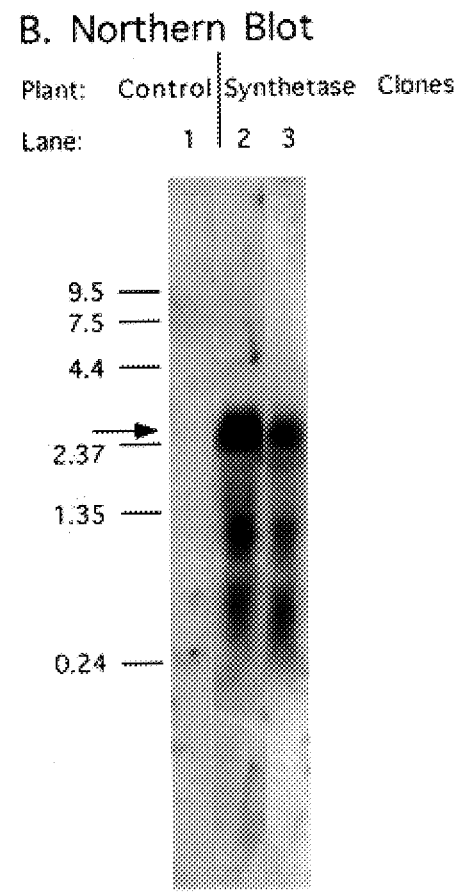
FIG. 27

TRANSGENIC PLANTS CO-EXPRESSING A FUNCTIONAL HUMAN 2-5A SYSTEM

RELATED APPLICATIONS

This application for U.S. patent is a continuation-in-part of U.S. patent application Ser. No. 08/198,973 filed on Feb. 18, 1994, now abandoned, which is a continuation-in-part of U.S. patent application Ser. No. 08/028,086 filed on Mar. 8, 1993, now abandoned.

FIELD OF THE INVENTION

The present invention relates to isolated 2-5A-dependent RNases having the ability to bind 2-5A and/or cleave single stranded RNA when bound to 2-5A, encoding sequences therefor, recombinant nucleotide molecules, recombinant vectors, recombinant cells, antiviral transgenic plants which express, for example, antiviral animal amino acid sequences which have activity similar or identical to 2-5A-dependent RNase, 2-5A synthetase and/or PKR, and antiviral transgenic tobacco plants which show resistance to, for example, the tobacco etch virus (TEV), the tobacco mosaic virus (TMV) and the alfalfa mosaic virus (AlMV).

BACKGROUND

Control of RNA degradation is a critical cell function, and gene expression is often regulated at the level of RNA stability. See, e.g., Sha, G. and Kamen R., *Cell,* 46:659–667 (1986). Nevertheless, relatively little is known about the biochemical pathways that mediate RNA degradation in mammalian or plant systems. For instance, most if not all of the ribonucleases responsible for mRNA turnover in mammalian or plant cells remain unidentified. This was reviewed in Brawerman, G., *Cell,* 57:9–10 (1989).

Presently, the 2-5A system is believed to be the only well-characterized RNA degradation pathway from higher animals including man. See FIG. 1. See also, e.g., Kerr, I. M. and Brown, R. E., *Prod. Natl. Acad. Sci. USA,* 75:256–260 (1978) and Cayley, P. J. et al.: *Biophys Res. Commun.,* 108:1243–1250 (1982); reviewed in Sen, G. C. and Lengyel, P., *J. Biol. Chem.,* 267:5017–5020 (1992). The activity of the 2-5A system is believed to be mediated by an endoribonuclease known as 2-5A-dependent RNase. See Clemens, M. J. and Williams, B. R. G., *Cell,* 13:565–572 (1978). 2-5A-dependent RNase is a unique enzyme in that it requires 2-5A, unusual oligoadenylates with 2',5' phosphodiester linkages, $p_n(A2'p)_nA$, for ribonuclease activity. See Kerr, I. M. and Brown, R. E., *Prod. Natl. Acad. Sci. USA,* 75:256–260 (1978). 2-5A is produced from ATP by a family of synthetases in reactions requiring double-stranded RNA (dsRNA). See FIG. 1. See also Hovanessian, A. G. et al., *Nature,* 256:537–539 (1977); Marie, I. and Hovanessian, A. G., *J. Bio. Chem.,* 267:9933–9939 (1992). 2-5A is unstable in cells and in cell-free systems due to the combined action of 2',5'-phosphodiesterase and 5'-phosphatase. See Williams, B. R. G. et al.; *Eur. J. Biochem.,* 92:455–562 (1978); and Johnson, M. I. and Hearl, W. G., *J. Biol. Chem.,* 262:8377–8382 (1987). The interaction of 2-5A-dependent RNase and 2-5A($K_d$=4×10$^{-11}$M), Silverman, R. H. et al., *Biol. Chem.,* 263:7336–7341 (1988), is highly specific. See Knight, M. et al., *Nature,* 288:189–192 (1980). 2-5A-dependent RNase is believed to have no detectable RNase activity until it is converted to its active state by binding to 2-5A. See Silverman, R. H., *Anal. Biochem.,* 144:450–460 (1985). Activated 2-5A-dependent RNase cleaves single-stranded regions of RNA 3' of UpNp, with preference for UU and UA sequences. See Wreschner, D. H. et al., *Nature,* 289:414–417 (1981a); and Floyd-Smith, G. et al., *Science,* 212:1020–1032 (1981). Analysis of inactive 2-5A-dependent RNase from mouse liver revealed it to be a single polypeptide of approximately 80 kDa. See Silverman, R. H. et al., *Biol. Chem.,* 263:7336–7341 (1988).

Although full scope and biological significance of the 2-5A system remains unknown, studies on the molecular mechanisms of interferon action have provided at least some of the functions. Interferons α, or Y are believed to induce the accumulation of both 2-5A-dependent RNase, Jacobsen, H. et al., *Virology,* 125:496–501 (1983A) and Floyd-Smith, G., *J. Cellular Biochem.,* 38:12–21 (1988), and 2-5A synthetases, Hovanessian, A. G. et al., *Nature,* 268:537–539 (1977), reviewed in Sen, G. C. and Lengyel, P., *J. Biol. Chem.,* 267:5017–5020 (1992). Furthermore, several investigations have implicated the 2-5A system in the mechanism by which interferon inhibits the replication of picornaviruses. Indeed, 2-5A per se and highly specific 2-5A mediated rRNA cleavage products were induced in interferon-treated, encephalomyocarditis virus (EMCV)-infected cells. See Williams, B. R. G., *Nature,* 282:582–586 (1979); Wreschner, D. H. et al., *Nucleic Acids Res.,* 9:1571–1581 (1981b); and Silverman, R. H. et al., *Eur. J. Biochem.,* 124:131–138 (1982a). In addition, expression of 2-5A synthetase cDNA inhibited the replication of picornaviruses, Chebath, J., *Nature,* 330:587–588 (1987) and Rysiecki, E. F. et al., *J. Interferon Res.,* 9:649–657 (1989), and the introduction of a 2-5A analogue inhibitor of 2-5A-dependent RNase into cells reduced the interferon-mediated inhibition of EMCV replication. See Watling, D. et al., *EMBO J.,* 4:431–436 (1985). Further, 2-5A-dependent RNase levels were correlated with the anti-EMCV activity of interferon, Kumar, R. et al., *J. Virol.,* 62:3175–3181 (1988), and EMCV-derived dsRNA both bound to and activated 2-5A synthetase in interferon-treated, infected cells. See Bribaudo, G. et al., *J. Virol.,* 65:1948–1757 (1991).

The 2-5A system, however, almost certainly provides functions beyond the antipicornavirus activity of interferons. For instance, introduction of 2-5A into cells, Hovanessian, A. G. and Wood, J. N., *Virology,* 101:81–90 (1980), or expression of 2-5A synthetase cDNA, Rysiecki, G. et al., *J. Interferon Res.,* 9:649–657 (1989), inhibits cell growth rates. Moreover, 2-5A-dependent RNase levels are elevated in growth arrested cells, Jacobsen, H. et al., *Proc. Natl. Acad. Sci. USA,* 80:4954–4958 (1983b), and 2-5A synthetase, Stark, G. et al., *Nature,* 278:471–473 (1979), and 2-5A-dependent RNase levels are induced during cell differentiation. See, e.g., Krause, D. et al., *Eur. J. Biochem.,* 146:611–618 (1985). Therefore, interesting correlations exist between 2-5A-dependent RNase and the fundamental control of cell growth and differentiation suggesting that the 2-5A system may function in general RNA metabolism. The ubiquitous presence of the 2-5A system in reptiles, avians and mammalians certainly supports a wider role for the pathway. See, for example, Cayley, P. J. et al., *Biochem. Biophys. Res. Commun.,* 108:1243–1250 (1982).

While it is presently believed that the 2-5A system is the only well-characterized RNA degradation pathway from higher animals, the dsRNA-dependent protein kinase enzyme, known as PKR, is also thought to have antiviral effects in higher animals. Like the 2-5A synthetase enzyme, it is believed that PKR is stimulated by dsRNA. It is believed that activated PKR phosphorylates the alpha subunit of translation factor eIF$_2$-alpha, which indirectly inhibits protein synthesis initiation. It is believed that interferons α, and Y induce the accumulation of PKR. See Hovanessian et al.: *J. Interferon Res.,* 9:641–647 (1989).

Like the 2-5A system, the PKR system is also likely to provide functions beyond the antipicornavirus activity of interferons. See Meurs, E. F. et al.: *J. Virology,* 66:5805–5814 (1992). For example, expression of mutant forms of PKR in NIH 3T3 cells resulted in tumor formation when injected into nude mice. See Meurs, E. F. et al.: *Proc. Natl. Acad. Sci USA,* 90:232–236 (1993).

In short, the 2-5A system and the PKR system inhibit viral protein synthesis. This is believed to be accomplished by the 2-5A system by degrading mRNA and rRNA whereas the PKR system is believed to accomplish this by indirectly inhibiting protein synthesis initiation.

Viral plant diseases are pandemic and their severity varies from mild symptoms to plant death. The majority of plant viruses are believed to have single stranded RNA genomes. Moreover, it is currently believed that plants are void of the three enzymes discussed above, i.e., PKR, 2-5A synthetase and 2-5A-dependent RNase. See Cayley, P. J. et al.: *Biochem. Biophys. Res. Commun.,* 108:1243–1250 (1982) and Devach, Y. et al.: *Biochemistry,* 24:593–599 (1985); but see Crum, C. et al.: *J. Biol. Chem.,* 263:13440–13443 (1988); Hiddinga, H. J. et al.: *Science,* 241:451–453 (1988); Sela, I.: *TIBS,* pp. 31–33 (February 1981); and Devach, Y. et al.: *Science,* 216:1415–1416.

The interferon family of cytokines are believed to induce an antiviral state in cells of higher vertebrates. J. Vilcek, G. C. Sen, *In Virology,* B. Fields, ed. (Raven, New York, 1995). Virus infected cells produce and secrete interferons α and β, which are believed to signal uninfected cells that a virus infection has occurred. Interferons are thought to bind to specific cell surface receptors, activating Jak-STAT signal transduction pathways which induce interferon-stimulated genes. Darnell, J. E. et al.: *Science,* 264:1415 (1994). The proteins encoded by these genes are believed to be responsible for the biological effects of interferons, including the antiviral responses. The 2-5A system, see Kerr, I. M. et al.: *Proc. Natl. Acad. Sci. USA,* 75:256 (1978), is one such interferon-induced, antiviral pathway present in cells of reptiles, avians and mammals. Cayley et al.: *Biochem. Biophys. Res. Commun.,* 108:1243 (1982). Two types of enzymes are believed to be essential for a functional 2-5A system: 1) any one of several 2-5A synthetases, which require dsRNA to produce 2-5A, a series of 5'-phosphorylated, 2',5'-linked oligoadenylates, A. G. Hovanessian, A. G. et al.: *Nature,* 268:537 (1977), and Marie, I. et al.: *J. Biol. Chem.,* 267:9933 (1992); and 2) the 2-5A-dependent Rnase L. Clemens, M. J. et al.: *Cell,* 13:565 (1978), Slattery et al.: *Proc. Natl. Acad. Sci. USA,* 76:4778 (1978), and Zhou, A. et al.: *Cell,* 72:753 (1993). 2-5A is thought to activate Rnase L which cleaves viral and cellular single-stranded RNAs, predominantly after UpNp sequences. Floyd-Smith, G. E. et al.: *Science,* 212:1020 (1981); and Wreschner, D. H. et al.: *Nature,* 289:414 (1981). Because virus-infected cells often contain dsRNA activators of 2-5A synthetase, see, e.g., Gribaudo G. et al.: *J. Virol.,* 65:1748 (1991), for instance as replicative intermediates of RNA viruses, RNA degradation by Rnase L is believed to frequently occur in interferon-treated, virus-infected cells. See Wreschner, D. H. et al.: *Nucleic Acids Res.,* 9:1571 (1981); and Silverman, R. H. et al.: *Eur. J. Biochem.,* 124:131 (1982). It is believed that the 2-5A system inhibits replication of the picornaviruses, encephalomyocarditis virus and mengo virus in interferon-treated mammalian cells. Chebath, J. et al.: *Nature,* 330:587 (1987); Rysiecki, G. et al.: *J. Interferon Res.,* 9:649 (1989); Coccia, E. M. et al., *Virology,* 179:228 (1990); and Hassel, B. A. et al.: *EMBO J.,* 12:3297 (1993).

RNase L, assayed by 2-5A binding activity, was not detected in tobacco, *Nicotiana glutinosa* and *N. tabacum.* See Cayley et al.: *Biochem. Biophys. Res. Commun.,* 108:1243 (1982). Furthermore, 2-5A synthetase was not detected in such plants, and 2-5A synthetase was not detected in control, tobacco mosaic virus (TMV)-infected, interferon-treated or poly (I):poly (C)-treated plants. Plants therefore appear to lack a 2-5A system or an equivalent of the mammalian 2-5A system.

Previously, expression in potato of rat 2-5A synthetase mRNA, without co-expression of RNase L., was correlated with possible partial resistance to potato virus X (PVX) in some, but not all transgenic plants. See Truve, E. et al.: *Bio/Technology,* 11:1048 (1993). The biochemical basis for both this perceived effect and for a possible anti-TMV effect of 2',5'-oligoadenylate in non-transgenic *N. glutinosa* leaf disks has not been established. See Y. Devash, et al.: *Science* 216: 1415–1416 (1982). Although plant oligoadenylates are believed to exist, they appear to differ from 2-5A, see, e.g., Y. Devash et al.: *Biochem.,* 24:593 (1985). It is therefore presently believed that plants do not produce or express 2-5A synthesis and RNase L.

Notwithstanding the importance of 2-5A-dependant RNase to the 2-5A system, 2-5A-dependent RNase enzymes having ribonuclease function have not been isolated, purified or sequenced heretofore. Consequently, there is a demand for isolated, active 2-5A-dependent RNases and their complete amino acid sequences, as well as a demand for encoding sequences for active 2-5A-dependent RNases. There is also a demand for transgenic plants which are immune or resistant to viruses, such as transgenic tobacco plants that are immune or resistant to viruses such as the picornaviruses, tobacco mosaic virus (TMV), tobacco etch virus (TEV) and alfalfa mosaic virus (AIMV).

SUMMARY OF THE INVENTION

In brief, the present invention alleviates and overcomes certain of the above-mentioned problems and shortcomings of the present state of the art through the discovery of novel, isolated 2-5A-dependent RNases and encoding sequences therefor.

Broadly speaking, the novel 2-5A-dependent RNases of the instant invention are involved in the fundamental control of single stranded RNA decay in animal cells, such as mammals, and are also present in animal cells, such as avian and reptilian cells. More particularly, the novel 2-5A dependent RNases of the present invention have the ability to degrade single stranded RNA, mainly 3'of UpUp or UpAp sequences, after they are activated by binding to 5'-phosphorylated,2',5'-linked oligoadenylates (hereinafter "2-5A". As a result, it is believed that the novel 2-5A dependent RNase are useful in connection with inhibition of cell growth rates, viral replication and in connection with interferon treatment of viral infection and cancer. As used herein, the term "2-5A-dependent RNase(s)" is used in a broad sense and is meant to include any amino acid sequence which includes a 2-5A binding domain and/or ribonuclease function when the 2-5A-dependent RNase is activated by 2-5A. The term 2-5A-dependent RNase also includes the term "RNase L" and is used interchangeably with the term "2-5A-dependent RNase."

The novel 2-5A dependent RNases of the present invention are protein enzyme having molecular weights on the order of between about 74 KDa (murine) and about 84 KDa (human), as determined by gel electrophoresis migration and/or prediction from their respective encoding nucleotide sequences. For example, a human 2-5A-dependent RNase of the instant invention has a molecular weight of about 83,539 Da as determined from the amino acid sequence predicted from the encoding sequence therefor, whereas the murine 2-5A-dependent RNase has a molecular weight of about 74 KDa as determined by gel electrophoresis migration and from prediction of the amino acid sequence from the encoding sequence. While an about 74 KDa molecular weight is reported herein for a murine 2-5A-dependent RNase, it should nevertheless be appreciated that the reported molecular weight is for an incomplete murine 2-5A-dependent RNase. It is nevertheless believed that once completely sequenced, i.e., when an about 84 amino acid end region is identified, the molecular weight of a complete murine 2-5A-dependent RNase will be similar to that of human, i.e., about 84 KDa.

It should also be readily apparent to those versed in this art, however, that since gel electrophoresis migration has been employed to determine molecular weight of a murine 2-5A-dependent RNase, the 74 KDa molecular weight is only an estimate based upon relative migration.

The amino acid sequence for human 2-5A-dependent RNase protein is depicted in FIG. 3 and Table 1. The encoding sequence for the human 2-5A-dependent RNase protein is also set forth in Table 1. The mRNA for human 2-5A-dependent RNase is about 5.0 Kb in size. The virtually complete amino acid sequence for the murine 2-5A-dependent RNase protein and the encoding sequence therefor is depicted in Table 2. The mRNA for murine 2-5A-dependent RNase is about 5.7 Kb in size.

Analysis of the amino acid sequences f the 2-5A-dependent RNases of the present invention have revealed several characteristics unique to the 2-5A-dependent RNases. For example, it has been discovered that the novel 2-5A dependent RNases of the instant invention include the following unique domains which span between the amino terminus and the caroxy terminus. For instance, it has been discovered that there are at least four and possibly as many as nine or more ankyrin repeats, of which three lie closest to the amino terminus. However, while four ankyrin repeats have been discovered, it is believed that there may be additional ankyrin repeats that may total, for instance, about eight or more when the amino acid sequences of the 2-5A-dependent RNases of the present invention are further analyzed. It is believed that these ankyrin repeats may possibly function in protein-protein interaction. Ankyrin repeat 1 generally lies between amino acids designated as 58–90 in Tables 1 and 2. Ankyrin repeat 2 generally lies between amino acids designated as 91–123 in Tables 1 and 2. Ankyrin repeat 3 generally lies between amino acids designated as 124–156 in Tables 1 and 2. Ankyrin repeat 4 generally lies between amino acids designated as 238 and 270 in Tables 1 and 2. See also FIGS. 10A and 10B.

It has also been discovered that the novel 2-5A dependent RNases include a cysteine rich region (which has homology to zinc fingers) that lies closer to the carboxy terminus than the amino terminus which may possibly function in RNA recognition or in formation of protein dimers. The cysteine rich region is believed to include about 5 or 6 cysteine residues which generally lie between amino acids designated as 395–444 in the human sequence as reported in Table 1 and FIG. 4, or between amino acids designated as 401–436 in the murine sequence as reported in Table 2 and FIG. 4.

Still further, it has been discovered that the novel 2-5A dependent RNases include a duplicated phosphate binding (2 P-loops) motif which lies generally within the ankyrin repeat motifs. It is believed that the two P-loops are in the same orientation and constitute the binding domain necessary for binding 2-5A. It is further believed that each P-loop motif includes a lysine residue which is essential for maximum 2-5A binding activity. The lysine residues are designated as 240 and 274 in Tables 1 and 2.

It has been further discovered that the 2-5A-dependent RNase proteins contain an amino acid region which follows the cysteine rich region that is believed to be homologous to protein kinases. Within this region, there is believed to be separate domains designated as domains VI and VII which generally lie between amino acid residues designated as 470–504 in Tables 1 and 2. More particularly, as to the human sequence of 2-5A-dependent RNase, domain VI generally lies between amino acid residues designated as 501–504, as reported in Table 1 and FIG. 4. As to the murine sequence of the 2-5A-dependent RNase, domain VI generally lies between amino acids designated as 470–489 and domain VII generally lies between amino acid residues designated as 499–502, as reported in Table 2 and FIG. 4.

It has also been discovered that there is limited homology between the amino acid sequences for the 2-5A-dependent RNases of the present invention and RNase E, encoded by the altered mRNA stability (ams)/rne gene of E. Coli. Uniquely, the limited homology is generally conserved between the murine and human amino acid sequences for 2-5A-dependent RNases and generally lies between a 200 amino acid region. More particularly, for the human sequence, (the amion acid region spans amino acid residues designated as 160–349 in Table 1 and FIGS. 9A and 9B. With respect to the murine sequence, the amino acid region spans amino acid residues designated as 160–348 in Table 2 and FIGS. 9A and 9B.

It has been further discovered and is believed that almost the entire, if not complete, amino acid sequences of the novel 2-5A-dependent RNase proteins of the instant invention are necessary for ribonuclease function. For example, it is believed that, when an about 84 amino acid region at the carboxy terminus is present in the human 2-5A-dependent RNase, the human 2-5A-dependent RNase has ribonuclease function in the presence of 2-5A. In contrast, when the murine 2-5A-dependent RNase lacks the about 84 amino acid region at the carboxy terminus, it lacks ribonuclease function.

With respect to the binding activity of a murine 2-5A-dependent RNase protein to 2-5A, it has been discovered that, when one P-loop is deleted from the repeated P-loop motif of a murine 2-5A-dependent RNase protein, nearly all 2-5A binding activity is lost, and that when both P-loops are deleted, virtually complete activity is lost. However, it has been found that, even though the carboxy terminus portion of the amino acid sequence of a murine 2-5A-dependent RNase protein following the repeated P-loop motif has been deleted, partial 2-5A binding activity is maintained.

It has been further discovered that when lysine residues 240 and 274 are replaced with asparagine residues in both P-loop motifs, significant 2-5A binding activity of a murine 2-5A-dependent RNase protein is lost. It has been further discovered, however, that when either lysine residue 240 or 274 is replaced in either P-loop motif, only partial 2-5A binding activity is lost. It is therefore believed that the presence of both P-loop motifs in the amino acid sequences for the 2-5A dependent RNases of the present invention plays an important role in 2-5A binding activity. It is further believed that the presence of lysine residues 240 and 274 in each P-loop motif plays an important role for enhanced 2-5A binding activity. It is also believed that the presence of virtually the entire amino acid sequence of the 2-5A-dependent RNases of the present invention provides for even further enhanced 2-5A binding activity, as well as provides for ribonuclease function.

In addition, the present invention relates to the cloning of murine and human 2-5A-dependent RNases and novel murine and human clones. Recombinant and naturally occurring forms of 2-5A-dependent RNase displayed virtually identical 2-5A binding properties and ribonuclease specificities.

The present invention further contemplates the use of the novel isolated, 2-5A-dependent RNases and encoding sequences therefor, as well as analogs and active fragments thereof, for use, for instance, 1.) in gene therapy for human and animal diseases including viral disease and cancer, 2.) as genetic markers for human disease due to perhaps cancer or viral infection, 3.) to develop plants and animals resistant to certain viruses, and 4.) as enzymes in connection with research and development, such as for studying the structure of RNA. In one manner to accomplish the above, and as contemplated by the present invention, the encoding sequences of the instant invention may be utilized in ex vivo therapy, i.e., to develop recombinant cells using encoding sequence of the present invention using techniques known to those versed in this art. In another manner which may be employed to accomplish the above, the encoding sequences of the present invention may be combined with an appropriate promoter to form a recombinant molecule and inserted into a suitable vector for introduction into an animal, plant, or other lower life forms also using techniques known to those skilled in this art. Of course, other suitable methods of means known to those versed in this art may be selected to accomplish the above-stated objectives or other objectives for which the novel 2-5A-dependent RNases and encoding sequences of the present invention are suited.

The present invention also contemplates novel transgenic plants, as indicated above, which are resistant to viruses such as the picornaviruses. Generally speaking, the transgenic plants of the present invention include any inserted nucleotide sequence encoding any type of antiviral amino acid sequence, including proteins. Preferably, the antiviral nucleotide sequences introduced into plants in accordance with the present invention are animal antiviral genes, such as those genes which are stimulated in response to interferon production and/or treatment. These include, for example, those animal antiviral genes that encode 2-5A-synthetase, 2-5A-dependent RNase, and PKR. These interferon-regulated proteins, 2-5A-synthetase, 2-5A-dependent RNase and PKR (the dsRNA-dependent protein kinase) have recognized antiviral effects in higher animals and are believed to have antiviral effects in the transgenic plants of the present invention. PKR is stimulated by dsRNA to phosphorylate translation factor eIF2 which indirectly inhibits protein synthesis initiation. On the other hand, 2-5A synthetase is activated by dsRNA resulting in the production of "2-5A," $p_xA(2'p5'A)_y$ wherein x=about 1 to about 3 and y≧about 2, from ATP. The 2-5A then activates an endoribonuclease entitled 2-5A dependent RNase (also known as RNase L or nuclease F). The activated ribonuclease degrades mRNA and rRNA thus inhibiting protein synthesis.

These above-described pathways are particularly effective at inhibiting viruses in animals with single stranded RNA genomes that replicate through dsRNA intermediates, such as the picornaviruses, and are believed to be effective at inhibiting similar types of viruses that infect plants. This belief is premised upon the understanding that most single stranded RNA plant viruses produce double stranded structures during replication by their viral replicases, see Dawson, W. O. et al.: Acad. Press, 38:307–342 (1990), and that plant viruses are similar to animal viruses in structure, composition and mechanism of replication in cells. In addition, even viral so-called single-stranded RNA may contain secondary structures which could activated PKR and 2-5A synthetase leading to widespread plant protection against plant viruses. It is believed that co-expression of 2-5A-dependent RNase and 2-5A-synthetase, will lead to the destruction of viral mRNA and viral genomic RNA thereby protecting the transgenic plants of the present invention from viruses. Moreover, it is believed that expression of PKR by the transgenic plants of the present invention will inhibit viral protein synthesis leading to inhibition of virus replication and protection of the transgenic plants. The present invention is therefore premised in part upon the belief that plant virus RNAs activate 2-5A-synthetase and PKR in the transgenic plants of the instant invention leading to immunity against virus infection. Furthermore, expression of 2-5A synthetase alone or 2-5A-dependent RNase alone or PKR alone may protect plants against viruses, perhaps by binding to viral RNA, such as viral replicative intermediates thereby blocking viral replication. Moreover, expression of only the dsRNA binding domains of PKR and/or of 2-5A-synthetase may similarly protect the transgenic plants of the present invention against viral infection.

It should therefore be appreciated by those versed in this art that novel transgenic plants which are resistant to viral infection can now be produced in accordance with the present invention. It is believed that the effectiveness of the anti-viral protection can be enhanced or even maximized when at least the three-above animal antiviral genes are inserted into plants to form exemplary transgenic plants of the present invention, since the animal antiviral proteins encode by these three animal antiviral genes interfere with different stages of the viral life cycles. Moreover, these animal antiviral proteins or amino acid sequences are believed likely to be safe to give or introduce into animals, including humans, since these antiviral proteins or amino acid sequences are naturally occurring in humans as well as in other mammals, avians and reptiles.

While the present invention is described herein with reference to the particular sequences disclosed, it should nevertheless be understood by those skilled in this art that the present invention contemplates variations to the amino acid and/or nucleotide sequences which do not destroy 2-5A synthetase activity, PKR activity and/or 2-5A-dependent ribonuclease activity. Therefore, the present invention contemplates any analogs, parts or fragments of 2-5A-dependent RNase, 2-5A synthetase, and PKR which are active, such as any active part, and any encoding sequences therefor. In other words, the present invention includes, among other things, any amino acid sequence, any nucleotide sequence and any transgenic plant which have the ability to accomplish the objectives of the instant invention. For example, the instant invention includes any amino acid sequence which has antiviral activity and any nucleotide sequence which encodes therefor and those transgenic plants that express such nucleotide sequences. More specifically, the present invention includes, for instance: 1.) any animal amino acid sequence which has the ability to inhibit or interfere with viral replication such as those amino acid sequences that have activity similar or identical to PKR activity, 2-5A synthetase activity and/or 2-5A ribonuclease activity, and any nucleotide sequence which encodes for an amino acid sequence having any such activity; and 2.) any transgenic plant having any animal antiviral nucleotide sequence which encodes any such amino acid sequence which has any such antiviral activity.

In accordance with a further feature contemplated by the present invention, novel transgenic plants, such as transgenic tobacco plants, having the ability to express a functional 2-5A system for conferring to such transgenic plants immunity to or resistance against viral infection have been surprisingly discovered. More particularly, transgenic tobacco plants having the ability to express functional 2-5A-dependent RNase (RNase L) and functional 2-5A synthetase to confer resistance against, e.g., the tobacco mosaic virus (TMV), the tobacco etch virus (TEV) and the alfalfa mosaic virus (AIMV) have been discovered. It has been surprisingly discovered that these unique transgenic tobacco plants are more resistant and immune to infection by TMV, TEV and AIMV than similar plants, which are not transgenic and with no ability to express such a 2-5A system.

Expression of the 2-5A system in plants in accordance with the present invention appears to have several apparent advantages compared to alternative plant antiviral strategies utilized heretofore. The most common approach involves pathogen-derived resistance, Sanford, J. C. et al.: *J. Theor. Biol.*, 113:395 (1985), in which plants are transformed to express certain viral-coded proteins or antisense RNAs, Wilson, T. M. A. et al.: *Proc. Natl. Acad. Sci. USA*, 90:3134 (1993); and Hull, R. et al.: *Crit. Rev. Plant Sci.*, 11:17 (1992). A potential limitation of this approach has been virus recombination that may occur in the plants resulting in possibly a more virulent virus, expansion of the host range of a virus or vector specificity. See Greene, A. E. et al.: *Science*, 263:1423 (1994); White, K. A. et al.: *Proc. Natl. Acad. Sci. USA*, 91:3642 (1994); and Tepfer, M. et al.: *Bio/Technology*, 11:1125 (1993). These risks, in general, are not considered to be high. See Falk, B. W. et al.: *Science*, 263:1395 (1994). However, even in instances of substantial resistance to virus infection, protection is usually limited to the virus from which the protein or antisense RNA is derived, or to closely related strains. In contrast, the transgenic plants containing the functional 2-5A system of the present invention are predicated upon the realization that immunity to and resistance against any plant virus that produces dsRNA in the infected cell may be provided. Most plant viruses, including those in the economically important potyvirus group, are positive sense, single-stranded RNA viruses which produce a dsRNA intermediate during their replicative process. Furthermore, because plant viruses are naive to a functional 2-5A system, it is believed that these viruses are likely to be even more vulnerable to it than viruses of higher vertebrates. It is therefore believed that expression of a functional 2-5A system in transgenic plants may uniquely provide a broad range of resistance against viral infections. Accordingly, the transgenic plant strategy according to the present invention provides a unique and advantageous approach for protecting crops and other plants against virus infections in the field.

The above features and advantages of the present invention will be better understood with reference to the accompanying FIGS., Detailed Description and Examples. It should also be understood that the particular methods, amino acid sequences, encoding sequences, constructs, vectors, recombinant cells, and antiviral transgenic plants illustrating the invention are exemplary only and not to be regarded as limitations of the invention.

BRIEF DESCRIPTION OF THE FIGS.

The file of this patent contains at least one drawing executed in color. Copies of this patent with color drawing (s) will be provided by the Patent and Trademark Office upon request and payment of the necessary fee.

Reference is now made to the accompanying FIGS. in which is shown illustrative embodiments of the present invention from which its novel features and advantages will be apparent.

Figure 1:
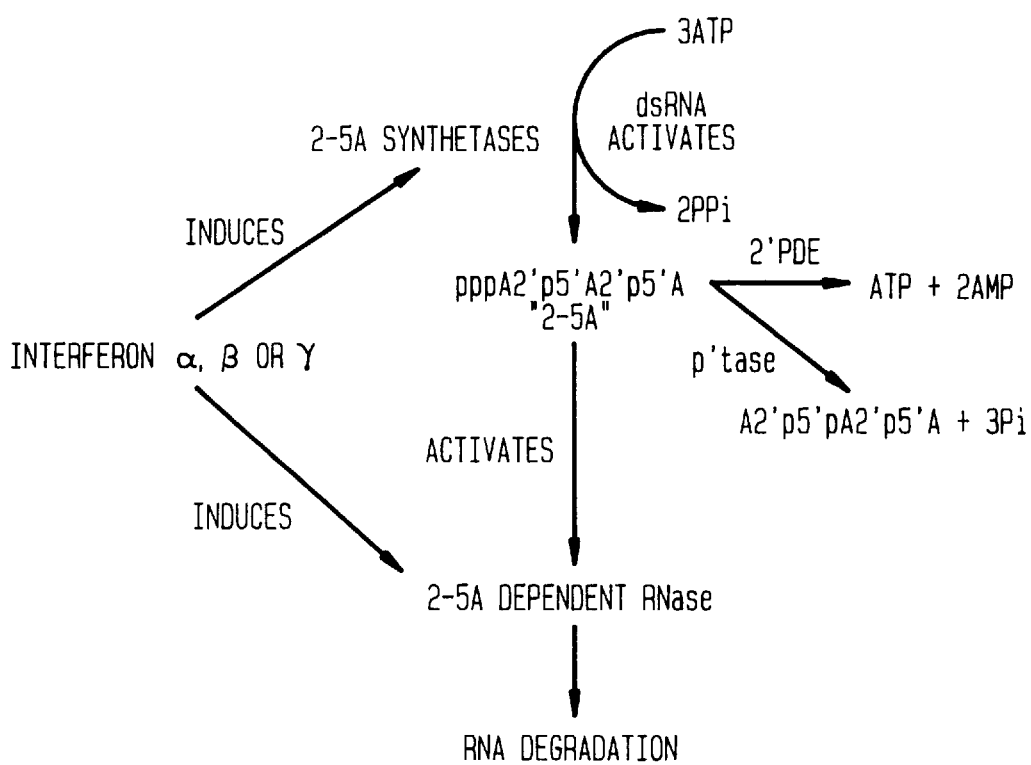
FIG. 1 is the 2-5A system: a ribonuclease pathway which is believed to function in the molecular mechanism of interferon action. 5'-phosphatase, p'tase; 2'-5'-phosphodiesterase, 2'-PDE.
Figure 2A:
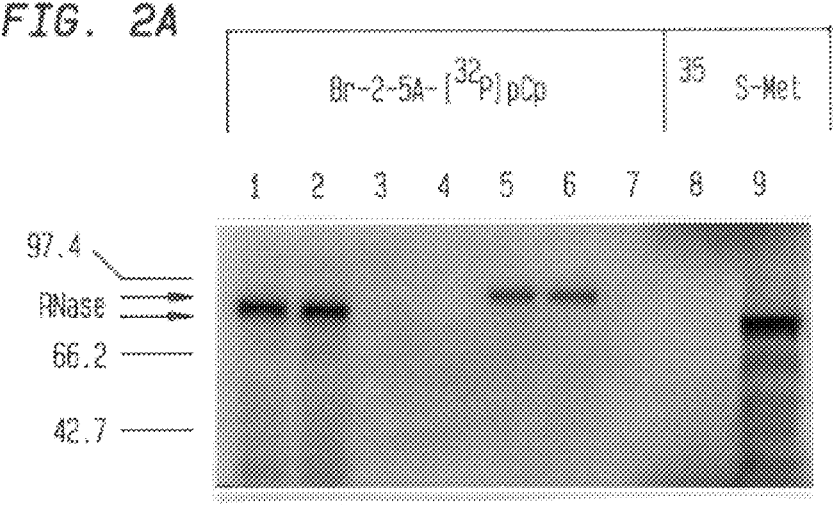
FIGS. 2A and 2B are a comparison of 2-5A binding activity of recombinant and naturally occurring forms of murine 2-5A-dependent RNase.

FIG. 2A is a specific affinity of truncated murine 2-5A-dependent RNase for 2-5A. UV covalent crosslinking of the $^{32}$P-2-5A probe (lanes 1–7) to protein is performed after translation reactions in wheat germ extract (5 $\mu$l) with murine 2-5A-dependent RNase mRNA (from clone ZB1) (lanes 1–3) or without added RNA (lane 4) or in extract of interferon treated mouse L cells (100 $\mu$g of protein) (lanes 5–7). Reactions are without added competitor (lanes 1, 4, and 5) or in the presence of either timer core. (A2'p)$_2$A, (100 nM) (lanes 2 and 6) or timer 2-5A, p$_3$(A2'p)$_2$A (100 nM) (lanes 3 and 7). Lanes 8 and 9 are produced by incubating the wheat germ extract with $^{35}$S-methionine in the absence or presence of 2-5A-dependent RNase mRNA, respectively.

Figure 2B:
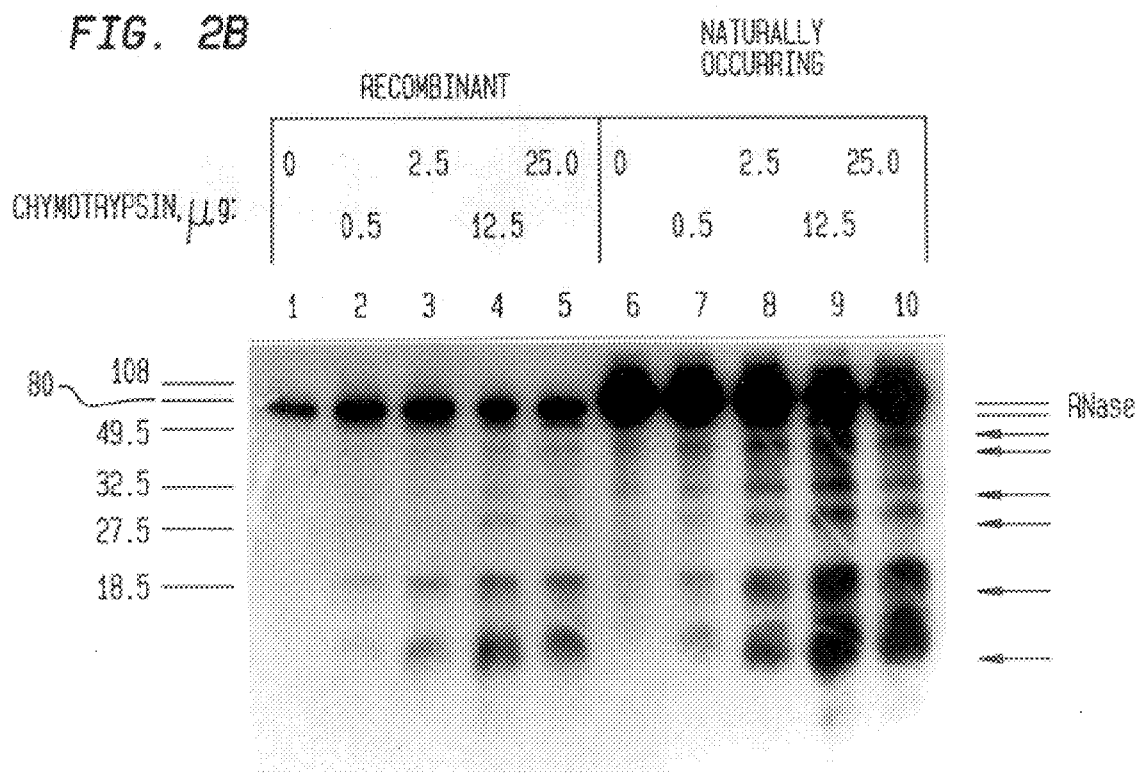

FIG. 2B are identical chymotrypsin cleavage products and are obtained from recombinant and naturally occurring form of 2-5A-dependent RNase. Partial chymotrypsin digests (arrows) are performed on truncated 2-5A-dependent RNase (clone ZB1) produced in wheat germ extract ("Recombinant") and murine L cell 2-5A-dependent RNase ("Naturally occurring") after crosslinking to the 2-5A probe and purification from gels.

Figure 3A:
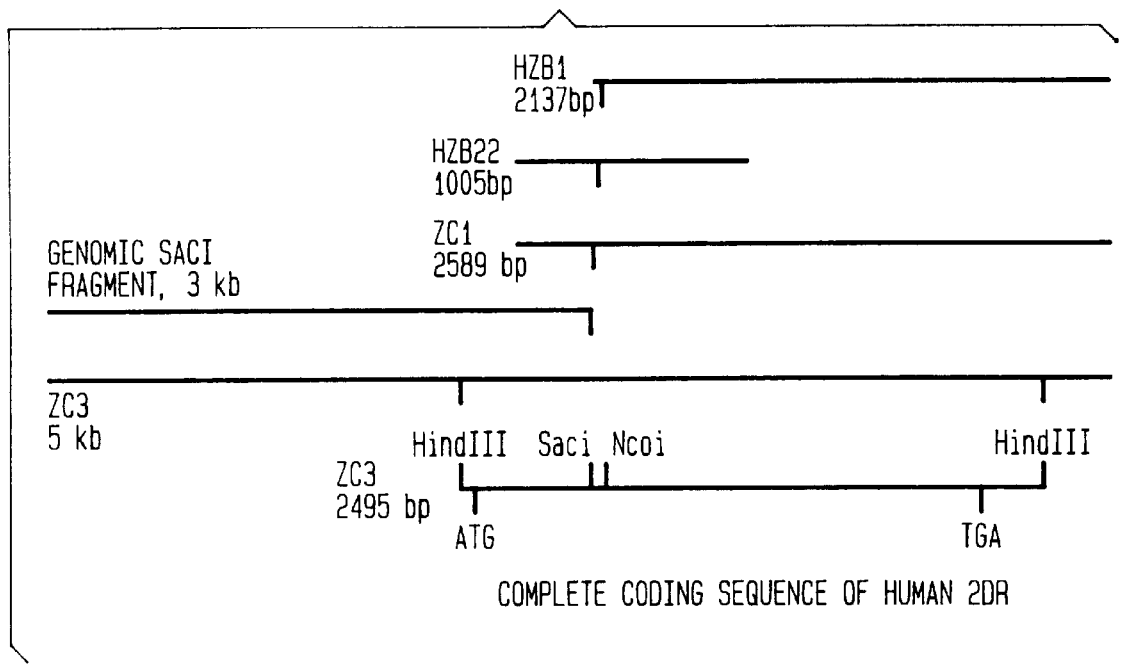
Figure 3B:
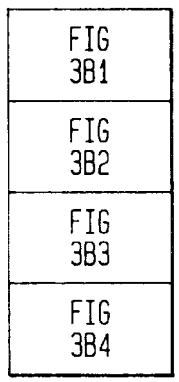
Figure 4:
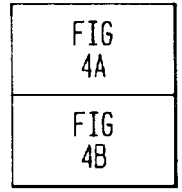

FIGS. 3A and 3B are clonings of the complete coding sequence for human 2-5A-dependent RNase.

FIG. 3A is the construction of a human 2-5A-dependent RNase clone. The initial human 2-5A-dependent RNase clone. The initial human 2-5A-dependent RNase cDNA cone, HZB1, is isolated from an adult human kidney cDNA library in λgt10 using radiolabeled murine 2-5A-dependant RNase cDNA (clone ZB1) as probe. See Example. Radiolabeled HZB1 DNA is used to isolate a partially overlapping cDNA clone, HZB22, which is fused to HZB1 DNA at the NcoI site to form clone ZC1. The 5'-region of the coding sequence is obtained from a genomic SacI fragment isolated using a radiolabeled HZB22 DNA fragment as probe. Fusion of the genomic SACI fragment with ZC1 at the indicated SacI site produces clone ZC3. The coding sequence with some flanking sequences is then subcloned as a HindIII fragment into pBluescript (KS(+) (Strategene) resulting in clone ZC5. The restriction map for the composite clone, ZC5, is shown. Clone HZB1 includes nucleotides designated as 658–2223 in Table I which encode for amino acids designated as 220–741 in Table I. Clone HZB22 includes a nucleotide sequence which encodes for amino acids designated as 62–397 in Table I. Clone ZC1 includes a nucleotide sequences which encode for amino acids designated as 1–741 in Table I.

FIGS. 3B1, 3B2, 3B3 and 3B4 are nucleotide sequence and predicted amino acid sequence of human 2-5A-dependent RNase with flanking nucleotide sequences. The numbers to the right indicate the positions of nucleotides and amino acid residues.

FIGS. 4A and 4B are alignment of the predicted amino acid sequences for murine and human forms of 2-5A- dependent RNase. The positions of the repeated P-loop motifs, the cysteine (Cys)-rich regions with homology to zinc fingers, and the regions of homology to protein kinase domains VI and VII are indicated. Amino acid residues which are important components of the indicated domains are represented in bold type and are italicized. Identical amino acid residues in murine and human 2-5A-dependent RNase are indicated with colon (:) symbols adjacent therebetween.

Figure 5A:
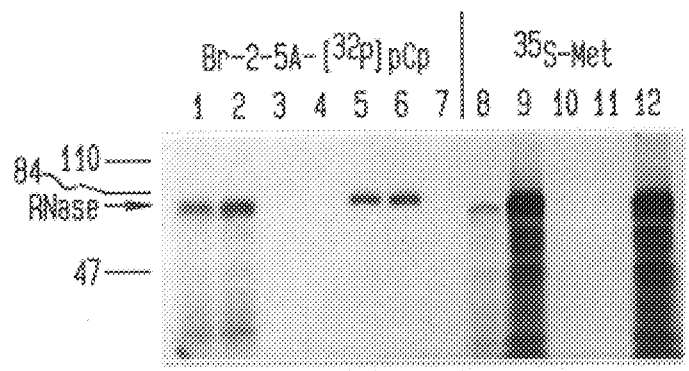
Figure 5B:
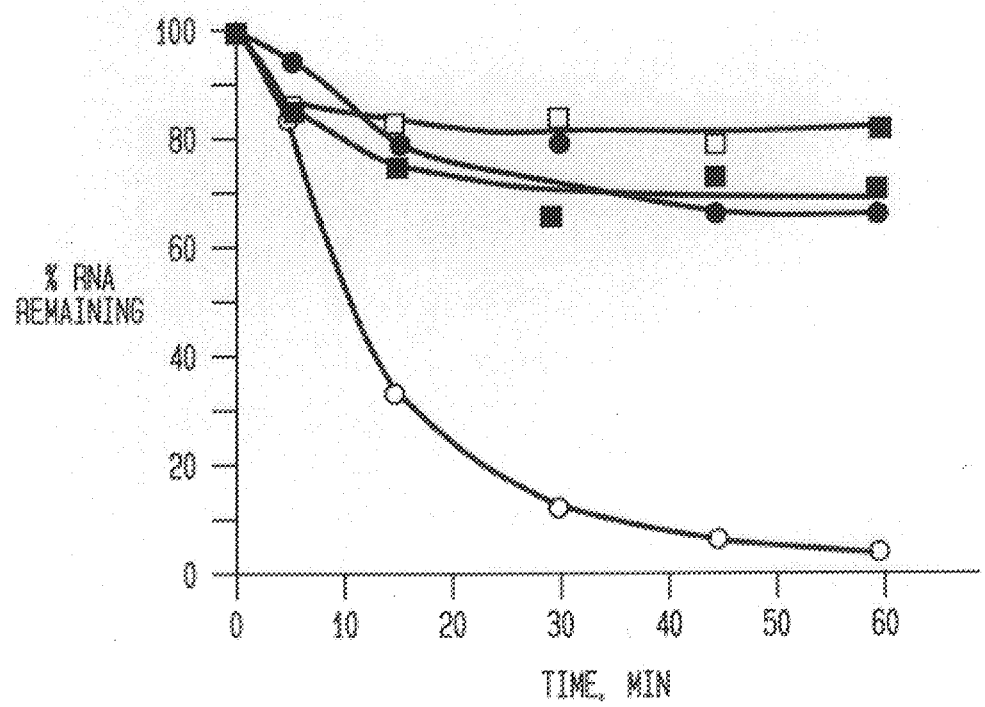

FIGS. 5A and 5B are 2-5A binding properties and ribonuclease activity of recombinant human 2-5A-dependent RNase produced in vitro.

FIG. 5A is specific affinity of recombinant human 2-5A-dependent RNase for 2-5A. Crosslinking of the 2-5A probe (lanes 1–7) to protein is performed after translation reaction in wheat germ extract (5 λl) with human 2-5A-dependent RNase mRNA (lanes 1–3) or without added RNA (lane 4) or in extract of human interferon a treated (1000 units per ml for 16 h) human HeLa cells (350 μg of protein) (lanes 5–7). Reactions were without added competitor (lanes 1, 4, and 5) or in the presence of either timer core, (A2'p)$_2$A, (100 nM) (lanes 2 and 6) or timer 2-5A, p$_3$(A2'p)$_2$A (100 nM) (lanes 3 and 7). Incubations with $^{35}$S-methionine are shown in lanes 8 to 12. Lane 8 is with wheat germ extract and human 2-5A-dependent RNase mRNA. Reticulocyte lysate preadsorbed to 2-5A-cellulose is incubated with human 2-5A-dependent RNase mRNA in the absence (lane 9) or presence (lane 10) of cycloheximide, or in the absence of added mRNA (lane 11). Lane 12 shows human 2-5A-dependent RNase which is produced in the nonadsorbed, crude reticulocyte lysate. The positions and relative molecular masses (in kDa) of the marker proteins are indicated.

FIG. 5B is reticulocyte lysate pretreated to remove endogenous 2-5A-dependent RNase and is incubated in the absence of added mRNA (■), in the presence of human 2-5A-dependent RNase mRNA without inhibitor (○, □) or in the presence of both 2-5A-dependent RNase mRNA and cycloheximide (50 μg per ml (●). See Example I. Subsequently, the recombinant 2-5A-dependent RNase (or controls) is adsorbed to 2-5A-cellulose and ribonuclease assays are performed after extensive washing of the matrix to reduce general nuclease activity. Radiolabeled substrate RNA was either poly(U) (○, ●, ■) or poly(C) (□).

Figure 6A:
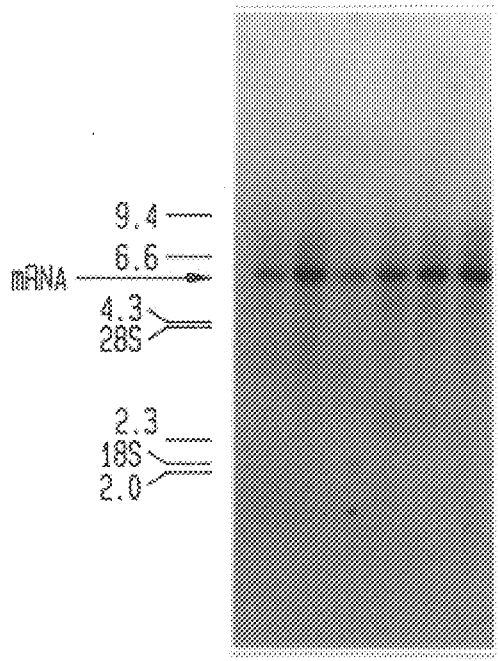
Figure 6B:
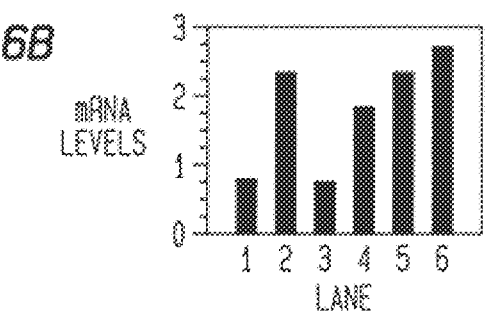
Figure 6C:
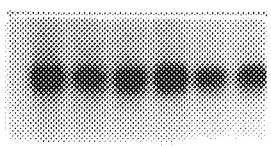

FIGS. 6A, 6B and 6C show levels of 2-5A-dependent RNase mRNA which are induced by interferon treatment of murine L929 cells even in the presence of cycloheximide.

FIG. 6A is a northern blot prepared with poly(A)$^+$RNA (4 μg per lane) that is isolated from murine L929 cells treated with murine interferon (α+) (1000 units per ml) and/or cycloheximide (50 μg per ml) for different durations (indicated) which is probed with radiolabeled murine 2-5A-dependent RNase cDNA. Interferon, IFN; cycloheximide, CHI.

FIG. 6B shows levels of 2-5A-dependent RNase which are estimated from the autoradiogram shown in panel (a) with a video camera and QuickCapture and Image computer programs.

FIG. 6C shows levels of glyceraldehyde-3-phosphate dehydrogenase (GAPDH) mRNA as determined in the same blot shown in panel (A).

Figure 7B:
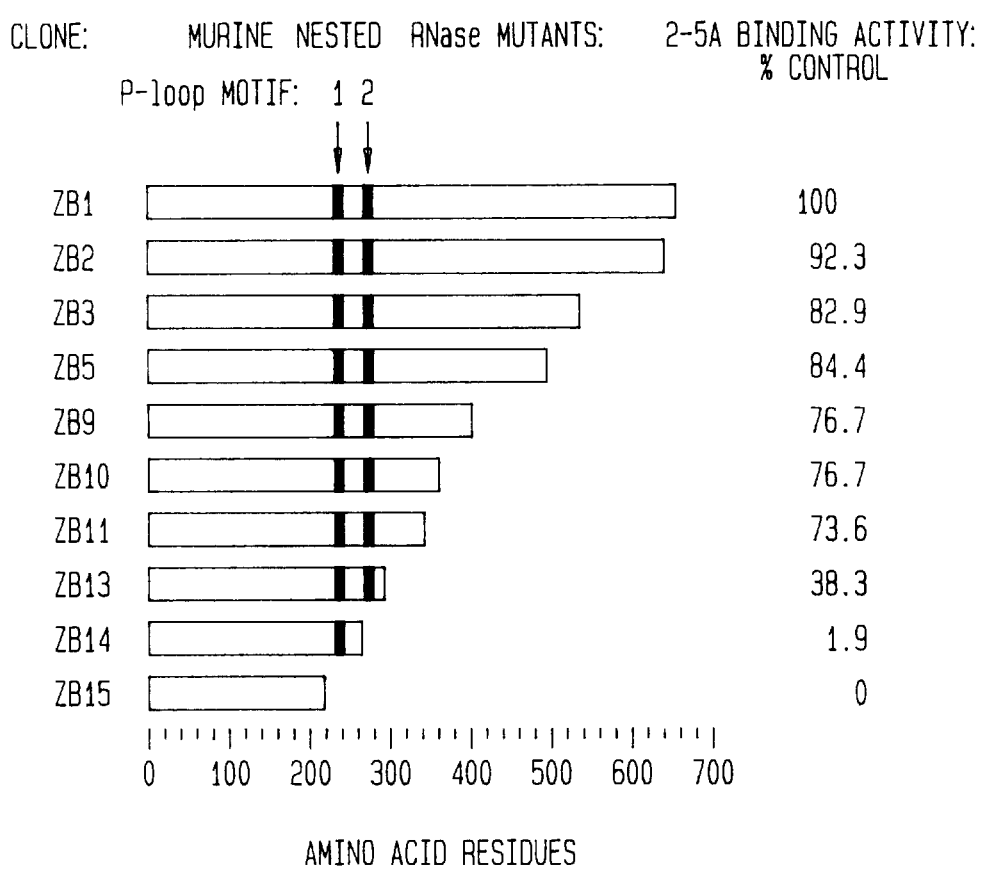

FIGS. 7A and 7B are the truncated, recombinant murine 2-5A-dependent RNase, clone ZB1, and murine L cell 2-5A-dependent RNase having identical 2-5A binding activities localized to a repeated P-loop motif.

FIG. 7A shows incubations of truncated 2-5A-dependent RNase, clone ZB1, ("Recombinant") which is produced in wheat germ extract (upper panel) or of murine L cell 2-5A-dependent RNase (labeled "Naturally Occurring," lower panel) with the $^{32}$P-2-5A probe, (2.4 nM), are in the absence of presence of unlabeled 2',5'-phosphodiester linked oligonucleotides (as indicated) followed by uv covalent crosslinking. Autoradiograms of the dried SDS/10% polyacrylamide gels are shown. Concentrations of the oligonucleotide competitors are indicated. It is inosine.

FIG. 7B shows a truncated series of murine 2-5A-dependent RNase mutants (ZB1 to ZB15) which is produced in wheat germ extract which are assayed for 2-5A binding activity by a filter binding method. See Example and Knight et al. 1980). The positions of the P-loop motifs and the lengths of the translation products are indicated. Clone ZB1 encodes for amino acids designated as 1–656 in Table 2, except for the last 5 amino acid residues which are Lys, Pro, Leu, Ser, and Gly. Clone ZB2 encodes for amino acids designated as 1–619 in Table 2. Clone ZB3 encodes for amino acids designated as 1–515 in Table 2. Clone ZB5 encodes for amino acids designated as 1–474 in Table 2. Clone ZB9 encodes for amino acids designated as 1–403 in Table 2. Clone ZB10 encodes for amino acids designated as 1–365 in Table 2. Clone ZB13 encodes for amino acids designated as 1–294 in Table 2. Clone ZB14 encodes for amino acids designated as 1265 in Table 2. Clone ZB15 encodes for amino acids designated as 1–218 in Table 2.

Figure 8A:
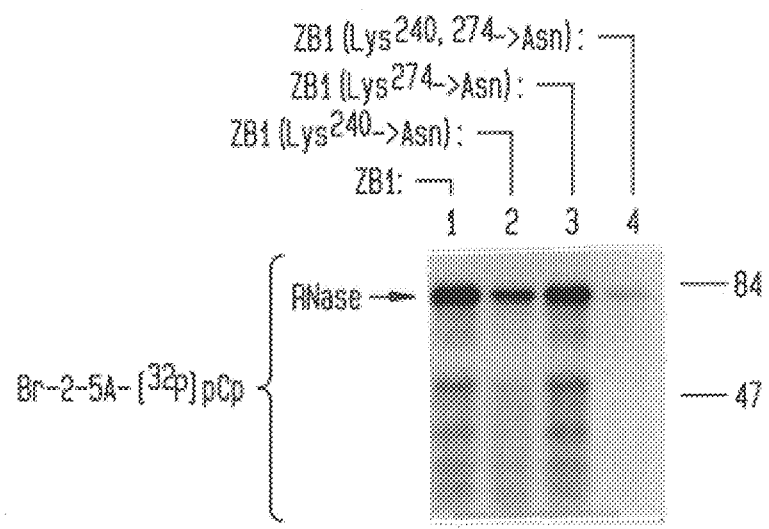
Figure 8B:
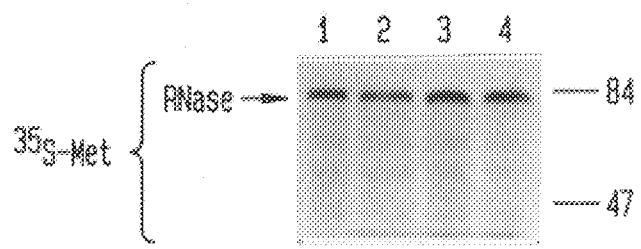

FIGS. 8A and 8B are substitution mutations of the lysine residues in the P-loop motifs of 2-5A-dependent RNase.

FIG. 8A shows the truncated murine 2-5A-dependent RNase, clone ZB1, and lysine to asparagine substitution mutants of clone ZB1, which are synthesized in wheat germ extract. In (A) unlabeled translation products are covalently crosslinked to the bromine-substituted, $^{32}$P-labeled 2-5A probe, Br-2-5A-[$^{32}$P]pCp. See Nolan-Sordan et al., 1990.

FIG. 8B shows the mRNA species which are translated in the presence of $^{35}$-S-methionine in separate reactions. Autoradiograms of the dried, SDS/polyacrylamide gels are shown. The order and positions of the translation products (labelled ("RNase") and the relative molecular masses (in kDa) of the protein markers are indicated.

Figures 9A, 9B:
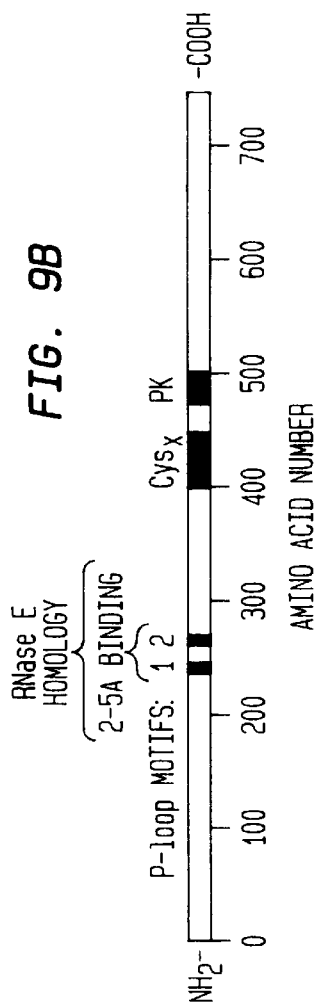

FIGS. 9A and 9B are a comparison of the amino acid sequences of RNase E ad 2-5A-dependent RNase.

FIG. 9A shows identical and conservative matches which are shown between E. coli RNase E and the murine and human forms of 2DR.

FIG. 9B is a model for the structure and function of 2DR. Abbreviations: P-loop motifs, a repeated sequence with homology to P-loops; Cys$_x$, a cysteine-rich region with homology to certain zinc fingers; PK, homology to protein kinase domains VI and VII.

FIGS. 10A and 10B are a comparison of the amino acid sequences of the ankyrin repeats in the human and murine 2-5A-dependent RNase proteins.

FIG. 10A shows murine and human forms of 2-5A-dependent RNases containing four ankyrin repeats. Homology between the ankyrin consensus sequence and the murine and human forms of 2-5A-dependent RNase are indicated. ψ, hydrophobic amino acids.

FIG. 10B is a model showing the relative positions of the four ankyrin repeats in 2-5A-dependent RNase in comparison to the position of the proposed 2-5A binding domain (↑) (the repeated P-loop motif); Cys$_x$, the cysteine-rich region; PK, the protein kinase homology region, and the carboxyterminal region required for RNase activity.

Figure 11:
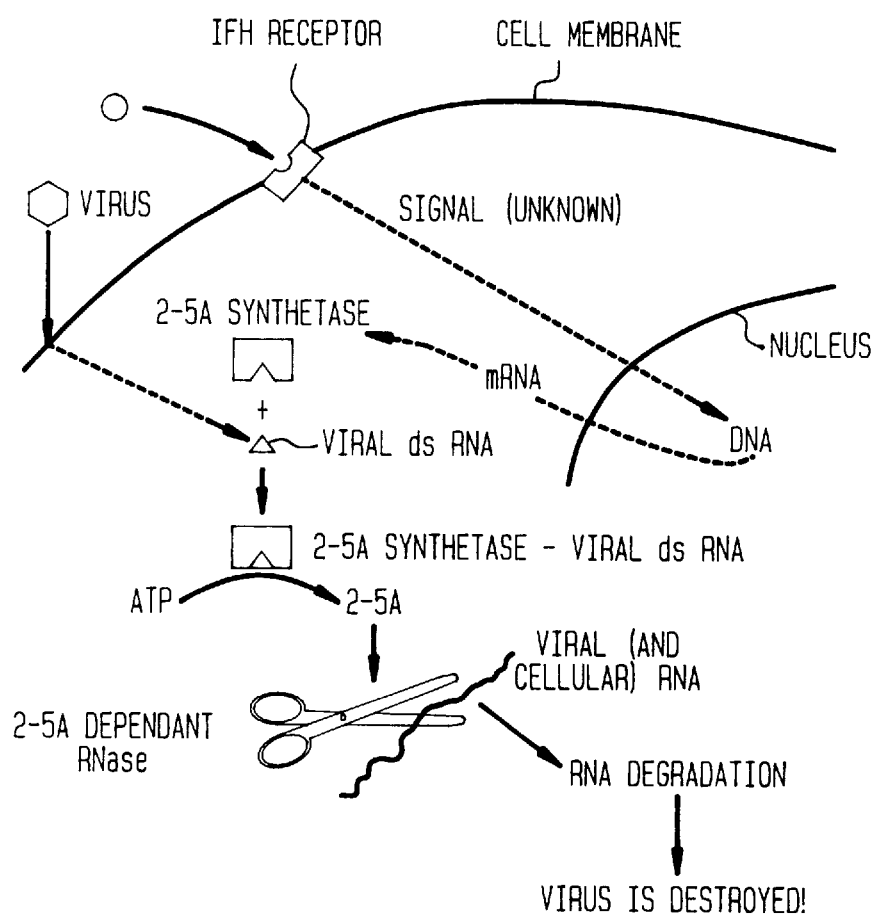

FIG. 11 shows the role of 2-5A-dependent RNase in the anti-viral response of cells to interferon treatment. Interferon binds to specific cell surface receptors resulting in the generation of a signal which activates a set of genes in the cell nucleus. The genes for 2-5A synthetase are thus activated producing inactive, native 2-5A synthetase. Interferon treatment of the cell also activates the 2-5A-dependent RNase gene (not shown in the FIGS.) Subsequently, the interferon-treated cells is infected by a virus. The virus produces double stranded RNA (dsRNA) during its replicative cycle. The viral dsRNA then activates the 2-5A synthetase resulting in the production of 2-5A. The 2-5A then activates the 2-5A-dependent RNase to degrade the viral RNA thus destroying the virus itself.

Figure 12:
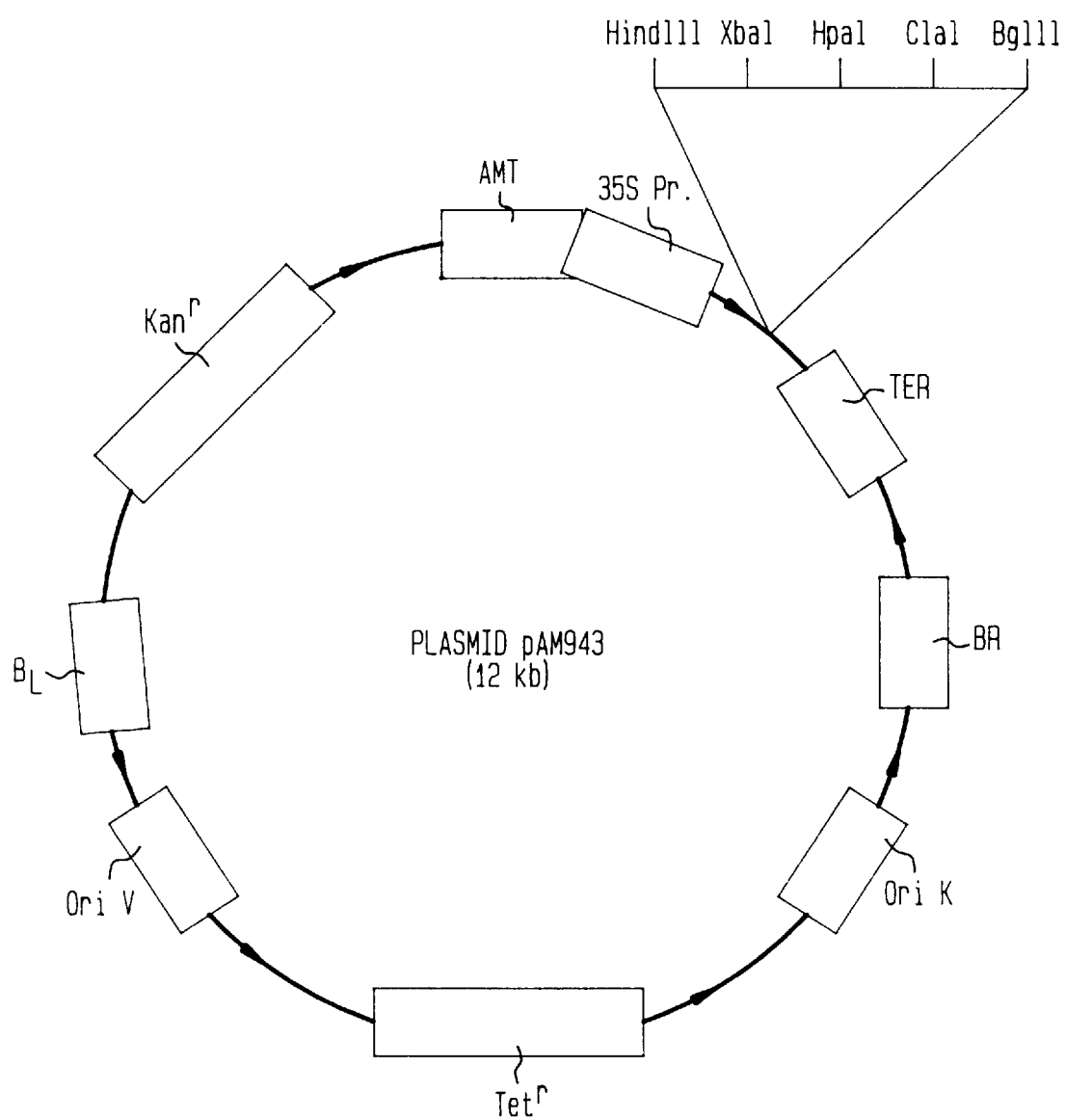

FIG. 12 depicts a physical map of T: based binary vector pAM943 which is about 12 Kbp. Abbreviations: $B_L$, left border; AMT, promotor of adenyl methyl transferase gene from Chlorella virus; 35S, promoter for 35S RNA from Cauliflower mosaic virus; TER, RNA termination signal; Ovi V and Ori K origins of DNA replication.

Figure 13:
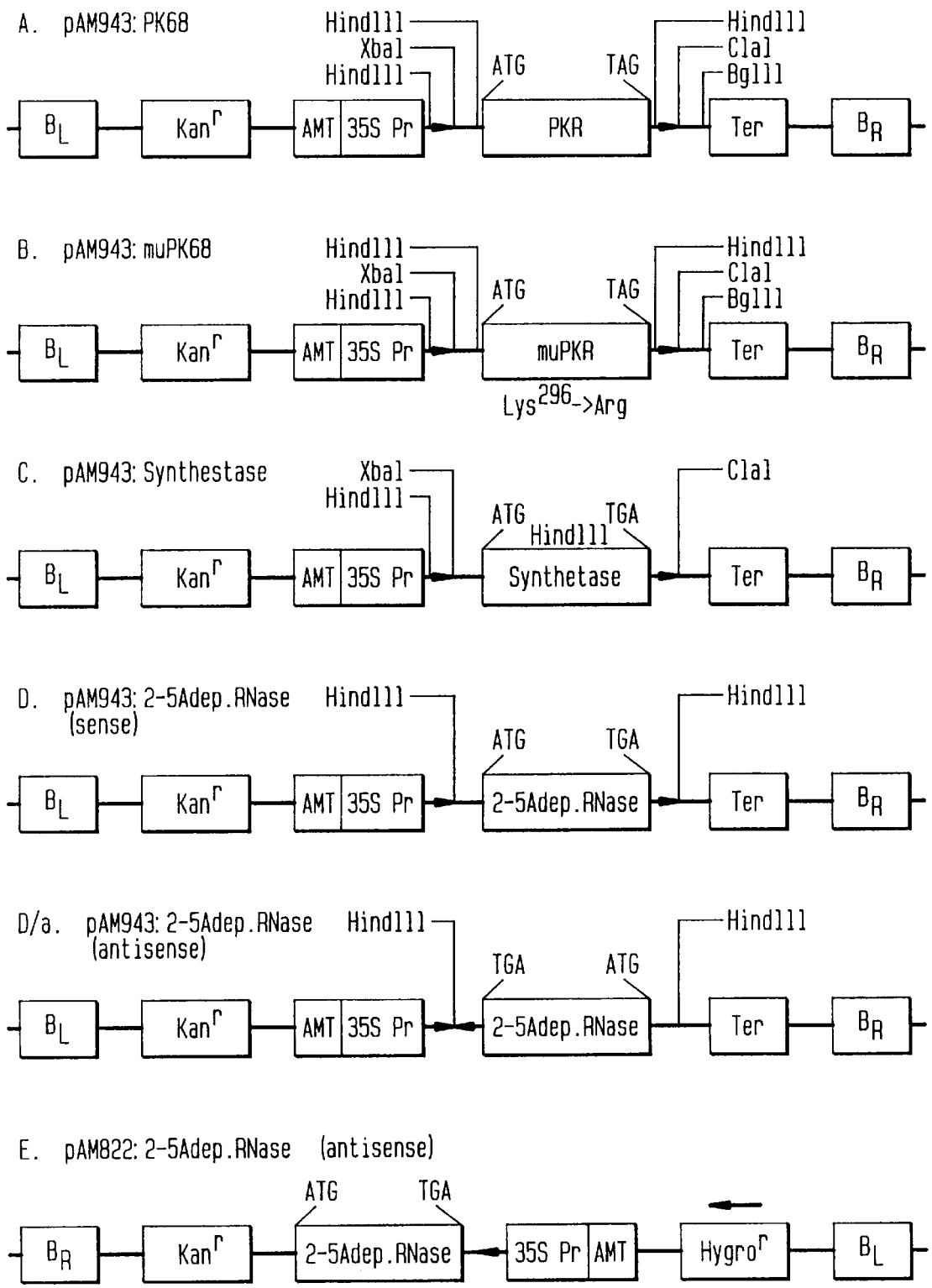

FIG. 13 depicts physical maps of portions of certain recombinant plasmid constructs containing cDNAs encoding mammalian antiviral proteins and showing the important DNA elements in between right border and left border of T-DNAs that re transferred to plant genomes. FIG. 13A depicts a certain portion of plasmid pAM943:PK68; FIG. 13B depicts a certain portion of plasmid pAM943:muPK68; FIG. 13C depicts a certain portion of plasmid pAM943:Synthetase; FIG. 13D depicts a certain portion of plasmid pAM943:2-5A-dep. RNase (sense); FIG. 13D/a depicts a certain portion of plasmid pAM943:2-5A-dep. RNase and FIG. 13E depicts pAM822:2-5A dep. RNase (antisense). Abbreviations: $B_L$, left border; $B_R$, right border; Kan$^r$, kanamycin resistance; Hygro$^r$, hygromycin resistance; AMT, promoter of adenyl methyl transferase gene from Chlorella virus; 35S, promoter for 35S RNA from Cauliflower mosaic virus; PKR, cDNA to human PKR; muPKR, cDNA to a lysine (amino acid #296) to arginine mutant form of PKR; Synthetase, cDNA to human PKR; muPKR, cDNA to a lysine (amino acid #296) to arginine mutant form of PKR; Synthetase, cDNA to a lower molecular weight form of human 2-5A-synthetase; 2-5Adep. RNase, cDNA to human 2-5A-dependent RNase; TER, RNA termination signal.

Figure 14:
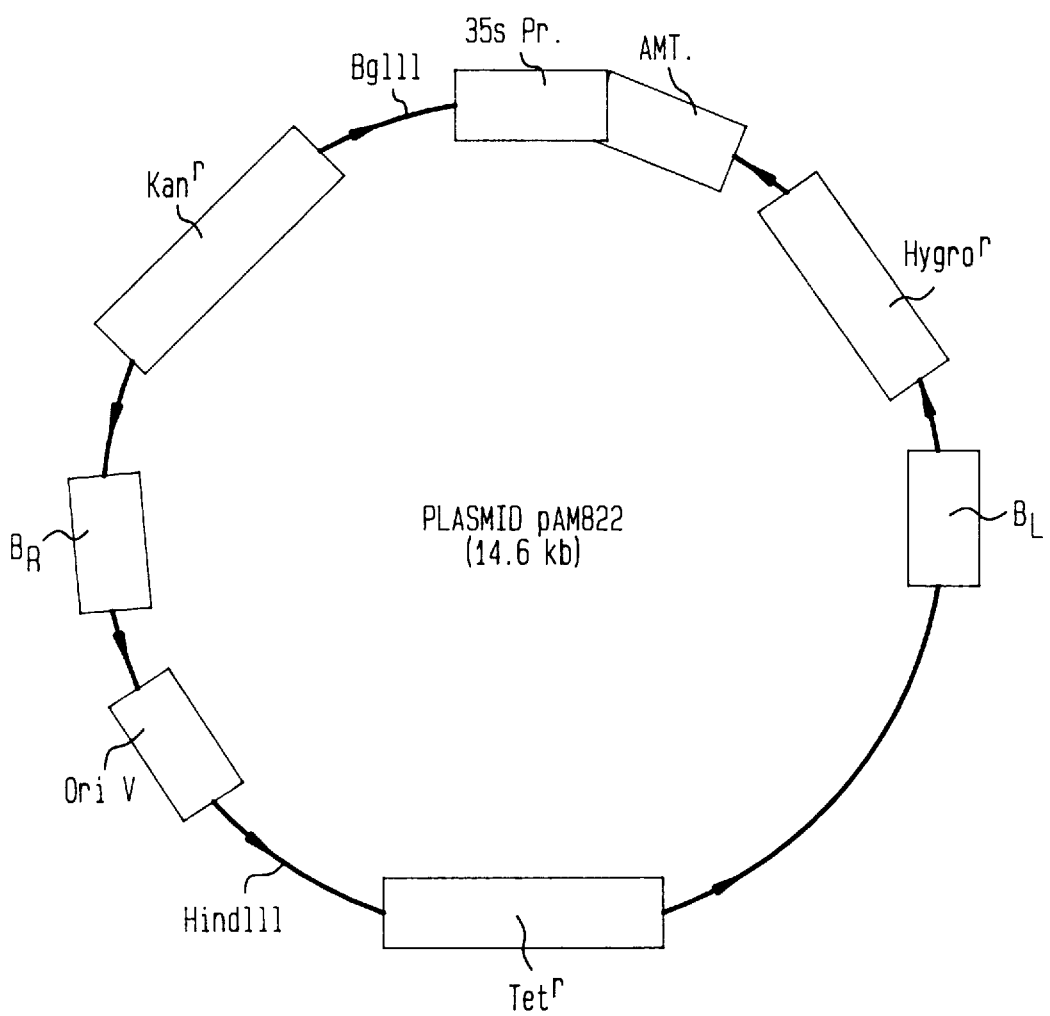

FIG. 14 shows a physical map of Ti based binary vector pAM822 which is about 14.6 Kbp. Abbreviations: $B_L$, left border; $B_R$, right border, Kan$^r$, kanamycin resistance; Hygro$^r$, hygromycin resistance; Tet$^r$, tetracycline resistance; AMT, promoter of adenyl methyl transferase gene from Chlorella virus; 35S, promoter for 35S RNA from Cauliflower mosaic virus; TER, RNA termination signal; Ovi V, origin of DNA replication.

Figure 15:

FIG. 15 shows expression of human 2-5A-synthetase DNA cDNA intransgenic tobacco plants as determined by measuring mRNA levels in a Northern blot. Construct C (pAM943:Synthetase) was introduced into the plants. Total RNA was prepared from the leaves of control (labeled "C") and transgenic plants using RNASTAT-60 (Tel-Test B., Inc.). Thirty $\mu$g of RNA was treated with glyoxal and separated in a 1.5% agarose gel. After electrophoresis RNA was transferred to Magnagraph (MSI) Nylon membrane and probed with human 2-5A-synthetase cDNA labeled with [$\alpha$-$^{32}$P]dCTP by random priming. Autoradiograms were made from the dried blots.

Figure 16:
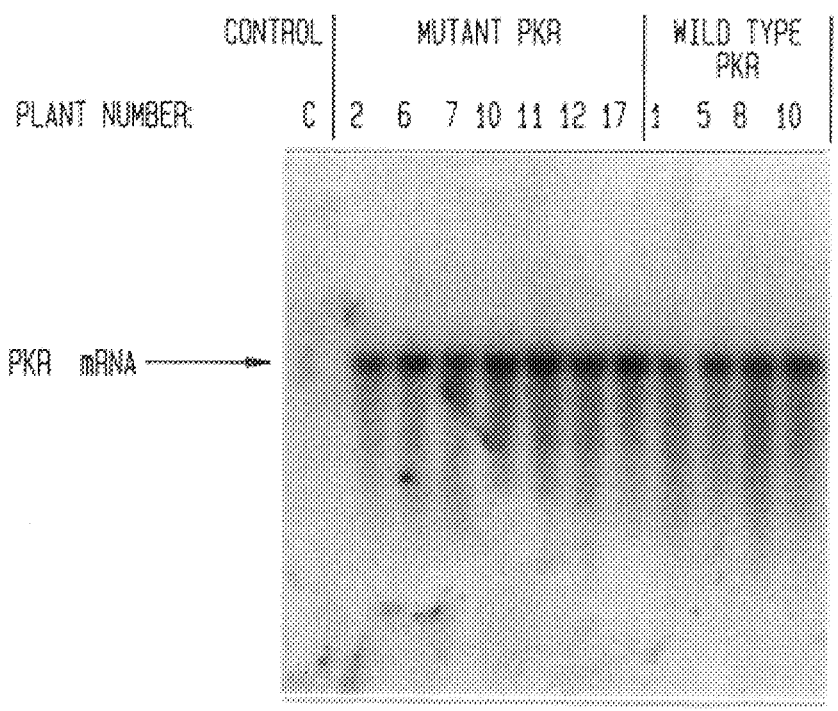

FIG. 16 shows expression of mutant and wild type forms of human PKR cDNA in transgenic tobacco plants as determined by measuring mRNA levels in a Northern blot. Constructs A (pAM943:PK68) and B (pAM943:muPK68) encoding wild type and mutant (lysine at position 296 to arginine) forms of PKR, respectively, were introduced into the plants. Total RNA was prepared from the leaves of control (labeled "C") and transgenic plants using RNASTAT-60 (Tel-Test B., Inc. Thirty $\mu$g of RNA was treated with glyoxal and separated in a 1.5% agarose gel. After electrophoresis RNA was transferred to Magnagraph (MSI) Nylon membrane and probed with human PKR cDNA labeled with [$\alpha$-$^{32}$P]dCTP by random priming. Autoradiograms were made from the dried blots.

Figure 17:
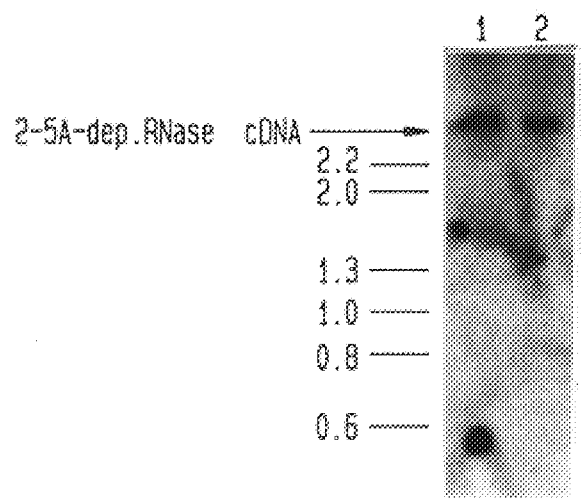

FIG. 17 shows a presence of 2-5A-dependent RNase cDNA in transgenic plants as determined on a Southern blot. Genomic DNA was isolated from leaves of transgenic plants containing construct D/a (pAM943:2-5A-dep.RNase, antisense) using CTAB (cetyltrimethylammonium bromide) following the method of Rogers and Bendich (1988, Plant Molecular Biology Manual, A6, pp. 1–10, Kluwar Academic Publisher, Dordrecht). Ten $\mu$g of genomic DNA was digested with HindIII for 5 h at 37° C. and fractionated in a 1% agarose gel followed by transfer to Magnagraph (nylon transfer membrane, Micron Separations, Inc.) using a capillary transfer method. The cDNA for 2-5A-dependent RNase (from plasmid pZC5) was labeled by random priming with [$\alpha$-$^{32}$P]dCTP (3,000 Ci/mmole) using a Prime-a-gene kit from (Promega) according to the protocol supplied by the company. The labeled 2-5A-dependent RNase cDNA (Specific activity of $1.0 \times 10^{9-}$ c.p.m. per $\mu$g DNA) was washed and an autoradiogram was made from the dried membrane. The sizes (in kilobases) and the positions of the DNA markers are indicated. The band indicated as "2-5A-dep. RNase cDNA" (see arrow) was absent in Southern blots of control plants (data not shown).

FIG. 18 depicts a cDNA coding sequence for human p68 kinase mRNA (PKR).

FIG. 19 depicts a translation product of the complete coding sequence for human p68 kinase mRNA (PKR) of FIG. 18.

FIGS. 20A and 20B depict a coding sequence for human 2-5A synthetase cDNA.

FIG. 21 depicts a translation product of the coding sequence for human 2-5A-synthetase of FIGS. 20A and 20B.

Figure 22A:
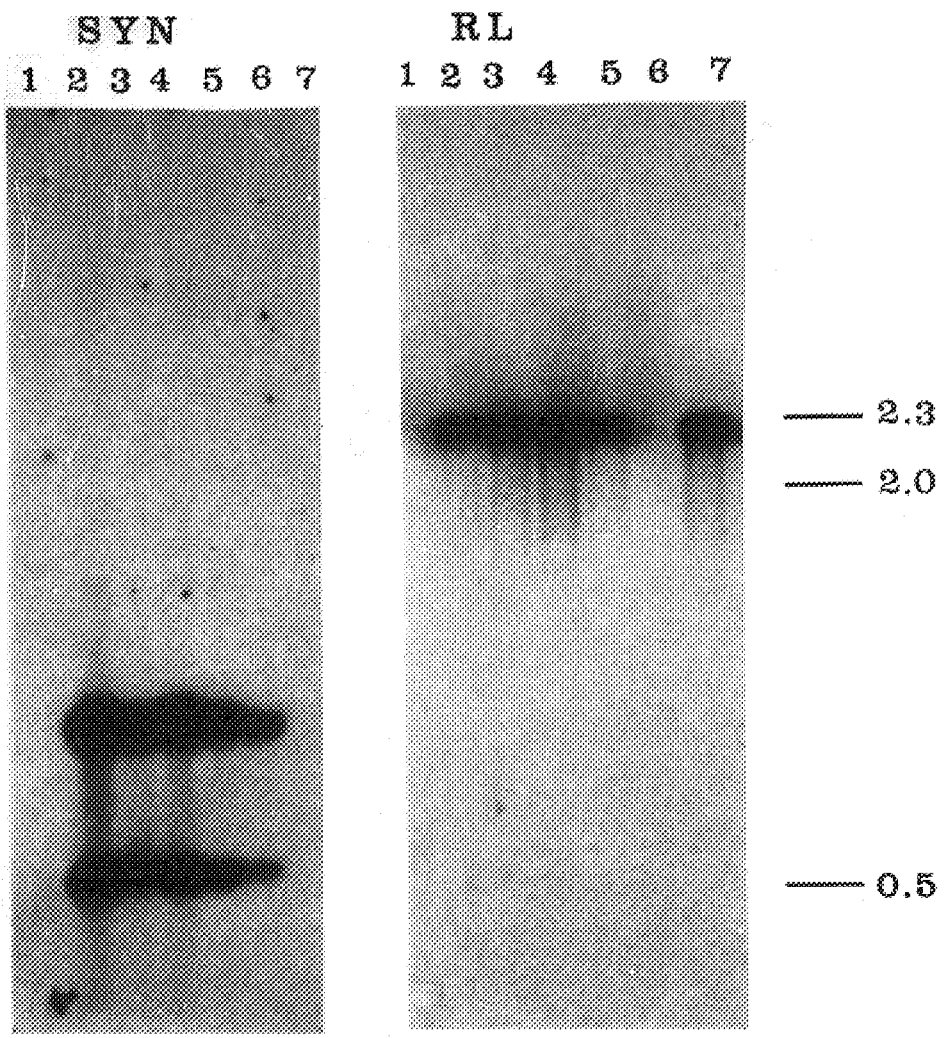
Figure 22B:
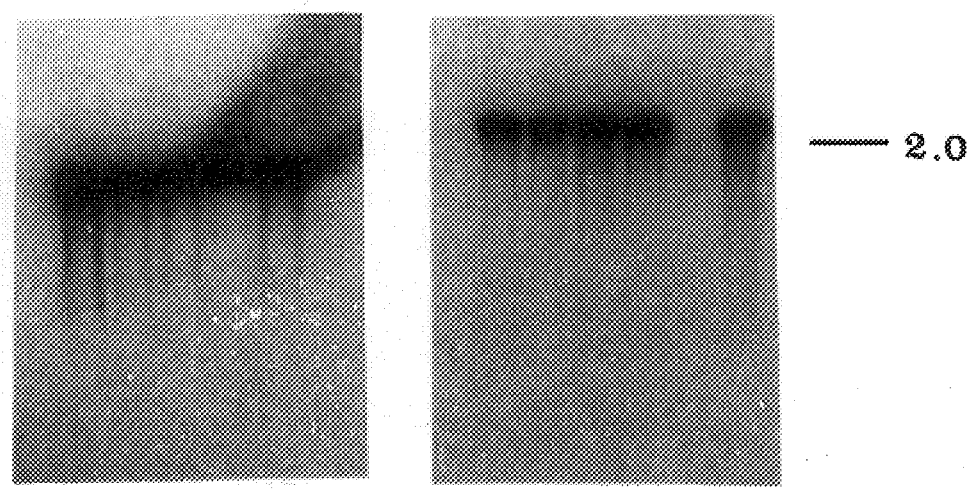
Figure 22C:
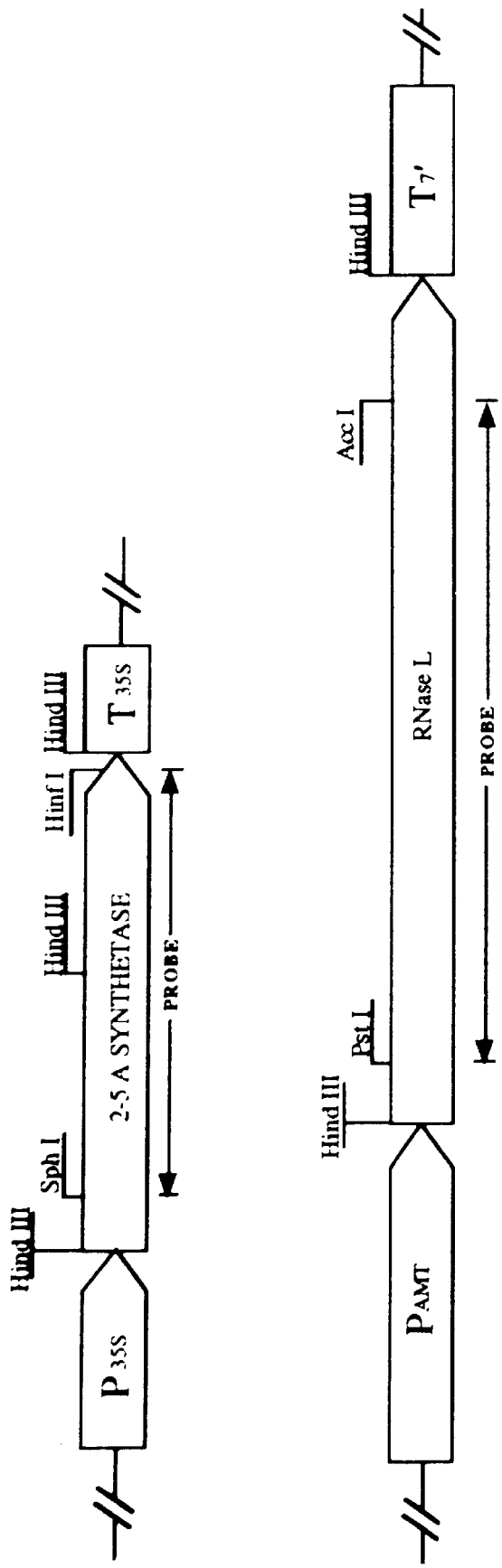

FIGS. 22A, 22B and 22C. Verification of transgenic tobacco plants. 22A is Southern blot of transgenic plants. Total genomic DNA is digested with Hind III, is electrophoresed on 1% agarose gel, is transferred to a membrane and hybridized with $^{32}$P-labeled random primed fragments generated from the 2-5A synthetase or RNase L cDNAs. Numbers at right are size markers in kbp. 22B is a Northern blot analysis of the transgenic plants. Total cellular RNA is isolated and is electrophoresed on a 1% formaldehyde gel, is transferred to a membrane and is hybridized with the same probe as in 22A. Lane 1, control tobacco plant; Lanes 2–5 transgenic plants expressing both 2-5A synthetase and RNase L; Lane 6, transgenic plant expressing 2-5A synthetase only; Lane 7, transgenic plant expressing RNase L only. SYN 2-5A synthetase; RL, RNase L. 22C is A partial map of the expression plasmid is shown.

Figure 23:
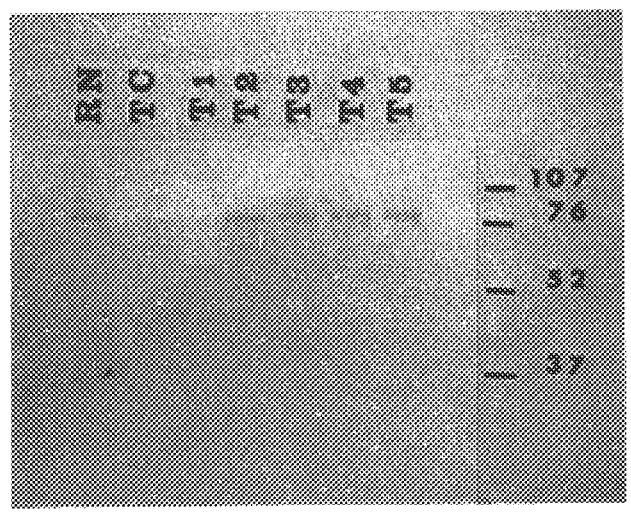

FIG. 23. Immunodetection of RNase L protein in transgenic plants. Total protein extracts from the transgenic plants are fractionated by SDS/PAGE and blotted onto a nitrocellulose membrane and probed with a monoclonal antibody reagent to recombinant human RNase L protein, which are expressed in and isolated from insect cells. Dong, B. et al.: *J. Biol. Chem.*, 269:14153 (1994). Numbers at the right are protein size markers in kDa. RN human RNase L protein (200 ng); TC, protein extract from control tobacco plant; T1–T5, protein extracts from transgenic tobacco plants; T1, transgenic plants expressing 2-5A synthetase only, T2, transgenic plant expressing RNase L only, T3–T5, plants expressing both 2-5A synthetase and RNase L.

Figure 24:
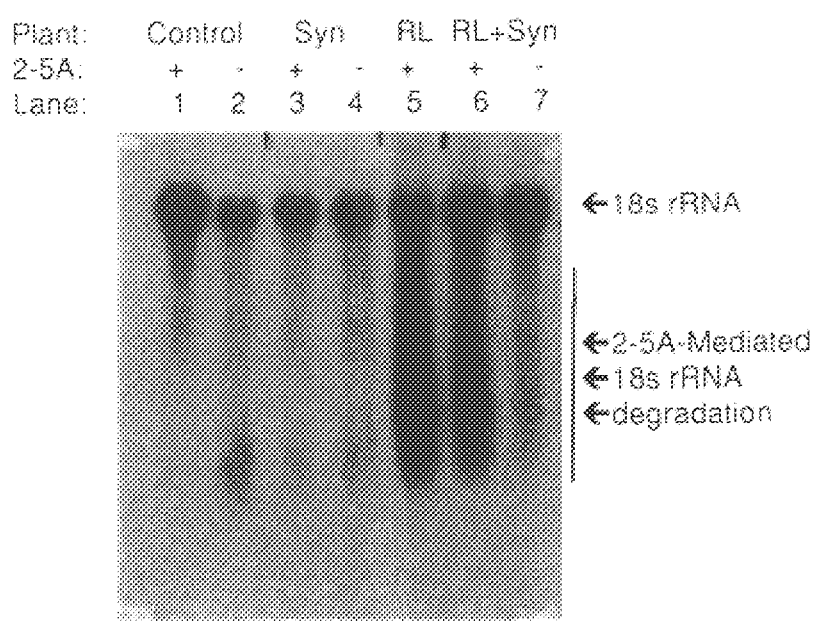

FIG. 24. 2-5A induce degradation of rRNA in transgenic plants expressing RNase L protein. Leaves are injected with about 2.5 μM 2-5A, total RNA is extracted after 3 hr and probed with $^{32}$P-labeled 18S cDNA. Lanes 1–2, control plant, lanes 3 and 4, plant expressing only 2-5A synthetase (Syn); lane 5, plant expressing only RNase L (RL); lanes 6–7, plants expressing both 2-5A synthetase and RNase L (Syn+RL).

Figure 25:
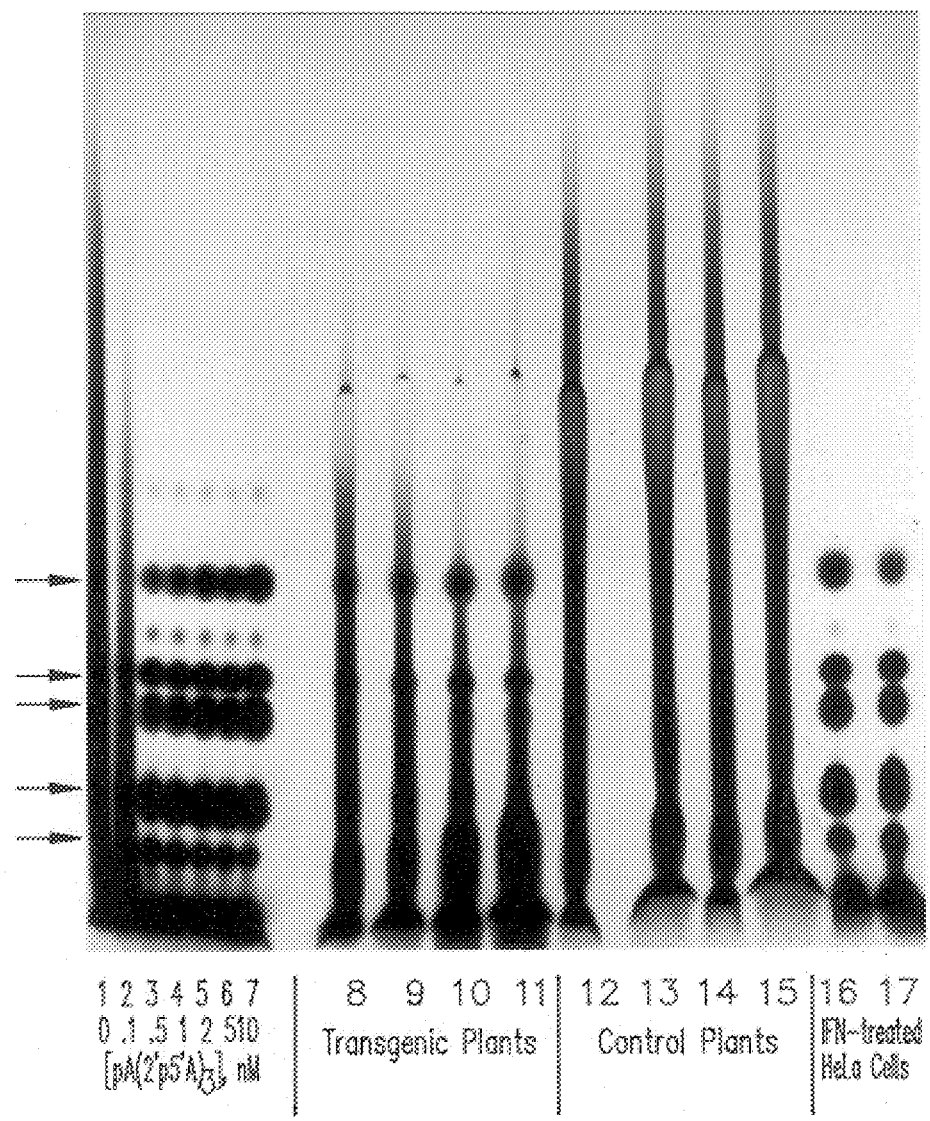

FIG. 25. Transgenic plants produce functional, human recombinant 2-5A synthetase. Extracts of plants containing cDNA to both human RNase L and 2-5A synthetase (lanes 8–11), of control plants that are transformed with vector alone (lanes 12–15), and of interferon treated human HeLa cells (lanes 16 and 17) are assayed for 2-5A synthetase activity. 2-5A synthetase activity in extracts of transgenic plants is determined by a functional assay for 2-5A. Plants extracts are prepared by homogenizing leaves in NP40 lysis buffer containing: about 0.5% (v/v) Non-idet P-40, about 90 mM KCI, about 5 mM magnesium acetate, about 20 mM Tris-HCI, pH about 7.5, about 5 mM 2-mercaptoethanol, and about 10 μg per ml leupeptin. The total cell lysates are centrifuged at about 10,000×g for about 10 min at about 4° C., the supernatants are collected and the protein concentration is determined as described in Bradford, M. et al.: *Anal. Biochem.*, 72:248 (1976). Extracts of interferon-treated (about 200 units per ml human interferon alpha for about 18 hr) human HeLa cells is prepared by the same method, except cells are disrupted by vortex mixing. 2-5A synthetase assays are performed by incubating about 200 μg (protein) extract per assay adjusted to about 65 μls with NP40 lysis buffer, with about 65 μl (per assay) of about 20 mM Tris-HCI, pH about 7.5, about 50 mM KCI, about 5 mM magnesium acetate, about 4 mM magnesium chloride, about 5 mM 2-mercaptoethanol, about 10% (v/v) glycerol. About 2 mM ATP, about 20 μg per ml poly (I): poly (C) for about 24 hr at about 30° C. Reactions are terminated, and proteins are denatured and removed, by heating reaction mixtures to about 100° C. for about 5 min followed by centrifugation at about 10,000×g for about 10 min. Supernatants are removed and concentrated in a speed-vac (Savant) to about 20 μl. 2-5A is then assayed by a 2-5A dependent ribonuclease L assay. Concentrated supernatants (about 5 and about 10 μl per plant), or dilutions of authentic 2-5A (pA(2'p5'A)$_3$), are incubated in a final volume of about 25 μl with about 1 μg of recombinant human RNase L, Dong, B. et al.: *J. Biol. Chem.*, 269:14153 (1994), in buffer (about 90 mM KCI, about 10 mM magnesium acetate, about 20 mM Tris-HCI, pH about 7.5, about 8 mM 2-mercaptoethanol, and about 10 μg per ml leupeptin) containing about 0.2 mM of poly(U)-($^{32}$P)-pCp prepared, as described in Silverman, R. H. et al.: *Anal. Biochem.*, 144:450 (1985) and incubated at about 30° C. for about 2 hr. Reactions are terminated with about 7.5 μl stop buffer, boiled for about 5 min, centrifuged briefly, and about 3 μl is loaded to 6% polyacrylamide/urea gels. After electrophoresis, X-ray film is exposed to the gel. 2-5A is monitored by its ability to activate RNase L, which are expressed and isolated from insect cells, Dong, B. et al.: *J. Biol. Chem.*, 269:14153 (1994), to cleave poly (U) to discrete products (arrows). Lanes 1–7 show activation of RNase L by authentic pA(2'p5'A)$_3$. An autoradiogram of the sequencing gel is shown.

Figure 26A:
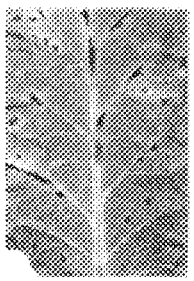
Figure 26B:
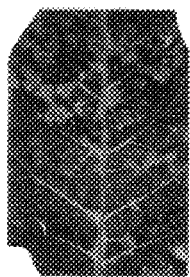
Figure 26C:
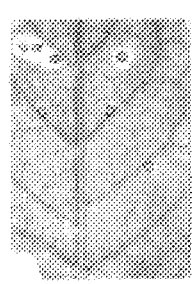
Figure 26D:
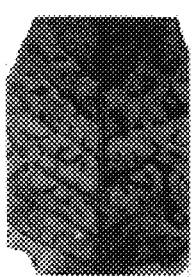
Figure 26E:
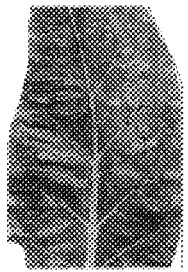
Figure 26F:
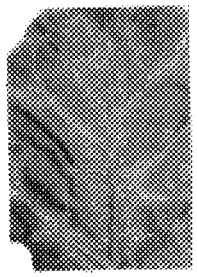
Figure 26G:
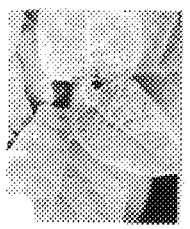
Figure 26H:
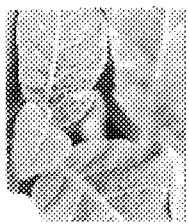

FIGS. 26A–26H. Virus-inoculated leaves showing local lesions. Leaves from transgenic or control plants are mechanically inoculated with either TEV (FIGS. 26A, 26B, 26G and 26H), TMV (FIGS. 26C and 26D), or AIMV (FIGS. 26E and 26F). Transgenic plants are grown in a greenhouse. Leaves from these plants are cut at the petiole and placed in petri dishes on moist filter papers. Leaves that are maintained in petri dishes for the incubation period remain in good physiological condition. The leaves are inoculated with an about 1:200, 1:1000 and 1:150 dilution of freshly prepared extracts from tobacco leaves systemically infected with tobacco etch virus (TEV, severe strain, ATCC#PV69), TMV, common strain), and alfalfa mosaic virus (AIMV, Nebraska strain) respectively. Six of six control plants become systemically infected when inoculated with sap diluted 1:10,000, 1:100,000, and 1:15,000, respectively. Following inoculation with virus, the leaves are rinsed with water, and petri dishes are sealed with stretched parafilm and placed in an incubator at about 22° C. for about 7 days under about 18 hr light. FIGS. 26A, 26C and 26E are plants expressing both 2-5A synthetase and RNase L; FIG. 26G, plant expressing 2-5A synthetase alone; FIG. 26H, plant expressing RNase L alone. Control plants, FIGS. 26B, 26D and 26F are transgenic for the vector-alone construct.

FIG. 27 illustrates (A) southern blot of genomic DNA and (B) northern blot of total RNA of control plants (lanes 1) and two plants that were transgenic for human 2-5A-synthetase probed with human 2-5A synthetase cDNA (lanes 2 and 3).

Figure 28:
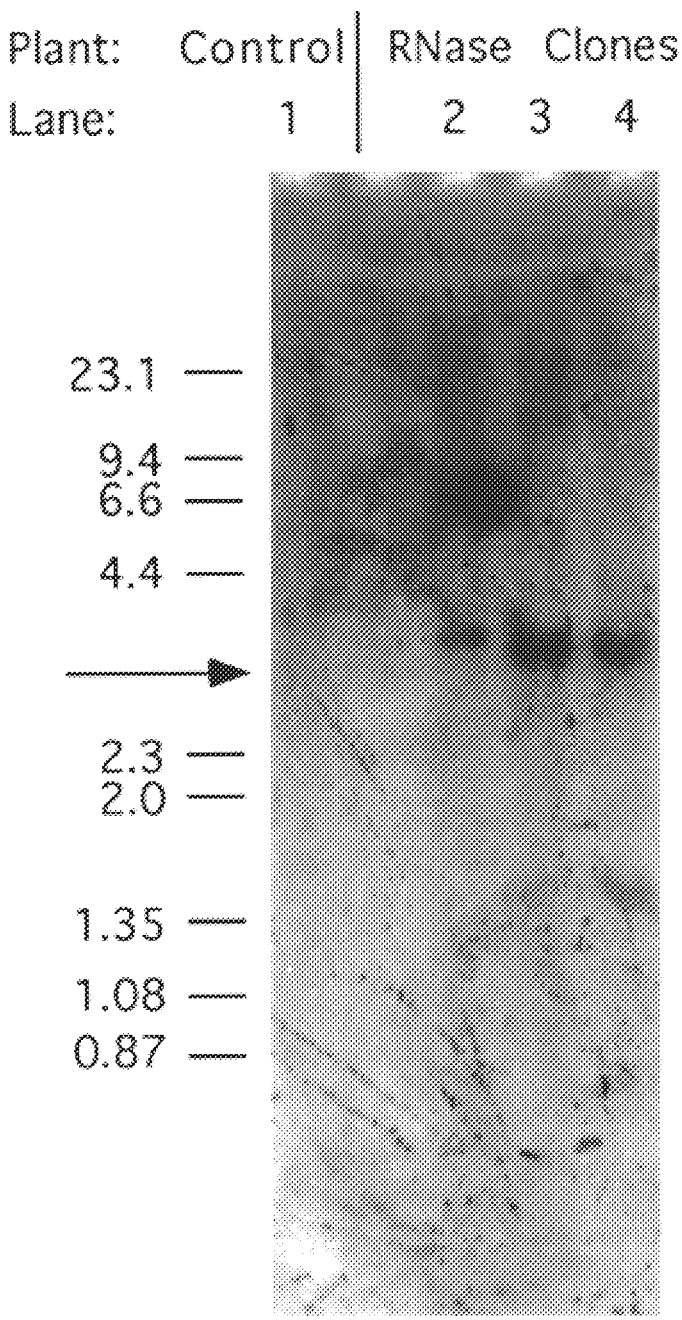

FIG. 28 illustrates southern blot of genomic DNA from control plant (lane 1) and three plants that are transgenic for human RNase L (lanes 2–4) probed with human RNase L cDNA.

Figure 29:
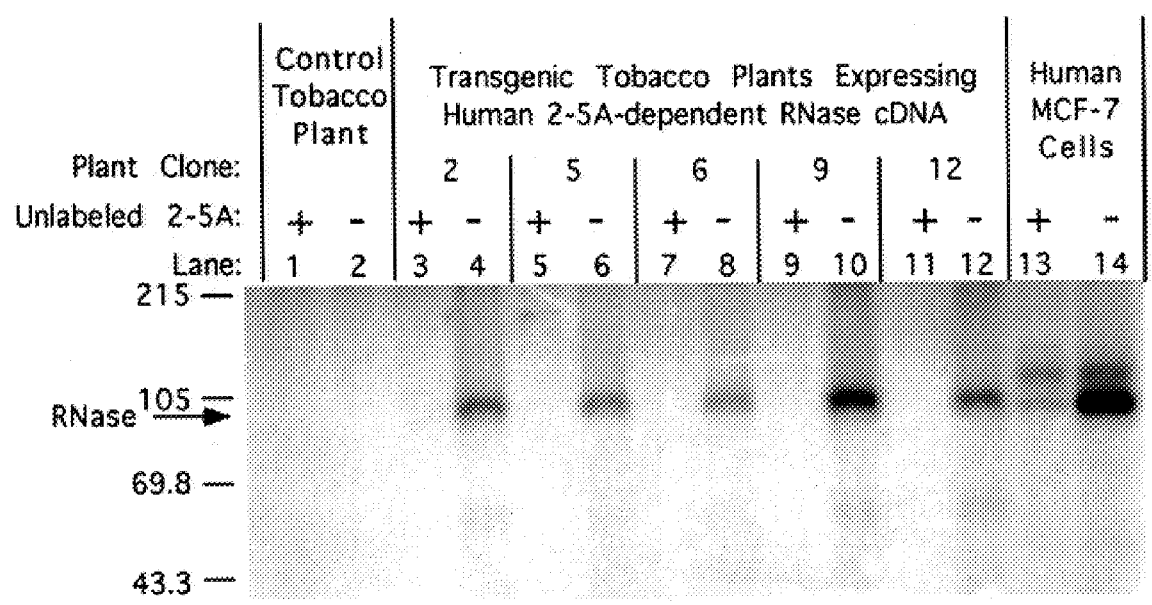

FIG. 29 illustrates detection of RNase L after covalent crosslinking to a $^{32}$P-labeled 2-5A probe. Extracts of control plants (lanes 1 and 2), of plants transgenic for human RNase L cDNA (2-5A-dependent RNase) (lanes 3–12) or of human MCF-7 cells (lanes 13 and 14) is incubated with $^{32}$P-labeled 2-5A probe under ultraviolet light to induce crosslinking with RNase L. Specificity of crosslinking is determined with an excess of unlabeled 2-5A (as indicated). The positions and molecular masses (in kDa) of the protein markers and the position of RNase L (arrow) are indicated on the autoradiogram of the dried SDS/polyacrylamide gel.

Figure 30:
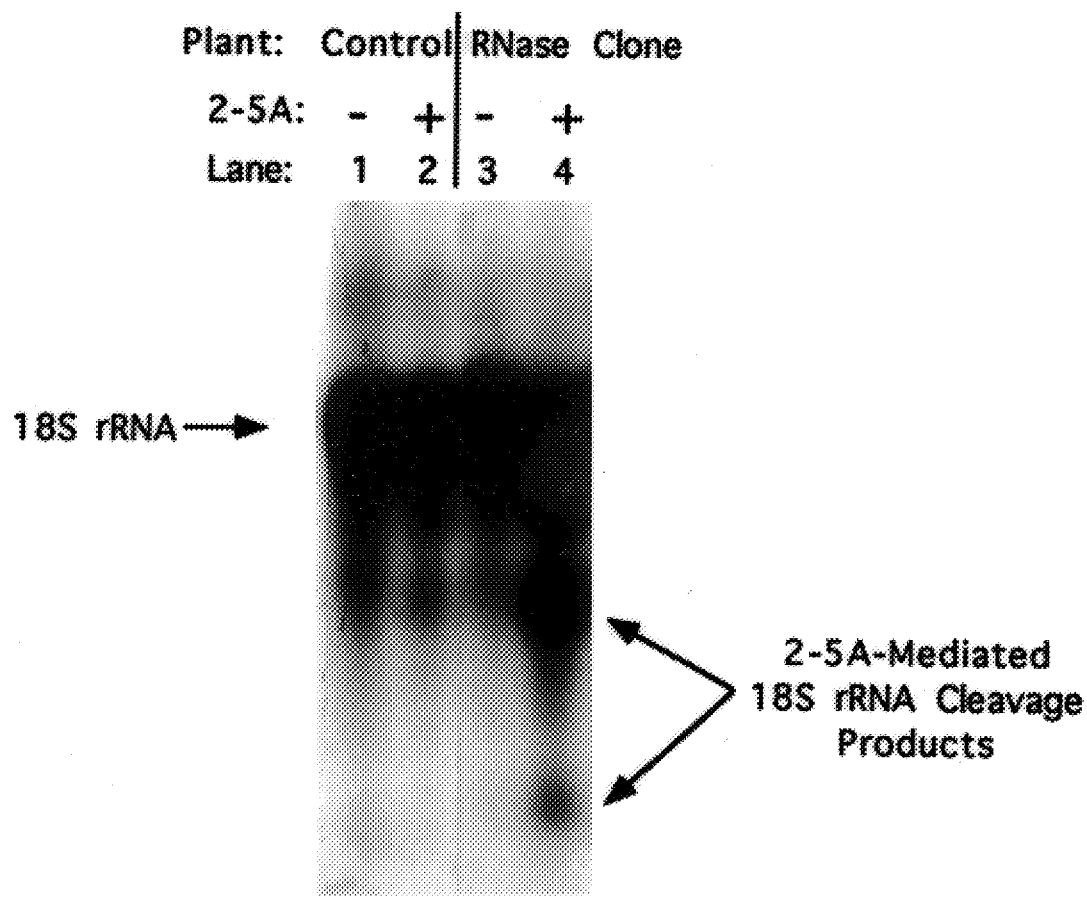

FIG. 30 illustrates that RNase L in cut leaves is activated to cleave rRNA by incubation in a solution containing 2-5A. A northern blot probed with $^{32}$P-labeled cDNA to 18C rRNA is shown. The cut leaves are from a control plant (lanes 1 and 2) or from a plant transgenic for human RNase L cDNA (lanes 3 and 4). The presence or absence of 2-5A and the position of the 2-5A-mediated rRNA cleavage products are shown.

DETAILED DESCRIPTION

By way of illustrating and providing a more complete appreciation of the present invention and many of the attendant advantages thereof, the following Detailed Description and Examples are given concerning the novel 2-5A-dependent RNases, encoding sequences therefor, recombinant nucleotide molecules, constructs, vectors, recombinant nucleotide molecules, antiviral transgenic plants and methods.

Because 2-5A-dependent RNase is very low in abundance (one five-hundred-thousandth of the total protein in mouse liver, Silverman, R. H. et al., *J. Biol. Chem.*, 263:7336–7341 (1988)), its cloning requires the development of a sensitive screening method. Murine L929 cells are selected as the source of mRNA due to high basal levels of 2-5A-dependent RNase. A protocol to enhance 2-5A-dependent RNase mRNA levels is developed based on the observation that optimal induction of 2-5A-dependent RNase is obtained by treating cells with both interferon and cycloheximide, then with medium alone. See Example. The cDNA library is screened by an adaptation of techniques developed for cloning DNA binding proteins, Singh, H. et al., *Cell*, 52:415–423 (1988); Singh H. et al., *BioTechniques*, 7:252–261 (1989), in which a bromine-substituted $^{32}$P-labeled 2-5A analogue ("2-5A probe"), Example and Nolan-Sorden, N. L. et al., *Anal. Biochem.*, 184:298–304 (1990), replaced a radiolabeled oligodeoxyribonucleotide. A single clone (ZB1) is thus isolated from about three million plaques. The protein expressed from the ZB1 clone, transferred from plaques to filter-lifts, shows reactivity to both the 2-5A probe and to a highly purified polyclonal antibody directed against 2-5A-dependent RNase.

To obtain recombinant protein for characterization, the cDNA is transcribed and translated in cell-free systems. See Example. 2-5A binding activity is then determined by covalently crosslinking the 2-5A probe to the protein with uv light, for example, Nolan-Sorden, N.L. et al., *Anal. Biochem.*, 184:298–304 (1990). The recombinant 74 kDa protein produced in a wheat germ extract shows specific affinity for the 2-5A probe. See FIG. 2A, lanes 1 to 3. A core derivative of 2-5A lacking 5'-phosphoryl groups, $(A2'p)_2A$, fails to interfere with binding of the protein to the 2-5A probe whereas trimer 205A, $p_3(A2'p)_2A$, completely prevents probe binding. See FIG. 2A, lanes 2 and 3, respectively.

There is no detectable 2-5A binding proteins in the wheat germ extract as shown in the incubation without added RNA, FIG. 2A, lane 4. For comparison, a similar profile of 2-5A binding activity is obtained for the 80 kDa 2-5A-dependent RNase from murine L929 cells, incubated without added oligonucleotide or with $(A2'p)_2A$ or $p_3(A2'p)_2A$ as competitors. See FIG. 2A, lanes 5 to 7. The $^{35}$S-labeled translation product is shown in FIG. 2A, lane 9. In a further comparison, covalent linkage of the 2-5A probe to the about 74 kDa protein and to murine L929 cell 2-5A-dependent RNase followed by partial digestion with chymotrypsin produces an identical pattern of six labeled peptides. See FIG. 2B. Similarly, partial digestion of the two labeled proteins with S. aureus V8 protease also produces identical patterns of labeled cleavage products. These results and the apparent molecular weight of about 74 kDa for the recombinant protein, as compared to about 80 kDa for 2-5A-dependent RNase, see FIG. 2A, suggests that the about 74 kDa protein is a truncated, or partial clone for 2-5A-dependent RNase.

To obtain the entire coding sequence for human 2-5A-dependent RNase, a composite DNA containing genomic and cDNA is constructed. See FIG. 3A. The initial cDNA portion of the human 2-5A-dependent RNase clone (HZB1) is obtained by screening a human kidney cDNA library with radiolabeled murine 2-5A-dependent RNase cDNA. See Example. A genomic clone, containing the 5'-part of the coding sequence, is isolated with radiolabeled human 2-5A-dependent RNase cDNA. The nucleotide and predicted amino acid sequences of human 2-5A-dependent RNase are determined, FIG. 3B, resulting an open reading frame encoding a protein of 83,539 Da.

A comparison is made between the predicted amino acid sequences of the human and murine forms of 2-5A-dependent RNase in order to identify and evaluate the conserved regions of the proteins. See FIG. 4. The murine cDNA, clone ZB1, contains about 88% of the coding sequence for 2-5A-dependent RNase to which an additional twenty-eight 3'-codons are added from a murine genomic clone. Alignment of the murine and human forms of 2-5A-dependent RNase indicates about 65% identity between the overlapping regions. See FIG. 4. In addition, there is 73% identity between the corresponding nucleotide sequences for murine and human 2-5A-dependent RNase. The apparent translation start codons for both the murine and human 2-5A-dependent RNases, are in an appropriate context for translational initiation, namely ACCATGG and GTCATGG, respectively. See FIG. 3B. See also, for example, Kozak, M., *Cell*, 44:283–292 (1986). In addition, both the human and murine 2-5A-dependent RNase sequences contain in-frame stop codons upstream of the translation start sites. See FIG. 3B.

The 2-5A binding properties of the recombinant and naturally occurring forms of human 2-5A-dependent RNase are compared by uv covalent crosslinking to the 2-5A probe. The recombinant human 2-5A-dependent RNase produces in wheat germ extract shows specific affinity for 2-5A. See FIG. 5A, lanes 1 to 3. Radiolabeling of the cloned human 2-5A-dependent RNase with the 2-5A probe is not prevented by $(A2'p)_2A$. See FIG. 5A, lanes 1 and 2. In contrast, addition of trimer 2-5A, $p_3(A2'p)_2A$, effectively competes with the 2-5A probe for binding to the recombinant 2-5A-dependent RNase. See lane 3. The same pattern of 2-5A binding activity is obtained with 2-5A-dependent RNase in an extract of interferon-treated human HeLa cells. See FIG. 5A, lanes 5 to 7. The apparent molecular weights of HeLa cell 2-5A-dependent RNase and $^{35}$S-labeled recombinant human 2-5A-dependent RNase produced in reticulocyte lysate are believed to be exactly the same (about 80 kDa). See FIG. 5A, lanes 5 and 9. The recombinant human 2-5A-dependent RNase produced in wheat germ extract migrates slightly faster probably due to post-translational modifications. See FIG. 5A, lanes 1, 2 and 8.

To demonstrate and characterize the ribonuclease activity of the cloned 2-5A-dependent RNase, translation is performed in a reticulocyte lysate instead of a wheat germ extract due to the substantially greater efficiency of protein synthesis in the former system. See FIG. 5A, compare lanes 9 and 8. Prior to translation, endogenous reticulocyte 2-5A-dependent RNase is removed by adsorbing the lysate to the affinity matrix, 2-5A-cellulose. See Example. See also, Silverman, R. H., *Anal. Biochem.*, 144:450–460 (1985). The treatment with 2-5A-cellulose effectively removes all measurable endogenous 2-5A-dependent RNase activity from the lysate, as determined by 2-5A-dependent ribonuclease assays, and FIG. 5B. In addition, the adsorption-depletion protocol did not reduce translational efficiency. FIG. 5A, lanes 9 and 12 show the $^{35}$S-translation products produced in the 2-5A-cellulose-pretreated and untreated lysates, respectively.

Ribonuclease assays with recombinant 2-5A-dependent RNase are performed after immobilizing and purifying the translation product on the activating affinity matrix, 2-5A-cellulose. It was previously shown that murine L cell 2-5A-dependent RNase bound to 2-5A-cellulose, resulting in ribonuclease activity against poly(U) but not poly(C). See Silverman, R. H., *Anal. Biochem.*, 144:450–460 (1985). Furthermore, by washing 2-5A-dependent RNase:2-5A-cellulose prior to adding the substrate the level of general, non-2-5A-dependent RNase, is greatly reduced. See Silverman, R. H., *Anal. Biochem.*, 144:450–460 (1985). Incubations of lysate in the absence of added mRNA or in the presence of both human 2-5A-dependent RNase mRNA and cycloheximide resulted in only low levels of poly(U) breakdown. See FIG. 5B. In addition, it is shown that cycloheximide completely prevented 2-5A-dependent RNase synthesis. See FIG. 5A, lane 10. In contrast, translation of the human 2-5A-dependent RNase MRNA, in the absence of inhibitor, results in substantial ribonuclease activity against poly(U) but not against poly(C).

See FIG. 5B. The poly(U) is degraded with a half-life of about 10 minutes whereas only 20% of the poly(C) is degraded after one hour of incubation. Binding of recombinant 2-5A-dependent RNase to the affinity matrix was also shown by monitoring the presence of the $^{35}$S-labeled translation product. These results are believed to demonstrate that the recombinant human 2-5A-dependent RNase produced in vitro is a functional and potent ribonuclease. Furthermore, both recombinant and naturally occurring forms of 2-5A-dependent RNase are capable of cleaving poly(U) but not poly(C). See FIG. 5B. See also Silverman, R. H., *Anal. Biochem.*, 144:450–460 (1985) and Floyd-Smith, G. et al., *Science*, 212:1020–1032 (1981).

To determine if 2-5A-dependent RNase mRNA levels are regulated by interferon, a northern blot from murine L929 cells treated with interferon and cycloheximide is probed with the radiolabeled murine 2-5A-dependent RNase cDNA. See FIG. 6. 2-5A-dependent RNase mRNA levels are enhanced three-fold by interferon (α+β) treatment even in the presence of cycloheximide. See FIGS. 6A and B, compare lanes 1 and 2). Regulation of 2-5A-dependent RNase mRNA levels by interferon as a function of time is demonstrated (FIGS. 6A and B, lanes 3 to 6. Maximum 2-5A-dependent RNase mRNA levels are observed after 14 hours of interferon treatment. See FIGS. 6A and B, lane 6. A similar increase in levels of 2-5A-dependent RNase per se is observed after interferon treatment of the cells. Relatively invariant levels of GAPDH mRNA indicates that equivalent levels of RNA are present in every lane of the blot. See FIG. 6C. These results are believed to show that the induction of 2-5A-dependent RNase expression is a primary response to interferon treatment. The murine and human 2-5A-dependent RNase mRNAs are determined from northern blots to be 5.7 kb and 5.0 kb in length, respectively. See FIG. 6A. The 2-5A-dependent RNase coding sequences, therefore, comprise only about 40% the nucleotide sequences contained in the mRNAs.

The 2-5A binding functions of the recombinant and naturally occurring forms of murine 2-5A-dependent RNase are characterized by covalent crosslinking to the 2-5A probe in the presence of unlabeled 2-5A or 2-5A analogues as competitors. See FIG. 7A. Interestingly, although the about 74 kDa truncated 2-5A-dependent RNase is missing about 84 amino acids from its carboxy-terminus, see FIG. 4, it nonetheless possesses a 2-5A binding activity indistinguishable from that of naturally occurring 2-5A-dependent RNase. See FIG. 7A. Trimer 2-5A[p$_3$(A2'p)$_2$A], at about 20 nM effectively prevents the 2-5A probe from binding to either protein. See FIG. 7A, lane 8. In comparison, a 500-fold higher concentration of (A2'p)$_2$A (10 μM) is required to prevent probe binding to both proteins. See lane 13. The dimer species, p$_3$A2'pA, is unable to prevent the 2-5A probe from binding to the proteins even at a concentration of 10 μM (lane 18). However, the inosine analogue, p$_3$I2'pA2'pA, Imai, J. et al., *J. Biol. Chem.*, 260:1390–1393 (1985), is able to prevent probe binding to both proteins but only when added at a concentration of about 1.0 μM (lane 22).

To further define sequences involved in 2-5A binding, nested 3'-deletions of the murine 2-5A-dependent RNase cDNA, clone ZB1, are constructed, transcribed in vitro, and expressed in a wheat germ extract. See FIG. 7B. The different deletion clones produces comparable amounts of polypeptide as monitored by incorporation of $^{35}$S-methionine. The levels of 2-5A binding activity are determined with the 2-5A probe in both a filter binding assay, Knight, M. et al., *Nature*, 288:189–192 (1980), and the uv crosslinking assay, Nolan-Sorden, N. L. et al., *Anal. Biochem.*, 184:298–304 (1990), with similar results. See FIG. 7B. Expression of clone ZB11, encoding amino acid residues 1 to 342, results in a loss of only about 26% of the 2-5A binding activity as compared to clone ZB1 (amino acids 1 to 656). See FIG. 7B. Clones intermediate in length between ZB1 and ZB11 all result in significant levels of 2-5A binding activity. In contrast, protein produced from ZB13 (amino acids 1 to 294) results in only about 38.3% of the 2-5A binding activity of clone ZB1, suggesting that a region important for the 2-5A binding function is affected. Indeed, clone ZB14 produced a protein encoding amino acids 1 to 265 which is nearly inactive in the 2-5A binding assay (only 1.9% of th activity of clone ZB1). Interestingly, the significant decrease in 2-5A binding activity observed with ZB14 occurs with the deletion of one of two P-loop motifs; nucleotide binding domains in many proteins. See FIGS. 4 and 7B. See also Saraste, M. et al., *TIBS*, 14:430–434 (1990). Deletion of both P-loop motifs in clone ZB15 results in protein (amino acids 1 to 218) which is completely lacking in 2-5A binding activity. See FIG. 7B.

To probe the involvement of the consensus lysine residues in the P-loop motifs in 2-5A binding activity, site-directed mutagenesis is performed on the truncated form of murine 2-5A-dependent RNase encoded by clone ZB1. Previously, it is reported that substitution mutations of the conserved lysine residues in P-loop motifs of eucaryotic initiation factor 4A and for *Bacillus anthracis* adenylyl cyclase results in a loss of ATP binding and catalytic activities, respectively. See Rozen et al., *Mol. Cell. Biol.*, 9:4061–4063 (1989) and Xia, Z. and Storm, D. R., *J. Biol. Chem.*, 265:6517–6520 (1990). In the former study the invariant lysine residue is mutated to asparagine. See Rozen et al., *Mol. Cell. Biol.*, 9:4061–4063 (1989). We substituted, individually and together, the consensus lysines with asparagines at positions 240 and 274 in the two P-loop motifs of 2-5A-dependent RNase. See FIG. 8 and the Example. Analysis of the effects of these mutations on 2-5A binding activity is determined by covalently crosslinking the $^{32}$P-2-5A probe to the in vitro translation products under uv light. See FIG. 8A. See also Nolan-Sorden, N. L. et al., *Anal. Biochem.*, 184:298–304 (1990). Similar levels of proteins are synthesized from the different mRNA species as shown in separate reactions containing $^{35}$S-methionine. See FIG. 8B. The three mutant forms of 2-5A-dependent RNase shows reduced binding to the 2-5A probe. See FIG. 8A, lanes 2 to 4. Clone ZB1 (Lys$^{240}$→Asn), FIG. 8A, lane 2, expresses a mutant 2-5A-dependent RNase with a substantially reduced affinity for 2-5A; about 48.4% of the activity of clone ZB1 as determined by phosphorimager analysis (Molecular Dynamics) of the dried gel. A more modest reduction in 2-5A binding activity, to 79% of the control value, is obtained from clone ZB1(Lys$^{274}$→Asn). See FIG. 8A, lane 3. In contrast, 2-5A binding activity from clone ZB1(Lys$^{240,274}$→Asn), FIG. 8A, lane 4, in which both conserved lysine residues are replaced with asparagine residues, is reduced to only 12.2% of the activity of clone ZB1 (averaged from three separate experiments). These results suggest that the lysine residues at positions 240 and 274 function within the context of a repeated P-loop motif in the binding of 2-5A to 2-5A-dependent RNase.

The molecular cloning and expression of 2-5A-dependent RNase, the terminal factor in the 2-5A system and a key enzyme in the molecular mechanisms of interferon action is described. See FIG. 1. The recombinant proteins produced in vitro are demonstrated to possess 2-5A binding properties identical to naturally occurring forms of murine and human 2-5A-dependent RNase. See FIGS. 2, 5A, and 7. In addition, linkage of a $^{32}$P-2-5A analogue to a truncated murine 2-5A-dependent RNase and to murine L cell 2-5A-dependent RNase followed by partial proteolysis reveals identical patterns of labeled peptides. See FIG. 2B. Furthermore, the full-length recombinant human 2-5A-dependent RNase isolated on the activating, affinity matrix, 2-5A-cellulose, shows potent ribonuclease activity towards poly(U) but none against poly(C). See FIG. 5B. Similarly, it is previously demonstrated that murine L cell 2-5A-dependent RNase was activated by 2-5A-cellulose resulting in the cleavage of poly(U), but not of poly(C). See Silverman, R. H., *Anal. Biochem.*, 144:450–460 (1985). The full-length human 2-5A-dependent RNase, which is produced in reticulocyte lysate, had the same apparent molecular weight as did naturally occurring 2-5A-dependent RNase. See FIG. 5A. However, the actual molecular mass of human 2-5A-dependent RNase is determined from the predicted amino acid sequence, FIG. 3B, to be about 83,539 Da.

Previously, it was reported that interferon enhances levels of 2-5A-dependent RNase by between two- to twenty-fold depending on the cell type. See Silverman, R. H. et al., *Eur. J. Biochem.*, 126:333–341 (1982b) and Jacobsen, H. et al., *Viroloy*, 125:496–501 (1983a). Results presented herein suggest that the gene for 2-5A-dependent RNase may be an interferon-stimulated gene. See FIG. 6. Levels of 2-5A-dependent RNase mRNA in murine L929 cells are elevated as a function of time of interferon (α+β) treatment by a factor of about three. Furthermore, the induction appeared to be a primary response to interferon treatment because it is observed in the presence of cycloheximide. Therefore, interferon is believed to regulate the 2-5A pathway by elevating levels of both 2-5A synthetases, Hovanessian, A. G. et al., *Nature,* 268:537–539 (1977), and 2-5A-dependent RNase, Jacobsen, H. et al., *Virology,* 125:496–501 (1983a). See FIGS. 1, 6 and 11.

The cloning of 2-5A-dependent RNase reveals several features of the protein. The 2-5A binding domain is of particular interest because it is the ability of 2-5A-dependent RNase to be activated by 2-5A that sets it apart from other nucleases. By expressing nested 3'-deletions of murine 2-5A-dependent RNase, a region between amino acids residues 218 and 294 which is believed to be critical for 2-5A binding activity is identified. See FIG. 7B. Interestingly, the identified region contains a repeated P-loop motif, one from residues 229 to 241 and another from residues 253 to 275. See FIG. 4 and Table 2. When the latter P-loop motif (amino acids 253–275) is partially deleted, there is a precipitous decline in 2-5A binding activity. See clone ZB14 in FIG. 7B.

The homology with P-loops is believed to be highly conserved between the human and murine forms of 2-5A-dependent RNase; thus underscoring the belief of the importance of this region for 2-5A binding activity. See FIG. 4. The similarity to P-loops consists of the tripeptides, glycine-lysine-threonine, preceded by glycine-rich sequences. In this regard, the unusual feature of 2-5A-dependent RNase is that the P-loop motif is repeated and are in the same orientation. Adenylyl cyclase from Bacillus anthracis also contains a duplicated P-loop motif, however, the two sequences are in opposite orientation and are overlapping. See Xia, Z. and Storm, D. R., *J. Biol. Chem.,* 265:6517–6520 (1990).

The relative importance of the conserved P-loop lysines (at positions 240 and 274) are evaluated by site-directed mutagenesis of the murine 2-5A-dependent RNase, clone ZB1. Although individual substitution mutations of the two lysines significantly reduced 2-5A binding activity, replacing both of the lysines with asparagine residues in the same mutant RNase severely represses 2-5A binding. See FIG. 8. Perhaps the trimer 2-5A requirement for activation of most forms of 2-5A-dependent RNase could be explained if the first and third adenylyl residues of 2-5A interact with the separate P-loop sequences inducing conformational changes in 2-5A-dependent RNase. In this regard, dimer 2-5A neither binds 2-5A-dependent RNase efficiently nor does it activate 2-5A-dependent RNase, FIG. 7A; Kerr, I. M. and Brown, R. E., *Prod. Natl. Acad. Sci. U.S.A.,* 75:265–260 (1978) and Knight, M. et al., *Nature,* 288:189–192 (1980), perhaps because it is too short to span the two P-loop motifs. Alternately, the residual 2-5A binding activity observed in the point mutants, ZB1(Lys$^{240}$→Asn) and ZB1 (Lys$^{274}$→Asn), and the very low affinity of the double mutant, ZB1(Lys$^{240,274}$→Asn) for 2-5A, could indicate that the two P-loop motifs are parts of separate 2-5A binding domains.

Homology with protein kinase domains VI and VII is also identified in 2-5A-dependent RNase. See FIG. 4. See also Hanks, S. K. et al., *Science,* 241:42–52 (1988). Although domain VI is believed to be involved in ATP binding, this region in 2-5A-dependent RNase is believed not to be important for 2-5A binding because its deletion caused only a minimal reduction in affinity for 2-5A. See FIG. 7B. However, a modest (two-fold) stimulatory effect of ATP on 2-5A-dependent RNase activity has been reported. See Wreschner, D. H. et al., *Eur. J. Biochem.,* 124:261–268 (1982) and Krause, D. et al., *J. Biol. Chem.,* 261:6836–6839 (1986). The latter report indicated that ATP was not required for 2-5A-dependent RNase activity but may act to stabilize the enzyme. Therefore, the region of homology with protein kinases could perhaps bind ATP resulting in stimulation of ribonuclease activity through stabilization of the enzyme.

A consensus zinc finger domain, reviewed in Evans, R. M. and Hollenberg, S. M., *Cell,* 52:1–3 (1988), consisting of six cysteine residues with the structure $CX_4CX_3CX_{17}CX_3CX_3C$ (amino acid residues 401–436 in Table 2 ) is identified in the murine form of 2-5A-dependent RNase. See FIG. 4. The homologous region in the human form of 2-5A-depenent RNase is $CX_{11}CX_{25}CX_3CX_6C$ (amino acid numbers 395 to 444 in Table 1 ). Because zinc fingers are nucleic acid binding domains, the cysteine-rich region in 2-5A-dependent RNase could be involved in binding to the RNA substrate. Alternatively, the cysteine-rich domain in 2-5A-dependent RNase could mediate formation of 2-5A-dependent RNase dimers. Analysis of crude preparations of 2-5A-dependent RNase suggest that 2-5A-dependent RNase may form dimers in concentrated but not in dilute extracts. See Slattery, E. et al., *Proc. Natl. Acad. Sci. U.S.A.,* 76:4778–4782 (1979) and Wreschner, D. H. et al., *Eur. J. Biochem.,* 124:261–268 (1982).

Comparison between the amino acid sequences of other ribonucleases with 2-5A-dependent RNase identifies some limited homology with RNase E, an endoribonuclease from *E. coli.* See FIG. 9A. See also Apirion D. and Lassar, A. B., *J. Biol. Chem.,* 253:1738–1742 (1978) and Claverie-Martin, F. et al., *J. Biol. Chem.* 266:2843–2851 (1991). The homology with RNase E is relatively conserved between the human and murine forms of 2-5A-dependent RNase and spans a region of about 200 amino acid residues. Within these regions there are 24 and 32% identical plus conservative matches, with some gaps, between RNase E and the human and murine forms of 2-5A-dependent RNase, respectively. See FIG. 9A.

The rne gene which encodes RNase E and the altered mRNA stability (ams) gene, Ono, M. and Kumano, M., *J. Mol. Biol.*, 129:343–357 (1979), map to the same genetic locus. See Mudd E. A. et al., *Mol. Microbiol.*, 4:2127–2135 (1990); Babitzke, P. and Kushner, S. R., *Proc. Natl. Acad. Sci. U.S.A.*, 88:1–5 (1991) and Taraseviciene, L. et al., *Mol. Microbiol.*, 5:851–855 (1991). RNase E is required for both efficient mRNA turnover and rRNA processing in *E. coli*. See Mudd E. A. et al., *Mol. Microbiol.*, 4:2127–2135 (1990) and Babitzke, P. and Kushner, S. R., *Proc. Natl. Acad. Sci. U.S.A.*, 88:1–5 (1991). The cleavage specificities of 2-5A-dependent RNase and RNase E are similar in that 2-5A-dependent RNase cleaves mainly after UU or UA, Wreschner, D. H. et al., *Nature*, 289:414–417 (1981a) and Floyd-Smith, G. et al., *Science*, 212:1020–1032 (1981), and RNase E usually cleaves within the central AUU sequence of (G or A)AUU(A or U), Ehretsmann, C. P. et al., *Genes & Development*, 6:149–159 (1992). The location of the RNase E homology and other identified features in 2-5A-dependent RNase are shown. See FIG. 9B. These findings raise the possibility that RNase E may be the ancestral precursor of 2-5A-dependent RNase. In this regard, there are indications of 2',5'-oligoadenylates in *E. coli*. See Brown, R. E. and Kerr, I. M., *Process in Clinical and Biological Research*, 202:3–10 (1985) and Trujillo, M. A. et al., *Eur. J. Biochem.*, 169:167–173 (1987). However, the evolutionary distribution of a complete 2-5A system (i.e. 2-5A synthetase and 2-5A-dependent RNase) is reported to begin only with reptiles or possibly amphibia. See Cayley, P. J. et al., *Biochem. Biophys. Res. Commun.*, 108:1243–1250 (1982).

Endoribonucleases play a controlling role in RNA metabolism by catalyzing the rate-limiting steps in RNA decay. See Brawerman, G., *Cell*, 57:9–10 (1989). 2-5A-dependent RNase is a uniquely regulated endoribonuclease which mediates effects of interferon against picornaviruses. It functions by binding 2-5A and subsequently degrades both viral and cellular RNA. See Wreschner, D. H. et al., *Nucleic Acids Res.*, 9:1571–1581 (1981b). In addition, the 2-5A system may be involved in the antiproliferative effects of interferon and in the fundamental control of RNA stability. Cellular levels of 2-5A-dependent RNase and/or 2-5A-synthetase are regulated during interferon-treatment, Hovanessian, A. G. et al., *Nature*, 268:537–539 (1977) and Jacobsen, H. et al., *Virology*, 125:496–501 (1983a), cell growth arrest, Stark, G. et al., *Nature*, 278:471–473 (1979) and Jacobsen, H. et al., *Proc. Natl. Acad. Sci. U.S.A.*, 80:4954–4958 (1983b), cell differentiation, Krause, D. et al., *Eur. J. Biochem.*, 146:611–618 (1985), changing hormone status, e.g., Stark, G. et al., *Nature*, 278:471–473 (1979), and liver regeneration, Etienne-Smekens, M. et al., *Proc. Natl. Acad. Sci. U.S.A.*, 80:4609–4613 (1983). However, basal levels of 2-5A-dependent RNase and 2-5A synthetase are present in most if not all mammalian cells. The existence of multiple forms of 2-5A synthetase with different intracellular locations, Hovanessian, A. G. et al., *EMBO J.*, 6:1273–1280 (1987), could indicate diverse functions for the 2-5A system. Similarly, the ubiquitous presence of the 2-5A system in higher animals suggests an important function for 2-5A-dependent RNase, Cayley, P. J. et al., *Biochem. Biophys. Res. Commun.*, 108:1243–1250 (1982). For instance, 2-5A-dependent RNase cleaves rRNA at specific sites in intact ribosomes, Wreschner, D. H. et al., *Nucleic Acids Res.*, 9:1571–1581 (1981b) and Silverman, R. H. et al., *J. Virol.*, 46:1051–1055 (1983), possibly affecting translation rates. The transient nature of 2-5A, Williams, B. R. G. et al., *Eur. J. Biochem.*, 92:455–562 (1978), and its growth inhibitory effect after introduction into cells, Hovanessian, A. G. and Wood, J. N., *Virology*, 101:81–89 (1980), indicate that the 2-5A system is a tightly regulated pathway.

Example I

The source of mRNA for preparing the cDNA library is murine L929 cells grown in EMEM (Whittaker, Inc.) and supplemented with about 10% FBS (Gibco-BRL), and antibiotics. The cells are treated with about 50 µg per ml of cycloheximide and 1000 units per ml of murine interferon ($\alpha+\beta$) ($1.3\times10^7$ units per mg protein: Lee Biomolecular) for about 2.5 hours to increase levels of 2-5A-dependent RNase mRNA. Total RNA was then isolated, e.g. Chomczynski, P. and Sacchi, N., *Anal. Biochem.*, 162:156–159 (1987), from which poly(A)$^+$ RNA is prepared by oligo(dT)-cellulose chromatography as described. See Sambrook, J. et al., *Cold Spring Harbor Laboratory Press* (1989). Synthesis of the first strand of cDNA is done by using reverse transcriptase as described (Superscript; BRL) except that 5-methyl-dCTP is substituted for dCTP and an XhoI-oligo-dT adapter-primer (Stratagene) is used. Synthesis of the second strand of cDNA and ligation of EcoRI linker was as described (Stratagene). The cDNA is digested with EcoRI and XhoI and unidirectionally cloned into predigested λZAPII vector (Stratagene). The library is packaged by using Giagpack Gold extract and titered on PLK-F bacteria.

The cDNA library is screened directly without prior amplification at a density of about 25,000 phage per 150 mm plate. Phage are grown for 3.5 hours at about 42° C. until plaques are visible. Nitrocellulose filters saturated in IPTG (10 mM) and then dried, are overlaid on the plates and growth was continued for an additional 4 to 6 hours at 37° C. The filters are processed by a modification of the methods of Singh, H. et al., *Cell*, 52:415–423 (1988) and Singh, H. et al., *BioTechniques*, 7:252–261 (1989). Filters are washed in ice-cold binding buffer (about 20 mM Tris-HC1, about pH 7.5, about 20 mM magnesium acetate, about 50 mM potassium chloride, about 1 mM EDTA, about 50 mM β-mercaptoethanol, about 0.1 mM PMSF, about 5% glycerol) containing about 6M guanidine-HCl for about 20 min. The solution containing the filters is then diluted two-fold with binding buffer and washing on ice is continued for about an additional 5 minutes; serial two-fold. dilutions were continued until the guanidine concentration was about 187 mM. The filters are then washed twice with binding buffer, and incubated with binding buffer containing about 5% nonfat milk for one hour at about room temperature. The filters are then washed twice with binding buffer and incubated in binding buffer (supplemented with about 0.25% nonfat dry milk and about 0.02% sodium azide) containing p(A2'p)$_2$(br$^8$A2'p)$_2$A3'-[32P]Cp (the "2-5A probe"), Nolan-Sorden, N. L. et al., *Anal. Biochem.*, 184:298–304 (1990), at about $2\times10^5$ counts per minute per ml (about 3,000 Ci per mmole) at about 4° C. with shaking for about 24 hours. The filters are washed twice with binding buffer and then twice with water before air drying and exposing to film.

Murine L929 cells are treated with about 1000 units per ml interferon ($\alpha+\beta$) with or without about 50 pg per ml of cycloheximide and the total RNA is then isolated as described. See Chomczynski, P. and Sacchi, N., *Anal. Biochem.*, 162:156–159 (1987). Poly(A)$^+$ RNA is prepared by oligo(dT)-cellulose chromatography, as described in Sambrook, J. et al., *Cold Spring Harbor Laboratory Press* (1989), and is separated on glyoxal agarose gels and transferred to Nytran membranes. RNA is immobilized on the membrane by uv crosslinking (Stratalinker, Stratagene). The murine 2-5A-dependent RNase cDNA is $^{32}$P-labeled by random priming and then hybridized to the filter [about 50% formamide, about 10% dextran sulphate, Denhardt's solution about 1% SDS, 6× SSPE, Sambrook, J. et al., *Cold Spring Harbor Laboratory Press* (1989), about 250 µg per ml salmon sperm DNA] at about 42° C.

The Human 2-5A-dependent RNase cDNA clone, HZB1, is isolated from an adult human kidney cDNA library in λgt10 with radiolabeled (random primed) murine 2-5A-dependent RNase cDNA (clone ZB1) as probe, Sambrook, J. et al., *Cold Spring Harbor Laboratory Press* (1989). Clone HBZ22 is isolated using radiolabeled HZB1 DNA as probe. The genomic human 2-5A-dependent RNase clone is isolated from a human placenta cosmid library in vector pVE15 (Stratagene) with a radiolabeled fragment of HZB22 DNA as probe. The murine genomic 2-5A-dependent RNase clone is isolated from a mouse 129SV genomic library in vector λFIXII (Stratagene) with a radiolabeled fragment of 2-5A-BP cDNA (clone ZB1) as probe. Subcloning of DNA is in Bluescript vectors (Stratagene).

Transcription of plasmids with phage RNA polymerases is in the presence of mGppppG as described (Promega) except that reaction mixtures are supplemented with 15% dimethyl sulfoxide and incubations are at about 37° C. for about 90 minutes. RNA is purified through Sephadex G50 spun-columns and ethanol precipitated prior to translation. Protein synthesis was performed, as described (Promega), at about 30° C. for about one hour in micrococcal nuclease-pretreated rabbit reticulocyte lysate or in an extract of wheat germ at about room temperature for about one hour and then at about 40° C. for about 12 hours. Translation reactions contain about 50 µM zinc sulfate. Endogenous 2-5A-dependent RNase in the reticulocyte lysated is removed by adsorption to about 30 µM of $p_2(A2'p)_3A$ covalently attached to cellulose (2-5A-cellulose), prepared as described in Wells, J. A. et al., *J. Biol. Chem.*, 259:1363–1370 (1984) and Silverman, R. H. and Krause, D., *I. R. L. Press. Oxford. England*, pp. 149–193 (1987), for about one hour on ice as described. See Silverman, R. H., *Anal. Biochem.*, 144:450–460 (1985). The 2-5A-dependent RNase:2-5A-cellulose complex is removed by twice centrifuging at about 400×g for about 5 minutes at about 2° C. The supernatant completely lacking in measurable levels of 2-5A-dependent RNase. See FIG. 5.

The set of nested 3'-deletions of the truncated murine 2-5A-dependent RNase cDNA, ZB1, is generated with exonuclease III/S1 nuclease digestion followed by filling-in with Klenow DNA Polymerase using the "Erase-A-Base" system (Promega).

The synthesis of the 2-5A probe, $p(A2'p)_2(br^8A2'p)_2A$ [32P]Cp, and its crosslinking to 2-5A-dependent RNase is performed exactly as described. See Nolan-Sorden, N. L. et al., *Anal. Biochem.*, 184:298–304 (1990). Briefly, the 2-5A probe, about 0.7 to 2.5 nM at 3,0009 Ci/mmole, is incubated for about one hour on ice with cell extract prepared as described, Silverman, R. H. and Krause, D., *I.R.L. Press, Oxford, England, pp.* 149–193 (1987), in the absence or presence of unlabeled oligonucleotide competitors. Covalent crosslinking is done under a uv lamp (308 nm) for one hour on ice and the proteins are separated on SDS/10% polyacrylamide gels. Filter assays for 2-5A binding activity using the 2-5A probe for about one hour on ice, as described in Knight, M. et al., *Nature*, 288:189–192 (1980).

Protease digestions are performed on gel-purified proteins in a gel, as described by Cleveland, D. W. et al., *J. Biol. Chem.*, 252:1102–1106 (1977).

The ribonuclease assay with 2-5A-cellulose is performed, as described by Silverman, R. H., *Anal. Biochem.*, 144:450–460 (1985). Briefly, lysates are adsorbed to about 30 µM of 2-5A-cellulose on ice for about two hours. The matrix is then washed three times by centrifuging and resuspending in buffer A. See Silverman, R. H., *Anal. Biochem.*, 144:450–460 (1985). The matrix is then incubated with poly(U)-[$^{32}$P]Cp or poly(C)-[$^{32}$P]Cp (both at about 16 µM in nucleotide equivalents) at about 30° C. and the levels of acid-precipitable radioactive RNA are determined by filtration on glass-fiber filters.

The Sanger dideoxy sequencing method is used to determine the DNA sequences (Sequenase, United States Biomedical).

The lysines in the truncated murine 2-5A-dependent RNase, clone ZB1, at positions 240 and 274 are mutated, individually and together, to asparagine residues. Mutants ZB1(Lys$^{274}$→Asn) and the double mutant, ZB1(Lys$^{240,274}$→Asn), are obtained with mutant oligonucleotides after subcloning ZB1 cDNA into pALTER-1 as described (Promega). Mutant ZB1(Lys$^{240}$→Asn) is obtained after polymerase chain reaction amplification of a segment of ZB1 with an upstream primer containing a unique HincII site attached to the mutant sequence and a second primer downstream of a unique BglII site. The HincII- and BGlII-digested polymerase chain reaction product and similarly-digested clone ZB1 are then ligated. The specific mutations are: for codon 240, AAA→AAC and for codon 274, AAG→AAC. Mutants are confirmed by DNA sequencing.

Example II

Seeds of tobacco (*Nicotiana tabacum* cv. Wisconsin) and Ti based binary vectors pAM943 and pAM822 were obtained from Dr. Amit Mitra, Department of Plant Pathology, University of Nebraska, Lincoln, Nebr. The *Agrobacterium tumefaciens* LBA4404 and the *E. coli* strains K802 and MM294 were purchased from Clonetech, Palo Alto, Calif. and Stragene, LaJolla, Calif. The plant tissue culture medium Murashige and Skoog's ready mix (MS media) was purchased from Sigma Chemical Company, St. Louis, Mo. The human cDNAs for PKR, the lysine→arginine mutant PKR, and 2-5A synthetase were obtained from Dr. B. R. G. Williams, Department of Cancer Biology, The Cleveland Clinic Foundation. See, for example, Meurs, E. et al.: *Cell,* 62:379–390 (1990); Chong, K. L. et al.: *EMBO J.,* 11:1553–1562 (1992); Rysieki, G. et al.: *J. Interferon Res.,* 9:649–657 (1989); Benech, P. et al.: *EMBO J.,* 4:2249–2256 (1985); and Saunders, M. E. et al.: *EMBO J.,* 4:1761–1768 (1985). The human cDNA for 2-5A dependent RNase, as shown in FIG. 3A, was cloned in Dr. R. H. Silverman's laboratory in the Department of Cancer Biology and is the property of The Cleveland Clinic Foundation. See, Zhou, A. et al.: *Cell,* 72:753–765 (1993).

The expression vector pAM943 is used to obtain Agrobacterium-mediated transfer of T DNA containing the cDNAs and kanamycin resistance marker gene. The physical map of the plasmid vector pAM943 shows its elements. See FIG. 12. The plasmid pAM943 contains a dual promoter consisting of the adenyl methyl transferase (AMT) gene promoter of Chlorella virus and the wild type 35S promoter of Cauliflower mosaic virus. The vector also contains the gene for kanamycin resistance to select the transformed plants. Initially, the cDNAs are subcloned in pAM943 and amplified in *E. coli* strains K802 or MM294 using tetracycline resistance as the selectable marker. The Agrobacterium cells are transformed with the recombinant pAM943 plasmids and selected by growth in medium containing about 5 µg/ml of tetracycline, about 10 µg/ml of kanamycin and about 25 µg/ml of streptomycin.

To subclone cDNAs for PKR (PK68), a lysine→arginine mutant PKR (muPk68; the mutant PKR protein binds to dsRNA but has no kinase activity and will thus function as a control), and a low molecular weight form of 2-5A-synthetase (synthetase), the plasmids pKS(+)PKR, pKS(+) muPKR, and pKS(+)synthetase are digested first with XbaI and than with ClaI restriction endonucleases, the cDNA fragments are purified from low melting point agarose gels and subcloned in sense orientation at XbaI and ClaI sites of pAM943. See FIG. 13. The recombinant plasmids, e.g., construct A, pAM943:PK68, construct B, pAM943:muPK68, and contruct C, pAM943:synthetase, which correspond to the constructs depicted in FIG. 13A–C, respectively, are used to transform *Agrobacterium tumefaciens* LBA4404. The resultant bacteria, identified as AG68, AGmu68 and AGsyn, respectively, are used for tobacco leaf disc transformations. Production of the recombinant plasmids, i.e., construct A, pAM943:PK68, construct B, pAM943:muPK68, and construct C pAM943:synthetase, is described in greater detail hereinafter.

To subclone cDNA for 2-5A-dependent RNase, the plasmid pKS(+)2C5 DNA is digested with HindIII enzyme and subcloned in the HindIII site of pAM943 in both orientations, see FIG. 13, and the recombinant plasmids, construct D, pAM943:2-5A-dep. RNase sense and construct D/a, pAM943:2-5A-dep. RNase antisense, both of which correspond to constructs D and D/a, respectively, in FIG. 13D and D/a, are used to transform Agrobacterium to obtain the bacteria called AG2DR sense and AG2DR antisense, respectively. Production of the recombinant plasmids, i.e., construct D, pAM943:2-5A-dep. RNase sense, construct D/a, pAM943:2-5A-dep. RNase antisense, and construct E, pAM822:2-5A dep. RNase antisense, is also described in greater detail hereinafter.

The competent Agrobacterium cells are prepared and transformation follows the method of, for example, An, G. et al.: *Plant Molecular Biology Manual*, AD:1–19 (1988). The presence of recombinant plasmids in the transformed Agrobacterium cells is confirmed by preparing plasmid DNA and by performing PCR using specific complementary oligonucleotides and by observing restriction enzyme digests.

The physical map of plasmid pAM822, one of the vectors used to deliver the reverse orientation cDNA for 2-5A dependent RNase into plant cells by electroporation, is also shown. See FIGS. 13E and 14. To subclone cDNA for 2-5A-dependent RNase into pAM822 the entire coding region of 2-5A-dependent RNase was PCR amplified using two oligonucleotide primers containing BamHI restriction sites before ATG (start codon) and after TGA (stop codon). The product was digested with BamHI and subcloned at BglII site of pAM822 vector. The cDNA used for 2-5A-dependent RNase is in plasmid pZC5 referenced in Zhou et al. *Cell* 72, 753–765 (1994), the human form of the cDNA. The sequence is also disclosed herein. The plasmid pAM822 contains a second selectable marker gene, the hygromycin resistance gene, permitting the construction of plants containing both 2-5A-synthetase and 2-5A-dependent RNase cDNAs. Insertion of pAM822:2-5Adep. RNase (FIG. 13E), containing 2-5A-dependent RNase cDNA, into kanamycin-resistant, transgenic tobacco leaf discs containing 2-5A-synthetase cDNA is thus performed.

Tobacco plants are grown aseptically in Murashige and Skoog's medium, known as MS medium, containing about 3% sucrose (MSO medium) and about 0.8% agar in plastic boxes (Phytatray) at about 28° C. under cycles consisting of about 16 hr of light and about 8 hr of dark in a growth chamber. Leaves bigger than about 2" long are cut into about 2 to 3 $cm^2$ pieces under the MSO medium and 6–8 leaf pieces are placed in a 6 cm Petri dish containing about 2 ml of MSO medium and holes are made in the leaf pieces with a sterile pointed forcep. Overnight cultures of AG68, AGmu68, AGSyn, AG2DR sense and AG2DR antisense are grown in LB (L broth) containing about 50 $\mu$M of acetosyringone and appropriate antibiotics at about 28° C. in a waterbath. One hundred microliter of overnight culture is added to each of the Petri dishes containing leaf pieces. Incubation is at about 28° C. under diffuse light in the growth chamber for about 2 days. Leaf pieces are washed extensively with MSO medium and transferred to solid agar for selection in shoot regeneration medium [MSO; about 0.5 mg/l BAP (benzylaminopurine); about 200 $\mu$g/ml kanamycin; about 200 $\mu$g/ml carbenicillin; and about 100 $\mu$g/ml of cefotaxine], under diffuse light at about 28° C. in the growth chamber. Within about 3 weeks, regeneration of plantlets is observed. When the plantlets are about 2–3 cm long they are transferred to root-inducing, hormone-free MSO solid agar medium containing about 200 $\mu$g/ml kanamycin and about 200 $\mu$g/ml carbenicillin. The transgenic plants expressing 2-5A synthetase are substantially transformed to introduce the cDNA for 2-5A-dependent RNase (with pAM943:2-5Adep.RNase sense, construct D; FIG. 13D). Alternatively, the vector pAM822 (FIG. 14) containing the 2-5A-dependent RNase cDNA in sense orientation and the hygromycin resistance gene is used to transform 2-5A-synthetase containing plants. This allows selection in hygromycin containing MSO media. Tissue culture and regeneration of plants are done as described above. Transgenic plants are grown to produce flowers and seeds to demonstrate the transfer of the antiviral genes or nucleotide sequences to subsequent generations. Although specific plasmid constructs are described herein, the present invention is intended to include any plant vector including those with inducible promoters.

Expression of PKR, mutant PKR, 2-5A-synthetase, and 2-5A-dependent RNase in plants that are 4" to 5" tall are tested in protein extracts of leaves (supernatant of 10,000×g centrifugation). Results of Northern and Southern blot assays and functional binding assays for 2-5A-dependent RNase are reported in Tables I–V. See also FIG. 15 wherein expression of human 2-5A synthetase cDNA in transgenic tobacco plants as determined by measuring the mRNA levels in a Northern blot is shown. FIG. 16, on the other hand, shows expression of mutant and wild type forms of human PKR cDNA in transgenic tobacco plants as determined by measuring mRNA levels in a Northern blot. FIG. 17 depicts presence of 2-5A-dependent RNase cDNA in transgenic tobacco plants as determined on a Southern blot.

TABLE I

Transgenic Tobacco Plants Expressing
Wild Type and Mutant Forms of Human PKR cDNA
(plasmid pAM943:PK68) FIG. 13A
(plasmid pAM943:muPK68) FIG. 13B

| Transgenic: | Plant: (clone #) | Southern Blot: (presence of DNA) | Northern Blot: (expression of mRNA) |
| --- | --- | --- | --- |
| Mutant PKR: | 1 | + | N.T. |
| (plasmid | 2 | ++ | + |
| pAM943:PK68) | 4 | N.T. | N.T. |
| FIG. 13A | 6 | N.T. | + |
| | 7 | N.T. | + |
| | 10 | N.T. | + |

TABLE I-continued

Transgenic Tobacco Plants Expressing
Wild Type and Mutant Forms of Human PKR cDNA
(plasmid pAM943:PK68) FIG. 13A
(plasmid pAM943:muPK68) FIG. 13B

| Transgenic: | Plant: (clone #) | Southern Blot: (presence of DNA) | Northern Blot: (expression of mRNA) |
|---|---|---|---|
|  | 11 | N.T. | + |
|  | 12 | N.T. | + |
|  | 17 | N.T. | + |
| Wild Type | 1 | N.T. | + |
| PKR: | 2 | N.T. | N.T. |
| (plasmid | 5 | N.T. | + |
| pAM943:muPK68) | 6 | N.T. | N.T. |
| FIG. 13B | 7 | N.T. | N.T. |
|  | 8 | N.T. | + |
|  | 10 | N.T. | + |
|  | 20 | N.T. | N.T. |
|  | 22 | N.T. | N.T. |

N.T., Not Tested

TABLE II

Transgenic Tobacco Plants Expressing
Human 2-5A-Synthetase cDNA
(Plasmid pAM943:synthetase - FIG. 13C)

| Plant: (clone #) | Southern Blot: (presence of DNA) | Northern Blot: (expression of mRNA) |
|---|---|---|
| 1 | ++ | + |
| 3 | ± | N.T. |
| 4 | + | ++ |
| 5 | ± | N.T. |
| 6 | ± | N.T. |
| 7 | ± | N.T. |
| 8 | +++ | + |
| 9 | + | N.T. |
| 10 | + | + |
| 12 | + | N.T. |
| 13 | + | N.T. |
| 14 | ++ | − |
| 15 | + | ± |
| 16 | + | − |
| 17 | N.T. | ++ |
| 18 | N.T. | ++ |
| a | N.T. | N.T. |
| b | N.T. | N.T. |
| c | N.T. | N.T. |
| d | N.T. | N.T. |

N.T., Not Tested.

TABLE III

Transgenic Tobacco Plants Containing
Sense or Antisense Orientation Human
2-5A-Dependent RNase cDNA
(plasmid pAM943:2-5A-dep. RNase sense - FIG. 13D)
(plasmid pAM943:2-5A-dep. RNase antisense - FIG. 13D/a)

| Transgenic: | Plant: (clone #) | Southern (presence of DNA) | Northern (expression of mRNA) | 2-5A-Binding Assay: (protein activity |
|---|---|---|---|---|
| Antisense: | 1 | + | N.T. | N.T. |
|  | 2 | + | N.T. | N.T. |
|  | 3 | + | N.T. | N.T. |
|  | 4 | + | N.T. | N.T. |
|  | 5 | + | N.T. | N.T. |
|  | a | N.T. | N.T. | N.T. |
|  | b | N.T. | N.T. | N.T. |
|  | c | N.T. | N.T. | N.T. |
| Sense: | Z1 | + | − | + |
|  | Z2 | ++ | − | ++ |
|  | Z3 | ++ | N.T. | ++ |
|  | Z4 | + | N.T. | N.T. |
|  | Z5 | N.T. | N.T. | +++ |
|  | Z6 | N.T. | N.T. | ++ |
|  | Z7 | N.T. | N.T. | +/− |

N.T., Not Tested.

TABLE IV

Transgenic Tobacco Plants Containing Both Human
2-5A-Synthetase and Human 2-5A-Dependent RNase cDNA
(plasmid pAM943:synthetase - FIG. 13C)
(plasmid pAM943:2-5A-dep. RNase sense - FIG. 13D)

| | Southern Blots: | | Northern Blot: | |
|---|---|---|---|---|
| Plant: (clone #) | (2-5A-Syn DNA) | (2-5A-Dep. RNase DNA) | (2-5A Syn. mRNA) | (2-5A-dep. RNase mRNA |
| 14/1 | N.T. | − | + | − |
| 14/2 | N.T. | − | + | − |
| 14/3 | N.T. | N.T. | N.T. | N.T. |
| 14/4 | N.T. | N.T. | N.T. | N.T. |
| 14/5 | N.T. | N.T. | N.T. | N.T. |
| 14/6 | N.T. | N.T. | N.T. | N.T. |
| 15/1 | N.T. | − | + | − |
| 15/2 | N.T. | − | + | − |
| 15/3 | N.T. | − | + | − |
| 15/4 | N.T. | N.T. | + | − |
| 15/5 | N.T. | N.T. | N.T. | N.T. |

TABLE IV-continued

Transgenic Tobacco Plants Containing Both Human
2-5A-Synthetase and Human 2-5A-Dependent RNase cDNA
(plasmid pAM943:synthetase - FIG. 13C)
(plasmid pAM943:2-5A-dep. RNase sense - FIG. 13D)

| Plant: (clone #) | Southern Blots: | | Northern Blot: | |
|---|---|---|---|---|
| | (2-5A-Syn DNA) | (2-5A-Dep. RNase DNA) | (2-5A Syn. mRNA) | (2-5A-dep. RNase mRNA) |
| 15/6 | N.T. | – | + | – |
| 15/7 | N.T. | – | N.T. | N.T. |

N.T., Not Tested.

Assays of dsRNA-dependent autophosphorylation of PKR, 2-5A synthetase activated with dsRNA, and 2-5A-dependent RNase by UV-crosslinking to radioactive 2-5A, see Nolan-Sorden et al.: *Analytical Biochemists*, (184):298–304 (1990), may be performed on the leaf extracts. The levels of the proteins may also be determined by Western blot analysis using the antibodies against PKR, 2-5A-synthetase and 2-5A-dependent RNase.

To demonstrate the expression of 2-5A-dependent RNase in transgenic plants containing construct D, pAM943:2-5A-dep. RNase sense, as depicted in FIG. 13D, functional assays that measure binding of radiolabeled 2-5A analog to 2-5A-dependent RNase are performed. See Tables III and V. Results show the presence of 2-5A-dependent RNase in transgenic plants Z1, Z2, Z3, Z5 and Z6. It is believed that the highest levels of human, recombinant 2-5A dependent RNase are in plant Z5. See Table V.

TABLE V

Functional Expression of 2-5A-Dependent RNase
in Transgenic Tobacco Plants ad Determined
by a 2-5A Binding Assay
(plasmid pAM943:2-5A-dep. RNase sense - FIG. 13D)

| Plant; | 2-5A Binding Activity[a]: |
|---|---|
| Z1 | 662 |
| Z2 | 1,618 |
| Z3 | 1,545 |
| Z5 | 2,575 |
| Z6 | 1,547 |
| Z7 | 31 |

[a]Tobacco plants contain construct D, pAM943:2-5Adep. RNase (sense). 2-5A binding assays are performed by the filter binding method of Knight, M. et al. Nature (288):189–192 (1980) with modifications. A $^{32}$P-labeled and bromine substituted 2-5A analog, p(A2'p)$_2$(br$^8$A2'p)$_2$A3'-$^{32}$p]Cp, about 15,000 counts per min per assay, at about 3,000 Ci per mmole, Nolan-Sorden, N. L., et al. Anal. Biochem., (184):298–304 (1990), is incubated with plant extracts, containing about 100 micrograms of protein per assay, on ice for about 4 h. The reaction mixtures are then transferred to nitrocellulose filteres which are washed twice in distilled water and dried and the amount of 2-5A probe bound to the 2-5A-dependent RNase on the filters is measured by scintillation counting, Silverman, R. H. and Krause, D., In, Clemens, M. J., Morris, A. G., and Gearing, A. J. H., (eds.), Lymphokines and Interferons - A Practical Approach, I.R.L. Press, Oxford, pp. 149–193 (1987). Data is presented as counts per min of labeled 2-5A bound to 2-5A-dependent RNase expressed in the transgenic plants. Background radioactivity from extracts of control plants 705 counts per min, consisting of nonspecific binding of 2-5A, is subtracted from these data.

To further confirm that the transgenic plants containing 2-5A-dependent RNase cDNA express functional 2-5A-dependent RNase protein or an amino acid sequence, an affinity labeling method is performed (data not shown). In this method, 2-5A-binding activity is determined on a Western blot with a bromine-substituted, $^{32}$P-labeled 2-5A analog (the "probe"), as described in Nolan-Sorden, N. L. et al.: *Anal. Biochem.*, 184:298–304 (1990). More particularly, leaves are collected from transgenic plants containing 2-5A-dependent RNase cDNA and they are homogenized in NP40 lysis buffer, see Silverman, R. H. and Krause, D. (1987) In, Clemens, M. J., Morris, A. G., and Gearing, A. J. H., (eds.), *Lymphokines and Interferons-A Practical Approach*, I.R.I., Press, Oxford, pp. 149–193, supplemented with about 5 mM ascorbic acid, about 1 mM cysteine, about 2 µg per ml leupeptin, about 100µ per ml phenylmethyleulfonyl fluoride, and about 2 µg per ml pepstatin. Extracts are clarified by centrifugation at about 10,000×g for about 10 min. Supernatants of the extracts, about 100 µg of protein per assay, are separated by SDS/10% polyacrylamide gel electrophoresis, followed by transfer of the proteins to Immobilon-P membrane filters (Millipore Corp., Bedford, Mass.). The filter is then incubated with about 4×10$^5$ c.p.m. per ml of $^{32}$P-labeled 2-5A probe for about 24 h at about 4° C., according to Zhou, A. et al.: *Cell* 73:753–765 (1993). The autoradiograms of the washed and dried filters show the presence of functional human 2-5A-dependent RNase visible to about 80 kDa bands, in plants Z3, Z5, and Z6 (data not shown).

Antiviral activity of the plants are determined by rubbing celite powder coated with Tobacco mosaic virus (ATCC) and Tobacco Etch virus (from Dr. Amit Mitra, Nebraska). The plants are monitored for symptoms of viral infection on leaves from control and transgenic plants and are documented in photographs.

The plasmids described and the transformed Agrobacterium strains can be used to transform any other plants into virus-resistant plants. Exemplary of plants that may be transformed in accordance with the present invention include vegetable plants like corn, potato, carrot, lettuce, cabbage, broccoli, cauliflower, bean, squash, pumpkin, pepper, onion, tomato, pea, beet, celery, cucumber, turnip and radish plants, fruit plants like banana, apple, pear, plum, apricot, peach, nectarine, cherry, key lime, orange, lemon, lime, grapefruit, grape, berry, and melon plants, grain plants like wheat, barley, rice, oat and rye plants, grass, flowers, trees, shrubs and weeds such as laboratory weeds like Arabidopsis. It should therefore be understood that the present invention includes any plant into which any nucleotide sequence encoding an amino acid having antiviral activity has been introduced to form transgenic plants having immunity or resistance against viral infection.

Construction of pAM943:PKR (Construct A) and pAM943:MuPKR (construct B)

The plasmids pKS(+)PKR and pKS(+)muPKR, encoding wild type PKR and a lysine to arginine at codon 296 mutant form of PKR, respectively, present in *E. coli* cells (obtained from Dr. B. R. G. Williams, Cleveland Clinic, Cleveland, Ohio) are prepared by standard methods. See, for example, Katze, M. G. et al.: *Mol. Cell Biol.*, 11:5497–5505 (1991) for generation of muPKR, lysine-296→arginine mutant (K296R), by site specific mutagenesis as described. The PKR nucleotide sequence utilized to construct plasmids pKS(+)PKR and pKS(+)muPKR is depicted in FIG. 18. To determine the ability of a plant translation apparatus to synthesize PKR protein, capped PKR mRNA is produced from linearized pKS(+)PKR by in vitro transcription. The RNA is then translated in wheat germ extract (obtained from Promega Corp., Madison, Wis.) in the presence of $^{35}$S-methionine. Synthesis of the $^{35}$S-labeled PKR is detected in an autoradiogram of the dried, SDS/polyacrylamide gel.

The cDNAs encoding PKR and muPKR are excised from plasmids pKS(+)PKR and pKS(+)muPKR by digesting with KpnI and XbaI. The resulting DNA fragments containing the entire coding sequences for PKR and muPKR are purified from a low melting point agarose gel. To generate cDNAs containing at the 5' end XbaI and at the 3' end ClaI sites, the PKR cDNA and muPKR cDNA are then digested with ClaI and purified. The resulting digested PKR cDNA and muPKR cDNA are then force cloned into XbaI and ClaI digested pAM943 by DNA ligation. The resulting plasmids, FIG. 13, constructs A and B, are used to transform *Agrobacterium tumefaciens* strain LBA4404 (Clonetech, Palo Alto, Calif.). Recombinant plasmids are prepared from transformed *Agrobacterium tumefaciens* bacteria by standard methods and the presence of PKR and muPKR cDNA is confirmed by PCR analysis and restriction enzyme digests of the isolated plasmids.

Construction of pAM943:Synthetase (construct C)

The plasmid ptac-15 containing the human cDNA illustrated in FIG. 20 for a small form of 2-5A-synthetase (producing a 1.8 kb mRNA) (obtained from Dr. B. R. G. Williams, Cleveland Clinic, Cleveland, Ohio) is prepared by standard methods and is digested with BamHI and EcoRI. The synthetase cDNA is purified from a low melting point agarose gel by standard methods and is then subcloned into plasmid pKS(+) (Strategene, La Jolla, Calif.) in BamHI and EcoRI sites. The resulting recombinant plasmid DNA (pKS (+)synthetase) is digested with XbaI and ClaI and the 2-5A synthetase cDNA is purified from a low melting point agarose gel and is then subcloned into XbaI and ClaI digested pAM943 to produce construct C (FIG. 13). Recombinant plasmids are prepared from transformed *Agrobacterium tumefaciens* bacteria by standard methods and the presence of 2-5A-synthetase cDNA is confirmed by PCR analysis and by restriction enzyme digests of the isolated plasmids.

Construction of pAM943:2-5Adep.RNase sense (construct D) and pAM943:2-5Adep.RNase antisense (construct D/a)

The plasmid pKS(+)ZC5 encoding a complete coding sequence for human 2-5A-dependent RNase is digested with HindIII. The 2.5 kbp cDNA for 2-5A-dependent RNase is purified in a low melting point agarose gel and is then subcloned in HindIII digested pAM943 in both sense (forward) and antisense (reverse) orientations to produce pAM943:2-5Adep.RNase sense (construct D) and pAM943:2-5Adep.RNase antisense (construct D/a), as depicted in FIG. 13D and D/a, respectively. Transformed Agrobacterium are determined to contain the 2-5A-dependent RNase cDNA by restriction enzyme digests and by PCR analysis.

Construction of pAM822:2-5Adep.RNase antisense (construct E)

Polymerase chain reactions (PCR) are performed on plasmid pKS(+)ZC5 encoding human 2-5A-dependent RNase to generate HindIII and BamHI sites on the two ends of the cDNA and to reduce 5' and 3' untranslated sequences. The PCR primers used are:

ID SEQ NO:7:

2DR-5 5'-TCATGCTCGAGAAGCTTGGATCCACC-ATGGAGAGCAGGGAT-3'; and

ID SEQ NO:8:

H2DR-4 5'-GATACTCGAGAAGCTTGCATCCTCAT-CAGCACCCAGGGCTGG-3'.

The PCR product (about 2.25 kbp) is purified on a low melting point agarose gel and is then digested with HindIII and is then subcloned into HindIII digested plasmid pKS(+). The resulting plasmid, pKS:pZC5 is digested with BamHI and the 2-5A-dependent RNase cDNA fragment is purified and cloned into BglII digested pAM822. Recombinants isolated in the reverse (antisense) orientation give pAM822:2-5Adep.RNase antisense (construct E). See FIG. 13E.

As to the nucleotide sequences disclosed herein, A means adenine; C means cytosine; G means guanine; T means thymine; and U means uracil. With respect to the disclosed amino acid sequences, A means ala or alanine; R means arg or arginine; N means asn or asparagine; D means asp or aspartic acid; C means cys or cysteine; E means glu or glutamic acid; Q means gln or glutamine; G means gly or glycine; H means his or histidine; I means ile or isoleucine; L means leu or leucine; K means lys or Lysine; M means met or methionine; F means phe or phenylalanine; P means pro or proline; S means ser or serine; T means thr or threonine; W means trp or tryptophan; Y means tyr or tyrosine; and V means val or valine.

The following listed materials are on deposit under the terms of the Budapest Treaty with the American Type Culture Collection (ATCC), 12301 Parklawn Drive, Rockville, Md. 20852, U.S.A., and have been assigned the following Accession Numbers.

| Plasmid DNA | ATCC No. | Deposit Date | Viability Date |
| --- | --- | --- | --- |
| pAM943:PK68 (Plasmid pA) | 75996 | 21 Dec. 1994 | 13 Jan. 1995 |
| pAM943:muPK68 (Plasmid pB) | 75997 | 21 Dec. 1994 | 13 Jan. 1995 |
| pAM943:Synthetase (Plasmid pC) | 75998 | 21 Dec. 1994 | 13 Jan. 1995 |
| pAM943:2-5Adep.RNase (Plasmid pD) | 75999 | 21 Dec. 1994 | 13 Jan. 1995 |
| Z9*, expressing, human 2-5A-dependent RNase cDNA | 97047 | 01 Feb. 1995 | 07 Feb. 1995 |
| 15/2** expressing human 2-5A-synthetase cDNA | 97041 | 01 Feb. 1995 | 07 Feb. 1995 |

*this seed contains construct D, shown in FIG. 13, which is pAM943:2-5Adep.RNase
**this seed contains construct C, shown in FIG. 13, which is pAM943:Synthetase

TABLE 1

Human 2-5A-depedent RNase

SEQ ID NO: 1:, SEQ ID NO: 2:, SEQ ID NO: 3: and SEQ ID NO: 4:

```
       -103 aatcccaacttacactcaaagct
tctttgattaagtgctaggagataaatttgcattttctca
aggaaaaggctaaaagtggtagcaggtggcatttaccgtc
ATG   GAG   AGC   AGG   GAT   CAT   AAC   AAC   CCC   CAG        30
Met   Glu   Ser   Arg   Asp   His   Asn   Asn   Pro   Gln        10
```

TABLE 1-continued

Human 2-5A-depedent RNase

| | | | | | | | | | |
|---|---|---|---|---|---|---|---|---|---|
| GAG | GGA | CCC | ACG | TCC | TCC | AGC | GGT | AGA | AGG | 60 |
| Glu | Gly | Pro | Thr | Ser | Ser | Ser | Gly | Arg | Arg | 20 |
| GCT | GCA | GTG | GAA | GAC | AAT | CAC | TTG | CTG | ATT | 90 |
| Ala | Ala | Val | Glu | Asp | Asn | His | Leu | Leu | Ile | 30 |
| AAA | GCT | GTT | CAA | AAC | GAA | GAT | GTT | GAC | CTG | 120 |
| Lys | Ala | Val | Gln | Asn | Glu | Asp | Val | Asp | Leu | 40 |
| GTC | CAG | CAA | TTG | CTG | GAA | GGT | GGA | GCC | AAT | 150 |
| Val | Gln | Gln | Leu | Leu | Glu | Gly | Gly | Ala | Asn | 50 |
| GTT | AAT | TTC | CAG | GAA | GAG | GAA | GGG | GGC | TGG | 180 |
| Val | Asn | Phe | Gln | Glu | Glu | Glu | Gly | Gly | Trp | 60 |
| ACA | CCT | CTG | CAT | AAC | GCA | GTA | CAA | ATG | AGC | 210 |
| Thr | Pro | Leu | His | Asn | Ala | Val | Gln | Met | Ser | 70 |
| AGG | GAG | GAC | ATT | GTG | GAA | CTT | CTG | CTT | CGT | 240 |
| Arg | Glu | Asp | Ile | Val | Glu | Leu | Leu | Leu | Arg | 80 |
| CAT | GGT | GCT | GAC | CCT | GTT | CTG | AGG | AAG | AAG | 270 |
| His | Gly | Ala | Asp | Pro (CCT)* | Val | Leu | Arg | Lys | Lys | 90 |
| AAT | GGG | GCC | ACG | CTT | TTT | ATC | CTC | GCA | GCG | 300 |
| Asn | Gly | Ala | Thr | Leu (Pro)* | Phe | Ile | Leu | Ala | Ala | 100 |
| ATT | GCG | GGG | AGC | GTG | AAG | CTG | CTG | AAA | CTT | 330 |
| Ile | Ala | Gly | Ser | Val | Lys | Leu | Leu | Lys | Leu | 110 |
| TTC | CTT | TCT | AAA | GGA | GCA | GAT | GTC | AAT | GAG | 360 |
| Phe | Leu | Ser | Lys | Gly | Ala | Asp | Val | Asn | Glu | 120 |
| TGT | GAT | TTT | TAT | GGC | TTC | ACA | GCC | TTC | ATG | 390 |
| Cys | Asp | Phe | Tyr | Gly | Phe | Thr | Ala | Phe | Met | 130 |
| GAA | GCC | GCT | GTG | TAT | GGT | AAG | GTC | AAA | GCC | 420 |
| Glu | Ala | Ala | Val | Tyr | Gly | Lys | Val | Lys | Ala | 140 |
| CTA | AAA | TTC | CTT | TAT | AAG | AGA | GGA | GCA | AAT | 450 |
| Leu | Lys | Phe | Leu | Tyr | Lys | Arg | Gly | Ala | Asn | 150 |
| GTG | AAT | TTG | AGG | CGA | AAG | ACA | AAG | GAG | GAT | 480 |
| Val | Asn | Leu | Arg | Arg | Lys | Thr | Lys | Glu | Asp | 160 |
| CAA | GAG | CGG | CTG | AGG | AAA | GGA | GGG | GCC | ACA | 510 |
| Gln | Glu | Arg | Leu | Arg | Lys | Gly | Gly | Ala | Thr | 170 |
| GCT | CTC | ATG | GAC | GCT | GCT | GAA | AAA | GGA | CAC | 540 |
| Ala | Leu | Met | Asp | Ala | Ala | Glu | Lys | Gly | His | 180 |
| GTA | GAG | GTC | TTG | AAG | ATT | CTC | CTT | GAT | GAG | 570 |
| Val | Glu | Val | Leu | Lys | Ile | Leu | Leu | Asp | Glu | 190 |
| ATG | GGG | GCA | GAT | GTA | AAC | GCC | TGT | GAC | AAT | 600 |
| Met | Gly | Ala | Asp | Val | Asn | Ala | Cys | Asp | Asn | 200 |
| ATG | GGC | AGA | AAT | GCC | TTG | ATC | CAT | GCT | CTC | 630 |
| Met | Gly | Arg | Asn | Ala | Leu | Ile | His | Ala | Leu | 210 |
| CTG | AGC | TCT | GAC | GAT | AGT | GAT | GTG | GAG | GCT | 660 |
| Leu | Ser | Ser | Asp | Asp | Ser | Asp | Val | Glu | Ala | 220 |
| ATT | ACG | CAT | CTG | CTG | CTG | GAC | CAT | GGG | GCT | 690 |
| Ile | Thr | His | Leu | Leu | Leu | Asp | His | Gly | Ala | 230 |
| GAT | GTC | AAT | GTG | AGG | GGA | GAA | AGA | GGG | AAG | 720 |
| Asp | Val | Asn | Val | Arg | Gly | Glu | Arg | Gly | Lys | 240 |
| ACT | CCC | CTG | ATC | CTG | GCA | GTG | GAG | AAG | AAG | 750 |
| Thr | Pro | Leu | Ile | Leu | Ala | Val | Glu | Lys | Lys | 250 |
| CAC | TTG | GGT | TTG | GTG | CAG | AGG | CTT | CTG | GAG | 780 |
| His | Leu | Gly | Leu | Val | Gln | Arg | Leu | Leu | Glu | 260 |
| CAA | GAG | CAC | ATA | GAG | ATT | AAT | GAC | ACA | GAC | 810 |
| Gln | Glu | His | Ile | Glu | Ile | Asn | Asp | Thr | Asp | 270 |
| AGT | GAT | GGC | AAA | ACA | GCA | CTG | CTG | CTT | GCT | 840 |
| Ser | Asp | Gly | Lys | Thr | Ala | Leu | Leu | Leu | Ala | 280 |
| GTT | GAA | CTC | AAA | CTG | AAG | AAA | ATC | GCC | GAG | 870 |
| Val | Glu | Leu | Lys | Leu | Lys | Lys | Ile | Ala | Glu | 290 |
| TTG | CTG | TGC | AAA | CGT | GGA | GCC | AGT | ACA | GAT | 900 |
| Leu | Leu | Cys | Lys | Arg | Gly | Ala | Ser | Thr | Asp | 300 |
| TGT | GGG | GAT | CTT | GTT | ATG | ACA | GCG | AGG | CGG | 930 |
| Cys | Gly | Asp | Leu | Val | Met | Thr | Ala | Arg | Arg | 310 |
| AAT | TAT | GAC | CAT | TCC | CTT | GTG | AAG | GTT | CTT | 960 |
| Asn | Tyr | Asp | His | Ser | Leu | Val | Lys | Val | Leu | 320 |
| CTC | TCT | CAT | GGA | GCC | AAA | GAA | GAT | TTT | CAC | 990 |
| Leu | Ser | His | Gly | Ala | Lys | Glu | Asp | Phe | His | 330 |
| CCT | CCT | GCT | GAA | GAC | TGG | AAG | CCT | CAG | AGC | 1020 |
| Pro | Pro | Ala | Glu | Asp | Trp | Lys | Pro | Gln | Ser | 340 |
| TCA | CAC | TGG | GGG | GCA | GCC | CTG | AAG | GAT | CTC | 1050 |
| Ser | His | Trp | Gly | Ala | Ala | Leu | Lys | Asp | Leu | 350 |
| CAC | AGA | ATA | TAC | CGC | CCT | ATG | ATT | GGC | AAA | 1080 |
| His | Arg | Ile | Tyr | Arg | Pro | Met | Ile | Gly | Lys | 360 |
| CTC | AAG | TTC | TTT | ATT | GAT | GAA | AAA | TAC | AAA | 1110 |
| Leu | Lys | Phe | Phe | Ile | Asp | Glu | Lys | Tyr | Lys | 370 |
| ATT | GCT | GAT | ACT | TCA | GAA | GGA | GGC | ATC | TAC | 1140 |
| Ile | Ala | Asp | Thr | Ser | Glu | Gly | Gly | Ile | Tyr | 380 |
| CTG | GGG | TTC | TAT | GAG | AAG | CAA | GAA | GTA | GCT | 1170 |

TABLE 1-continued

Human 2-5A-depedent RNase

| | | | | | | | | | | |
|---|---|---|---|---|---|---|---|---|---|---|
| Leu | Gly | Phe | Tyr | Glu | Lys | Gln | Glu | Val | Ala | 390 |
| GTG | AAG | ACG | TTC | TGT | GAG | GGC | AGC | CCA | CGT | 1200 |
| Val | Lys | Thr | Phe | Cys | Glu | Gly | Ser | Pro | Arg | 400 |
| GCA | CAG | CGG | GAA | GTC | TCT | TGT | CTG | CAA | AGC | 1230 |
| Ala | Gln | Arg | Glu | Val | Ser | Cys | Leu | Gln | Ser | 410 |
| AGC | CGA | GAG | AAC | AGT | CAC | TTG | GTG | ACA | TTC | 1260 |
| Ser | Arg | Glu | Asn | Ser | His | Leu | Val | Thr | Phe | 420 |
| TAT | GGG | AGT | GAG | AGC | CAC | AGG | GGC | CAC | TTG | 1290 |
| Tyr | Gly | Ser | Glu | Ser | His | Arg | Gly | His | Leu | 430 |
| TTT | GTG | TGT | GTC | ACC | CTC | TGT | GAG | CAG | ACT | 1320 |
| Phe | Val | Cys | Val | Thr | Leu | Cys | Glu | Gln | Thr | 440 |
| CTG | GAA | GCG | TGT | TTG | GAT | GTG | CAC | AGA | GGG | 1350 |
| Leu | Glu | Ala | Cys | Leu | Asp | Val | His | Arg | Gly | 450 |
| GAA | GAT | GTG | GAA | AAT | GAG | GAA | GAT | GAA | TTT | 1380 |
| Glu | Asp | Val | Glu | Asn | Glu | Glu | Asp | Glu | Phe | 460 |
| GCC | CGA | AAT | GTC | CTG | TCA | TCT | ATA | TTT | AAG | 1410 |
| Ala | Arg | Asn | Val | Leu | Ser | Ser | Ile | Phe | Lys | 470 |
| GCT | GTT | CAA | GAA | CTA | CAC | TTG | TCC | TGT | GGA | 1440 |
| Ala | Val | Gln | Glu | Leu | His | Leu | Ser | Cys | Gly | 480 |
| TAC | ACC | CAC | CAG | GAT | CTG | CAA | CCA | CAA | AAC | 1470 |
| Tyr | Thr | His | Gln | Asp | Leu | Gln | Pro | Gln | Asn | 490 |
| ATC | TTA | ATA | GAT | TCT | AAG | AAA | GCT | GCT | CAC | 1500 |
| Ile | Leu | Ile | Asp | Ser | Lys | Lys | Ala | Ala | His | 500 |
| CTG | GCA | GAT | TTT | GAT | AAG | AGC | ATC | AAG | TGG | 1530 |
| Leu | Ala | Asp | Phe | Asp | Lys | Ser | Ile | Lys | Trp | 510 |
| GCT | GGA | GAT | CCA | CAG | GAA | GTC | AAG | AGA | GAT | 1560 |
| Ala | Gly | Asp | Pro | Gln | Glu | Val | Lys | Arg | Asp | 520 |
| CTA | GAG | GAC | CTT | GGA | CGG | CTG | GTC | CTC | TAT | 1590 |
| Leu | Glu | Asp | Leu | Gly | Arg | Leu | Val | Leu | Tyr | 530 |
| GTG | GTA | AAG | AAG | GGA | AGC | ATC | TCA | TTT | GAG | 1620 |
| Val | Val | Lys | Lys | Gly | Ser | Ile | Ser | Phe | Glu | 540 |
| GAT | CTG | AAA | GCT | CAA | AGT | AAT | GAA | GAG | GTG | 1650 |
| Asp | Leu | Lys | Ala | Gln | Ser | Asn | Glu | Glu | Val | 550 |
| GTT | CAA | CTT | TCT | CCA | GAT | GAG | GAA | ACT | AAG | 1680 |
| Val | Gln | Leu | Ser | Pro | Asp | Glu | Glu | Thr | Lys | 560 |
| GAC | CTC | ATT | CAT | CGT | CTC | TTC | CAT | CCT | GGG | 1710 |
| Asp | Leu | Ile | His | Arg | Leu | Phe | His | Pro | Gly | 570 |
| GAA | CAT | GTG | AGG | GAC | TGT | CTG | AGT | GAC | CTG | 1740 |
| Glu | His | Val | Arg | Asp | Cys | Leu | Ser | Asp | Leu | 580 |
| CTG | GGT | CAT | CCC | TTC | TTT | TGG | ACT | TGG | GAG | 1770 |
| Leu | Gly | His | Pro | Phe | Phe | Trp | Thr | Trp | Glu | 590 |
| AGC | CGC | TAT | AGG | ACG | CTT | CGG | AAT | GTG | GGA | 1800 |
| Ser | Arg | Tyr | Arg | Thr | Leu | Arg | Asn | Val | Gly | 600 |
| AAT | GAA | TCC | GAC | ATC | AAA | ACA | CGA | AAA | TCT | 1830 |
| Asn | Glu | Ser | Asp | Ile | Lys | Thr | Arg | Lys | Ser | 610 |
| GAA | AGT | GAG | ATC | CTC | AGA | CTA | CTG | CAA | CCT | 1860 |
| Glu | Ser | Glu | Ile | Leu | Arg | Leu | Leu | Gln | Pro | 620 |
| GGG | CCT | TCT | GAA | CAT | TCC | AAA | AGT | TTT | GAC | 1890 |
| Gly | Pro | Ser | Glu | His | Ser | Lys | Ser | Phe | Asp | 630 |
| AAG | TGG | ACG | ACT | AAG | ATT | AAT | GAA | TGT | GTT | 1920 |
| Lys | Trp | Thr | Thr | Lys | Ile | Asn | Glu | Cys | Val | 640 |
| ATG | AAA | AAA | ATG | AAT | AAG | TTT | TAT | GAA | AAA | 1950 |
| Met | Lys | Lys | Met | Asn | Lys | Phe | Tyr | Glu | Lys | 650 |
| AGA | GGC | AAT | TTC | TAC | CAG | AAC | ACT | GTG | GGT | 1980 |
| Arg | Gly | Asn | Phe | Tyr | Gln | Asn | Thr | Val | Gly | 660 |
| GAT | CTG | CTA | AAG | TTC | ATC | CGG | AAT | TTG | GGA | 1210 |
| Asp | Leu | Leu | Lys | Phe | Ile | Arg | Asn | Leu | Gly | 670 |
| GAA | CAC | ATT | GAT | GAA | GAA | AAG | CAT | AAA | AAG | 2040 |
| Glu | His | Ile | Asp | Glu | Glu | Lys | His | Lys | Lys | 680 |
| ATG | AAA | TTA | AAA | ATT | GGA | GAC | CCT | TCC | CTG | 2070 |
| Met | Lys | Leu | Lys | Ile | Gly | Asp | Pro | Ser | Leu | 690 |
| TAT | TTT | CAG | AAG | ACA | TTT | CCA | GAT | CTG | GTG | 2100 |
| Tyr | Phe | Gln | Lys | Thr | Phe | Pro | Asp | Leu | Val | 700 |
| ATC | TAT | GTC | TAC | ACA | AAA | CTA | CAG | AAC | ACA | 2130 |
| Ile | Tyr | Val | Tyr | Thr | Lys | Leu | Gln | Asn | Thr | 710 |
| GAA | TAT | AGA | AAG | CAT | TTC | CCC | AAA | ACC | CAC | 2160 |
| Glu | Tyr | Arg | Lys | His | Phe | Pro | Lys | Thr | His | 720 |
| AGT | CCA | AAC | AAA | CCT | CAG | TGT | GAT | GGA | GCT | 2190 |
| Ser | Pro | Asn | Lys | Pro | Gln | Cys | Asp | Gly | Ala | 730 |
| GGT | GGG | GCC | AGT | GGG | TTG | GCC | AGC | CCT | GGG | 2220 |
| Gly | Gly | Ala | Ser | Gly | Leu | Ala | Ser | Pro | Gly | 740 |
| TGC | 2223 | | | | | | | | | |
| Cys | 741 | | | | | | | | | |

| | |
|---|---|
| tgatggactgatttgctggagttcagggaactact | 2258 |
| tattagctgtagagtccttggcaaatcacaacat | 2292 |
| tctgggcctttaactcaccaggttgcttgtgagggat | 2330 |
| gagttgcatagctgatatgtcagtccctggcatcgtg | 2367 |
| tattccatatgtctataacaaaagcaatatatacccag | 2405 |

TABLE 1-continued

Human 2-5A-depedent RNase

| | |
|---|---|
| actacactagtccataagctttacccactaactggga | 2442 |
| ggacattctgctaagattccttttgtcaattgcaccaa | 2480 |
| aagaatgagtgccttgacccctaatgctgcatatgtt | 2517 |
| acaattctctcacttaattttcccaatgatcttgcaaa | 2555 |
| acagggattatcatccccatttaagaactgaggaacc | 2592 |
| tgagactcagagagtgtgagctactggcccaagattat | 2630 |
| tcaatttatacctagcactttataaatttatgtggtg | 2667 |
| ttattggtacctctcatttgggcaccttaaaacttaac | 2705 |
| tatcttccagggctcttccagatgaggcccaaaacat | 2742 |
| atataggggttccaggaatctcattcattcattcagta | 2780 |
| tttattgagcatctagtataagtctgggcactggatg | 2817 |
| catgaatt | 2825 |

*It is believed that the original codon number 95, i.e. CTT encoding the amino acid number 95, i.e. leucine, is correct, however the alternative codon in parenthesis shown above codon number 95, i.e. CCT encoding the alternative amino acid in parenthesis shown below amino acid number 95, i.e. proline may also exist at this position (see page 81).
SEQ ID NO: 1: represents the DNA encoding sequence for the human 2-5A-dependent RNase protein. SEQ ID NO: 2: represents the amino acid sequence encoded by the DNA sequence designated SEQ ID NO: 1:. SEQ ID NO: 3: represents the DNA sequence, represented by SEQ ID NO: 1:, having the alternative codon number 95, CCT. SEQ ID NO: 4: represents the amino acid sequence encoded by SEQ ID NO: 3:, having the alternative amino acid number 95, proline.

TABLE 2

Murine 2-5A-dependent RNase (partial)

| | |
|---|---|
| SEQ ID NO:5. and SEQ ID NO:6: | |
| -163 | |
| attcggcacgaggaaggtgccaattactagctcccttctttattcgtgta | |
| ctgatgagatgtcagaagacagaacataatcagcccaatccctactccaa | |
| gactctcattgtgtcccaagaaacacacgtgtgcatttcccaaggaaaa | |
| ggcattgaggacc ATG GAG ACC CCG GAT TAT | 18 |
| Met Glu Thr Pro Asp Tyr | 6 |
| AAC ACA CCT GGA GGT GGA ACC CCA TCA GCG | 48 |
| Asn Thr Pro Gln Gly Gly Thr Pro Ser Ala | 16 |
| GGA AGT CAG AGG ACC GTT GTC GAA GAT GAT | 78 |
| Gly Ser Gln Arg Thr Val Val Glu Asp Asp | 26 |
| TCT TCG TTG ATC AAA GCT GTT CAG AAG GGA | 108 |
| Ser Ser Leu Ile Lys Ala Val Gln Lys Gly | 36 |
| GAT GTT GTC AGG GTC CAG CAA TTG TTA GAA | 138 |
| Asp Val Val Arg Val Gln Gln Leu Leu Glu | 46 |
| AAA GGG GCT GAT GCC AAT GCC TGT GAA GAC | 168 |
| Lys Gly Ala Asp Ala Asn Ala Cys Glu Asp | 56 |
| ACC TGG GGC TGG ACA CCT TTG CAC AAC GCA | 198 |
| Thr Trp Gly Trp Thr Pro Leu His Asn Ala | 66 |
| GTG CAA GCT GGC AGG GTA GAC ATT GTG AAC | 228 |
| Val Gln Ala Gly Arg Val Asp Ile Val Asn | 76 |
| CTC CTG CTT AGT CAT GGT GCT GAC CCT CAT | 258 |
| Leu Leu Leu Ser His Gly Ala Asp Pro His | 86 |
| CGG AGG AAG AAG AAT GGG GCC ACC CCC TTC | 288 |
| Arg Arg Lys Lys Asn Gly Ala Thr Pro Phe | 96 |
| ATC ATT GCT GGG ATC CAG GGA GAT GTG AAA | 318 |
| Ile Ile Ala Gly Ile Gln Gly Asp Val Lys | 106 |
| CTG CTC GAG ATT CTC CTC TCT TGT GGT GCA | 348 |
| Leu Leu Glu Ile Leu Leu Ser Cys Gly Ala | 116 |
| GAC GTC AAT GAG TGT GAC GAG AAC GGA TTC | 378 |
| Asp Val Asn Glu Cys Asp Glu Asn Gly Phe | 126 |
| ACG GCT TTC ATG GAA GCT GCT GAG CGT GGT | 408 |
| Thr Ala Phe Met Glu Ala Ala Glu Arg Gly | 136 |
| AAC GCT GAA GCC TTA AGA TTC CTT TTT GCT | 438 |
| Asn Ala Glu Ala Leu Arg Phe Leu Phe Ala | 146 |
| AAG GGA GCC AAT GTG AAT TTG CGA CGA CAG | 468 |
| Lys Gly Ala Asn Val Asn Leu Arg Arg Gln | 156 |
| ACA ACG AAG GAC AAA AGG CGA TTG AAG CAA | 498 |
| Thr Thr Lys Asp Lys Arg Arg Leu Lys Gln | 166 |
| GGA GGC GCC ACA GCT CTC ATG AGC GCT GCT | 528 |
| Gly Gly Ala Thr Ala Leu Met Ser Ala Ala | 176 |
| GAG AAG GGC CAC CTG GAA GTC CTG AGA ATT | 558 |
| Glu Lys Gly His Leu Glu Val Leu Arg Ile | 186 |
| CTC CTC AAT GAC ATG GCA GCA GAA GTC GAT | 588 |
| Leu Leu Asn Asp Met Lys Ala Glu Val Asp | 196 |
| GCT CGG GAC AAC ATG GGC AGA AAT GCC CTG | 618 |

TABLE 2-continued

Murine 2-5A-dependent RNase (partial)

| | |
|---|---|
| Ala Arg Asp Asn Met Gly Arg Asn Ala Leu | 206 |
| ATC CGT ACT CTG CTG AAC TGG GAT TGT GAA | 648 |
| Ile Arg Thr Leu Leu Asn Trp Asp Cys Glu | 216 |
| AAT GTG GAG GAG ATT ACT TCA ATC CTG ATT | 678 |
| Asn Val Glu Glu Ile Thr Ser Ile Leu Ile | 226 |
| CAG CAC GGG GCT GAT GTT AAC GTG AGA GGA | 708 |
| Gln His Gly Ala Asp Val Asn Val Arg Gly | 236 |
| GAA AGA GGG AAA ACA CCC CTC ATC GCA GCA | 738 |
| Glu Arg Gly Lys Thr Pro Leu Ile Ala Ala | 246 |
| GTG GAG AGG AAG CAC ACA GGC TTG GTG CAG | 768 |
| Val Glu Arg Lys His Thr Gly Leu Val Gln | 256 |
| ATG CTC CTG AGT CGG GAA GGC ATA AAC ATA | 798 |
| Met Leu Leu Ser Arg Glu Gly Ile Asn Ile | 266 |
| GAT GCC AGG GAT AAC GAG GGC AAG ACA GCT | 828 |
| Asp Ala Arg Asp Asn Glu Gly Lys Thr Ala | 276 |
| CTG CTA ATT GCT GTT GAT AAA CAA CTG AAG | 858 |
| Leu Leu Ile Ala Val Asp Lys Gln Leu Lys | 286 |
| GAA ATT GTC CAG TTG CTT CTT GAA AAG GGA | 888 |
| Glu Ile Val Gln Leu Leu Leu Glu Lys Gly | 296 |
| GCT GAT AAG TGT GAC GAT CTT GTT TGG ATA | 918 |
| Ala Asp Lys Cys Asp Asp Leu Val Trp Ile | 306 |
| GCC AGG AGG AAT CAT GAC TAT CAC CTT GTA | 948 |
| Ala Arg Arg Asn His Asp Tyr His Leu Val | 316 |
| AAG CTT CTC CTC CCT TAT GTA GCT AAT CCT | 978 |
| Lys Leu Leu Leu Pro Tyr Val Ala Asn Pro | 326 |
| GAC ACC GAC CCT CCT GCT GGA GAC TGG TCG | 1008 |
| Asp Thr Asp Pro Pro Ala Gly Asp Trp Ser | 336 |
| CCT CAC AGT TCA CGT TGG GGG ACA GCC TTG | 1038 |
| Pro His Ser Ser Arg Trp Gly Thr Ala Leu | 346 |
| AAA AGC CTC CAC AGT ATG ACT CGA CCC ATG | 1068 |
| Lys Ser Leu His Ser Met Thr Arg Pro Met | 356 |
| ATT GGC AAA CTC AAG ATC TTC ATT CAT GAT | 1098 |
| Ile Gly Lys Leu Lys Ile Phe Ile His Asp | 366 |
| GAC TAT AAA ATT GCT GGC ACT TCC GAA GGG | 1128 |
| Asp Tyr Lys Ile Ala Gly Thr Ser Glu Gly | 376 |
| GCT GTC TAC CTA GGG ATC TAT GAC AAT CGA | 1158 |
| Ala Val Tyr Leu Gly Ile Tyr Asp Asn Arg | 386 |
| GAA GTG GCT GTG AAG GTC TTC CGT GAG AAT | 1188 |
| Glu Val Ala Val Lys Val Phe Arg Glu Asn | 396 |
| AGC CCA CGT GGA TGT AAG GAA GTC TCT TGT | 1218 |
| Ser Pro Arg Gly Cys Lys Glu Val Ser Cys | 406 |
| CTG CGG GAC TGC GGT GAC CAC AGT AAC TTA | 1248 |
| Leu Arg Asp Cys Gly Asp His Ser Asn Leu | 416 |
| GTG GCT TTC TAT GGA AGA GAG GAC GAT AAG | 1278 |
| Val Ala Phe Tyr Gly Arg Glu Asp Asp Lys | 426 |
| GGC TGT TTA TAT GTG TGT GTG TCC CTG TGT | 1308 |

TABLE 2-continued

Murine 2-5A-dependent RNase (partial)

| | |
|---|---|
| Gly Cys Leu Tyr Val Cys Val Ser Leu Cys | 436 |
| GAG TGG ACA CTG GAA GAG TTC CTG AGG TTG | 1338 |
| Glu Trp Thr Leu Glu Glu Phe Leu Arg Leu | 446 |
| CCC AGA GAG GAA CCT GTG GAG AAC GGG GAA | 1368 |
| Pro Arg Glu Glu Pro Val Glu Asn Gly Glu | 456 |
| GAT AAG TTT GCC CAC AGC ATC CTA TTA TCT | 1398 |
| Asp Lys Phe Ala His Ser Ile Leu Leu Ser | 466 |
| ATA TTT GAG GGT GTT CAA AAA CTA CAC TTG | 1428 |
| Ile Phe Glu Gly Val Gln Lys Leu His Leu | 476 |
| CAT GGA TAT TCC CAT CAG GAC CTG CAA CCA | 1458 |
| His Gly Tyr Ser His Gln Asp Leu Gln Pro | 486 |
| CAA AAC ATC TTA ATA GAT TCC AAG AAA GCT | 1488 |
| Gln Asn Ile Leu Ile Asp Ser Lys Lys Ala | 496 |
| GTC CGG CTG GCA GAT TTT GAT CAG AGC ATC | 1518 |
| Val Arg Leu Ala Asp Phe Asp Gln Ser Ile | 506 |
| CGA TGG ATG GGA GAG TCA CAG ATG GTC AGG | 1548 |
| Arg Trp Met Gly Glu Ser Gln Met Val Arg | 516 |
| AGA GAC TTG GAG GAT CTT GGA CGG CTG GTT | 1578 |
| Arg Asp Leu Glu Asp Leu Gly Arg Leu Val | 526 |
| CTC TAC GTG GTA ATG AAA GGT GAG ATC CCC | 1608 |
| Leu Tyr Val Val Met Lys Gly Glu Ile Pro | 536 |
| TTT GAG ACA CTA AAG ACT CAG AAT GAT GAA | 1638 |
| Phe Glu Thr Leu Lys Thr Gln Asn Asp Glu | 546 |
| GTG CTG CTT ACA ATG TCT CCA GAT GAG GAG | 1668 |
| Val Leu Leu Thr Met Ser Pro Asp Glu Glu | 556 |
| ACT AAG GAC CTC ATT CAT TGC CTG TTT TCT | 1698 |
| Thr Lys Asp Leu Ile His Cyc Leu Phe Ser | 566 |
| CCT GGA GAA AAT GTC AAG AAC TGC CTG GTA | 1728 |
| Pro Gly Glu Asn Val Lys Asn Cys Leu Val | 576 |
| GAC CTG CTT GGC CAT CCT TTC TTT TGG ACT | 1758 |
| Asp Leu Leu Gly His Pro Phe Phe Trp Thr | 586 |
| TGG GAG AAC CGC TAT AGA ACA CTC CGG AAT | 1788 |
| Trp Glu Asn Arg Tyr Arg Thr Leu Arg Asn | 596 |
| GTG GGA AAT GAA TCT GAC ATC AAA GTA CGG | 1818 |
| Val Gly Asn Glu Ser Asp Ile Lys Val Arg | 606 |
| AAA TGT AAA AGT GAT CTT CTC AGA CTA CTG | 1848 |
| Lys Cys Lys Ser Asp Leu Leu Arg Leu Leu | 616 |
| CAG CAT CAG ACA CTT GAG CCT CCC AGA AGC | 1878 |
| Gln His Gln Thr Leu Glu Pro Pro Arg Ser | 626 |
| TTT GAC CAG TGG ACA TCT AAG ATC GAC AAA | 1908 |
| Phe Asp Gln Trp Thr Ser Lys Ile Asp Lys | 636 |
| AAT GTT ATG GAT GAA ATG AAT CAT TTC TAC | 1938 |
| Asn Val Met Asp Glu Met Asn His Phe Tyr | 646 |
| GAA AAG AGA AAA AAA AAC CCT TAT CAG GAT | 1968 |
| Glu Lys Arg Lys Lys Asn Pro Tyr Gln Asp | 656 |
| ACT GTA GGT GAT CTG CTG AAG TTT ATT CGG | 1998 |
| Thr Val Gly Asp Leu Leu Lys Phe Ile Arg | 666 |
| AAT ATA GGC GAA CAC ATC AAT GAG GAA AAA | 2028 |
| Asn Ile Gly Glu His Ile Asn Glu Glu Lys | 676 |
| AAG CGG GGG | 2037 |
| Lys Arg Gly | 679 |

SEQ ID NO:5: represents the DNA sequence encoding Murine 2-5A-dependent RNase (partial). SEQ ID NO:6: represents the amino acid sequence encoded by SEQ ID NO:5:.

Example III

The Ti based binary vector, plasmid pAM943 (Mitra, A. et al.: *Plant Mol Biol,* 26:85–93 (1994)) containing a dual promoter consisting of the upstream region of the gene for adenyl methyl transferase (AMT) of Chlorella virus and the minimum length of 35S promoter is used as the cloning vector for this study. See FIG. 13. The vector also contains the gene for kanamycin resistance for selection of the transformed plants. Bacterial strains used are the *Agrobacterium tumefaciens* strain, LBA4404 and the *Escherichia coli* strain MM294 (Clonetech). The human cDNA encoding a low molecular weight form of 2-5A synthetase is a gift from Drs. B. R. G. Williams (Cleveland, Ohio) and Dirk Gewert (London, England) and the cDNA for human RNase L is previously reported in Zhou, A. et al.: *Cell,* 72:753–765 (1993).

The plant tissue culture medium, Murashige and Skoog's ready mix (MS media), is from Sigma Co. Seeds of *Nicoti-ana tabacum* cv. Wisconsin 38 are grown aseptically in MS in 0.8% agarose medium supplemented with 3% sucrose (MSO medium) in plastic boxes in a growth chamber at about 25° C. under cycles consisting of about 16 hours of light and about eight hours of dark cycle.

The XbaI-ClaI fragment of human cDNA for 2-5A synthetase is directionally cloned at XbaI, ClaI sites of pAM943. See FIG. 13C. The human cDNA for RNase L is subcloned at the HindIII site of pAM943 and the recombinant plasmid with the cDNA in sense orientation is selected. See FIG. 13D. The plasmids are grown in MM294 strain of *E. coli* and then introduced into *Agrobacterium tumefaciens* LBA4404 as described in An, G. et al.: *Binary Vectors,* In: S. B. Selvin, R. A. Schilperoort and D. P. S. Verma (eds), *Plant Molecular Biology Manual,* Martinus Nijhoff, Dordrecht, The Netherland, pp. A-3:1–19 (1988). Agrobacterium cells transformed with either pAM943:Synthetase or pAM943:2-5Adep.RNase are grown in LB medium containing tetracycline (5 μg per ml), kanamycin (10 μg per ml) and streptomycin (25 μg per ml). Tobacco leaf discs are transformed following an Agrobacterium-leaf disc co-culture method. See, An, G. et al.: *Binary Vectors,* In: S. B. Selvin, R. A. Schilperoort and D. P. S. Verma (eds), *Plant Molecular Biology Manual,* Martinus Nijhoff, Dordrecht, The Netherland, pp. A-3:1–19 (1988). The leaf discs are washed extensively with MSO medium and incubated on MSO solid agar selection and shoot regeneration medium containing BAP(benzylaminopurine) (0.5 mg per 1), kanamycin (200 μg per ml), carbenicillin (200 μg per ml) and cefotaxeme (200μ per ml) in parafilm-covered Petri dishes under diffuse light at 25° C. in a growth chamber. The regenerated plantlets are transferred to MSO solid agar selection and hormone free medium and later monitored for the presence of the cDNAs.

For southern blots, DNA from leaves of control and transformed plants are prepared as described in Robert, S. O. et al.: Extraction of DNA from plant tissues, In: S. B. Gelvin, R. A. Schilperoort and D. P. S. Verma (eds), Plant Molecular Biology Manual, Martinus Nijhoff, Dordrecht, The Netherland, pp. A6:1–10 (1988). After digestion of HindIII, the DNA fragments are separated in 1% agarose gel and transferred to Nytran membranes (Scheilcher & Schuell). For northern blots, total RNA is extracted from the leaves using RNA-State 60 reagent (Tel-Test, B. Inc.). Glyoxal treated RNA is fractionated in agarose gels and transferred to Nytran filters. The cDNAs are $^{32}$P-labeled using a multiprime DNA labelling kit (Promega) and used as probes.

2-5A synthetase expressed in the leaves of transgenic tobacco plants are isolated on the activating affinity matrix, poly(I):poly(C)-cellulose as described in Silverman, R. H. et al.: Analysis of anti-viral mechanisms: Interferon-regulated 2',5'-oligoadenylate and protein kinase systems, In: M. J. Clemens, A. G. Morris, Gearing, A. F. H. (eds), Lymphokines and Interferons: A Practical Approach, pp. 149–193, Oxford: IRL Press (1987). Incubation with ATP allows the synthesis of 2-5A measured in a competition binding assay in which unlabeled 2-5A produced in the incubations competes with a radiolabeled 2-5A analog for binding to mouse liver RNase L on nitrocellulose discs. See, Knight, M. et al.: *Nature,* 288:189–192 (1980). Standard curves are prepared with known amounts of unlabeled 2-5A added as competitor.

To measure RNase L levels in the extracts of the leaves, cross-linking is performed of a bromine-substituted and 32P-labeled 2-5A probe, $(A2'p)_2(br^8A2'p)_2A3'$-$[^{32}P]Cp$, to RNase L under ultraviolet light. See, Nolan-Sorden, N. L. et al.: *Anal Biochem,* 184:298–304 (1990). Extracts of leaves from control and transgenic plants and from the human breast cancer cell line, MCF7, are prepared as described in Silverman, R. H. et al.: Analysis of anti-viral mechanisms: Interferon-regulated 2',5'-oligoadenylate and protein kinase systems, In: M. J. Clemens, A. G. Morrs, Gearing, A. F. H. (eds), Lymphokines and Interferons: A Practical Approach, pp. 149–193, Oxford: IRL Press (1987). Assays are in presence or absence of unlabeled $p_3(A2'p)_2A$,(100 nM). The mixtures are exposed to ultraviolet light for about one hour on ice, proteins are separated on SDS-polyacrylamide (10%) gels, and the dried gels are used to expose X-ray film.

Leaves from control and transgenic plants are cut and allowed to take up 2-5A [1 μM of $p_3(A2'p)_3A$] through the petiole for about seven hours at room temperature under fluorescent light. Total RNA is prepared and used to prepare northern blots. THe RNA in the blots is hybridized to a $^{32}P$ labeled human 18S rRNA cDNA probe (the cDNA is provided by Dr. John Thaden, Baltimore).

Transgenic plants expressing 2-5A synthetase or RNase L are grown in a temperature controlled greenhouse. Six-week old plants are inoculated with a 1:500 or 1:5000 dilution of freshly prepared extracts from tobacco leaves systemically infected with tobacco etch virus (TEV, severe strain, ATCC#PV69) and tobacco mosaic virus (TMV, common strain), respectively. Virus titer in the systemically-infected upper leaves are determined by ELISA 21 days after inoculation. Rabbit polyclonal antibodies are used against either TMV coat protein (CP) or TEV cylindrical inclusion protein (CI). Standard curves are constructed using TMV CP or TEV CI proteins.

To produce transgenic tobacco plants, cDNAs for a small form of human 2-5A synthetase and for the human RNase L are individually subcloned into the plant express plasmid, pAM943. See FIG. 13 (Mitra, A. et al.: Plant Mol Biol, 26:85–93 (1994)). In this vector, transcription of the inserted cDNA is driven by a bipartite promoter consisting of the adenyl methyl transferase (AMT) of Chlorella virus fused with the 35S promoter of Cauliflower mosaic virus (FIG. 13). Plants are regenerated from leaf discs transformed separately with Agrobacterium containing either of the two cDNAs following selection with kanamycin. Southern blots are performed on the total genomic DNA isolated from the plants nd digested with HindIII to establish that integration of the cDNAs has occurred. The transformed plants show the presence of 2-5A synthetase cDNA or RNase L cDNA at the expected sizes whereas the control plants are negative. See FIGS. 27A and 28, respectively.

To demonstrate that the 2-5A synthetase cDNA is transcribed in the transgenic plants, northern blots are performed on the total RNA isolated from these plants. See FIG. 27B. A major transcript of about 2.5 kb is clearly seen in the synthetase expressing plants. See FIG. 27B, lanes 2 and 3 are from representative plants. No cross-hybridizing RNA species are detected in the control plant. See FIG. 27B, lane 1. To determine if 2-5A synthetase activity is present in these plants, enzyme assays are performed on crude extracts of the leafs. See Table V below. The 2-5A synthetase is isolated on the activating affinity matrix, poly(I):poly(C)-cellulose. See, for example, Silverman, R. H. et al.: Analysis of anti-viral mechanisms: Interferon-regulated 2',5'-oligoadenylate and protein kinase systems, In: M. J. Clemens, A. G. Morrs, Gearing, A. F. H. (eds), Lymphokines and Interferons: A Practical Approach, pp. 149–193, Oxford: IRL Press (1987). Production of 2-5A oligomers from ATP is measured in a highly specific radiobinding assay (Knight, M. et al.: Nature, 288: 189–192 (1980). Results showed significant 2-5A synthetase activity only in the transgenic plants. See Table V.

TABLE V 2-5A synthetase activity, mRNA, and DNA in transgenic tobacco plants

| | 2-5A (pmol/mg protein/h) | mRNA (Northern) | cDNA (Southern) |
|---|---|---|---|
| Control Plant | <1 | – | – |
| Transgenic Synthetase 15/1 | 9.4 | + | + |
| Transgenic Synthetase 15/2 | 17.9 | + | + |
| Transgenic Synthetase 15/3 | 11.1 | + | + |
| Transgenic Synthetase 15/4 | 16.7 | + | + |
| Transgenic Synthetase 15/6 | 25.0 | + | + |

Expression of RNase L is detected using a bromine substituted, $^{32}P$-labeled 2-5A probe. See, Nolan-Sorden, N. L. et al.: Anal Biochem, 184:298–304 (1990). Covalent crosslinking of the 2-5A probe to RNase L is achieved using UV light. See, Nolan-Sorden, N. L. et al.: Anal Biochem, 184:298–304 (1990). The 83.5 kDa RNase L is clearly detected in the transgenic plants, but is absent in the control plants. See FIG. 29. Specificity of the binding of the 2-5A probe to the RNase L is demonstrated by incubating the plant extract with an excess of unlabeled 2-5A. See FIG. 29. Competition between the unlabeled 2-5A and the 2-5A probe prevents the radiolabeling of the RNase L. RNase L from human MCF-7 cells is shown for comparison. See FIG. 29, lanes 13 and 14.

To monitor uptake of 2-5A, leaves are cut at the base of the petiole and then placed in a solution of $^{32}P$-labeled 2-5A probe for about three hours at room temperature under light. The petiole was cut further and autoradiograms were made from the lamina. Uptake and translocation of the 2-5A probe is readily apparent through veins to all parts of lamina (data now shown). Catalytic activity of RNase L in the intact leaves is determined after allowing unlabeled 2-5A, $p_3A$ $(2'p5'A)_3$ (1 μM), to be taken up by cut leaves for seven hours. Total RNA is extracted and northern blots are prepared and then probed with $^{32}P$-labeled cDNA to 18S rRNA. Results show that 2-5A induce degradation of the 18S rRNA to discrete cleavage products in the RNase L expressing plants, but not in the control plant. See FIG. 30. Previous studies report a similar degradation of 18S rRNA induced in mammalian cells by activation of RNase L. See, Wreschner, D. H. et al.: Nucl Acids Res, 9:1571–1581 (1981). These results appear to demonstrate that both human 2-5A synthetase and RNase L may be expressed as functionally active proteins in plants.

To monitor viral resistance, individual leaves from control and transgenic plants are inoculated using diluted extracts prepared from TEV-infected leaves or TMV-infected leaves. All inoculated plants, both control and transgenic, show typical symptoms within one week indicating systemic viral infection. Virus concentrations are determined 21 days after inoculation by ELISA using standard curves constructed from purified viruses. Representative data from these experiments are shown in Table VI below. Results show no significant difference in viral yields in the transgenic plants compared with the control plants.

TABLE VI

Virus growth assays from control and transgenic plants

| Plants: | Virus Concentration* | |
|---|---|---|
| | TEV: | TMV: |
| Transgenic RNase L, 2 | 38 | 448 |
| Transgenic RNase L, 5 | 38 | 474 |
| Transgenic RNase L, 6 | 31 | 422 |
| Transgenic RNase L, 12 | 30 | 420 |
| Transgenic Synthetase, 15/1 | 36 | 418 |
| Transgenic Synthetase, 15/2 | 25 | 454 |
| Transgenic Synthetase, 15/5 | 34 | 438 |
| Transgenic Synthetase, 15/6 | 36 | 442 |
| Control | 37 | 468 |

*Virus amounts are expressed as μg of viral antigen per g of fresh tissue. A minimum of three leaves are assayed from each plant. ELISAs are repeated two times and each sample is determined in duplicate. Control: virus assays on leaves of plants transformed with the vector alone. Zero time samples consisting of extract of inoculated leaves rinsed with water and immediately processed for ELISAs, gives values of 0.8 and 1.4 for TEV and TMV in these assays, respectively.

In this Example III, neither 2-5A synthetase activity (Table V) nor RNase L activity, as measured either by 2-5A binding, see FIG. 29, or by 2-5A-dependent ribonuclease activities, see FIG. 30, is detectable in leaves of control Nicotiana tabacum plants. Devash et al. also reported an absence of any protein that can bind 2-5A in tobacco plants. See, Devash, Y. et al.: *J. Biol Chem*, 259:3482–3486 (1984). Southern and northern blots probed with human 2-5A synthetase cDNA or RNase L cDNA are also negative. See FIGS. 27 and 28. These results appear to support the report of Cayley, P. J. et al.: *Biochem Biophys Res Commun*, 108:1243–1250 (1982), which shows an absence of 2-5A synthetase activity or 2-5A binding activity (a measure of RNase L) in *Nicotiana glutinosa* and *Nicotiana tabacum* cv. xanthi-nc. In addition, no 2-5A synthetase is detected and no 2-5A is detected in control, TMV-infected, interferon-treated or poly(I):poly(C)-treated plants. See, Cayley, P. J. et al.: *Biochem Biophys Res Commun*, 108:1243–1250 (1982). Definitive evidence for the existence of a 2-5A pathway requires, as a minimum, both an enzyme capable of synthetizing 2-5A [defined as $p_xA(2'p5'A)y$ where x=1 to 3; y≧2] and a ribonuclease activity that is dormant until activated by 2-5A. Any studies heretofore that establish these minimal criteria for plants has not been uncovered. Therefore, either a 2-5A system exists in plants, but is sufficiently different from that in higher vertebrates that it has thus far escaped detection or that the 2-5A system does not exist in plants. In this regard, oligoadenylates that are substantially different from 2-5A have been found in tobacco plants (Devash, Y. et al.: *J. Biol Chem*, 259:3482–3486 (1984)) and 2',5'-oligoadenylates have been reported to inhibit plant cell-free protein synthesis (Truve, E. et al.: *Arch Virol*, 9S:41–50 (1994)), TMV replication (Devash, Y. et al.: *Science*, 216:1415–1416 (1982); Devash, Y. et al.: *J. Biol Chem*, 259:3482–3486 (1984); and Devach, Y. et al.: *Meth Enz*, 119:759–761 (1986)) or to induce of cytokine activities and stress proteins in plants (Kulaeva, O. N. et al.: *Plant Mol Biol*, 20:383–393 (1992).

Human 2-5A synthetase and RNase L in separate transgenic plants are expressed. Stable introduction of the cDNAs into the plant genome is confirmed in Southern blots, see FIGS. 27A and 28, and expression is determined by northern blotting and by functional enzyme assays. Expression of RNase L is obtained by both specific 2-5A binding assay, producing an 83 kDa labeled protein, see FIG. 29, and by 2-5A dependent breakdown of rRNA in intact leaves, see FIG. 30. The absence of rRNA cleavage in the RNase L+ plants without addition of 2-5A indicates that the enzyme is in its dormant state until activation occurs. These findings also suggest an absence of 2-5A per se in the plants; thus confirming other reports. See, for example, Cayley, P. J. et al.: *Biochem Biophys Res Commun*, 108:1243–1250 (1982); and Devash, Y. et al.: *J. Biol Chem*, 259:3482–3486 (1984).

These findings appear to support the feasibility of transferring a complete functional 2-5A system, i.e., RNase L plus 2-5A-synthetase to plants. See Example IV. All of the transgenic plants appear to grow well and produce flowers. Co-expression of both 2-5A synthetase and RNase L, is believed to provide a broad range of protection against plant viruses because activation of 2-5A synthetase require dsRNA structure without any sequence specificity and many types of viruses produce dsRNA during the replicative cycles. See Example IV. Previously, Truve, E. et al.: *Bio/Technology*, 11:1048–1052 (1993); and Truve, E. et al.: *Arch Virol*, 9S:41–50 (1994), reported that expression in plants of rat 2-5A-synthetase alone (i.e., without coexpression of RNase L) provided some antiviral activities. In contrast, in this Example III, inhibition of TMV or TEV replication is not observed in tobacco plants expressing 2-5A-synthetase alone or RNase L alone (see Table VI). The results of this Example III are consistent with the present belief that both 2-5A synthetase and RNase L are necessary in a functional 2-5A system.

Example IV

A binary plant transformation/expression vector, Hoekema A. et al.: *Nature*, 303:179 (1983), designated as pAM2280 and contains both the 2-5A synthetase and RNase L cDNAs is driven by the cauliflower mosaic virus 35S promoter, see Sanders, P. et al.: *Nucl. Acids Res.*, 15:1534 (1987) and the chlorella virus adenine methyltransferase gene promoter, Mitra, A. et al.: *Plant Mol. Bio.*, 26:85 (1994), respectively, is constructed.

The coding regions of original plasmids, pBabe.El.6S (a gift from B. R. G. Williams, Cleveland) and pzC5 (Zhou, A. et al.: *Cell* (72): 753 (1993), encoding a low molecular weight species of human 2-5A synthetase and human RNase L, respectively, are used to construct a binary plant transformation/expression vector pAM2200. *E. coli* Mc1000 containing Vector pAM2200 was deposited on Mar. 4, 1998, with the American Type Culture Collection (ATCC), 10801 University Boulevard, Manassas, Va. 20110-2209, U.S.A., and has been assigned ATCC Accession Number 98686. The binary plasmid contains a neomycin phosphotransferase plant selectable marker gene which is driven by the T-DNA gene nopaline synthase promoter. Mitra, A. et al.: *Mol. Gen. Genet.*, 215:294 (1989). This plasmid is used to produce transgenic tobacco plants by Agrobacterium-mediated transformation of axenically grown tobacco seedlings. Horsch, R. et al.: *Science*, 227:1229 (1985). Transformed tobacco plants are selected on MS plates containing about 300 μg/ml kanamycin. See Murasighe, F. et al.: *Physiol. Plant.*, 15:473 (1962).

Young tobacco seedlings (N. tabacum, petit Havana SR-1), Maliga, P. et al.: *Plant Sci. Let.*, 44:78 (1978), are transformed using the Agrobacterium co-cultivation method. Horsch, R. et al.: *Science*, 227:1229 (1985). The human 2-5A system cDNAs is believed to have no effect on the transformation frequency or normal growth and development of the transgenic tobacco plants. Primary transformants are grown to maturity and are allowed to self-pollinate. All are believed to produce viable seeds. Kanamycin-resistant R1 seedlings are grown in a greenhouse and are analyzed for transgene expression and virus resistance.

Southern blot analysis, Southern, E. M., et al.: *J. Mol. Biol.,* 98:503 (1985), of the transgenic plants is believed to show that all of the kanamycin-resistant plants contain intact and unmodified inserts, see FIG. 22A, indicating appropriate integration of the transgenes into plant chromosomes.

Integration of the plasmid DNA into plant DNA is determined by Southern blot analysis. Southern, E. M. et al.: *J. Mol. Biol.,* 98:503 (1985). Five grams of fresh plant tissue are used to prepare DNA. See Guillemaut, P. et al.: *Plant Mol. Biol. Reptr.,* 10:60 (1992). Briefly, plant tissue is ground in liquid nitrogen and is thawed in extraction buffer (about 100 mM sodium acetate, pH about 4.8, about 50 mM EDTA, pH about 8.0, about 500 mM NaCl, about 2% PVP-40; the mixture adjusted to pH about 5.5, then SDS is added to about 1.4% and cysteine to about 10 mM), it is then incubated at about 65° C. for about 20 minutes, and it is then centrifuged. About one-half volume of about 3M potassium acetate, pH about 4.8, is added to the supernatant and the mixture is incubated at about 0° C. for about 1 hr. The DNA is recovered by ethanol precipitation, which is dissolved in THE and is then centrifuged overnight in a cesium chloride gradient. DNA is digested with Hind III, it is separated on a 1% agarose gel, and it is then transferred to a Zeta-probe membrane (Bio-Rad) according to the manufacturer's recommendations. The membrane is hybridized with a randomly labeled DNA probe, Feinberg, A. P., et al.: *Anal. Biochem.,* 132:6 (1983), using the human 2-5A synthetase and RNase L cDNAs as templates.

In order to determine expression of 2-5A synthetase and RNase L cDNAs in transgenic tobacco plants, total RNA is prepared from fifteen independently transformed plants. See Logemann, J. et al.: *Anal Biochem.,* 163:16 (1987). RNA extraction buffer contains about 8M guanidinium chloride, about 20 MM MES, about 20 mM EDTA and about 50 mM B-mercaptoethanol, pH about 7.0. Aliquots of RNA samples are separated on formaldehyde gels and they are transferred to the Zeta-probe membranes and are probed with DNA fragments as in southern blots.

Northern blot analysis indicates that most of the transgenic tobacco plants are believed to produce mRNA for both 2-5A synthetase and RNase L, although a few are believed to express only the 2-5A synthetase or the RNase L mRNAs. See FIG. 22B.

Expression of RNase L protein in transgenic tobacco is monitored by probing western blots with a monoclonal antibody to human RNase. Dong, B. et al.: *J. Biol. Chem.,* 269:14153 (1994).

A total cellular protein extract is prepared by grinding transformed plant tissue in liquid nitrogen and thawing in protein extraction buffer (about 0.5M sucrose, about 0.1% ascorbic acid, about 0.1% cysteine-HCl, about 0.01M Tris-HCl, pH about 7.5), Mitra, A. et al.: *Mol. Gen. Genet.,* 215:294 (1989), in the presence of about 15 μg phenylmethyl sulfonylflouride (PMSF). The homogenate is centrifuged at about 14,000×g for about 30 min at about 4° C. and the supernatant containing the soluble proteins is recovered and is concentrated using a Microcon (Amicon) concentrator. Protein concentration in the extract is quantified by the Bradford method. Bradford, *M.: Anal. Biochem.,* 72:248 (1976). Extracts containing about 200 μg of total protein are separated on a 12.5% acrylamide gel, Lamelli, U. K.: *Nature,* 227:680 (1970), along with about 200 ng recombinant RNase L protein as a standard. The resolved proteins are transferred to a nitrocellulose membrane using a Bio-Rad trans-blot apparatus at about 250 mA for about 1 hr. The membrane is immersed in a blocking solution (about 5% non-fat dry milk in Tris buffered saline) and is incubated at about 28° C. for about 1 hr. The membrane is then washed and is incubated with about a 1:5000 dilution of a mouse monoclonal antibody which is prepared against human RNase L antigen. Dong, B. et al.: *J. Biol. Chem.,* 269:14153 (1994). Following incubation with antibody, the membrane is placed in the biotinylated goat anti-mouse antibody solution for about 1 hr at about 28° C. with gentle agitation. The membrane is washed, is incubated in a streptavidin-biotinylated alkaline phosphatase complex for about 1 hr, and is followed by immersion in a color development solution until purple bands become visible.

The transgenic plants expressing RNase L mRNA also express the nuclease protein. See FIG. 23. The RNase L which is produced in plants containing both the synthetase and nuclease cDNAs (FIG. 23, lanes T3–T5) as well as in plants containing only the nuclease cDNA (FIG. 23, lane T2) co-migrate with authentic human, recombinant RNase L (FIG. 23, lane RN). Dong, B. et al.: *J. Biol. Chem.,* 269:14153 (1994). The immunoblot appears to show a single protein band of about 80 kDa in protein extracts from transgenic plants. Proteins in control plant extracts do not appear to react with the anti-RNase L antibody (FIG. 23, lane TC), which supports the current belief that tobacco plants do not have an RNase L homologue.

Functional expression of RNase L in transgenic tobacco plants is detected by 2-5A-induced breakdown of 18S ribosomal RNA (rRNA) in detached leaves that are injected with 2-5A. See FIG. 24. Transgenic leaves are injected with about 2.5 μM $p_3A(2'p5'A)_3$ and are incubated for about 3 hrs before total RNA is prepared. Degradation of rRNA is demonstrated by probing the total RNA on a northern blot with a radiolabeled cDNA to 18S rRNA (a gift of John Thaden, Baltimore). Injection of 2-5A appears to result in the degradation of rRNA only in transgenic plants expressing both the 2-5A synthetase and RNase L (FIG. 24, lane 6) or only RNase L (FIG. 24, lane 5), but not in control plants which are transformed with vector along (FIG. 24, lane 1) or plants expressing only 2-5A synthetase (FIG. 24, lane 3). In addition, plants expressing RNase L are believed to have specific 2-5A binding activity that is absent in control, non-transgenic plants. It is therefore surprisingly discovered that introduction of the human RNase L cDNA into transgenic plants leads to production of a functional RNase L enzyme.

To determine if 2-5A synthetase is present in the transgenic tobacco plants, functional assays for the enzyme are performed. 2-5A synthetase activity in extracts of transgenic plants is determined by a functional assay for 2-5A. Plants extracts are prepared by homogenizing leaves in NP40 lysis buffer containing: about 0.5% (v/v) Non-idet P-40, about 90 mM KCI, about 5 mM magnesium acetate, about 20 mM Tris-HCI, pH about 7.5, about 5 mM 2-mercaptoethanol, and about 10 μg per ml leupeptin. The total cell lysates are centrifuged at about 10,000×g for about 10 min at about 4° C., the supernatants are collected and the protein concentration is determined. See Bradford, M. et al.: *Anal. Biochem.,* 72:248 (1976). Extracts of interferon-treated (about 200 units per ml human interferon alpha for about 18 hr) human HeLa cells are prepared by the same method, except cells are disrupted by vortex mixing. 2-5A synthetase assays are performed by incubating about 200 μg (protein)

extract per assay which are adjusted to about 65 μls with NP40 lysis buffer, with about 65 μl (per assay) of about 20 mM Tris-HCI, pH about 7.5, about 50 mM KCI, about 5 mM magnesium acetate, about 4 mM magnesium chloride, about 5 mM 2-mercaptoethanol, about 10% (v/v) glycerol, about 2 mM ATP, about 20 μg per ml poly (I): poly (C) for about 24 hr at about 30° C. Reactions are terminated, and proteins are denatured and removed, by heating reaction mixtures to 100 C. for 5 min followed by centrifugation at 10,000×g for 10 min. Supernatants are removed and concentrated in a speed-vac (Savant) to 20 μl. 2-5A is then assayed by a 2-5A dependent ribonuclease L assay. Concentrated supernatants (about 5 and about 10 μl per plant), or dilutions of authentic 2-5A (pA(2'p5'A)$_3$), are incubated in a final volume of about 25 μl with about 1 μg of recombinant human RNase L, Dong B. et al.: *J. Biol. Chem.*, 269:14153 (1994), in buffer (about 90 mM KCI, about 10 mM magnesium acetate, about 20 mM Tris-HCI, pH about 7.5, about 8 mM 2-mercaptoethanol, and about 10 μg per ml leupeptin) containing about 0.2 mM of poly(U)-($^{32}$P)-pCp which is prepared as described in Silverman, R. H.: *Anal. Biochem.*, 144:450 (1985), and is incubated at about 30° C. for about 2 hr. Reactions are terminated with about 7.5 μl stop buffer, are boiled for about 5 min, are centrifuged briefly, and about 3 μl is loaded to about 6% polyacrylamide/urea gels. After electrophoresis, X-ray film is exposed to the gel.

Extracts of leaves are incubated in buffer containing ATP and poly(I):poly (C), an activator of 2-5A synthetase. Hovanessian, A. G. et al.: *Nature*, 268:537 (1977); and Marie, I. et al. *J. Biol. Chem.*, 267:9933 (1992). After removing the protein from the reaction mixtures, 2-5A is assayed by its ability to activate recombinant human RNase L, which is isolated from transfected insect cells. See Dong, B. et al.: *J. Biol. Chem.*, 269:14153 (1994) and FIG. 25. For comparison, authentic 2-5A (pA(2'p5'A)$_3$) is incubated with RNase L, resulting in the production of discrete poly (U) cleavage products, see FIG. 25, lanes 1–7. Extracts of plants transgenic for both human 2-5A synthetase and RNase L (FIG. 25, lanes 8–11) or for 2-5A synthetase alone are believed to produce functional 2-5A. Identical poly(U) cleavage products are observed with authentic 2-5A (FIG. 25, lanes 1–7) and with 2-5A synthetase assays from interferon-treated human HeLa cells (FIG. 25, lanes 16,17). These results appear to demonstrate production of functional 2-5A synthetase in transgenic tobacco plants.

In contrast, extracts of control plants which are transformed with vector only do not appear to produce 2-5A, as indicated by the lack of specific poly(U) breakdown products (FIG. 25, lanes 12–15); thereby supporting the belief that 2-5A synthetase is absent in tobacco. See Cayley et al.: *Biochem. Biophys. Res. Commun.*, 108:1243 (1982).

To monitor viral resistance, leaves are manually inoculated with three different types of plant viruses: tobacco etch virus (TEV), a member of the potyvirus group; TMV, a member of the tobamovirus group; and alfalfa mosaic virus (AIMV), a member of the bromovirus group. See R. E. F. Matthews, Plant Virology, Academic Press Inc., NY, 1991.

Transgenic plants are grown in a greenhouse. Leaves from these plants are cut at the petiole and placed in petri dishes on moist filter papers. Leaves are maintained in petri dishes for the incubation period and remain in good physiological condition. The leaves are inoculated with a 1:200, 1:1000 and 1:150 dilution of freshly prepared extracts from tobacco leaves systemically infected with TEV (severe strain), ATCC#PV69, TMV (common strain), and AIMV (Nebraska strain), respectively. Six of six control plants become systemically infected when inoculated with sap diluted 1:10,000, 1:100,000, and 1:15,000, respectively. Following inoculation with virus, the leaves are rinsed with water, petri dishes are sealed with stretched parafilm, and are placed in an incubator at about 22° C. for about 7 days under about 18 hr light.

Leaves from a total of forty-eight kanamycin-resistant R1 progeny plants expressing both 2-5A synthetase and RNase L, or either proteins alone, are tested. A composite picture from representative plants is shown in FIG. 26. Infection of plants expressing both proteins induce necrotic local lesions (FIG. 26, panels a, c, e), whereas plants expressing only one protein, (FIG. 26, panels g, h) or control plants (FIG. 26, panels b, d, f) produce typical systemic infections.

In nature, TEV and AIMV are not believed to produce local lesions in tobacco plants. See R. E. F. Matthews, Plant Virology, Academic Press Inc., NY, 1991. TMV is believed to produce local lesions in tobacco plants containing the N or N' gene. Sela, I. et al.: *Adv. Virus Res.*, 24:177 (1981). However, the tobacco cultivar that is used (SR-1) does not contain the N gene and hence is a systemic host for TMV. The necrotic lesions that are produced by different viruses are morphologically distinct. Lesions that are produced by AIMV, in addition, are smaller than those of TEV and TMV. Lesions in transgenic plants appear quickly, within about 48 hours, whereas TMV lesions in hypersensitive control plants (*N. tabacum*, var Samsun NN and Xanthi nc) appear only after about 72 hours. There appears to be a direct correlation between the inoculum concentrations and number of local lesions.

Necrotic lesions in transgenic plants are believed to be formed because viral dsRNAs activates the 2-5A synthetase resulting in subsequent RNA decay by RNase L. Activation of the 2-5A system in plants may be achieved either by extensive secondary structure in viral genomic RNAs or by double-stranded replicative intermediates which are formed during viral replication. For all three viruses inoculated, no virus is detected in leaf tissues between lesions by ELISA with virus-specific antibodies. To ascertain that virus in transgenic tobacco plants expressing the human 2-5A system do not undergo alterations or mutation, virus is recovered from single lesions and reinoculated onto control plants. The three recovered viruses produce typical symptoms and systemic infection in control plants. It is therefore believed that transgenic plants expressing a functional 2-5A system selectively destroy a small number of cells that are initially invaded by virus infection, leading to the formation of necrotic lesions. That is, the interferon regulated 2-5A system is believed to induce cell suicide as a defense against viruses.

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 2928 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 104..2326

( x i ) SEQUENCE DESCRIPTION: SEQ ID NO:1:

```
AATCCAACT  TACACTCAAA  GCTTCTTTGA  TTAAGTGCTA  GGAGATAAAT  TTGCATTTTC        60

TCAAGGAAAA  GGCTAAAAGT  GGTAGCAGGT  GGCATTTACC  GTC ATG GAG AGC AGG         115
                                                Met Glu Ser Arg
                                                  1

GAT CAT AAC AAC CCC CAG GAG GGA CCC ACG TCC TCC AGC GGT AGA AGG             163
Asp His Asn Asn Pro Gln Glu Gly Pro Thr Ser Ser Ser Gly Arg Arg
  5              10                  15                  20

GCT GCA GTG GAA GAC AAT CAC TTG CTG ATT AAA GCT GTT CAA AAC GAA             211
Ala Ala Val Glu Asp Asn His Leu Leu Ile Lys Ala Val Gln Asn Glu
                25                  30                  35

GAT GTT GAC CTG GTC CAG CAA TTG CTG GAA GGT GGA GCC AAT GTT AAT             259
Asp Val Asp Leu Val Gln Gln Leu Leu Glu Gly Gly Ala Asn Val Asn
            40                  45                  50

TTC CAG GAA GAG GAA GGG GGC TGG ACA CCT CTG CAT AAC GCA GTA CAA             307
Phe Gln Glu Glu Glu Gly Gly Trp Thr Pro Leu His Asn Ala Val Gln
        55                  60                  65

ATG AGC AGG GAG GAC ATT GTG GAA CTT CTG CTT CGT CAT GGT GCT GAC             355
Met Ser Arg Glu Asp Ile Val Glu Leu Leu Leu Arg His Gly Ala Asp
    70                  75                  80

CCT GTT CTG AGG AAG AAG AAT GGG GCC ACG CTT TTT ATC CTC GCA GCG             403
Pro Val Leu Arg Lys Lys Asn Gly Ala Thr Leu Phe Ile Leu Ala Ala
85                  90                  95                 100

ATT GCG GGG AGC GTG AAG CTG CTG AAA CTT TTC CTT TCT AAA GGA GCA             451
Ile Ala Gly Ser Val Lys Leu Leu Lys Leu Phe Leu Ser Lys Gly Ala
                    105                 110                 115

GAT GTC AAT GAG TGT GAT TTT TAT GGC TTC ACA GCC TTC ATG GAA GCC             499
Asp Val Asn Glu Cys Asp Phe Tyr Gly Phe Thr Ala Phe Met Glu Ala
                120                 125                 130

GCT GTG TAT GGT AAG GTC AAA GCC CTA AAA TTC CTT TAT AAG AGA GGA             547
Ala Val Tyr Gly Lys Val Lys Ala Leu Lys Phe Leu Tyr Lys Arg Gly
            135                 140                 145

GCA AAT GTG AAT TTG AGG CGA AAG ACA AAG GAG GAT CAA GAG CGG CTG             595
Ala Asn Val Asn Leu Arg Arg Lys Thr Lys Glu Asp Gln Glu Arg Leu
        150                 155                 160

AGG AAA GGA GGG GCC ACA GCT CTC ATG GAC GCT GCT GAA AAA GGA CAC             643
Arg Lys Gly Gly Ala Thr Ala Leu Met Asp Ala Ala Glu Lys Gly His
165                 170                 175                 180

GTA GAG GTC TTG AAG ATT CTC CTT GAT GAG ATG GGG GCA GAT GTA AAC             691
Val Glu Val Leu Lys Ile Leu Leu Asp Glu Met Gly Ala Asp Val Asn
                    185                 190                 195

GCC TGT GAC AAT ATG GGC AGA AAT GCC TTG ATC CAT GCT CTC CTG AGC             739
Ala Cys Asp Asn Met Gly Arg Asn Ala Leu Ile His Ala Leu Leu Ser
```

-continued

```
                   200                      205                         210
TCT  GAC  GAT  AGT  GAT  GTG  GAG  GCT  ATT  ACG  CAT  CTG  CTG  CTG  GAC  CAT       787
Ser  Asp  Asp  Ser  Asp  Val  Glu  Ala  Ile  Thr  His  Leu  Leu  Leu  Asp  His
               215                      220                      225

GGG  GCT  GAT  GTC  AAT  GTG  AGG  GGA  GAA  AGA  GGG  AAG  ACT  CCC  CTG  ATC       835
Gly  Ala  Asp  Val  Asn  Val  Arg  Gly  Glu  Arg  Gly  Lys  Thr  Pro  Leu  Ile
          230                      235                      240

CTG  GCA  GTG  GAG  AAG  AAG  CAC  TTG  GGT  TTG  GTG  CAG  AGG  CTT  CTG  GAG       883
Leu  Ala  Val  Glu  Lys  Lys  His  Leu  Gly  Leu  Val  Gln  Arg  Leu  Leu  Glu
245                      250                      255                      260

CAA  GAG  CAC  ATA  GAG  ATT  AAT  GAC  ACA  GAC  AGT  GAT  GGC  AAA  ACA  GCA       931
Gln  Glu  His  Ile  Glu  Ile  Asn  Asp  Thr  Asp  Ser  Asp  Gly  Lys  Thr  Ala
                    265                      270                      275

CTG  CTG  CTT  GCT  GTT  GAA  CTC  AAA  CTG  AAG  AAA  ATC  GCC  GAG  TTG  CTG       979
Leu  Leu  Leu  Ala  Val  Glu  Leu  Lys  Leu  Lys  Lys  Ile  Ala  Glu  Leu  Leu
               280                      285                      290

TGC  AAA  CGT  GGA  GCC  AGT  ACA  GAT  TGT  GGG  GAT  CTT  GTT  ATG  ACA  GCG      1027
Cys  Lys  Arg  Gly  Ala  Ser  Thr  Asp  Cys  Gly  Asp  Leu  Val  Met  Thr  Ala
          295                      300                      305

AGG  CGG  AAT  TAT  GAC  CAT  TCC  CTT  GTG  AAG  GTT  CTT  CTC  TCT  CAT  GGA      1075
Arg  Arg  Asn  Tyr  Asp  His  Ser  Leu  Val  Lys  Val  Leu  Leu  Ser  His  Gly
     310                      315                      320

GCC  AAA  GAA  GAT  TTT  CAC  CCT  CCT  GCT  GAA  GAC  TGG  AAG  CCT  CAG  AGC      1123
Ala  Lys  Glu  Asp  Phe  His  Pro  Pro  Ala  Glu  Asp  Trp  Lys  Pro  Gln  Ser
325                      330                      335                      340

TCA  CAC  TGG  GGG  GCA  GCC  CTG  AAG  GAT  CTC  CAC  AGA  ATA  TAC  CGC  CCT      1171
Ser  His  Trp  Gly  Ala  Ala  Leu  Lys  Asp  Leu  His  Arg  Ile  Tyr  Arg  Pro
               345                      350                      355

ATG  ATT  GGC  AAA  CTC  AAG  TTC  TTT  ATT  GAT  GAA  AAA  TAC  AAA  ATT  GCT      1219
Met  Ile  Gly  Lys  Leu  Lys  Phe  Phe  Ile  Asp  Glu  Lys  Tyr  Lys  Ile  Ala
          360                      365                      370

GAT  ACT  TCA  GAA  GGA  GGC  ATC  TAC  CTG  GGG  TTC  TAT  GAG  AAG  CAA  GAA      1267
Asp  Thr  Ser  Glu  Gly  Gly  Ile  Tyr  Leu  Gly  Phe  Tyr  Glu  Lys  Gln  Glu
               375                      380                      385

GTA  GCT  GTG  AAG  ACG  TTC  TGT  GAG  GGC  AGC  CCA  CGT  GCA  CAG  CGG  GAA      1315
Val  Ala  Val  Lys  Thr  Phe  Cys  Glu  Gly  Ser  Pro  Arg  Ala  Gln  Arg  Glu
390                      395                      400

GTC  TCT  TGT  CTG  CAA  AGC  AGC  CGA  GAG  AAC  AGT  CAC  TTG  GTG  ACA  TTC      1363
Val  Ser  Cys  Leu  Gln  Ser  Ser  Arg  Glu  Asn  Ser  His  Leu  Val  Thr  Phe
405                      410                      415                      420

TAT  GGG  AGT  GAG  AGC  CAC  AGG  GGC  CAC  TTG  TTT  GTG  TGT  GTC  ACC  CTC      1411
Tyr  Gly  Ser  Glu  Ser  His  Arg  Gly  His  Leu  Phe  Val  Cys  Val  Thr  Leu
               425                      430                      435

TGT  GAG  CAG  ACT  CTG  GAA  GCG  TGT  TTG  GAT  GTG  CAC  AGA  GGG  GAA  GAT      1459
Cys  Glu  Gln  Thr  Leu  Glu  Ala  Cys  Leu  Asp  Val  His  Arg  Gly  Glu  Asp
          440                      445                      450

GTG  GAA  AAT  GAG  GAA  GAT  GAA  TTT  GCC  CGA  AAT  GTC  CTG  TCA  TCT  ATA      1507
Val  Glu  Asn  Glu  Glu  Asp  Glu  Phe  Ala  Arg  Asn  Val  Leu  Ser  Ser  Ile
          455                      460                      465

TTT  AAG  GCT  GTT  CAA  GAA  CTA  CAC  TTG  TCC  TGT  GGA  TAC  ACC  CAC  CAG      1555
Phe  Lys  Ala  Val  Gln  Glu  Leu  His  Leu  Ser  Cys  Gly  Tyr  Thr  His  Gln
     470                      475                      480

GAT  CTG  CAA  CCA  CAA  AAC  ATC  TTA  ATA  GAT  TCT  AAG  AAA  GCT  GCT  CAC      1603
Asp  Leu  Gln  Pro  Gln  Asn  Ile  Leu  Ile  Asp  Ser  Lys  Lys  Ala  Ala  His
485                      490                      495                      500

CTG  GCA  GAT  TTT  GAT  AAG  AGC  ATC  AAG  TGG  GCT  GGA  GAT  CCA  CAG  GAA      1651
Leu  Ala  Asp  Phe  Asp  Lys  Ser  Ile  Lys  Trp  Ala  Gly  Asp  Pro  Gln  Glu
               505                      510                      515

GTC  AAG  AGA  GAT  CTA  GAG  GAC  CTT  GGA  CGG  CTG  GTC  CTC  TAT  GTG  GTA      1699
Val  Lys  Arg  Asp  Leu  Glu  Asp  Leu  Gly  Arg  Leu  Val  Leu  Tyr  Val  Val
```

```
                         520                          525                          530
AAG  AAG  GGA  AGC  ATC  TCA  TTT  GAG  GAT  CTG  AAA  GCT  CAA  AGT  AAT  GAA        1747
Lys  Lys  Gly  Ser  Ile  Ser  Phe  Glu  Asp  Leu  Lys  Ala  Gln  Ser  Asn  Glu
          535                     540                     545

GAG  GTG  GTT  CAA  CTT  TCT  CCA  GAT  GAG  GAA  ACT  AAG  GAC  CTC  ATT  CAT        1795
Glu  Val  Val  Gln  Leu  Ser  Pro  Asp  Glu  Glu  Thr  Lys  Asp  Leu  Ile  His
     550                          555                     560

CGT  CTC  TTC  CAT  CCT  GGG  GAA  CAT  GTG  AGG  GAC  TGT  CTG  AGT  GAC  CTG        1843
Arg  Leu  Phe  His  Pro  Gly  Glu  His  Val  Arg  Asp  Cys  Leu  Ser  Asp  Leu
565                      570                     575                          580

CTG  GGT  CAT  CCC  TTC  TTT  TGG  ACT  TGG  GAG  AGC  CGC  TAT  AGG  ACG  CTT        1891
Leu  Gly  His  Pro  Phe  Phe  Trp  Thr  Trp  Glu  Ser  Arg  Tyr  Arg  Thr  Leu
                    585                          590                     595

CGG  AAT  GTG  GGA  AAT  GAA  TCC  GAC  ATC  AAA  ACA  CGA  AAA  TCT  GAA  AGT        1939
Arg  Asn  Val  Gly  Asn  Glu  Ser  Asp  Ile  Lys  Thr  Arg  Lys  Ser  Glu  Ser
               600                     605                     610

GAG  ATC  CTC  AGA  CTA  CTG  CAA  CCT  GGG  CCT  TCT  GAA  CAT  TCC  AAA  AGT        1987
Glu  Ile  Leu  Arg  Leu  Leu  Gln  Pro  Gly  Pro  Ser  Glu  His  Ser  Lys  Ser
               615                     620                     625

TTT  GAC  AAG  TGG  ACG  ACT  AAG  ATT  AAT  GAA  TGT  GTT  ATG  AAA  AAA  ATG        2035
Phe  Asp  Lys  Trp  Thr  Thr  Lys  Ile  Asn  Glu  Cys  Val  Met  Lys  Lys  Met
     630                     635                     640

AAT  AAG  TTT  TAT  GAA  AAA  AGA  GGC  AAT  TTC  TAC  CAG  AAC  ACT  GTG  GGT        2083
Asn  Lys  Phe  Tyr  Glu  Lys  Arg  Gly  Asn  Phe  Tyr  Gln  Asn  Thr  Val  Gly
645                      650                     655                          660

GAT  CTG  CTA  AAG  TTC  ATC  CGG  AAT  TTG  GGA  GAA  CAC  ATT  GAT  GAA  GAA        2131
Asp  Leu  Leu  Lys  Phe  Ile  Arg  Asn  Leu  Gly  Glu  His  Ile  Asp  Glu  Glu
                    665                     670                     675

AAG  CAT  AAA  AAG  ATG  AAA  TTA  AAA  ATT  GGA  GAC  CCT  TCC  CTG  TAT  TTT        2179
Lys  His  Lys  Lys  Met  Lys  Leu  Lys  Ile  Gly  Asp  Pro  Ser  Leu  Tyr  Phe
               680                     685                     690

CAG  AAG  ACA  TTT  CCA  GAT  CTG  GTG  ATC  TAT  GTC  TAC  ACA  AAA  CTA  CAG        2227
Gln  Lys  Thr  Phe  Pro  Asp  Leu  Val  Ile  Tyr  Val  Tyr  Thr  Lys  Leu  Gln
          695                     700                     705

AAC  ACA  GAA  TAT  AGA  AAG  CAT  TTC  CCC  CAA  ACC  CAC  AGT  CCA  AAC  AAA        2275
Asn  Thr  Glu  Tyr  Arg  Lys  His  Phe  Pro  Gln  Thr  His  Ser  Pro  Asn  Lys
     710                     715                     720

CCT  CAG  TGT  GAT  GGA  GCT  GGT  GGG  GCC  AGT  GGG  TTG  GCC  AGC  CCT  GGG        2323
Pro  Gln  Cys  Asp  Gly  Ala  Gly  Gly  Ala  Ser  Gly  Leu  Ala  Ser  Pro  Gly
725                      730                     735                          740

TGC  TGATGGACTG  ATTTGCTGGA  GTTCAGGGAA  CTACTTATTA  GCTGTAGAGT                        2376
Cys

CCTTGGCAAA  TCACAACATT  CTGGGCCTTT  TAACTCACCA  GGTTGCTTGT  GAGGGATGAG                2436

TTGCATAGCT  GATATGTCAG  TCCCTGGCAT  CGTGTATTCC  ATATGTCTAT  AACAAAAGCA                2496

ATATATACCC  AGACTACACT  AGTCCATAAG  CTTTACCCAC  TAACTGGGAG  GACATTCTGC                2556

TAAGATTCCT  TTTGTCAATT  GCACCAAAAG  AATGAGTGCC  TTGACCCCTA  ATGCTGCATA                2616

TGTTACAATT  CTCTCACTTA  ATTTTCCCAA  TGATCTTGCA  AAACAGGGAT  TATCATCCCC                2676

ATTTAAGAAC  TGAGGAACCT  GAGACTCAGA  GAGTGTGAGC  TACTGGCCCA  AGATTATTCA                2736

ATTTATACCT  AGCACTTTAT  AAATTTATGT  GGTGTTATTG  GTACCTCTCA  TTTGGGCACC                2796

TTAAAACTTA  ACTATCTTCC  AGGGCTCTTC  CAGATGAGGC  CCAAAACATA  TATAGGGGTT                2856

CCAGGAATCT  CATTCATTCA  TTCAGTATTT  ATTGAGCATC  TAGTATAAGT  CTGGGCACTG                2916

GATGCATGAA  TT                                                                        2928
```

( 2 ) INFORMATION FOR SEQ ID NO:2:

(  i  ) SEQUENCE CHARACTERISTICS:
  ( A ) LENGTH: 741 amino acids
  ( B ) TYPE: amino acid
  ( D ) TOPOLOGY: linear (  i i  ) MOLECULE TYPE: protein (  x i  ) SEQUENCE DESCRIPTION: SEQ ID NO:2:

```
Met Glu Ser Arg Asp His Asn Asn Pro Gln Glu Gly Pro Thr Ser Ser
 1               5                  10                  15

Ser Gly Arg Arg Ala Ala Val Glu Asp Asn His Leu Leu Ile Lys Ala
                20                  25                  30

Val Gln Asn Glu Asp Val Asp Leu Val Gln Gln Leu Leu Glu Gly Gly
            35                  40                  45

Ala Asn Val Asn Phe Gln Glu Glu Gly Gly Trp Thr Pro Leu His
    50                  55                  60

Asn Ala Val Gln Met Ser Arg Glu Asp Ile Val Glu Leu Leu Leu Arg
 65                  70                  75                  80

His Gly Ala Asp Pro Val Leu Arg Lys Lys Asn Gly Ala Thr Leu Phe
                85                  90                  95

Ile Leu Ala Ala Ile Ala Gly Ser Val Lys Leu Leu Lys Leu Phe Leu
            100                 105                 110

Ser Lys Gly Ala Asp Val Asn Glu Cys Asp Phe Tyr Gly Phe Thr Ala
            115                 120                 125

Phe Met Glu Ala Ala Val Tyr Gly Lys Val Lys Ala Leu Lys Phe Leu
    130                 135                 140

Tyr Lys Arg Gly Ala Asn Val Asn Leu Arg Arg Lys Thr Lys Glu Asp
145                 150                 155                 160

Gln Glu Arg Leu Arg Lys Gly Gly Ala Thr Ala Leu Met Asp Ala Ala
                165                 170                 175

Glu Lys Gly His Val Glu Val Leu Lys Ile Leu Leu Asp Glu Met Gly
            180                 185                 190

Ala Asp Val Asn Ala Cys Asp Asn Met Gly Arg Asn Ala Leu Ile His
            195                 200                 205

Ala Leu Leu Ser Ser Asp Asp Ser Asp Val Glu Ala Ile Thr His Leu
    210                 215                 220

Leu Leu Asp His Gly Ala Asp Val Asn Val Arg Gly Glu Arg Gly Lys
225                 230                 235                 240

Thr Pro Leu Ile Leu Ala Val Glu Lys Lys His Leu Gly Leu Val Gln
                245                 250                 255

Arg Leu Leu Glu Gln Glu His Ile Glu Ile Asn Asp Thr Asp Ser Asp
                260                 265                 270

Gly Lys Thr Ala Leu Leu Leu Ala Val Glu Leu Lys Leu Lys Lys Ile
            275                 280                 285

Ala Glu Leu Leu Cys Lys Arg Gly Ala Ser Thr Asp Cys Gly Asp Leu
    290                 295                 300

Val Met Thr Ala Arg Arg Asn Tyr Asp His Ser Leu Val Lys Val Leu
305                 310                 315                 320

Leu Ser His Gly Ala Lys Glu Asp Phe His Pro Pro Ala Glu Asp Trp
                325                 330                 335

Lys Pro Gln Ser Ser His Trp Gly Ala Ala Leu Lys Asp Leu His Arg
            340                 345                 350

Ile Tyr Arg Pro Met Ile Gly Lys Leu Lys Phe Phe Ile Asp Glu Lys
            355                 360                 365

Tyr Lys Ile Ala Asp Thr Ser Glu Gly Gly Ile Tyr Leu Gly Phe Tyr
    370                 375                 380
```

| | | | | | | | | | | | | | | |
|---|---|---|---|---|---|---|---|---|---|---|---|---|---|---|
| Glu 385 | Lys | Gln | Glu | Val | Ala 390 | Val | Lys | Thr | Phe | Cys 395 | Glu | Gly | Ser | Pro | Arg 400 |
| Ala | Gln | Arg | Glu | Val 405 | Ser | Cys | Leu | Gln | Ser 410 | Ser | Arg | Glu | Asn | Ser 415 | His |
| Leu | Val | Thr | Phe 420 | Tyr | Gly | Ser | Glu | Ser 425 | His | Arg | Gly | His | Leu 430 | Phe | Val |
| Cys | Val | Thr 435 | Leu | Cys | Glu | Gln | Thr 440 | Leu | Glu | Ala | Cys | Leu 445 | Asp | Val | His |
| Arg | Gly 450 | Glu | Asp | Val | Glu | Asn 455 | Glu | Glu | Asp | Glu | Phe 460 | Ala | Arg | Asn | Val |
| Leu 465 | Ser | Ser | Ile | Phe | Lys 470 | Ala | Val | Gln | Glu | Leu 475 | His | Leu | Ser | Cys | Gly 480 |
| Tyr | Thr | His | Gln | Asp 485 | Leu | Gln | Pro | Gln | Asn 490 | Ile | Leu | Ile | Asp | Ser 495 | Lys |
| Lys | Ala | Ala | His 500 | Leu | Ala | Asp | Phe | Asp 505 | Lys | Ser | Ile | Lys | Trp 510 | Ala | Gly |
| Asp | Pro | Gln 515 | Glu | Val | Lys | Arg | Asp 520 | Leu | Glu | Asp | Leu | Gly 525 | Arg | Leu | Val |
| Leu | Tyr 530 | Val | Val | Lys | Lys | Gly 535 | Ser | Ile | Ser | Phe | Glu 540 | Asp | Leu | Lys | Ala |
| Gln 545 | Ser | Asn | Glu | Glu | Val 550 | Val | Gln | Leu | Ser | Pro 555 | Asp | Glu | Glu | Thr | Lys 560 |
| Asp | Leu | Ile | His | Arg 565 | Leu | Phe | His | Pro | Gly 570 | Glu | His | Val | Arg | Asp 575 | Cys |
| Leu | Ser | Asp | Leu 580 | Leu | Gly | His | Pro | Phe 585 | Phe | Trp | Thr | Trp | Glu 590 | Ser | Arg |
| Tyr | Arg | Thr 595 | Leu | Arg | Asn | Val | Gly 600 | Asn | Glu | Ser | Asp | Ile 605 | Lys | Thr | Arg |
| Lys | Ser | Glu 610 | Ser | Glu | Ile | Leu 615 | Arg | Leu | Leu | Gln | Pro 620 | Gly | Pro | Ser | Glu |
| His 625 | Ser | Lys | Ser | Phe | Asp 630 | Lys | Trp | Thr | Thr | Lys 635 | Ile | Asn | Glu | Cys | Val 640 |
| Met | Lys | Lys | Met | Asn 645 | Lys | Phe | Tyr | Glu | Lys 650 | Arg | Gly | Asn | Phe | Tyr 655 | Gln |
| Asn | Thr | Val | Gly 660 | Asp | Leu | Leu | Lys | Phe 665 | Ile | Arg | Asn | Leu | Gly 670 | Glu | His |
| Ile | Asp | Glu 675 | Glu | Lys | His | Lys | Lys 680 | Met | Lys | Leu | Lys | Ile 685 | Gly | Asp | Pro |
| Ser | Leu 690 | Tyr | Phe | Gln | Lys | Thr 695 | Phe | Pro | Asp | Leu | Val 700 | Ile | Tyr | Val | Tyr |
| Thr 705 | Lys | Leu | Gln | Asn | Thr 710 | Glu | Tyr | Arg | Lys | His 715 | Phe | Pro | Gln | Thr | His 720 |
| Ser | Pro | Asn | Lys | Pro 725 | Gln | Cys | Asp | Gly | Ala 730 | Gly | Gly | Ala | Ser | Gly 735 | Leu |
| Ala | Ser | Pro | Gly 740 | Cys | | | | | | | | | | | |

( 2 ) INFORMATION FOR SEQ ID NO:3:

( i ) SEQUENCE CHARACTERISTICS:
        ( A ) LENGTH: 2928 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
    ( A ) NAME/KEY: CDS
    ( B ) LOCATION: 104..2326

( x i ) SEQUENCE DESCRIPTION: SEQ ID NO:3:

```
AATCCCAACT  TACACTCAAA  GCTTCTTTGA  TTAAGTGCTA  GGAGATAAAT  TTGCATTTTC                    60

TCAAGGAAAA  GGCTAAAAGT  GGTAGCAGGT  GGCATTTACC  GTC ATG GAG AGC AGG                       115
                                                    Met Glu Ser Arg
                                                     1

GAT CAT AAC AAC CCC CAG GAG GGA CCC ACG TCC TCC AGC GGT AGA AGG                           163
Asp His Asn Asn Pro Gln Glu Gly Pro Thr Ser Ser Ser Gly Arg Arg
  5              10                  15                  20

GCT GCA GTG GAA GAC AAT CAC TTG CTG ATT AAA GCT GTT CAA AAC GAA                           211
Ala Ala Val Glu Asp Asn His Leu Leu Ile Lys Ala Val Gln Asn Glu
                 25                  30                  35

GAT GTT GAC CTG GTC CAG CAA TTG CTG GAA GGT GGA GCC AAT GTT AAT                           259
Asp Val Asp Leu Val Gln Gln Leu Leu Glu Gly Gly Ala Asn Val Asn
             40                  45                  50

TTC CAG GAA GAG GAA GGG GGC TGG ACA CCT CTG CAT AAC GCA GTA CAA                           307
Phe Gln Glu Glu Glu Gly Gly Trp Thr Pro Leu His Asn Ala Val Gln
         55                  60                  65

ATG AGC AGG GAG GAC ATT GTG GAA CTT CTG CTT CGT CAT GGT GCT GAC                           355
Met Ser Arg Glu Asp Ile Val Glu Leu Leu Leu Arg His Gly Ala Asp
     70                  75                  80

CCT GTT CTG AGG AAG AAG AAT GGG GCC ACG CCT TTT ATC CTC GCA GCG                           403
Pro Val Leu Arg Lys Lys Asn Gly Ala Thr Pro Phe Ile Leu Ala Ala
 85                  90                  95                  100

ATT GCG GGG AGC GTG AAG CTG CTG AAA CTT TTC CTT TCT AAA GGA GCA                           451
Ile Ala Gly Ser Val Lys Leu Leu Lys Leu Phe Leu Ser Lys Gly Ala
                 105                 110                 115

GAT GTC AAT GAG TGT GAT TTT TAT GGC TTC ACA GCC TTC ATG GAA GCC                           499
Asp Val Asn Glu Cys Asp Phe Tyr Gly Phe Thr Ala Phe Met Glu Ala
             120                 125                 130

GCT GTG TAT GGT AAG GTC AAA GCC CTA AAA TTC CTT TAT AAG AGA GGA                           547
Ala Val Tyr Gly Lys Val Lys Ala Leu Lys Phe Leu Tyr Lys Arg Gly
         135                 140                 145

GCA AAT GTG AAT TTG AGG CGA AAG ACA AAG GAG GAT CAA GAG CGG CTG                           595
Ala Asn Val Asn Leu Arg Arg Lys Thr Lys Glu Asp Gln Glu Arg Leu
    150                 155                 160

AGG AAA GGA GGG GCC ACA GCT CTC ATG GAC GCT GCT GAA AAA GGA CAC                           643
Arg Lys Gly Gly Ala Thr Ala Leu Met Asp Ala Ala Glu Lys Gly His
165                 170                 175                 180

GTA GAG GTC TTG AAG ATT CTC CTT GAT GAG ATG GGG GCA GAT GTA AAC                           691
Val Glu Val Leu Lys Ile Leu Leu Asp Glu Met Gly Ala Asp Val Asn
                185                 190                 195

GCC TGT GAC AAT ATG GGC AGA AAT GCC TTG ATC CAT GCT CTC CTG AGC                           739
Ala Cys Asp Asn Met Gly Arg Asn Ala Leu Ile His Ala Leu Leu Ser
            200                 205                 210

TCT GAC GAT AGT GAT GTG GAG GCT ATT ACG CAT CTG CTG CTG GAC CAT                           787
Ser Asp Asp Ser Asp Val Glu Ala Ile Thr His Leu Leu Leu Asp His
        215                 220                 225

GGG GCT GAT GTC AAT GTG AGG GGA GAA AGA GGG AAG ACT CCC CTG ATC                           835
Gly Ala Asp Val Asn Val Arg Gly Glu Arg Gly Lys Thr Pro Leu Ile
    230                 235                 240

CTG GCA GTG GAG AAG AAG CAC TTG GGT TTG GTG CAG AGG CTT CTG GAG                           883
Leu Ala Val Glu Lys Lys His Leu Gly Leu Val Gln Arg Leu Leu Glu
245                 250                 255                 260

CAA GAG CAC ATA GAG ATT AAT GAC ACA GAC AGT GAT GGC AAA ACA GCA                           931
Gln Glu His Ile Glu Ile Asn Asp Thr Asp Ser Asp Gly Lys Thr Ala
                265                 270                 275
```

| | | | | | | | | | | | | | | | | |
|---|---|---|---|---|---|---|---|---|---|---|---|---|---|---|---|---|
| CTG | CTG | CTT | GCT | GTT | GAA | CTC | AAA | CTG | AAG | AAA | ATC | GCC | GAG | TTG | CTG | 979 |
| Leu | Leu | Leu | Ala 280 | Val | Glu | Leu | Lys | Leu 285 | Lys | Lys | Ile | Ala | Glu 290 | Leu | Leu | |
| TGC | AAA | CGT | GGA | GCC | AGT | ACA | GAT | TGT | GGG | GAT | CTT | GTT | ATG | ACA | GCG | 1027 |
| Cys | Lys | Arg 295 | Gly | Ala | Ser | Thr | Asp 300 | Cys | Gly | Asp | Leu | Val 305 | Met | Thr | Ala | |
| AGG | CGG | AAT | TAT | GAC | CAT | TCC | CTT | GTG | AAG | GTT | CTT | CTC | TCT | CAT | GGA | 1075 |
| Arg | Arg | Asn 310 | Tyr | Asp | His | Ser | Leu 315 | Val | Lys | Val | Leu | Leu 320 | Ser | His | Gly | |
| GCC | AAA | GAA | GAT | TTT | CAC | CCT | CCT | GCT | GAA | GAC | TGG | AAG | CCT | CAG | AGC | 1123 |
| Ala 325 | Lys | Glu | Asp | Phe | His 330 | Pro | Pro | Ala | Glu | Asp 335 | Trp | Lys | Pro | Gln | Ser 340 | |
| TCA | CAC | TGG | GGG | GCA | GCC | CTG | AAG | GAT | CTC | CAC | AGA | ATA | TAC | CGC | CCT | 1171 |
| Ser | His | Trp | Gly | Ala 345 | Ala | Leu | Lys | Asp | Leu 350 | His | Arg | Ile | Tyr | Arg 355 | Pro | |
| ATG | ATT | GGC | AAA | CTC | AAG | TTC | TTT | ATT | GAT | GAA | AAA | TAC | AAA | ATT | GCT | 1219 |
| Met | Ile | Gly | Lys 360 | Leu | Lys | Phe | Phe | Ile 365 | Asp | Glu | Lys | Tyr | Lys 370 | Ile | Ala | |
| GAT | ACT | TCA | GAA | GGA | GGC | ATC | TAC | CTG | GGG | TTC | TAT | GAG | AAG | CAA | GAA | 1267 |
| Asp | Thr | Ser 375 | Glu | Gly | Gly | Ile | Tyr 380 | Leu | Gly | Phe | Tyr | Glu 385 | Lys | Gln | Glu | |
| GTA | GCT | GTG | AAG | ACG | TTC | TGT | GAG | GGC | AGC | CCA | CGT | GCA | CAG | CGG | GAA | 1315 |
| Val | Ala 390 | Val | Lys | Thr | Phe | Cys 395 | Glu | Gly | Ser | Pro | Arg 400 | Ala | Gln | Arg | Glu | |
| GTC | TCT | TGT | CTG | CAA | AGC | AGC | CGA | GAG | AAC | AGT | CAC | TTG | GTG | ACA | TTC | 1363 |
| Val | Ser | Cys 405 | Leu | Gln | Ser | Ser | Arg 410 | Glu | Asn | Ser | His | Leu 415 | Val | Thr | Phe 420 | |
| TAT | GGG | AGT | GAG | AGC | CAC | AGG | GGC | CAC | TTG | TTT | GTG | TGT | GTC | ACC | CTC | 1411 |
| Tyr | Gly | Ser | Glu | Ser 425 | His | Arg | Gly | His | Leu 430 | Phe | Val | Cys | Val | Thr 435 | Leu | |
| TGT | GAG | CAG | ACT | CTG | GAA | GCG | TGT | TTG | GAT | GTG | CAC | AGA | GGG | GAA | GAT | 1459 |
| Cys | Glu | Gln | Thr 440 | Leu | Glu | Ala | Cys | Leu 445 | Asp | Val | His | Arg | Gly 450 | Glu | Asp | |
| GTG | GAA | AAT | GAG | GAA | GAT | GAA | TTT | GCC | CGA | AAT | GTC | CTG | TCA | TCT | ATA | 1507 |
| Val | Glu | Asn 455 | Glu | Glu | Asp | Glu | Phe 460 | Ala | Arg | Asn | Val | Leu 465 | Ser | Ser | Ile | |
| TTT | AAG | GCT | GTT | CAA | GAA | CTA | CAC | TTG | TCC | TGT | GGA | TAC | ACC | CAC | CAG | 1555 |
| Phe | Lys | Ala 470 | Val | Gln | Glu | Leu | His 475 | Leu | Ser | Cys | Gly | Tyr 480 | Thr | His | Gln | |
| GAT | CTG | CAA | CCA | CAA | AAC | ATC | TTA | ATA | GAT | TCT | AAG | AAA | GCT | GCT | CAC | 1603 |
| Asp 485 | Leu | Gln | Pro | Gln | Asn 490 | Ile | Leu | Ile | Asp | Ser 495 | Lys | Lys | Ala | Ala | His 500 | |
| CTG | GCA | GAT | TTT | GAT | AAG | AGC | ATC | AAG | TGG | GCT | GGA | GAT | CCA | CAG | GAA | 1651 |
| Leu | Ala | Asp | Phe | Asp 505 | Lys | Ser | Ile | Lys | Trp 510 | Ala | Gly | Asp | Pro | Gln 515 | Glu | |
| GTC | AAG | AGA | GAT | CTA | GAG | GAC | CTT | GGA | CGG | CTG | GTC | CTC | TAT | GTG | GTA | 1699 |
| Val | Lys | Arg | Asp 520 | Leu | Glu | Asp | Leu | Gly 525 | Arg | Leu | Val | Leu | Tyr 530 | Val | Val | |
| AAG | AAG | GGA | AGC | ATC | TCA | TTT | GAG | GAT | CTG | AAA | GCT | CAA | AGT | AAT | GAA | 1747 |
| Lys | Lys | Gly 535 | Ser | Ile | Ser | Phe | Glu 540 | Asp | Leu | Lys | Ala | Gln 545 | Ser | Asn | Glu | |
| GAG | GTG | GTT | CAA | CTT | TCT | CCA | GAT | GAG | GAA | ACT | AAG | GAC | CTC | ATT | CAT | 1795 |
| Glu | Val 550 | Val | Gln | Leu | Ser | Pro 555 | Asp | Glu | Glu | Thr | Lys 560 | Asp | Leu | Ile | His | |
| CGT | CTC | TTC | CAT | CCT | GGG | GAA | CAT | GTG | AGG | GAC | TGT | CTG | AGT | GAC | CTG | 1843 |
| Arg 565 | Leu | Phe | His | Pro | Gly 570 | Glu | His | Val | Arg | Asp 575 | Cys | Leu | Ser | Asp | Leu 580 | |
| CTG | GGT | CAT | CCC | TTC | TTT | TGG | ACT | TGG | GAG | AGC | CGC | TAT | AGG | ACG | CTT | 1891 |
| Leu | Gly | His | Pro | Phe 585 | Phe | Trp | Thr | Trp | Glu 590 | Ser | Arg | Tyr | Arg | Thr 595 | Leu | |

```
CGG  AAT  GTG  GGA  AAT  GAA  TCC  GAC  ATC  AAA  ACA  CGA  AAA  TCT  GAA  AGT   1939
Arg  Asn  Val  Gly  Asn  Glu  Ser  Asp  Ile  Lys  Thr  Arg  Lys  Ser  Glu  Ser
               600                      605                      610

GAG  ATC  CTC  AGA  CTA  CTG  CAA  CCT  GGG  CCT  TCT  GAA  CAT  TCC  AAA  AGT   1987
Glu  Ile  Leu  Arg  Leu  Leu  Gln  Pro  Gly  Pro  Ser  Glu  His  Ser  Lys  Ser
          615                      620                      625

TTT  GAC  AAG  TGG  ACG  ACT  AAG  ATT  AAT  GAA  TGT  GTT  ATG  AAA  AAA  ATG   2035
Phe  Asp  Lys  Trp  Thr  Thr  Lys  Ile  Asn  Glu  Cys  Val  Met  Lys  Lys  Met
     630                      635                      640

AAT  AAG  TTT  TAT  GAA  AAA  AGA  GGC  AAT  TTC  TAC  CAG  AAC  ACT  GTG  GGT   2083
Asn  Lys  Phe  Tyr  Glu  Lys  Arg  Gly  Asn  Phe  Tyr  Gln  Asn  Thr  Val  Gly
645                      650                      655                      660

GAT  CTG  CTA  AAG  TTC  ATC  CGG  AAT  TTG  GGA  GAA  CAC  ATT  GAT  GAA  GAA   2131
Asp  Leu  Leu  Lys  Phe  Ile  Arg  Asn  Leu  Gly  Glu  His  Ile  Asp  Glu  Glu
                    665                      670                      675

AAG  CAT  AAA  AAG  ATG  AAA  TTA  AAA  ATT  GGA  GAC  CCT  TCC  CTG  TAT  TTT   2179
Lys  His  Lys  Lys  Met  Lys  Leu  Lys  Ile  Gly  Asp  Pro  Ser  Leu  Tyr  Phe
               680                      685                      690

CAG  AAG  ACA  TTT  CCA  GAT  CTG  GTG  ATC  TAT  GTC  TAC  ACA  AAA  CTA  CAG   2227
Gln  Lys  Thr  Phe  Pro  Asp  Leu  Val  Ile  Tyr  Val  Tyr  Thr  Lys  Leu  Gln
          695                      700                      705

AAC  ACA  GAA  TAT  AGA  AAG  CAT  TTC  CCC  CAA  ACC  CAC  AGT  CCA  AAC  AAA   2275
Asn  Thr  Glu  Tyr  Arg  Lys  His  Phe  Pro  Gln  Thr  His  Ser  Pro  Asn  Lys
710                      715                      720

CCT  CAG  TGT  GAT  GGA  GCT  GGT  GGG  GCC  AGT  GGG  TTG  GCC  AGC  CCT  GGG   2323
Pro  Gln  Cys  Asp  Gly  Ala  Gly  Gly  Ala  Ser  Gly  Leu  Ala  Ser  Pro  Gly
725                      730                      735                      740

TGC  TGATGGACTG  ATTTGCTGGA  GTTCAGGGAA  CTACTTATTA  GCTGTAGAGT                  2376
Cys

CCTTGGCAAA  TCACAACATT  CTGGGCCTTT  TAACTCACCA  GGTTGCTTGT  GAGGGATGAG           2436

TTGCATAGCT  GATATGTCAG  TCCCTGGCAT  CGTGTATTCC  ATATGTCTAT  AACAAAAGCA           2496

ATATATACCC  AGACTACACT  AGTCCATAAG  CTTTACCCAC  TAACTGGGAG  GACATTCTGC           2556

TAAGATTCCT  TTTGTCAATT  GCACCAAAAG  AATGAGTGCC  TTGACCCCTA  ATGCTGCATA           2616

TGTTACAATT  CTCTCACTTA  ATTTTCCCAA  TGATCTTGCA  AAACAGGGAT  TATCATCCCC           2676

ATTTAAGAAC  TGAGGAACCT  GAGACTCAGA  GAGTGTGAGC  TACTGGCCCA  AGATTATTCA           2736

ATTTATACCT  AGCACTTTAT  AAATTTATGT  GGTGTTATTG  GTACCTCTCA  TTTGGGCACC           2796

TTAAAACTTA  ACTATCTTCC  AGGGCTCTTC  CAGATGAGGC  CCAAAACATA  TATAGGGGTT           2856

CCAGGAATCT  CATTCATTCA  TTCAGTATTT  ATTGAGCATC  TAGTATAAGT  CTGGGCACTG           2916

GATGCATGAA  TT                                                                   2928
```

(2) INFORMATION FOR SEQ ID NO:4:

(i) SEQUENCE CHARACTERISTICS:
        (A) LENGTH: 741 amino acids
        (B) TYPE: amino acid
        (D) TOPOLOGY: linear (ii) MOLECULE TYPE: protein (xi) SEQUENCE DESCRIPTION: SEQ ID NO:4:

```
Met  Glu  Ser  Arg  Asp  His  Asn  Asn  Pro  Gln  Glu  Gly  Pro  Thr  Ser  Ser
  1                 5                      10                      15

Ser  Gly  Arg  Arg  Ala  Ala  Val  Glu  Asp  Asn  His  Leu  Leu  Ile  Lys  Ala
                20                      25                      30

Val  Gln  Asn  Glu  Asp  Val  Asp  Leu  Val  Gln  Gln  Leu  Leu  Glu  Gly  Gly
          35                      40                      45
```

```
Ala  Asn  Val  Asn  Phe  Gln  Glu  Glu  Gly  Gly  Trp  Thr  Pro  Leu  His
         50                      55                      60

Asn  Ala  Val  Gln  Met  Ser  Arg  Glu  Asp  Ile  Val  Glu  Leu  Leu  Leu  Arg
 65                      70                      75                       80

His  Gly  Ala  Asp  Pro  Val  Leu  Arg  Lys  Lys  Asn  Gly  Ala  Thr  Pro  Phe
                    85                       90                       95

Ile  Leu  Ala  Ala  Ile  Ala  Gly  Ser  Val  Lys  Leu  Leu  Lys  Leu  Phe  Leu
                   100                      105                     110

Ser  Lys  Gly  Ala  Asp  Val  Asn  Glu  Cys  Asp  Phe  Tyr  Gly  Phe  Thr  Ala
              115                      120                     125

Phe  Met  Glu  Ala  Ala  Val  Tyr  Gly  Lys  Val  Lys  Ala  Leu  Lys  Phe  Leu
         130                     135                          140

Tyr  Lys  Arg  Gly  Ala  Asn  Val  Asn  Leu  Arg  Arg  Lys  Thr  Lys  Glu  Asp
145                          150                     155                     160

Gln  Glu  Arg  Leu  Arg  Lys  Gly  Gly  Ala  Thr  Ala  Leu  Met  Asp  Ala  Ala
                   165                     170                     175

Glu  Lys  Gly  His  Val  Glu  Val  Leu  Lys  Ile  Leu  Leu  Asp  Glu  Met  Gly
              180                     185                     190

Ala  Asp  Val  Asn  Ala  Cys  Asp  Asn  Met  Gly  Arg  Asn  Ala  Leu  Ile  His
              195                     200                     205

Ala  Leu  Leu  Ser  Ser  Asp  Asp  Ser  Asp  Val  Glu  Ala  Ile  Thr  His  Leu
210                          215                     220

Leu  Leu  Asp  His  Gly  Ala  Asp  Val  Asn  Val  Arg  Gly  Glu  Arg  Gly  Lys
225                     230                     235                     240

Thr  Pro  Leu  Ile  Leu  Ala  Val  Glu  Lys  Lys  His  Leu  Gly  Leu  Val  Gln
                   245                     250                     255

Arg  Leu  Leu  Glu  Gln  Glu  His  Ile  Glu  Ile  Asn  Asp  Thr  Asp  Ser  Asp
              260                     265                     270

Gly  Lys  Thr  Ala  Leu  Leu  Leu  Ala  Val  Glu  Leu  Lys  Leu  Lys  Lys  Ile
              275                     280                     285

Ala  Glu  Leu  Leu  Cys  Lys  Arg  Gly  Ala  Ser  Thr  Asp  Cys  Gly  Asp  Leu
         290                     295                     300

Val  Met  Thr  Ala  Arg  Arg  Asn  Tyr  Asp  His  Ser  Leu  Val  Lys  Val  Leu
305                          310                     315                     320

Leu  Ser  His  Gly  Ala  Lys  Glu  Asp  Phe  His  Pro  Pro  Ala  Glu  Asp  Trp
                   325                     330                     335

Lys  Pro  Gln  Ser  Ser  His  Trp  Gly  Ala  Ala  Leu  Lys  Asp  Leu  His  Arg
              340                     345                     350

Ile  Tyr  Arg  Pro  Met  Ile  Gly  Lys  Leu  Lys  Phe  Phe  Ile  Asp  Glu  Lys
         355                     360                     365

Tyr  Lys  Ile  Ala  Asp  Thr  Ser  Glu  Gly  Gly  Ile  Tyr  Leu  Gly  Phe  Tyr
370                          375                     380

Glu  Lys  Gln  Glu  Val  Ala  Val  Lys  Thr  Phe  Cys  Glu  Gly  Ser  Pro  Arg
385                          390                     395                     400

Ala  Gln  Arg  Glu  Val  Ser  Cys  Leu  Gln  Ser  Ser  Arg  Glu  Asn  Ser  His
                   405                     410                     415

Leu  Val  Thr  Phe  Tyr  Gly  Ser  Glu  Ser  His  Arg  Gly  His  Leu  Phe  Val
              420                     425                     430

Cys  Val  Thr  Leu  Cys  Glu  Gln  Thr  Leu  Glu  Ala  Cys  Leu  Asp  Val  His
              435                     440                     445

Arg  Gly  Glu  Asp  Val  Glu  Asn  Glu  Glu  Asp  Glu  Phe  Ala  Arg  Asn  Val
     450                     455                     460

Leu  Ser  Ser  Ile  Phe  Lys  Ala  Val  Gln  Glu  Leu  His  Leu  Ser  Cys  Gly
```

|     |     |     |     | 465 |     |     |     |     | 470 |     |     |     |     | 475 |     |     |     |     | 480 |
|-----|-----|-----|-----|-----|-----|-----|-----|-----|-----|-----|-----|-----|-----|-----|-----|-----|-----|-----|-----|

Tyr Thr His Gln Asp Leu Gln Pro Gln Asn Ile Leu Ile Asp Ser Lys
                    485                 490                 495

Lys Ala Ala His Leu Ala Asp Phe Asp Lys Ser Ile Lys Trp Ala Gly
            500                 505                 510

Asp Pro Gln Glu Val Lys Arg Asp Leu Glu Asp Leu Gly Arg Leu Val
        515                 520                 525

Leu Tyr Val Val Lys Lys Gly Ser Ile Ser Phe Glu Asp Leu Lys Ala
    530                 535                 540

Gln Ser Asn Glu Glu Val Val Gln Leu Ser Pro Asp Glu Glu Thr Lys
545                 550                 555                 560

Asp Leu Ile His Arg Leu Phe His Pro Gly Glu His Val Arg Asp Cys
                565                 570                 575

Leu Ser Asp Leu Leu Gly His Pro Phe Phe Trp Thr Trp Glu Ser Arg
            580                 585                 590

Tyr Arg Thr Leu Arg Asn Val Gly Asn Glu Ser Asp Ile Lys Thr Arg
        595                 600                 605

Lys Ser Glu Ser Glu Ile Leu Arg Leu Leu Gln Pro Gly Pro Ser Glu
    610                 615                 620

His Ser Lys Ser Phe Asp Lys Trp Thr Thr Lys Ile Asn Glu Cys Val
625                 630                 635                 640

Met Lys Lys Met Asn Lys Phe Tyr Glu Lys Arg Gly Asn Phe Tyr Gln
                645                 650                 655

Asn Thr Val Gly Asp Leu Leu Lys Phe Ile Arg Asn Leu Gly Glu His
            660                 665                 670

Ile Asp Glu Glu Lys His Lys Lys Met Lys Leu Lys Ile Gly Asp Pro
        675                 680                 685

Ser Leu Tyr Phe Gln Lys Thr Phe Pro Asp Leu Val Ile Tyr Val Tyr
    690                 695                 700

Thr Lys Leu Gln Asn Thr Glu Tyr Arg Lys His Phe Pro Gln Thr His
705                 710                 715                 720

Ser Pro Asn Lys Pro Gln Cys Asp Gly Ala Gly Gly Ala Ser Gly Leu
                725                 730                 735

Ala Ser Pro Gly Cys
            740

( 2 ) INFORMATION FOR SEQ ID NO:5:

( i ) SEQUENCE CHARACTERISTICS:
        ( A ) LENGTH: 2200 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 164..2200

( x i ) SEQUENCE DESCRIPTION: SEQ ID NO:5:

ATTCGGCACG AGGAAGGTGC CAATTACTAG CTCCCTTCTT TATTCGTGTA CTGATGAGAT    60

GTCAGAAGAC AGAACATAAT CAGCCCAATC CCTACTCCAA GACTCTCATT GTGTCCCAAA    120

GAAACACACG TGTGCATTTC CCAAGGAAAA GGCATTGAGG ACC ATG GAG ACC CCG    175
                                                                                    Met Glu Thr Pro
                                                                                      1

GAT TAT AAC ACA CCT CAG GGT GGA ACC CCA TCA GCG GGA AGT CAG AGG    223
Asp Tyr Asn Thr Pro Gln Gly Gly Thr Pro Ser Ala Gly Ser Gln Arg

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| ACC | GTT | GTC | GAA | GAT | GAT | TCT | TCG | TTG | ATC | AAA | GCT | GTT | CAG | AAG | GGA | 271  |
| Thr | Val | Val | Glu | Asp | Asp | Ser | Ser | Leu | Ile | Lys | Ala | Val | Gln | Lys | Gly |      |
|     |     |     |     | 25  |     |     |     |     | 30  |     |     |     |     | 35  |     |      |
| GAT | GTT | GTC | AGG | GTC | CAG | CAA | TTG | TTA | GAA | AAA | GGG | GCT | GAT | GCC | AAT | 319  |
| Asp | Val | Val | Arg | Val | Gln | Gln | Leu | Leu | Glu | Lys | Gly | Ala | Asp | Ala | Asn |      |
|     |     |     | 40  |     |     |     |     | 45  |     |     |     |     | 50  |     |     |      |
| GCC | TGT | GAA | GAC | ACC | TGG | GGC | TGG | ACA | CCT | TTG | CAC | AAC | GCA | GTG | CAA | 367  |
| Ala | Cys | Glu | Asp | Thr | Trp | Gly | Trp | Thr | Pro | Leu | His | Asn | Ala | Val | Gln |      |
|     |     | 55  |     |     |     |     | 60  |     |     |     |     |     | 65  |     |     |      |
| GCT | GGC | AGG | GTA | GAC | ATT | GTG | AAC | CTC | CTG | CTT | AGT | CAT | GGT | GCT | GAC | 415  |
| Ala | Gly | Arg | Val | Asp | Ile | Val | Asn | Leu | Leu | Leu | Ser | His | Gly | Ala | Asp |      |
|     |     | 70  |     |     |     | 75  |     |     |     |     | 80  |     |     |     |     |      |
| CCT | CAT | CGG | AGG | AAG | AAG | AAT | GGG | GCC | ACC | CCC | TTC | ATC | ATT | GCT | GGG | 463  |
| Pro | His | Arg | Arg | Lys | Lys | Asn | Gly | Ala | Thr | Pro | Phe | Ile | Ile | Ala | Gly |      |
| 85  |     |     |     | 90  |     |     |     |     | 95  |     |     |     |     |     | 100 |      |
| ATC | CAG | GGA | GAT | GTG | AAA | CTG | CTC | GAG | ATT | CTC | CTC | TCT | TGT | GGT | GCA | 511  |
| Ile | Gln | Gly | Asp | Val | Lys | Leu | Leu | Glu | Ile | Leu | Leu | Ser | Cys | Gly | Ala |      |
|     |     |     |     |     | 105 |     |     |     | 110 |     |     |     |     |     | 115 |      |
| GAC | GTC | AAT | GAG | TGT | GAC | GAG | AAC | GGA | TTC | ACG | GCT | TTC | ATG | GAA | GCT | 559  |
| Asp | Val | Asn | Glu | Cys | Asp | Glu | Asn | Gly | Phe | Thr | Ala | Phe | Met | Glu | Ala |      |
|     |     |     | 120 |     |     |     |     | 125 |     |     |     |     | 130 |     |     |      |
| GCT | GAG | CGT | GGT | AAC | GCT | GAA | GCC | TTA | AGA | TTC | CTT | TTT | GCT | AAG | GGA | 607  |
| Ala | Glu | Arg | Gly | Asn | Ala | Glu | Ala | Leu | Arg | Phe | Leu | Phe | Ala | Lys | Gly |      |
|     |     | 135 |     |     |     |     | 140 |     |     |     |     |     | 145 |     |     |      |
| GCC | AAT | GTG | AAT | TTG | CGA | CGA | CAG | ACA | ACG | AAG | GAC | AAA | AGG | CGA | TTG | 655  |
| Ala | Asn | Val | Asn | Leu | Arg | Arg | Gln | Thr | Thr | Lys | Asp | Lys | Arg | Arg | Leu |      |
|     |     | 150 |     |     |     | 155 |     |     |     |     | 160 |     |     |     |     |      |
| AAG | CAA | GGA | GGC | GCC | ACA | GCT | CTC | ATG | AGC | GCT | GCT | GAG | AAG | GGC | CAC | 703  |
| Lys | Gln | Gly | Gly | Ala | Thr | Ala | Leu | Met | Ser | Ala | Ala | Glu | Lys | Gly | His |      |
| 165 |     |     |     |     | 170 |     |     |     |     | 175 |     |     |     |     | 180 |      |
| CTG | GAA | GTC | CTG | AGA | ATT | CTC | CTC | AAT | GAC | ATG | AAG | GCA | GAA | GTC | GAT | 751  |
| Leu | Glu | Val | Leu | Arg | Ile | Leu | Leu | Asn | Asp | Met | Lys | Ala | Glu | Val | Asp |      |
|     |     |     |     | 185 |     |     |     |     | 190 |     |     |     |     | 195 |     |      |
| GCT | CGG | GAC | AAC | ATG | GGC | AGA | AAT | GCC | CTG | ATC | CGT | ACT | CTG | CTG | AAC | 799  |
| Ala | Arg | Asp | Asn | Met | Gly | Arg | Asn | Ala | Leu | Ile | Arg | Thr | Leu | Leu | Asn |      |
|     |     |     | 200 |     |     |     |     | 205 |     |     |     |     | 210 |     |     |      |
| TGG | GAT | TGT | GAA | AAT | GTG | GAG | GAG | ATT | ACT | TCA | ATC | CTG | ATT | CAG | CAC | 847  |
| Trp | Asp | Cys | Glu | Asn | Val | Glu | Glu | Ile | Thr | Ser | Ile | Leu | Ile | Gln | His |      |
|     |     | 215 |     |     |     |     | 220 |     |     |     |     | 225 |     |     |     |      |
| GGG | GCT | GAT | GTT | AAC | GTG | AGA | GGA | GAA | AGA | GGG | AAA | ACA | CCC | CTC | ATC | 895  |
| Gly | Ala | Asp | Val | Asn | Val | Arg | Gly | Glu | Arg | Gly | Lys | Thr | Pro | Leu | Ile |      |
|     |     | 230 |     |     |     | 235 |     |     |     |     | 240 |     |     |     |     |      |
| GCA | GCA | GTG | GAG | AGG | AAG | CAC | ACA | GGC | TTG | GTG | CAG | ATG | CTC | CTG | AGT | 943  |
| Ala | Ala | Val | Glu | Arg | Lys | His | Thr | Gly | Leu | Val | Gln | Met | Leu | Leu | Ser |      |
| 245 |     |     |     |     | 250 |     |     |     |     | 255 |     |     |     |     | 260 |      |
| CGG | GAA | GGC | ATA | AAC | ATA | GAT | GCC | AGG | GAT | AAC | GAG | GGC | AAG | ACA | GCT | 991  |
| Arg | Glu | Gly | Ile | Asn | Ile | Asp | Ala | Arg | Asp | Asn | Glu | Gly | Lys | Thr | Ala |      |
|     |     |     |     | 265 |     |     |     | 270 |     |     |     |     | 275 |     |     |      |
| CTG | CTA | ATT | GCT | GTT | GAT | AAA | CAA | CTG | AAG | GAA | ATT | GTC | CAG | TTG | CTT | 1039 |
| Leu | Leu | Ile | Ala | Val | Asp | Lys | Gln | Leu | Lys | Glu | Ile | Val | Gln | Leu | Leu |      |
|     |     |     | 280 |     |     |     |     | 285 |     |     |     |     | 290 |     |     |      |
| CTT | GAA | AAG | GGA | GCT | GAT | AAG | TGT | GAC | GAT | CTT | GTT | TGG | ATA | GCC | AGG | 1087 |
| Leu | Glu | Lys | Gly | Ala | Asp | Lys | Cys | Asp | Asp | Leu | Val | Trp | Ile | Ala | Arg |      |
|     |     | 295 |     |     |     |     | 300 |     |     |     |     | 305 |     |     |     |      |
| AGG | AAT | CAT | GAC | TAT | CAC | CTT | GTA | AAG | CTT | CTC | CTC | CCT | TAT | GTA | GCT | 1135 |
| Arg | Asn | His | Asp | Tyr | His | Leu | Val | Lys | Leu | Leu | Leu | Pro | Tyr | Val | Ala |      |
|     |     | 310 |     |     |     |     | 315 |     |     |     |     | 320 |     |     |     |      |
| AAT | CCT | GAC | ACC | GAC | CCT | CCT | GCT | GGA | GAC | TGG | TCG | CCT | CAC | AGT | TCA | 1183 |
| Asn | Pro | Asp | Thr | Asp | Pro | Pro | Ala | Gly | Asp | Trp | Ser | Pro | His | Ser | Ser |      |

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| 325 |     |     |     |     | 330 |     |     |     |     | 335 |     |     |     |     | 340 |      |
| CGT | TGG | GGG | ACA | GCC | TTG | AAA | AGC | CTC | CAC | AGT | ATG | ACT | CGA | CCC | ATG | 1231 |
| Arg | Trp | Gly | Thr | Ala | Leu | Lys | Ser | Leu | His | Ser | Met | Thr | Arg | Pro | Met |      |
|     |     |     | 345 |     |     |     |     | 350 |     |     |     |     |     | 355 |     |      |
| ATT | GGC | AAA | CTC | AAG | ATC | TTC | ATT | CAT | GAT | GAC | TAT | AAA | ATT | GCT | GGC | 1279 |
| Ile | Gly | Lys | Leu | Lys | Ile | Phe | Ile | His | Asp | Asp | Tyr | Lys | Ile | Ala | Gly |      |
|     |     |     | 360 |     |     |     |     | 365 |     |     |     |     |     | 370 |     |      |
| ACT | TCC | GAA | GGG | GCT | GTC | TAC | CTA | GGG | ATC | TAT | GAC | AAT | CGA | GAA | GTG | 1327 |
| Thr | Ser | Glu | Gly | Ala | Val | Tyr | Leu | Gly | Ile | Tyr | Asp | Asn | Arg | Glu | Val |      |
|     |     | 375 |     |     |     |     | 380 |     |     |     |     | 385 |     |     |     |      |
| GCT | GTG | AAG | GTC | TTC | CGT | GAG | AAT | AGC | CCA | CGT | GGA | TGT | AAG | GAA | GTC | 1375 |
| Ala | Val | Lys | Val | Phe | Arg | Glu | Asn | Ser | Pro | Arg | Gly | Cys | Lys | Glu | Val |      |
|     |     | 390 |     |     |     |     | 395 |     |     |     |     | 400 |     |     |     |      |
| TCT | TGT | CTG | CGG | GAC | TGC | GGT | GAC | CAC | AGT | AAC | TTA | GTG | GCT | TTC | TAT | 1423 |
| Ser | Cys | Leu | Arg | Asp | Cys | Gly | Asp | His | Ser | Asn | Leu | Val | Ala | Phe | Tyr |      |
| 405 |     |     |     |     | 410 |     |     |     |     | 415 |     |     |     |     | 420 |      |
| GGA | AGA | GAG | GAC | GAT | AAG | GGC | TGT | TTA | TAT | GTG | TGT | GTG | TCC | CTG | TGT | 1471 |
| Gly | Arg | Glu | Asp | Asp | Lys | Gly | Cys | Leu | Tyr | Val | Cys | Val | Ser | Leu | Cys |      |
|     |     |     |     | 425 |     |     |     |     | 430 |     |     |     |     | 435 |     |      |
| GAG | TGG | ACA | CTG | GAA | GAG | TTC | CTG | AGG | TTG | CCC | AGA | GAG | GAA | CCT | GTG | 1519 |
| Glu | Trp | Thr | Leu | Glu | Glu | Phe | Leu | Arg | Leu | Pro | Arg | Glu | Glu | Pro | Val |      |
|     |     |     | 440 |     |     |     |     | 445 |     |     |     |     | 450 |     |     |      |
| GAG | AAC | GGG | GAA | GAT | AAG | TTT | GCC | CAC | AGC | ATC | CTA | TTA | TCT | ATA | TTT | 1567 |
| Glu | Asn | Gly | Glu | Asp | Lys | Phe | Ala | His | Ser | Ile | Leu | Leu | Ser | Ile | Phe |      |
|     |     | 455 |     |     |     |     | 460 |     |     |     |     | 465 |     |     |     |      |
| GAG | GGT | GTT | CAA | AAA | CTA | CAC | TTG | CAT | GGA | TAT | TCC | CAT | CAG | GAC | CTG | 1615 |
| Glu | Gly | Val | Gln | Lys | Leu | His | Leu | His | Gly | Tyr | Ser | His | Gln | Asp | Leu |      |
|     |     | 470 |     |     |     |     | 475 |     |     |     |     | 480 |     |     |     |      |
| CAA | CCA | CAA | AAC | ATC | TTA | ATA | GAT | TCC | AAG | AAA | GCT | GTC | CGG | CTG | GCA | 1663 |
| Gln | Pro | Gln | Asn | Ile | Leu | Ile | Asp | Ser | Lys | Lys | Ala | Val | Arg | Leu | Ala |      |
| 485 |     |     |     |     | 490 |     |     |     |     | 495 |     |     |     |     | 500 |      |
| GAT | TTT | GAT | CAG | AGC | ATC | CGA | TGG | ATG | GGA | GAG | TCA | CAG | ATG | GTC | AGG | 1711 |
| Asp | Phe | Asp | Gln | Ser | Ile | Arg | Trp | Met | Gly | Glu | Ser | Gln | Met | Val | Arg |      |
|     |     |     |     | 505 |     |     |     |     | 510 |     |     |     |     | 515 |     |      |
| AGA | GAC | TTG | GAG | GAT | CTT | GGA | CGG | CTG | GTT | CTC | TAC | GTG | GTA | ATG | AAA | 1759 |
| Arg | Asp | Leu | Glu | Asp | Leu | Gly | Arg | Leu | Val | Leu | Tyr | Val | Val | Met | Lys |      |
|     |     |     | 520 |     |     |     |     | 525 |     |     |     |     | 530 |     |     |      |
| GGT | GAG | ATC | CCC | TTT | GAG | ACA | CTA | AAG | ACT | CAG | AAT | GAT | GAA | GTG | CTG | 1807 |
| Gly | Glu | Ile | Pro | Phe | Glu | Thr | Leu | Lys | Thr | Gln | Asn | Asp | Glu | Val | Leu |      |
|     |     | 535 |     |     |     |     | 540 |     |     |     |     | 545 |     |     |     |      |
| CTT | ACA | ATG | TCT | CCA | GAT | GAG | GAG | ACT | AAG | GAC | CTC | ATT | CAT | TGC | CTG | 1855 |
| Leu | Thr | Met | Ser | Pro | Asp | Glu | Glu | Thr | Lys | Asp | Leu | Ile | His | Cys | Leu |      |
|     |     | 550 |     |     |     |     | 555 |     |     |     |     | 560 |     |     |     |      |
| TTT | TCT | CCT | GGA | GAA | AAT | GTC | AAG | AAC | TGC | CTG | GTA | GAC | CTG | CTT | GGC | 1903 |
| Phe | Ser | Pro | Gly | Glu | Asn | Val | Lys | Asn | Cys | Leu | Val | Asp | Leu | Leu | Gly |      |
| 565 |     |     |     |     | 570 |     |     |     |     | 575 |     |     |     |     | 580 |      |
| CAT | CCT | TTC | TTT | TGG | ACT | TGG | GAG | AAC | CGC | TAT | AGA | ACA | CTC | CGG | AAT | 1951 |
| His | Pro | Phe | Phe | Trp | Thr | Trp | Glu | Asn | Arg | Tyr | Arg | Thr | Leu | Arg | Asn |      |
|     |     |     |     | 585 |     |     |     |     | 590 |     |     |     |     | 595 |     |      |
| GTG | GGA | AAT | GAA | TCT | GAC | ATC | AAA | GTA | CGG | AAA | TGT | AAA | AGT | GAT | CTT | 1999 |
| Val | Gly | Asn | Glu | Ser | Asp | Ile | Lys | Val | Arg | Lys | Cys | Lys | Ser | Asp | Leu |      |
|     |     |     | 600 |     |     |     |     | 605 |     |     |     |     | 610 |     |     |      |
| CTC | AGA | CTA | CTG | CAG | CAT | CAG | ACA | CTT | GAG | CCT | CCC | AGA | AGC | TTT | GAC | 2047 |
| Leu | Arg | Leu | Leu | Gln | His | Gln | Thr | Leu | Glu | Pro | Pro | Arg | Ser | Phe | Asp |      |
|     |     | 615 |     |     |     |     | 620 |     |     |     |     | 625 |     |     |     |      |
| CAG | TGG | ACA | TCT | AAG | ATC | GAC | AAA | AAT | GTT | ATG | GAT | GAA | ATG | AAT | CAT | 2095 |
| Gln | Trp | Thr | Ser | Lys | Ile | Asp | Lys | Asn | Val | Met | Asp | Glu | Met | Asn | His |      |
|     |     | 630 |     |     |     |     | 635 |     |     |     |     | 640 |     |     |     |      |
| TTC | TAC | GAA | AAG | AGA | AAA | AAA | AAC | CCT | TAT | CAG | GAT | ACT | GTA | GGT | GAT | 2143 |
| Phe | Tyr | Glu | Lys | Arg | Lys | Lys | Asn | Pro | Tyr | Gln | Asp | Thr | Val | Gly | Asp |      |

```
645                      650                      655                      660
CTG  CTG  AAG  TTT  ATT  CGG  AAT  ATA  GGC  GAA  CAC  ATC  AAT  GAG  GAA  AAA        2191
Leu  Leu  Lys  Phe  Ile  Arg  Asn  Ile  Gly  Glu  His  Ile  Asn  Glu  Glu  Lys
                    665                      670                      675

AAG  CGG  GGG                                                                          2200
Lys  Arg  Gly
```

( 2 ) INFORMATION FOR SEQ ID NO:6:

( i ) SEQUENCE CHARACTERISTICS:
        ( A ) LENGTH: 679 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met  Glu  Thr  Pro  Asp  Tyr  Asn  Thr  Pro  Gln  Gly  Gly  Thr  Pro  Ser  Ala
 1                    5                       10                      15

Gly  Ser  Gln  Arg  Thr  Val  Val  Glu  Asp  Ser  Ser  Leu  Ile  Lys  Ala
               20                       25                      30

Val  Gln  Lys  Gly  Asp  Val  Val  Arg  Val  Gln  Gln  Leu  Leu  Glu  Lys  Gly
               35                       40                      45

Ala  Asp  Ala  Asn  Ala  Cys  Glu  Asp  Thr  Trp  Gly  Trp  Thr  Pro  Leu  His
 50                       55                      60

Asn  Ala  Val  Gln  Ala  Gly  Arg  Val  Asp  Ile  Val  Asn  Leu  Leu  Leu  Ser
 65                    70                       75                         80

His  Gly  Ala  Asp  Pro  His  Arg  Arg  Lys  Lys  Asn  Gly  Ala  Thr  Pro  Phe
                    85                       90                      95

Ile  Ile  Ala  Gly  Ile  Gln  Gly  Asp  Val  Lys  Leu  Leu  Glu  Ile  Leu  Leu
               100                      105                     110

Ser  Cys  Gly  Ala  Asp  Val  Asn  Glu  Cys  Asp  Glu  Asn  Gly  Phe  Thr  Ala
               115                      120                     125

Phe  Met  Glu  Ala  Ala  Glu  Arg  Gly  Asn  Ala  Glu  Ala  Leu  Arg  Phe  Leu
      130                      135                     140

Phe  Ala  Lys  Gly  Ala  Asn  Val  Asn  Leu  Arg  Arg  Gln  Thr  Thr  Lys  Asp
145                      150                      155                     160

Lys  Arg  Arg  Leu  Lys  Gln  Gly  Gly  Ala  Thr  Ala  Leu  Met  Ser  Ala  Ala
               165                      170                     175

Glu  Lys  Gly  His  Leu  Glu  Val  Leu  Arg  Ile  Leu  Leu  Asn  Asp  Met  Lys
                    180                      185                     190

Ala  Glu  Val  Asp  Ala  Arg  Asp  Asn  Met  Gly  Arg  Asn  Ala  Leu  Ile  Arg
               195                      200                     205

Thr  Leu  Leu  Asn  Trp  Asp  Cys  Glu  Asn  Val  Glu  Glu  Ile  Thr  Ser  Ile
210                      215                      220

Leu  Ile  Gln  His  Gly  Ala  Asp  Val  Asn  Val  Arg  Gly  Glu  Arg  Gly  Lys
225                      230                      235                     240

Thr  Pro  Leu  Ile  Ala  Ala  Val  Glu  Arg  Lys  His  Thr  Gly  Leu  Val  Gln
                    245                      250                     255

Met  Leu  Leu  Ser  Arg  Glu  Gly  Ile  Asn  Ile  Asp  Ala  Arg  Asp  Asn  Glu
               260                      265                     270

Gly  Lys  Thr  Ala  Leu  Leu  Ile  Ala  Val  Asp  Lys  Gln  Leu  Lys  Glu  Ile
               275                      280                     285

Val  Gln  Leu  Leu  Leu  Glu  Lys  Gly  Ala  Asp  Lys  Cys  Asp  Asp  Leu  Val
               290                      295                     300

Trp  Ile  Ala  Arg  Arg  Asn  His  Asp  Tyr  His  Leu  Val  Lys  Leu  Leu  Leu
305                      310                      315                     320
```

Pro Tyr Val Ala Asn Pro Asp Thr Asp Pro Ala Gly Asp Trp Ser
            325                 330                 335

Pro His Ser Ser Arg Trp Gly Thr Ala Leu Lys Ser Leu His Ser Met
            340                 345                 350

Thr Arg Pro Met Ile Gly Lys Leu Lys Ile Phe Ile His Asp Asp Tyr
            355                 360                 365

Lys Ile Ala Gly Thr Ser Glu Gly Ala Val Tyr Leu Gly Ile Tyr Asp
            370                 375                 380

Asn Arg Glu Val Ala Val Lys Val Phe Arg Glu Asn Ser Pro Arg Gly
385                 390                 395                 400

Cys Lys Glu Val Ser Cys Leu Arg Asp Cys Gly Asp His Ser Asn Leu
                405                 410                 415

Val Ala Phe Tyr Gly Arg Glu Asp Asp Lys Gly Cys Leu Tyr Val Cys
            420                 425                 430

Val Ser Leu Cys Glu Trp Thr Leu Glu Glu Phe Leu Arg Leu Pro Arg
            435                 440                 445

Glu Glu Pro Val Glu Asn Gly Glu Asp Lys Phe Ala His Ser Ile Leu
            450                 455                 460

Leu Ser Ile Phe Glu Gly Val Gln Lys Leu His Leu His Gly Tyr Ser
465                 470                 475                 480

His Gln Asp Leu Gln Pro Gln Asn Ile Leu Ile Asp Ser Lys Lys Ala
                485                 490                 495

Val Arg Leu Ala Asp Phe Asp Gln Ser Ile Arg Trp Met Gly Glu Ser
            500                 505                 510

Gln Met Val Arg Arg Asp Leu Glu Asp Leu Gly Arg Leu Val Leu Tyr
            515                 520                 525

Val Val Met Lys Gly Glu Ile Pro Phe Glu Thr Leu Lys Thr Gln Asn
    530                 535                 540

Asp Glu Val Leu Leu Thr Met Ser Pro Asp Glu Thr Lys Asp Leu
545                 550                 555                 560

Ile His Cys Leu Phe Ser Pro Gly Glu Asn Val Lys Asn Cys Leu Val
                565                 570                 575

Asp Leu Leu Gly His Pro Phe Phe Trp Thr Trp Glu Asn Arg Tyr Arg
            580                 585                 590

Thr Leu Arg Asn Val Gly Asn Glu Ser Asp Ile Lys Val Arg Lys Cys
            595                 600                 605

Lys Ser Asp Leu Leu Arg Leu Leu Gln His Gln Thr Leu Glu Pro Pro
            610                 615                 620

Arg Ser Phe Asp Gln Trp Thr Ser Lys Ile Asp Lys Asn Val Met Asp
625                 630                 635                 640

Glu Met Asn His Phe Tyr Glu Lys Arg Lys Lys Asn Pro Tyr Gln Asp
                645                 650                 655

Thr Val Gly Asp Leu Leu Lys Phe Ile Arg Asn Ile Gly Glu His Ile
            660                 665                 670

Asn Glu Glu Lys Lys Arg Gly
            675

( 2 ) INFORMATION FOR SEQ ID NO:7:

( i ) SEQUENCE CHARACTERISTICS:
        ( A ) LENGTH: 190 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
Asp Arg Arg Lys Pro Arg Gln Asn Asn Arg Arg Asp Arg Asn Glu Arg
1               5                   10                  15

Arg Asp Thr Arg Ser Glu Arg Thr Glu Gly Ser Asp Asn Arg Glu Glu
            20                  25                  30

Asn Arg Arg Asn Arg Arg Gln Ala Gln Gln Gln Thr Ala Glu Thr Arg
        35                  40                  45

Glu Ser Arg Gln Gln Ala Glu Val Thr Glu Lys Ala Arg Thr Ala Asp
    50                  55                  60

Glu Gln Gln Ala Pro Arg Arg Glu Arg Ser Arg Arg Asn Asp Asp
65                  70                  75                  80

Lys Arg Gln Ala Gln Gln Glu Ala Lys Ala Leu Asn Val Glu Gln
                85                  90                  95

Ser Val Gln Glu Thr Glu Gln Glu Arg Val Arg Pro Val Gln Pro
                100                 105                 110

Arg Arg Lys Gln Arg Gln Leu Asn Gln Lys Val Arg Tyr Glu Gln Ser
            115                 120                 125

Val Ala Glu Glu Ala Val Val Ala Pro Val Val Glu Thr Val Ala
        130                 135                 140

Ala Glu Pro Ile Val Gln Glu Ala Pro Ala Pro Arg Thr Glu Leu Val
145                 150                 155                 160

Lys Val Pro Leu Pro Val Val Ala Gln Thr Ala Pro Glu Gln Gln Glu
                165                 170                 175

Glu Asn Asn Ala Asp Asn Arg Asp Asn Gly Gly Met Pro Ser
                180                 185                 190
```

( 2 ) INFORMATION FOR SEQ ID NO:8:

( i ) SEQUENCE CHARACTERISTICS:
( A ) LENGTH: 2562 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:8:

```
CAGTTTCTGG AGCAAATTCA GTTTGCCTTC CTGGATTTGT AAATTGTAAT GACCTCAAAA      60
CTTTAGCAGT TCTTCCATCT GACTCAGGTT TGCTTCTCTG GCGGTCTTCA GAATCAACAT     120
CCACACTTCC GTGATTATCT GCGTGCATTT TGGACAAAGC TTCCAACCAG GATACGGGAA     180
GAAGAAATGG CTGGTGATCT TTCAGCAGGT TTCTTCATGG AGGAACTTAA TACATACCGT     240
CAGAAGCAGG GAGTAGTACT TAAATATCAA GAACTGCCTA ATTCAGGACC TCCACATGAT     300
AGGAGGTTTA CATTTCAAGT TATAATAGAT GGAAGAGAAT TTCCAGAAGG TGAAGGTAGA     360
TCAAAGAAGG AAGCAAAAAA TGCCGCAGCC AAATTAGCTG TTGAGATACT TAATAAGGAA     420
AAGAAGGCAG TTAGTCCTTT ATTATTGACA CAACGAATT CTTCAGAAGG ATTATCCATG     480
GGGAATTACA TAGGCCTTAT CAATAGAATT GCCCAGAAGA AAAGACTAAC TGTAAATTAT     540
GAACAGTGTG CATCGGGGGT GCATGGGCCA GAAGGATTTC ATTATAAATG CAAAATGGGA     600
CAGAAAGAAT ATAGTATTGG TACAGGTTCT ACTAAACAGG AAGCAAAACA ATTGGCCGCT     660
AAACTTGCAT ATCTTCAGAT ATTATCAGAA GAAACCTCAG TGAAATCTGA CTACCTGTCC     720
TCTGGTTCTT TTGCTACTAC GTGTGAGTCC CAAAGCAACT CTTTAGTGAC CAGCACACTC     780
GCTTCTGAAT CATCATCTGA AGGTGACTTC TCAGCAGATA CATCAGAGAT AAATTCTAAC     840
```

-continued

| | | | | | |
|---|---|---|---|---|---|
| AGTGACAGTT | TAAACAGTTC | TTCGTTGCTT | ATGAATGGTC | TCAGAAATAA | TCAAAGGAAG | 900 |
| GCAAAAAGAT | CTTTGGCACC | CAGATTTGAC | CTTCCTGACA | TGAAAGAAAC | AAAGTATACT | 960 |
| GTGGACAAGA | GGTTTGGCAT | GGATTTTAAA | GAAATAGAAT | TAATTGGCTC | AGGTGGATTT | 1020 |
| GGCCAAGTTT | TCAAAGCAAA | ACACAGAATT | GACGGAAAGA | CTTACGTTAT | TAAACGTGTT | 1080 |
| AAATATAATA | ACGAGAAGGC | GGAGCGTGAA | GTAAAAGCAT | TGGCAAAACT | TGATCATGTA | 1140 |
| AATATTGTTC | ACTACAATGG | CTGTTGGGAT | GGATTTGATT | ATGATCCTGA | GACCAGTGAT | 1200 |
| GATTCTCTTG | AGAGCAGTGA | TTATGATCCT | GAGAACAGCA | AAAATAGTTC | AAGGTCAAAG | 1260 |
| ACTAAGTGCC | TTTTCATCCA | AATGGAATTC | TGTGATAAAG | GGACCTTGGA | ACAATGGATT | 1320 |
| GAAAAAGAA | GAGGCGAGAA | ACTAGACAAA | GTTTTGGCTT | TGGAACTCTT | TGAACAAATA | 1380 |
| ACAAAGGGG | TGGATTATAT | ACATTCAAAA | AAATTAATTC | ATAGAGATCT | TAAGCCAAGT | 1440 |
| AATATATTCT | TAGTAGATAC | AAAACAAGTA | AAGATTGGAG | ACTTTGGACT | TGTAACATCT | 1500 |
| CTGAAAAATG | ATGGAAAGCG | AACAAGGAGT | AGGGGAACTT | TGCGATACAT | GAGCCCAGAA | 1560 |
| CAGATTTCTT | CGCAAGACTA | TGGAAGGAA | GTGGACCTCT | ACGCTTGGG | GCTAATTCTT | 1620 |
| GCTGAACTTC | TTCATGTATG | TGACACTGCT | TTTGAAACAT | CAAAGTTTTT | CACAGACCTA | 1680 |
| CGGGATGGCA | TCATCTCAGA | TATATTTGAT | AAAAAGAAA | AAACTCTTCT | ACAGAAATTA | 1740 |
| CTCTCAAAGA | AACCTGAGGA | TCGACCTAAC | ACATCTGAAA | TACTAAGGAC | CTTGACTGTG | 1800 |
| TGGAAGAAAA | GCCCAGAGAA | AAATGAACGA | CACACATGTT | AGAGCCCTTC | TGAAAAAGTA | 1860 |
| TCCTGCTTCT | GATATGCAGT | TTTCCTTAAA | TTATCTAAAA | TCTGCTAGGG | AATATCAATA | 1920 |
| GATATTTACC | TTTTATTTTA | ATGTTTCCTT | TAATTTTTTA | CTATTTTTAC | TAATCTTTCT | 1980 |
| GCAGAAACAG | AAAGGTTTTC | TTCTTTTTGC | TTCAAAAACA | TTCTTACATT | TTACTTTTTC | 2040 |
| CTGGCTCATC | TCTTTATTTT | TTTTTTTTTT | TTTAAAGAC | AGAGTCTCGC | TCTGTTGCCC | 2100 |
| AGGCTGGAGT | GCAATGACAC | AGTCTTGGCT | CACTGCAACT | TCTGCCTCTT | GGGTTCAAGT | 2160 |
| GATTCTCCTG | CCTCAGCCTC | CTGAGTAGCT | GGATTACAGG | CATGTGCCAC | CCACCCAACT | 2220 |
| AATTTTTGTG | TTTTTAATAA | AGACAGGGTT | TCACCATGTT | GGCCAGGCTG | GTCTCAAACT | 2280 |
| CCTGACCTCA | AGTAATCCAC | CTGCCTCGGC | CTCCCAAAGT | GCTGGGATTA | CAGGGATGAG | 2340 |
| CCACCGCGCC | CAGCCTCATC | TCTTTGTTCT | AAAGATGGAA | AAACCACCCC | CAAATTTTCT | 2400 |
| TTTTATACTA | TTAATGAATC | AATCAATTCA | TATCTATTTA | TTAAATTTCT | ACCGCTTTTA | 2460 |
| GGCCAAAAAA | ATGTAAGATC | GTTCTCTGCC | TCACATAGCT | TACAAGCCAG | CTGGAGAAAT | 2520 |
| ATGGTACTCA | TTAAAAAAAA | AAAAAAAAG | TGATGTACAA | CC | | 2562 |

( 2 ) INFORMATION FOR SEQ ID NO:9:

( i ) SEQUENCE CHARACTERISTICS:
        ( A ) LENGTH: 551 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:9:

```
Met Ala Gly Asp Leu Ser Ala Gly Phe Phe Met Glu Glu Leu Asn Thr
 1               5                  10                  15

Tyr Arg Gln Lys Gln Gly Val Val Leu Lys Tyr Gln Glu Leu Pro Asn
             20                  25                  30

Ser Gly Pro Pro His Asp Arg Arg Phe Thr Phe Gln Val Ile Ile Asp
         35                  40                  45
```

```
Gly Arg Glu Phe Pro Glu Gly Glu Gly Arg Ser Lys Lys Glu Ala Lys
 50                  55                  60

Asn Ala Ala Ala Lys Leu Ala Val Glu Ile Leu Asn Lys Glu Lys Lys
 65                  70                  75                  80

Ala Val Ser Pro Leu Leu Thr Thr Thr Asn Ser Ser Glu Gly Leu
                 85                  90                  95

Ser Met Gly Asn Tyr Ile Gly Leu Ile Asn Arg Ile Ala Gln Lys Lys
             100                 105                 110

Arg Leu Thr Val Asn Tyr Glu Gln Cys Ala Ser Gly Val His Gly Pro
         115                 120                 125

Glu Gly Phe His Tyr Lys Cys Lys Met Gly Gln Lys Glu Tyr Ser Ile
     130                 135                 140

Gly Thr Gly Ser Thr Lys Gln Glu Ala Lys Gln Leu Ala Ala Lys Leu
145                 150                 155                 160

Ala Tyr Leu Gln Ile Leu Ser Glu Glu Thr Ser Val Lys Ser Asp Tyr
                 165                 170                 175

Leu Ser Ser Gly Ser Phe Ala Thr Thr Cys Glu Ser Gln Ser Asn Ser
             180                 185                 190

Leu Val Thr Ser Thr Leu Ala Ser Glu Ser Ser Ser Gly Asp Phe
         195                 200                 205

Ser Ala Asp Thr Ser Glu Ile Asn Ser Asn Ser Asp Ser Leu Asn Ser
    210                 215                 220

Ser Ser Leu Leu Met Asn Gly Leu Arg Asn Asn Gln Arg Lys Ala Lys
225                 230                 235                 240

Arg Ser Leu Ala Pro Arg Phe Asp Leu Pro Asp Met Lys Glu Thr Lys
                 245                 250                 255

Tyr Thr Val Asp Lys Arg Phe Gly Met Asp Phe Lys Glu Ile Glu Leu
             260                 265                 270

Ile Gly Ser Gly Gly Phe Gly Gln Val Phe Lys Ala Lys His Arg Ile
         275                 280                 285

Asp Gly Lys Thr Tyr Val Ile Lys Arg Val Lys Tyr Asn Asn Glu Lys
     290                 295                 300

Ala Glu Arg Glu Val Lys Ala Leu Ala Lys Leu Asp His Val Asn Ile
305                 310                 315                 320

Val His Tyr Asn Gly Cys Trp Asp Gly Phe Asp Tyr Asp Pro Glu Thr
                 325                 330                 335

Ser Asp Asp Ser Leu Glu Ser Ser Asp Tyr Asp Pro Glu Asn Ser Lys
             340                 345                 350

Asn Ser Ser Arg Ser Lys Thr Lys Cys Leu Phe Ile Gln Met Glu Phe
         355                 360                 365

Cys Asp Lys Gly Thr Leu Glu Gln Trp Ile Glu Lys Arg Arg Gly Glu
     370                 375                 380

Lys Leu Asp Lys Val Leu Ala Leu Glu Leu Phe Glu Gln Ile Thr Lys
385                 390                 395                 400

Gly Val Asp Tyr Ile His Ser Lys Lys Leu Ile His Arg Asp Leu Lys
                 405                 410                 415

Pro Ser Asn Ile Phe Leu Val Asp Thr Lys Gln Val Lys Ile Gly Asp
             420                 425                 430

Phe Gly Leu Val Thr Ser Leu Lys Asn Asp Gly Lys Arg Thr Arg Ser
         435                 440                 445

Lys Gly Thr Leu Arg Tyr Met Ser Pro Glu Gln Ile Ser Ser Gln Asp
     450                 455                 460

Tyr Gly Lys Glu Val Asp Leu Tyr Ala Leu Gly Leu Ile Leu Ala Glu
465                 470                 475                 480
```

```
            Leu  Leu  His  Val  Cys  Asp  Thr  Ala  Phe  Glu  Thr  Ser  Lys  Phe  Phe  Thr
                           485                      490                     495

Asp  Leu  Arg  Asp  Gly  Ile  Ile  Ser  Asp  Ile  Phe  Asp  Lys  Lys  Glu  Lys
                           500                      505                     510

Thr  Leu  Leu  Gln  Lys  Leu  Leu  Ser  Lys  Lys  Pro  Glu  Asp  Arg  Pro  Asn
                           515                      520                     525

Thr  Ser  Glu  Ile  Leu  Arg  Thr  Leu  Thr  Val  Trp  Lys  Lys  Ser  Pro  Glu
                   530                           535                     540

Lys  Asn  Glu  Arg  His  Thr  Cys
            545                      550
```

( 2 ) INFORMATION FOR SEQ ID NO:10:

( i ) SEQUENCE CHARACTERISTICS:
        ( A ) LENGTH: 1650 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:10:

```
AACTGAAACC  AACAGCAGTC  CAAGCTCAGT  CAGCAGAAGA  GATAAAAGCA  AACAGGTCTG      60

GGAGGCAGTT  CTGTTGCCAC  TCTCTCTCCT  GTCAATGATG  GATCTCAGAA  ATACCCCAGC     120

CAAATCTCTG  GACAAGTTCA  TTGAAGACTA  TCTCTTGCCA  GACACGTGTT  TCCGCATGCA     180

AATCGACCAT  GCCATTGACA  TCATCTGTGG  GTTCCTGAAG  GAAAGGTGCT  TCCGAGGTAG     240

CTCCTACCCT  GTGTGTGTGT  CCAAGGTGGT  AAAGGGTGGC  TCCTCAGGCA  AGGGCACCAC     300

CCTCAGAGGC  CGATCTGACG  CTGACCTGGT  TGTCTTCCTC  AGTCCTCTCA  GCACTTTTCA     360

GGATCAGTTA  AATCGCCGGG  GAGAGTTCAT  CCAGGAAATT  AGGAGACAGC  TGGAAGCCTG     420

TCAAAGAGAG  AGAGCACTTT  CCGTGAAGTT  TGAGGTCCAG  GCTCCACGCT  GGGGCAACCC     480

CCGTGCGCTC  AGCTTCGTAC  TGAGTTCGCT  CCAGCTCGGG  GAGGGGGTGG  AGTTCGATGT     540

GCTGCCTGCC  TTTGATGCCC  TGGGTCAGTT  GACTGGCAGC  TATAAACCTA  ACCCCCAAAT     600

CTATGTCAAG  CTCATCGAGG  AGTGCACCGA  CCTGCAGAAA  GAGGGCGAGT  TCTCCACCTG     660

CTTCACAGAA  CTACAGAGAG  ACTTCCTGAA  GCAGCGCCCC  ACCAAGCTCA  AGAGCCTCAT     720

CCGCCTAGTC  AAGCACTGGT  ACCAAAATTG  TAAGAAGAAG  CTTGGGAAGC  TGCCACCTCA     780

GTATGCCCTG  GAGCTCCTGA  CGGTCTATGC  TTGGGAGCGA  GGGAGCATGA  AAACACATTT     840

CAACACAGCC  CAAGGATTTC  GGACGGTCTT  GGAATTAGTC  ATAAACTACC  AGCAACTCTG     900

CATCTACTGG  ACAAAGTATT  ATGACTTTAA  AAACCCCATT  ATTGAAAAGT  ACCTGAGAAG     960

GCAGCTCACG  AAACCCAGGC  CTGTGATCCT  GGACCCGGCG  GACCCTACAG  GAAACTTGGG    1020

TGGTGGAGAC  CCAAAGGGTT  GGAGGCAGCT  GGCACAAGAG  GCTGAGGCCT  GGCTGAATTA    1080

CCCATGCTTT  AAGAATTGGG  ATGGGTCCCC  AGTGAGCTCC  TGGATTCTGC  TGGCTGAAAG    1140

CAACAGTACA  GACGATGAGA  CCGACGATCC  CAGGACGTAT  CAGAAATATG  GTTACATTGG    1200

AACACATGAG  TACCCTCATT  TCTCTCATAG  ACCCAGCACG  CTCCAGGCAG  CATCCACCCC    1260

ACAGGCAGAA  GAGGACTGGA  CCTGCACCAT  CCTCTGAATG  CCAGTGCATC  TTGGGGGAAA    1320

GGGCTCCAGT  GTTATCTGGA  CCAGTTCCTT  CATTTTCAGG  TGGGACTCTT  GATCCAGAGA    1380

AGACAAAGCT  CCTCAGTGAG  CTGGTGTATA  ATCCAAGACA  GAACCCAAGT  CTCCTGACTC    1440

CTGGCCTTCT  ATGCCCTCTA  TCCTATCATA  GATAACATTC  TCCACAGCCT  CACTTCATTC    1500

CACCTATTCT  CTGAAAATAT  TCCCTGAGAG  AGAACAGAGA  GATTTAGATA  AGAGAATGAA    1560
```

ATTCCAGCCT TGACTTTCTT CTGTGCACCT GATGGGAGGG TAATGTCTAA TGTATTATCA    1620

ATAACAATAA AAATAAAGCA AATACCAAAA    1650

( 2 ) INFORMATION FOR SEQ ID NO:11:

( i ) SEQUENCE CHARACTERISTICS:
        ( A ) LENGTH: 400 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:11:

```
Met Met Asp Leu Arg Asn Thr Pro Ala Lys Ser Leu Asp Lys Phe Ile
  1               5                  10                  15

Glu Asp Tyr Leu Leu Pro Asp Thr Cys Phe Arg Met Gln Ile Asp His
             20                  25                  30

Ala Ile Asp Ile Ile Cys Gly Phe Leu Lys Glu Arg Cys Phe Arg Gly
         35                  40                  45

Ser Ser Tyr Pro Val Cys Val Ser Lys Val Val Lys Gly Gly Ser Ser
     50                  55                  60

Gly Lys Gly Thr Thr Leu Arg Gly Arg Ser Asp Ala Asp Leu Val Val
 65                  70                  75                  80

Phe Leu Ser Pro Leu Thr Thr Phe Gln Asp Gln Leu Asn Arg Arg Gly
                 85                  90                  95

Glu Phe Thr Gln Glu Ile Arg Arg Gln Leu Glu Ala Cys Gln Arg Glu
            100                 105                 110

Arg Ala Leu Ser Val Lys Phe Glu Val Gln Ala Pro Arg Trp Gly Asn
            115                 120                 125

Pro Arg Ala Leu Ser Phe Val Leu Ser Ser Leu Gln Leu Gly Glu Gly
        130                 135                 140

Val Glu Phe Asp Val Leu Pro Ala Phe Asp Ala Leu Gly Gln Leu Thr
145                 150                 155                 160

Gly Ser Tyr Lys Pro Asn Pro Gln Ile Tyr Val Lys Leu Ile Glu Glu
                165                 170                 175

Cys Thr Asp Leu Gln Lys Glu Gly Glu Phe Ser Thr Cys Gly Thr Glu
            180                 185                 190

Leu Gln Arg Asp Phe Leu Lys Gln Arg Pro Thr Lys Leu Lys Ser Leu
        195                 200                 205

Ile Arg Leu Val Lys His Trp Thr Gln Asn Cys Lys Lys Lys Leu Gly
    210                 215                 220

Lys Leu Pro Pro Gln Tyr Ala Leu Glu Leu Leu Thr Val Tyr Ala Trp
225                 230                 235                 240

Glu Arg Gly Ser Met Lys Thr His Phe Asn Thr Ala Gln Gly Phe Arg
                245                 250                 255

Thr Val Leu Glu Leu Val Ile Asn Tyr Gln Gln Leu Cys Ile Tyr Trp
            260                 265                 270

Ile Lys Tyr Tyr Asp Phe Lys Asn Pro Ile Ile Glu Lys Tyr Leu Arg
        275                 280                 285

Arg Gln Leu Thr Lys Pro Arg Pro Val Ile Leu Lys Pro Ala Asp Pro
    290                 295                 300

Thr Gly Asn Leu Gly Gly Gly Asp Pro Lys Gly Trp Arg Gln Leu Ala
305                 310                 315                 320

Gln Glu Ala Glu Ala Trp Leu Asn Tyr Pro Cys Phe Lys Asn Trp Asp
                325                 330                 335
```

-continued

| | | | | | | | | | | | | | | | |
|---|---|---|---|---|---|---|---|---|---|---|---|---|---|---|---|
| Gly | Ser | Pro | Val 340 | Ser | Ser | Trp | Ile | Leu 345 | Leu | Ala | Glu | Ser | Asn 350 | Ser | Thr |
| Asp | Asp | Glu 355 | Thr | Asp | Asp | Pro | Arg 360 | Thr | Tyr | Gln | Lys | Tyr 365 | Gly | Tyr | Ile |
| Gly | Thr 370 | His | Glu | Tyr | Pro | His 375 | Phe | Ser | His | Arg | Pro 380 | Ser | Thr | Leu | Gln |
| Ala 385 | Ala | Ser | Thr | Pro | Gln 390 | Ala | Glu | Glu | Asp | Trp 395 | Thr | Cys | Thr | Ile | Leu 400 |

The present invention may, of course, be carried out in other specific ways than those herein set forth without departing from the spirit and essential characteristics of the invention. For example, the nucleotide sequences disclosed herein may be combined with other nucleotide sequences to generate heterologous nucleotide sequences for introduction into the genomes of plants to form transgenic plants. The present embodiments are, therefore, to be considered in all respects as illustrative and not restrictive and all changes coming within the meaning and equivalency range of the appended claims are intended to be embraced herein.

Having described our invention, we claim:

1. A transgenic plant, and any transgenic descendent of said transgenic plant, whose cells contain a functional 2-5A system for conferring to said transgenic plant and any transgenic descendent of said transgenic plant resistance to viral infection, said functional 2-5A system comprising:
   a.) a first nucleotide sequence encoding an amino acid sequence having 2-5A-dependent RNase activity;
   b.) a second nucleotide sequence encoding an amino acid sequence having 2-5A synthetase activity;
   said transgenic plant being more resistant against viral infection than a similar plant which does not contain said functional 2-5A system.

2. A transgenic plant of claim 1, said transgenic plant being a transgenic tobacco plant, and any transgenic descendant of said transgenic tobacco plant.

3. A transgenic plant of claim 2, said transgenic tobacco plant, and any transgenic descendant of said transgenic tobacco plant, being more resistant against the tobacco mosaic virus, the tobacco etch virus and the alfalfa mosaic virus than a similar tobacco plant which does not contain said functional 2-5A system.

4. A transgenic plant of claim 1, said first nucleotide sequence includes nucleotides designated as 104-2326 in SEQ ID NO: 1 or any part of this nucleotide sequence which encodes an amino acid sequence having human 2-5A-dependent RNase activity, and said second exogenous nucleotide sequence includes nucleotides designated as 1-1650 in SEQ ID NO: 10 or any part of this nucleotide sequence which encodes an amino acid sequence having human 2-5A-synthetase activity or the double stranded RNA binding domain of 2-5A-synthetase.

5. A transgenic plant of claim 1, said first nucleotide sequence includes nucleotides designated as 164-2200 in SEQ ID NO: 5 or any part of this nucleotide sequence which encodes an amino acid sequence having murine 2-5A-dependent RNase activity, and said second nucleotide sequence includes nucleotides designated as 1-1650 in SEQ ID NO: 10 or any part of this nucleotide sequence which encodes an amino acid sequence having human 2-5A-synthetase activity or the double stranded RNA binding domain of 2-5A-synthetase.

6. A transgenic plant of claim 1, said functional 2-5A system being pAM2200 vector having ATCC Accession No. 98686.

7. A vector for introduction into a plant, said vector containing a functional 2-5A system for conferring resistance against viral infection to a plant when said vector has been introduced effectively into a plant, said functional 2-5A system comprising:
   a.) a first nucleotide sequence encoding an amino acid sequence having 2-5A-dependent RNase activity; and
   b.) a second nucleotide sequence encoding an amino acid sequence having 2-5A synthetase activity.

8. A vector of claim 7, said vector being pAM2200 having ATCC Accession No. 98686.

9. A vector of claim 7, said first nucleotide sequence encoding an amino acid sequence having human 2-5A-dependent RNase activity and said second nucleotide sequence encoding an amino acid sequence having human 2-5A synthetase activity.

10. A vector of claim 7, said first nucleotide sequence encoding an amino acid sequence having murine 2-5A-dependent RNase activity and said second nucleotide sequence encoding an amino acid sequence having human 2-5A synthetase activity.

11. A transgenic plant of claim 1, said first nucleotide sequence encoding an amino acid sequence having human 2-5A-dependent RNase activity and said second nucleotide sequence encoding an amino acid sequence having human 2-5A synthetase activity.

12. A transgenic plant of claim 1, said first nucleotide sequence encoding an amino acid sequence having murine 2-5A-dependent RNase activity and said second nucleotide sequence encoding an amino acid sequence having human 2-5A synthetase activity.

13. A tobacco plant of claim 2, said first nucleotide sequence encoding an amino acid sequence having human 2-5A-dependent RNase activity and said second nucleotide sequence encoding an amino acid sequence having human 2-5A synthetase activity.

14. A tobacco plant of claim 2, said first nucleotide sequence encoding an amino acid sequence having murine 2-5A-dependent RNase activity and said second nucleotide sequence encoding an amino acid sequence having human 2-5A synthetase activity.

15. A transgenic plant of claim 6, said vector comprising a first nucleotide sequence encoding an amino acid sequence having human 2-5A-dependent RNase activity and a second nucleotide sequence encoding an amino acid sequence having human 2-5A synthetase activity.

16. A transgenic plant of claim 6, said vector comprising a first nucleotide sequence encoding an amino acid sequence having murine 2-5A-dependent RNase activity and a second nucleotide sequence encoding an amino acid sequence having human 2-5A synthetase activity.

* * * * *